United States Patent [19]
Ries et al.

[11] Patent Number: 6,114,532
[45] Date of Patent: Sep. 5, 2000

[54] BICYCLIC HETEROCYCLES, THE PREPARATION THEREOF, AND THEIR USE AS PHARMACEUTICALS

[75] Inventors: Uwe Ries, Biberach; Norbert Hauel, Schemmerhofen; Gerhard Mihm, Biberach; Henning Priepke, Warthausen; Klaus Binder, Wiesbaden; Jean-Marie Stassen, Warthausen; Wolfgang Weinen, Biberach; Rainer Zimmerman, Mittelbiberach, all of Germany

[73] Assignee: Boehringer Ingelheim Pharma KG, Ingelheim, Germany

[21] Appl. No.: 09/243,200

[22] Filed: Feb. 2, 1999

Related U.S. Application Data

[60] Provisional application No. 60/077,694, Mar. 12, 1998.

[30] Foreign Application Priority Data

Feb. 3, 1998 [DE] Germany .......................... 198 04 085
Jul. 30, 1998 [DE] Germany .......................... 198 34 325

[51] Int. Cl.$^7$ .................... C07D 209/18; C07D 235/16; C07D 413/06; C07D 401/12; C07D 307/01; C07D 263/56; A61K 31/4184
[52] U.S. Cl. .................... 546/162; 514/314; 514/367; 514/394; 548/306.1; 548/309.7
[58] Field of Search .................... 548/309.7; 546/162; 514/367

[56] References Cited

U.S. PATENT DOCUMENTS

| | | | |
|---|---|---|---|
| 3,972,890 | 8/1976 | Botta ............................... | 548/309.7 X |
| 3,993,469 | 11/1976 | Regel et al. ..................... | 548/309.7 X |
| 4,420,487 | 12/1983 | Shetty et al. ......................... | 424/273 B |
| 4,634,783 | 1/1987 | Fujii et al. .............................. | 549/475 |
| 4,728,741 | 3/1988 | Kaiser et al. ........................... | 548/305 |
| 4,851,406 | 7/1989 | Mertens, I et al. . | |
| 4,954,498 | 9/1990 | Mertens, II et al. .................... | 514/254 |
| 5,116,843 | 5/1992 | Mertens, III et al. ................. | 514/253 |
| 5,298,518 | 3/1994 | Miyake et al. .......................... | 514/381 |
| 5,342,851 | 8/1994 | Sanfilippo et al. ..................... | 514/370 |
| 5,434,150 | 7/1995 | Austel et al. ........................ | 514/228.5 |
| 5,466,813 | 11/1995 | Diehl et al. .............................. | 548/179 |
| 5,576,444 | 11/1996 | Himmelsbach et al. . | |

FOREIGN PATENT DOCUMENTS

| | | |
|---|---|---|
| 0 223 937 | 6/1987 | European Pat. Off. . |
| 0 275 888 | 7/1988 | European Pat. Off. . |
| 0 531 883 | 3/1993 | European Pat. Off. . |
| 0 540 051 | 5/1993 | European Pat. Off. . |
| 0 567 966 | 11/1993 | European Pat. Off. . |
| 0 655 439 | 5/1995 | European Pat. Off. . |
| 197 18 181 | 11/1998 | Germany . |
| 98 37075 | 8/1998 | WIPO . |

OTHER PUBLICATIONS

T. Nagahara, et al; "Dibasic (Amidinoary) Propanoic Acid Derivatives As Novel Blood Coagulation Facrtor Xa Inhibitors"; Journal of Medicinal Chemistry; 1994; pp. 1200–1207; vol. 37; Pub. American Chemical Society; US.

*Primary Examiner*—Floyd D. Higel
*Attorney, Agent, or Firm*—R. P. Raymond; A. R. Stempel; M-E. M. Devlin

[57] ABSTRACT

The present invention relates to 5-membered heterocyclic condensed benzoderivatives of formula

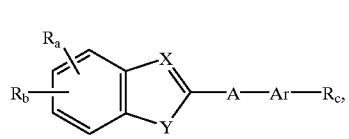

(I)

wherein $R_a$ to $R_c$, A, X and Y are defined as in claim 1, the tautomers, stereoisomers, mixtures thereof and the salts thereof, particularly the physiologically acceptable salts thereof with inorganic or organic acids or bases which have valuable properties.

The compounds of the above formula I wherein $R_c$ denotes a cyano group are valuable intermediates for preparing the other compounds of formula I, and the compounds of the above formula I wherein $R_c$ denotes one of the following amidino groups and the tautomers and stereoisomers thereof have valuable pharmacological properties, particularly an antithrombotic activity.

11 Claims, No Drawings

BICYCLIC HETEROCYCLES, THE PREPARATION THEREOF, AND THEIR USE AS PHARMACEUTICALS

RELATED APPLICATIONS

This application claims the benefit of U.S. provisional application Ser. No. 60/077,694, filed Mar. 12, 1998.

The present invention relates to new 5-membered heterocyclic condensed benzoderivatives of general formula

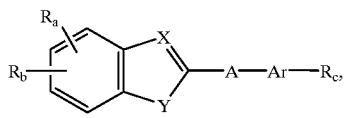

(I)

their tautomers, stereoisomers, mixtures thereof and the salts thereof, particularly the physiologically acceptable salts thereof with inorganic or organic acids or bases which have valuable properties.

The compounds of the above general formula I wherein $R_c$ denotes a cyano group are valuable intermediates for the preparation of the other compounds of general formula I, and the compounds of the above general formula I wherein $R_c$ denotes one of the following amidino groups, and the tautomers and stereoisomers thereof have valuable pharmacological properties, particularly an antithrombotic activity.

The present application thus relates to the new compounds of the above general formula I and the preparation thereof, pharmaceutical compositions containing the pharmacologically effective compounds and the use thereof.

In the above general formula

A denotes an oxygen or sulphur atom, a carbonyl, sulphinyl or sulphonyl group, an imino group optionally substituted by a $C_{1-3}$-alkyl group or a methylene group optionally mono- or disubstituted by a carboxy-$C_{1-3}$-alkyl- or $C_{1-3}$-alkoxycarbonyl-$C_{1-3}$-alkyl group, Ar denotes a phenylene or naphthylene group each optionally substituted by a fluorine, chlorine or bromine atom, by a trifluoromethyl, $C_{1-3}$-alkyl- or $C_{1-3}$-alkoxy group, a thienylene, thiazolylene, pyridinylene, pyrimidinylene, pyrazinylene or pyridazinylene group each optionally substituted in the carbon skeleton by a $C_{1-3}$-alkyl group, X denotes a nitrogen atom or an —$R_1C$= group wherein $R_1$ denotes a hydrogen, fluorine, chlorine, bromine or iodine atom, a $C_{1-3}$-alkyl or $C_{1-3}$-alkoxy group, Y denotes an oxygen or sulphur atom or an —$R_2N$— group, wherein $R_2$ denotes a hydrogen atom or a $C_{1-5}$-alkyl group, a $C_{1-3}$-alkyl group, which is substituted by a phenyl group optionally substituted by a carboxy or $C_{1-3}$-alkoxycarbonyl group, a $C_{1-5}$-alkyl group, which is substituted by a carboxy, $C_{1-3}$-alkoxycarbonyl, carboxy-$C_{1-3}$-alkoxycarbonyl, $C_{1-3}$-alkoxycarbonyl-$C_{1-3}$-alkoxycarbonyl, carboxy-$C_{1-3}$-alkyl-aminocarbonyl or $C_{1-3}$-alkoxycarbonyl-$C_{1-3}$-alkylaminocarbonyl group, or an n-$C_{2-4}$-alkyl group, which is terminally substituted by a di-($C_{1-3}$-alkyl)-amino, pyrrolidino, piperidino, morpholino, piperazino or N-$C_{1-3}$-alkyl-piperazino group, whilst the abovementioned cyclic groups may additionally be substituted by one or two $C_{1-3}$-alkyl groups, $R_a$ denotes a hydrogen atom or a $C_{1-3}$-alkyl group, $R_b$ denotes a $R_3$—CO—$C_{3-5}$-cycloalkylene, $R_3$—$SO_2$—$NR_4$, $R_3$—CO—$NR_4$, $R_5NR_6$—CO, $R_5NR_6$—$SO_2$— or $R_5NR_6$—CO—$C_{3-5}$-cycloalkylene group, wherein $R_3$ denotes a $C_{1-6}$-alkyl- or $C_{5-7}$-cycloalkyl group, a $C_{1-3}$-alkyl group, which is substituted by a $C_{5-7}$-cycloalkyl, phenyl, $C_{1-3}$-alkylamino, di-($C_{1-3}$-alkyl)-amino, carboxy-$C_{1-3}$-alkylamino, $C_{1-3}$-alkoxycarbonylamino, phenylsulphonylamino or tetrazolyl group, a $C_{1-3}$-alkyl group, which is substituted by a carboxy, $C_{1-3}$-alkoxycarbonyl, carboxy-$C_{1-3}$-alkoxy or $C_{1-3}$-alkoxy-carbonyl-$C_{1-3}$-alkoxy group, a $C_{1-3}$-alkyl group, which is substituted by an imidazolyl or benzimidazolyl group, whilst the imidazole moiety of the abovementioned groups may be substituted by one or two $C_{1-3}$-alkyl groups or by a carboxy-$C_{1-3}$-alkyl or $C_{1-3}$-alkoxycarbonyl-$C_{1-3}$-alkyl group, a phenyl group optionally mono or disubstituted by $C_{1-3}$-alkyl, $C_{1-3}$-alkoxy, trifluoromethyl, carboxy or $C_{1-3}$-alkoxycarbonyl groups, wherein the substituents may be identical or different, a phenyl group substituted by 3 or 4 methyl groups, a naphthyl, pyridinyl, pyrazolyl, quinolyl or isoquinolyl group each optionally substituted by a $C_{1-3}$-alkyl group, $R_4$ denotes a hydrogen atom, a $C_{1-5}$-alkyl or $C_{5-7}$-cycloalkyl group, a $C_{1-5}$-alkyl group, which is substituted by a carboxy group or by a $C_{1-5}$-alkoxycarbonyl group wherein the alkoxy moiety in the 2 or 3 position may additionally be substituted by a hydroxy group, a $C_{1-3}$-alkyl group, which is substituted by an aminocarbonyl, hydroxyaminocarbonyl, $C_{1-3}$-alkylamino-carbonyl, di-($C_{1-3}$-alkyl)-aminocarbonyl or $C_{5-7}$-alkylene-iminocarbonyl group, whilst the $C_{6-7}$-alkyleneimino moiety may additionally be substituted in the 4 position by a di-($C_{1-3}$-alkyl)-amino group, an optionally phenyl-substituted $C_{1-3}$-alkyl group, which is substituted in the alkyl moiety by a carboxy-$C_{1-3}$-alkoxycarbonyl, $C_{1-3}$-alkoxycarbonyl-$C_{1-3}$-alkoxycarbonyl, carboxy-$C_{1-3}$-alkylaminocarbonyl, N-($C_{1-3}$-alkyl)-carboxy-$C_{1-3}$-alkylaminocarbonyl, $C_{1-3}$-alkoxycarbonyl-$C_{1-3}$-alkylaminocarbonyl, N-($C_{1-3}$-alkyl)-$C_{1-3}$-alkoxycarbonyl-$C_{1-3}$-alkylaminocarbonyl, morpholinocarbonyl or 4-($C_{1-3}$-alkyl)-piperazinocarbonyl group, a $C_{1-3}$-alkyl group, which is substituted by a carboxy-$C_{1-3}$-alkylaminocarbonyl, N-($C_{1-3}$-alkyl)-carboxy-$C_{1-3}$-alkylaminocarbonyl, $C_{1-3}$-alkoxycarbonyl-$C_{1-3}$-alkylaminocarbonyl or N-($C_{1-3}$-alkyl)-$C_{1-3}$-alkoxycarbonyl-$C_{1-3}$-alkylamino-carbonyl group, which are additionally substituted at a carbon atom of the alkylamino moiety by a carboxy or $C_{1-3}$-alkoxycarbonyl group, a $C_{1-3}$-alkyl group, which is substituted by a di-($C_{1-3}$-alkyl)-aminocarbonyl group wherein an alkyl moiety may additionally be substituted in the 2 or 3 position by a di-($C_{1-3}$-alkyl)-amino group, a $C_{1-3}$-alkyl group, which is substituted by a 4-(morpholinocarbonyl-$C_{1-3}$-alkyl)-piperazinocarbonyl, N-($C_{1-3}$-alkyl)-pyrrolidinyl or N-($C_{1-3}$-alkyl)-piperidinyl group, or an n-$C_{2-4}$-alkyl group, which is terminally substituted by a di-($C_{1-3}$-alkyl)-amino, $C_{5-7}$-alkyleneimino or morpholino group, $R_5$ denotes a $C_{1-5}$-alkyl or $C_{5-7}$-cycloalkyl group, a phenyl-$C_{1-3}$-alkyl group, which may be substituted in the alkyl moiety by a carboxy or $C_{1-3}$-alkoxycarbonyl group, an n-$C_{2-4}$-alkyl group, which is substituted in the 2, 3 or 4 position by a hydroxy, $C_{1-3}$-alkylamino or di-($C_{1-3}$-alkyl)-amino group, a phenyl group optionally mono or disubstituted by a $C_{1-3}$-alkyl, $C_{1-3}$-alkoxy, trifluoromethyl, carboxy or $C_{1-3}$-alkoxycarbonyl group, wherein the substituents may be identical or different, a phenyl group substituted by 3 or 4 methyl groups, a naphthyl, pyridinyl, quinolyl or isoquinolyl group, $R_6$ denotes a $C_{1-5}$-alkyl group optionally substituted by a carboxy or $C_{1-3}$-alkoxycarbonyl group, a $C_{1-3}$-alkyl group, which is substituted in the alkyl moiety by a $C_{1-3}$-alkylaminocarbonyl, di-($C_{1-3}$-alkyl)-aminocarbonyl, carboxy-$C_{1-3}$-alkylaminocarbonyl or $C_{1-3}$-alkyloxycarbonyl-$C_{1-3}$-alkylaminocarbonyl group, or an n-$C_{2-4}$-alkyl group, which is substituted in the 2, 3 or 4 position by a hydroxy, $C_{1-3}$-alkylamino or di-($C_{1-3}$-alkyl)-amino group, or one of the groups $R_5$ or $R_6$ denotes a hydrogen atom, whilst the other one of the groups has the meanings given for $R_5$ and $R_6$ hereinbefore, or $R_5$ and $R_6$ together with the nitrogen atom between them denote a pyrrolidino or piperidino group optionally substituted by one or two $C_{1-3}$-alkyl groups, which may additionally be substituted by a carboxy-$C_{1-3}$-alkyl or $C_{1-3}$-alkoxy-$C_{1-3}$-alkyl group or on to which a benzene ring may be condensed via two adjacent carbon atoms, or $R_b$ denotes an amino, $C_{1-3}$-alkylamino or $C_{5-7}$-cycloalkyl-amino group, which may be substituted at the nitrogen atom by a phenylaminocarbonyl, N-phenyl-$C_{1-3}$-alkylaminocarbonyl, phenylsulphonylamino-$C_{1-3}$-alkylcarbonyl, $C_{1-3}$-alkyloxy-carbonyl-$C_{1-3}$-alkyl, N-($C_{3-5}$-cycloalkyl)-$C_{1-3}$-alkylamino-carbonyl, N-(hydroxycarbonyl-$C_{1-3}$-alkyl)-aminocarbonyl, N-($C_{1-3}$-alkoxycarbonyl-$C_{1-3}$-alkyl)-aminocarbonyl-$C_{3-5}$-cyclo-alkylamino group, a piperidino group substituted in the 4 position by a di-($C_{1-3}$-alkyl)-amino group, a piperazino group substituted in the 4 position by a $C_{1-3}$-alkyl group, a $C_{2-4}$-alkylsulphonyl group, which is substituted in the 2, 3 or 4 position by a di-($C_{1-3}$-alkyl)-amino group, a 4-oxo-3,4-dihydro-phthalazinyl-1-yl or 4-oxo-2,3-diaza-spiro[5.5]undec-1-en-1-yl group, a methyl group substituted by a $C_{5-7}$-cycloalkyleneiminocarbonyl group wherein the methyl group is substituted by a carboxy-$C_{1-3}$-alkyl or $C_{1-3}$-alkoxy-$C_{1-3}$-alkyl group, a carbonyl or methyl group substituted by a $C_{3-5}$-cycloalkyl or $C_{3-5}$-alkyl group, whilst the cycloalkyl moiety may additionally be substituted by a $C_{1-3}$-alkyl, carboxy-$C_{1-3}$-alkyl or $C_{1-3}$-alkoxycarbonyl-$C_{1-3}$-alkyl group and the methyl moiety is substituted by a $C_{1-3}$-alkoxy or $C_{1-4}$-alkylamino group, a $C_{5-7}$-cycloalkyl-N-(carboxy-$C_{1-3}$-alkoxy)-iminomethylene or $C_{5-7}$-cycloalkyl-N-($C_{1-3}$-alkoxycarbonyl-$C_{1-3}$-alkoxy)-iminomethylene group, which may additionally be substituted in the cycloalkyl moiety by a $C_{1-3}$-alkyl group, a phosphinyl group, which is substituted by a $C_{1-6}$-alkyl or $C_{5-7}$-cycloalkyl group and by a hydroxy, $C_{1-3}$-alkoxy, carboxy-$C_{1-3}$-alkoxy or $C_{1-3}$-alkoxycarbonyl-$C_{1-3}$-alkoxy group, a piperidino group wherein in the 2 position a methylene group is replaced by a carbonyl or sulphonyl group, a tetrazolyl group optionally substituted by a $C_{1-5}$-alkyl group, a phenyl or phenylsulphonyl group optionally mono or disubstituted by a $C_{1-3}$-alkyl, $C_{1-3}$-alkoxy, trifluoromethyl, carboxy or $C_{1-3}$-alkoxycarbonyl group, wherein the substituents may be identical or different, a sulphimidoyl group, which is substituted at the sulphur atom by a $C_{5-7}$-cycloalkyl group and may additionally be substituted at the nitrogen atom by a $C_{2-4}$-alkanoyl, carboxy-$C_{1-3}$-alkyl, $C_{1-3}$-alkoxycarbonyl-$C_{1-3}$-alkyl, carboxy-$C_{2-4}$-alkanoyl or $C_{1-3}$-alkoxycarbonyl-$C_{2-4}$-alkanoyl group, an imidazolyl group substituted in the 1 position by a carboxy-$C_{1-3}$-alkyl or $C_{1-3}$-alkoxycarbonyl-$C_{1-3}$-alkyl group, which may additionally be substituted by a $C_{1-5}$-alkyl group, a $C_{1-3}$-alkoxycarbonyl-$C_{1-3}$-alkyl group, which is substituted in the alkyl moiety by a $C_{5-7}$-cycloalkylaminocarbonyl group, a $C_{1-3}$-alkyl group, which is substituted by a 1-imidazolyl group, whilst the imidazolyl moiety may additionally be substituted by one or two $C_{1-3}$-alkyl groups, or in the 2 position by a 1-benzimidazolyl group substituted by a carboxy-$C_{1-3}$-alkyl or $C_{1-3}$-alkoxycarbonyl-$C_{1-3}$-alkyl group, or a furanyl-1-pyrazolyl group optionally substituted by a $C_{1-3}$-alkyl group, and $R_c$ denotes a cyano group or an amidino group, which may be substituted by a hydroxy group, by one or two $C_{1-3}$-alkyl groups, by one or two $C_{1-8}$-alkoxycarbonyl groups or by a group which can be cleaved in vivo, especially those compounds wherein A, X, Y and $R_a$ to $R_d$ are with the proviso as hereinbefore defined that Ar represents a 1,4-phenylene group, $R_3$ does not represent a pyrazolyl group or a naphthyl, pyridinyl, pyrazolyl, quinolyl or isoquinolyl group each substituted by a $C_{1-3}$-alkyl group and $R_b$ does not represent a furanyl-1-pyrazolyl group optionally substituted by a $C_{1-3}$-alkyl group.

The term "a group which can be cleaved in vivo from an imino or amino group" may refer, for example, to a hydroxy group, an acyl group such as the benzoyl or pyridinoyl group or a $C_{1-16}$-alkanoyl group such as the formyl, acetyl, propionyl, butanoyl, pentanoyl or hexanoyl group, an allyloxycarbonyl group, a $C_{1-16}$-alkoxycarbonyl group such as the methoxycarbonyl, ethoxycarbonyl, propoxycarbonyl, isopropoxycarbonyl, butoxycarbonyl, tert. butoxycarbonyl, pentoxycarbonyl, hexyloxycarbonyl, octyloxycarbonyl, nonyloxycarbonyl, decyloxycarbonyl, undecyloxycarbonyl, dodecyloxycarbonyl or hexadecyloxycarbonyl group, a phenyl-$C_{1-6}$-alkoxycarbonyl group such as the benzyloxycarbonyl, phenylethoxycarbonyl or phenylpropoxycarbonyl group, a $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl or $R_7CO$—O—($R_8CR_9$)—O—CO group, wherein $R_7$ denotes a $C_{1-8}$-alkyl, $C_{5-7}$-cycloalkyl, phenyl or phenyl-$C_{1-3}$-alkyl group, $R_8$ denotes a hydrogen atom, a $C_{1-3}$-alkyl, $C_{5-7}$-cycloalkyl or phenyl group and $R_0$ denotes a hydrogen atom or a $C_{1-3}$-alkyl group.

Moreover, the saturated alkyl and alkoxy moieties mentioned in the above definitions which contain more than 2 carbon atoms also include the branched isomers thereof, such as the isopropyl, tert.butyl, isobutyl group etc.

Preferred compounds of the abovementioned invention are those of general formula

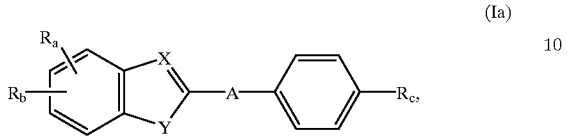

(Ia)

wherein

A, X, Y and $R_a$ to $R_c$ are as hereinbefore defined, especially those compounds of general formula Ia wherein A denotes a methylene group optionally substituted by a carboxy-$C_{1-3}$-alkyl or $C_{1-3}$-alkoxycarbonyl-$C_{1-3}$-alkyl group, or a carbonyl or imino group, X denotes a nitrogen atom or an —$R_1C=$ group, wherein $R_1$ denotes a hydrogen, fluorine, chlorine or bromine atom, a $C_{1-3}$-alkyl or $C_{1-3}$-alkoxy group, Y denotes an oxygen or sulphur atom or an —$R_2N$— group, wherein $R_2$ denotes a hydrogen atom or a $C_{1-5}$-alkyl group, a benzyl group, which may be substituted in the phenyl moiety by a carboxy or $C_{1-3}$-alkoxycarbonyl group, a $C_{1-5}$-alkyl group, which is substituted by a carboxy or $C_{1-3}$-alkoxycarbonyl group, a $C_{1-3}$-alkyl group, which is substituted by a carboxy-$C_{1-3}$-alkoxycarbonyl, carboxy-$C_{1-3}$-alkylaminocarbonyl or $C_{1-3}$-alkoxycarbonyl-$C_{1-3}$-alkylaminocarbonyl group, or an n-$C_{2-4}$-alkyl group, which is terminally substituted by a di-($C_{1-3}$-alkyl)-amino or morpholino group, $R_a$ denotes a hydrogen atom or a methyl group, $R_b$ denotes an $R_3$—CO—$C_{3-5}$-cycloalkylene, $R_3$—$SO_2$—$NR_4$, $R_3$—CO—$NR_4$, $R_5NR_6$—CO, $R_5NR_6$—$SO_2$ or $R_5NR_6$—CO—$C_{3-5}$-cycloalkylene group, wherein $R_3$ denotes a $C_{1-4}$-alkyl, cyclopentyl, cyclohexyl or benzyl group, a $C_{1-3}$-alkyl group, which is substituted by a tetrazolyl, carboxy, $C_{1-3}$-alkoxycarbonyl, carboxy-$C_{1-3}$-alkoxy, $C_{1-3}$-alkoxycarbonyl-$C_{1-3}$-alkoxy, carboxy-$C_{1-3}$-alkylamino, $C_{1-3}$-alkoxycarbonylamino group, a phenyl group optionally mono or disubstituted by methyl, methoxy, trifluoromethyl, carboxy or methoxycarbonyl groups, wherein the substituents may be identical or different, a phenyl group substituted by 3 or 4 methyl groups, a 5-pyrazolyl group optionally substituted by a $C_{1-3}$-alkyl group, a naphthyl, pyridinyl, quinolyl or isoquinolyl group, $R_4$ denotes a hydrogen atom, a $C_{1-5}$-alkyl or $C_{5-7}$-cycloalkyl group, a $C_{1-5}$-alkyl group, which is substituted by a carboxy group or by a $C_{1-5}$-alkoxycarbonyl group wherein the alkoxy moiety in the 2 or 3 position may additionally be substituted by a hydroxy group, a $C_{1-3}$-alkyl group, which is substituted by an aminocarbonyl, hydroxyaminocarbonyl or piperidinocarbonyl group, whilst the piperidino moiety may additionally be substituted in the 4 position by a dimethylamino group, a $C_{1-3}$-alkyl group, which is substituted by a carboxy-$C_{1-3}$-alkylaminocarbonyl, N-($C_{1-3}$-alkyl)-carboxy-$C_{1-3}$-alkylaminocarbonyl, $C_{1-3}$-alkoxycarbonyl-$C_{1-3}$-alkylaminocarbonyl, N-($C_{1-3}$-alkyl)-$C_{1-3}$-alkoxycarbonyl-$C_{1-3}$-alkylaminocarbonyl, morpholinocarbonyl or 4-($C_{1-3}$-alkyl)-piperazinocarbonyl group, a $C_{1-3}$-alkyl group, which is substituted by a carboxy-$C_{1-3}$-alkylaminocarbonyl, N-($C_{1-3}$-alkyl)-carboxy-$C_{1-3}$-alkylaminocarbonyl, $C_{1-3}$-alkoxycarbonyl-$C_{1-3}$-alkylaminocarbonyl or N-($C_{1-3}$-alkyl)-$C_{1-3}$-alkoxycarbonyl-$C_{1-3}$-alkylamino-carbonyl group, which are additionally substituted at a carbon atom of the alkylamino moiety by a carboxy or $C_{1-3}$-alkoxycarbonyl group, a $C_{1-3}$-alkyl group, which is substituted in the alkyl moiety by a di-($C_{1-3}$-alkyl)-aminocarbonyl group wherein an alkyl moiety may additionally be substituted in the 2 or 3 position by a di-($C_{1-3}$-alkyl)-amino group, a $C_{1-3}$-alkyl group, which is substituted in the alkyl moiety by a 4-(morpholinocarbonyl-$C_{1-3}$-alkyl)-piperazinocarbonyl or N-($C_{1-3}$-alkyl)-pyrrolidinyl group, or an n-$C_{2-3}$-alkyl group, which is terminally substituted by a di-($C_{1-3}$-alkyl)-amino, $C_{5-7}$-alkyleneimino or morpholino group, $R_5$ denotes a $C_{1-5}$-alkyl or $C_{5-7}$-cycloalkyl group, a phenyl-$C_{1-3}$-alkyl group, which may be substituted in the alkyl moiety by a carboxy or $C_{1-3}$-alkoxycarbonyl group, a phenyl, naphthyl, pyridinyl, quinolyl or isoquinolyl group and $R_6$ denotes a $C_{1-5}$-alkyl group optionally substituted by a carboxy or $C_{1-3}$-alkoxycarbonyl group, a $C_{1-3}$-alkyl group, which is substituted in the alkyl moiety by a $C_{1-3}$-alkylaminocarbonyl, di-($C_{1-3}$-alkyl)-aminocarbonyl, carboxy-$C_{1-3}$-alkylaminocarbonyl or $C_{1-3}$-alkyloxycarbonyl-$C_{1-3}$-alkylaminocarbonyl group, an n-$C_{2-3}$-alkyl group, which is substituted in the 2 or 3 position by a $C_{1-3}$-alkylamino or di-($C_{1-3}$-alkyl)-amino group, or one of the groups $R_5$ or $R_6$ denotes a hydrogen atom, whilst the other one of the groups has the meanings given for $R_5$ and $R_6$ hereinbefore, or $R_5$ and $R_6$ together with the nitrogen atom between them denote a pyrrolidino or piperidino group optionally substituted by a $C_{1-3}$-alkyl, carboxy-$C_{1-3}$-alkyl or $C_{1-3}$-alkoxy-$C_{1-3}$-alkyl group, onto which a benzene ring may additionally be condensed via two adjacent carbon atoms, or $R_b$ denotes an amino, methylamino, cyclopentylamino or cyclohexylamino group, substituted at the nitrogen atom by a phenylaminocarbonyl, N-phenyl-methylaminocarbonyl, phenylsulphonylaminomethylcarbonyl, hydroxycarbonyl-methylaminocarbonyl or $C_{1-3}$-alkyloxycarbonylmethylamino-carbonyl group, a piperidino group substituted in the 4 position by a di-($C_{1-3}$-alkyl)-amino group, a piperazino group substituted in the 4 position by a $C_{1-3}$-alkyl group, a $C_{2-3}$-alkylsulphonyl group, which is substituted in the 2 or 3 position by a di-($C_{1-3}$-alkyl)-amino group, a 4-oxo-3,4-dihydro-phthalazinyl-1-yl or 4-oxo-2,3-diaza-spiro[5.5]undec-1-en-1-yl group, a carbonyl or methyl group substituted by a cyclopentyl, cyclohexyl or $C_{3-5}$-alkyl group wherein the methyl moiety is substituted by a $C_{1-3}$-alkoxy or $C_{1-4}$-alkylamino group and the cycloalkyl moiety may additionally be substituted by a methyl, carboxymethyl or $C_{1-3}$-alkoxycarbonylmethyl group, a cyclohexyl-N-(carboxymethoxy)-iminomethylene or cyclohexyl-N-($C_{1-3}$-alkoxycarbonylmethoxy)-iminomethylene group, which may additionally be substituted by a methyl group in the cyclohexyl moiety, a phosphinyl group, which is substituted by a $C_{3-6}$-alkyl group and by a hydroxy, $C_{1-3}$-alkoxy, carboxymethoxy or $C_{1-3}$-alkoxycarbonylmethoxy group, a piperidino group wherein in the 2 position a methylene group is replaced by a carbonyl or sulphonyl group, a tetrazolyl group optionally substituted by a $C_{1-5}$-alkyl group, a phenyl or phenylsulphonyl group optionally substituted by a methyl group, a sulphimidoyl group, which is substituted at the sulphur atom by a cyclohexyl group and may additionally be substituted at the nitrogen atom by a $C_{2-4}$-alkanoyl, carboxymethyl, $C_{1-3}$-alkoxycarbonylmethyl, carboxy-$C_{2-3}$-alkanoyl or $C_{1-3}$-alkoxycarbonyl-$C_{2-3}$-alkanoyl group, an imidazolyl group substituted in the 1 position by a carboxymethyl or $C_{1-3}$-alkoxycarbonylmethyl group, which may additionally be substituted by a $C_{1-5}$-alkyl group, a $C_{1-3}$-alkoxycarbonyl-$C_{1-3}$-alkyl group, which is substituted in the alkyl moiety by a $C_{5-7}$-cycloalkylaminocarbonyl group, a $C_{1-3}$-alkyl group, which is substituted by a 1-imidazolyl group, whilst the imidazolyl moiety may additionally be substituted by one or two $C_{1-3}$-alkyl groups, or by a 1-benzimidazolyl group substituted in the 2 position by a carboxy-$C_{1-3}$-alkyl or $C_{1-3}$-alkoxycarbonyl-$C_{1-3}$-alkyl group, or a 5-furanyl-1-pyrazolyl group optionally substituted by a $C_{1-3}$-alkyl group and $R_c$ denotes a cyano group or an amidino group, which may be substituted by one or two $C_{1-3}$-alkyl groups, by one or two $C_{1-8}$-alkoxycarbonyl groups or by a hydroxy group, the tautomers, stereoisomers and salts thereof.

Particularly preferred compounds of general formula I are those wherein

A denotes a methylene or imino group,

X denotes a nitrogen atom or an —$R_1C$= group, wherein $R_1$ denotes a hydrogen, fluorine, chlorine or bromine atom or a methyl group, Y denotes an oxygen or sulphur atom or an —$R_2N$— group, wherein $R_2$ denotes a hydrogen atom, a methyl, benzyl, 4-carboxybenzyl or 4-methoxycarbonylbenzyl group, a $C_{1-3}$-alkyl group, which is substituted by a carboxy or $C_{1-3}$-alkoxycarbonyl group, a methyl group, which is substituted by a carboxymethylaminocarbonyl or $C_{1-3}$-alkoxycarbonylmethylaminocarbonyl group or an n-$C_{2-3}$-alkyl group, which is terminally substituted by a morpholino group, $R_a$ denotes a hydrogen atom, $R_b$ denotes an $R_3$—CO-(1,1-cyclopropylene), $R_3$—$SO_2$—$NR_4$, $R_3$—CO—$NR_4$, $R_5NR_6$—CO, $R_5NR_6$—$SO_2$ or $R_5NR_6$—CO—$C_{3-5}$-(1,1-cyclopropylene) group, wherein $R_3$ denotes a $C_{1-3}$-alkyl, cyclopentyl or cyclohexyl group, a methyl group, which is substituted by a tetrazolyl, carboxymethoxy, $C_{1-3}$-alkoxycarbonylmethoxy, carboxy-$C_{1-3}$-alkylamino, $C_{1-3}$-alkoxycarbonylamino group, a phenyl, naphthyl, pyridinyl, 1-methyl-5-pyrazolyl, quinolyl or isoquinolyl group, $R_4$ denotes a hydrogen atom, a $C_{1-3}$-alkyl or cyclopentyl group, a $C_{1-5}$-alkyl group, which is substituted by a carboxy group or by a $C_{1-3}$-alkoxycarbonyl group, a methyl group, which is substituted by a 4-dimethylaminopiperidinocarbonyl, morpholinocarbonyl, 4-methylpiperazino or 4-morpholinocarbonylmethyl-piperazinocarbonyl group, a $C_{1-3}$-alkyl group, which is substituted by a carboxymethylaminocarbonyl, N-($C_{1-3}$-alkyl)-carboxymethylaminocarbonyl, $C_{1-3}$-alkoxycarbonylmethylaminocarbonyl or N-($C_{1-3}$-alkyl)-$C_{1-3}$-alkoxycarbonylmethylaminocarbonyl group, a $C_{1-3}$-alkyl group, which is substituted by a di-($C_{1-3}$-alkyl)-aminocarbonyl group wherein an alkyl moiety is additionally substituted in the 2 or 3 position by a di-($C_{1-3}$-alkyl)-amino group, a $C_{1-3}$-alkyl group, which is substituted by a carboxymethylaminocarbonyl or $C_{1-3}$-alkoxycarbonylmethylamino-carbonyl group wherein the methyl group of the methylamino moiety is additionally substituted by an aminocarbonyl-methyl group, an n-$C_{2-3}$-alkyl group, which is terminally substituted by a di-($C_{1-3}$-alkyl)-amino, pyrrolidino or morpholino group, $R_5$ denotes a $C_{1-5}$-alkyl, cyclopentyl, cyclohexyl, phenyl, naphthyl, pyridinyl, quinolyl or isoquinolyl group, $R_6$ denotes a $C_{1-5}$-alkyl group optionally substituted by a carboxy or $C_{1-3}$-alkoxycarbonyl group, a $C_{1-3}$-alkyl group, which is substituted by a $C_{1-3}$-alkylaminocarbonyl, carboxymethylaminocarbonyl or $C_{1-3}$-alkyl-oxycarbonylmethylaminocarbonyl group, or $R_5$ and $R_6$ together with the nitrogen atom between them denote a pyrrolidino group substituted by a carboxymethyl or $C_{1-3}$-alkoxymethyl group or a pyrrolidino group onto which a benzene ring is additionally condensed via two adjacent carbon atoms, or $R_b$ denotes an N-pyrrolidinocarbonyl-methylamino, phenylsulphonyl, 4-oxo-2,3-diaza-spiro[5.5]undec-1-en-1-yl or $C_{3-5}$-alkyl-tetrazolyl group, a cyclohexylcarbonyl group, which is substituted by a methyl, carboxymethyl or $C_{1-3}$-alkoxycarbonylmethyl group, a cyclohexyl-N-(carboxymethoxy)-iminomethylene or cyclohexyl-N-($C_{1-3}$-alkoxycarbonylmethoxy)-iminomethylene group, which is additionally substituted by a methyl group in the cyclohexyl moiety, a phosphinyl group, which is substituted by a $C_{3-6}$-alkyl group and by a $C_{1-3}$-alkoxymethoxy group a sulphimidoyl group, which is substituted at the sulphur atom by a cyclohexyl group and additionally at the nitrogen atom by a $C_{2-4}$-alkanoyl group, or a 3-methyl-5-(furan-2-yl)-1-pyrazolyl group, and $R_c$ denotes an amidino group, the tautomers, stereoisomers and salts thereof.

Most particularly preferred compounds of general formula I are those wherein

A denotes a methylene group,

X denotes a nitrogen atom or an —HC= group,

Y denotes an oxygen or sulphur atom or an —$R_2$N— group, wherein $R_2$ denotes a hydrogen atom, a methyl, benzyl or $C_{1-3}$-alkoxycarbonylmethyl group, $R_a$ denotes a hydrogen atom, $R_b$ denotes a $R_5NR_6$—$SO_2$, $R_5NR_6$—CO, $R_3$—$SO_2$—$NR_4$, $R_3$—CO—$NR_4$ or $R_5NR_6$—CO—$C_{3-5}$-(1,1-cyclopropylene) group, wherein $R_3$ denotes a cyclopentyl, cyclohexyl, phenyl, naphthyl, 1-methyl-pyrazolyl, quinolyl or isoquinolyl group or a methyl group, which is substituted by a carboxymethylamino, $C_{1-3}$-alkoxycarbonyl-methylamino, carboxymethoxy, $C_{1-3}$-alkoxycarbonylmethoxy or tetrazolyl group, $R_4$ denotes a hydrogen atom or a methyl group, substituted by a carboxy, $C_{1-3}$-alkoxycarbonyl, morpholinocarbonyl, 4-dimethylamino-piperidinocarbonyl, 4-methyl-piperazinocarbonyl, 4-morpholinocarbonylmethyl-piperazinocarbonyl, carboxymethylaminocarbonyl, N-methyl-carboxymethylamino-carbonyl, $C_{1-3}$-alkoxycarbonylmethylaminocarbonyl, N-methyl-$C_{1-3}$-alkoxycarbonylmethylaminocarbonyl, N-($C_{1-3}$-alkyl)-N-(2-dimethylamino-ethyl)-aminocarbonyl, N-(1-carboxy-2-aminocarbonyl-ethyl)-aminocarbonyl or N-(1-$C_{1-3}$-alkoxycarbonyl-2-aminocarbonyl-ethyl)-aminocarbonyl group, or a cyclopentyl group, $R_5$ denotes a $C_{1-5}$-alkyl, phenyl or pyridyl group and $R_6$ denotes a $C_{1-5}$alkyl group, which may be terminally substituted by a carboxy or $C_{1-3}$-alkoxycarbonyl group, or a $C_{1-3}$-alkyl group substituted by a methylaminocarbonyl, carboxymethylaminocarbonyl or $C_{1-3}$-alkoxycarbonylmethylaminocarbonyl group or substituted in the 2 or 3 position by a dimethylamino group, or $R_5$ together with $R_6$ and the nitrogen atom between them denotes a 1-methyl-5-pyrazolyl group, a pyrrolidino group optionally substituted by a $C_{1-3}$-alkoxycarbonyl group or a pyrrolidino group onto which a benzene ring is condensed via two adjacent carbon atoms, or $R_b$ denotes a N-pyrrolidinocarbonyl-methylamino, phenylsulphonyl, 4-oxo-2,3-diaza-spiro[5.5]undec-1-en-1-yl or $C_{3-5}$-alkyl-tetrazolyl group, a cyclohexylcarbonyl group, which is substituted in the 1 position by a methyl, carboxymethyl or $C_{1-3}$-alkoxycarbonylmethyl group a cyclohexyl-N-(carboxymethoxy)-iminomethylene or cyclohexyl-N-($C_{1-3}$-alkoxycarbonylmethoxy)-iminomethylene group, which is additionally substituted in the cyclohexyl moiety by a methyl group, or a phosphinyl group, which is substituted by a $C_{3-6}$-alkyl group and by a $C_{1-3}$-alkoxymethoxy group, and $R_c$ denotes an amidino group, particularly those compounds of general formula I wherein A denotes a methylene group, X denotes a nitrogen atom or an —HC= group, Y denotes an oxygen or sulphur atom or an —$R_2$N— group, wherein $R_2$ denotes a hydrogen atom, a methyl, benzyl or $C_{1-3}$-alkoxycarbonylmethyl group, $R_a$ denotes a hydrogen atom, $R_b$ denotes an $R_{5a}NR_{6a}$—$SO_2$ group, wherein $R_{5a}$ denotes a $C_{1-3}$-alkyl or phenyl group and $R_{6a}$ denotes a $C_{1-5}$-alkyl group, which is terminally substituted by a carboxy or $C_{1-3}$-alkoxycarbonyl group or is substituted in the 2 or 3 position by a dimethylamino group, or $R_{5a}$ together with $R_{6a}$ and the nitrogen atom between them denotes a pyrrolidino group optionally substituted by a $C_{1-3}$-alkoxycarbonyl group or a pyrrolidino group onto which a benzene ring is condensed via two adjacent carbon atoms, or an $R_{3a}$—$SO_2$—$NR_{4a}$ group, wherein $R_{3a}$ denotes a cyclopentyl, cyclohexyl, phenyl, naphthyl, quinolyl or isoquinolyl group and $R_{4a}$ denotes a hydrogen atom or a methyl group which is substituted by a carboxy, $C_{1-3}$-alkoxycarbonyl, morpholinocarbonyl, 4-dimethylamino-piperidinocarbonyl, 4-methyl-piperazinocarbonyl, 4-morpholinocarbonylmethyl-piperazinocarbonyl, carboxymethylaminocarbonyl, N-methyl-carboxymethylaminocarbonyl, $C_{1-3}$-alkoxycarbonylmethyl-aminocarbonyl, N-methyl-$C_{1-3}$-alkoxycarbonylmethyl-aminocarbonyl, N-($C_{1-3}$-alkyl)-N-(2-dimethylamino-ethyl)-aminocarbonyl, N-(1-carboxy-2-aminocarbonyl-ethyl)-aminocarbonyl or N-(1-$C_{1-3}$-alkoxycarbonyl-2-aminocarbonyl-ethyl)-aminocarbonyl group, or a $R_{5b}NR_{6b}$—CO group, wherein $R_{5b}$ denotes a $C_{3-5}$-alkyl, phenyl or pyridyl group and $R_{6b}$ denotes a $C_{1-5}$-alkyl group or a $C_{1-3}$-alkyl group, which is substituted by a carboxy, $C_{1-3}$-alkoxycarbonyl, methylaminocarbonyl, carboxymethylaminocarbonyl or $C_{1-3}$-alkoxycarbonylmethylaminocarbonyl group or in the 2 or 3 position is also substituted by a dimethylamino group, or an $R_{3b}$—CO—$NR_{4b}$ group, wherein $R_{3b}$ denotes a phenyl group and $R_{4b}$ denotes a $C_{1-3}$-alkyl group, which is substituted by a carboxy or $C_{1-3}$-alkoxycarbonyl group, or $R_{3b}$ denotes a methyl group, which is substituted by a carboxymethylamino, $C_{1-3}$-alkoxycarbonylmethylamino, carboxymethoxy, $C_{1-3}$-alkoxycarbonylmethoxy or tetrazolyl group, and $R_{4b}$ denotes a cyclopentyl group, or a $R_{5c}NR_{6c}$—CO—$C_{3-5}$-(1,1-cyclopropylene) group, wherein $R_{5c}$ together with $R_{6c}$ and the nitrogen atom between them denotes a 1-methyl-5-pyrazolyl group, a pyrrolidino group optionally substituted by a $C_{1-3}$-alkoxycarbonyl group or a pyrrolidino group onto which a benzene ring is condensed via two adjacent carbon atoms, or $R_b$ denotes a N-pyrrolidinocarbonyl-methylamino, phenylsulphonyl, 4-oxo-2,3-diaza-spiro[5.5]undec-1-en-1-yl or $C_{3-5}$-alkyl-tetrazolyl group, a cyclohexylcarbonyl group, which is substituted in the 1 position by a methyl, carboxymethyl or $C_{1-3}$-alkoxycarbonylmethyl group a cyclohexyl-N-(carboxymethoxy)-iminomethylene or cyclohexyl-N-($C_{1-3}$-alkoxycarbonylmethoxy)-iminomethylene group, which is additionally substituted in the cyclohexyl moiety by a methyl group, a phosphinyl group, which is substituted by a $C_{3-6}$-alkyl group and by a $C_{1-3}$-alkoxymethoxy group, and $R_c$ denotes an amidino group, the tautomers, the stereoisomers and the salts thereof.

The following are examples of particularly preferred compounds:

(a) 4-[(5-(N-Carboxymethyl-quinolin-8-yl-sulphonylamino)-1-methyl-1H-benzimidazol-2-yl)-methyl]-benzamidine, (b) 4-[(5-(N-Carboxymethylaminoacetyl-quinolin-8-yl-sulphonylamino)-1-methyl-1H-benzimidazol-2-yl)-methyl]-benzamidine, (c) 4-[(5-(N-(2-Dimethylamino-ethyl)-benzenesulphonylamino)-1-benzyl-1H-benzimidazol-2-yl)-methyl]-benzamidine, (d) 4-[(5-(N-(2-Diethylamino-ethyl)-benzenesulphonylamino)-1-(carboxymethylaminocarbonyl)-methyl-1H-benzimidazol-2-yl)-methyl]-benzamidine, (e) 4-[(5-Pyrrolidinosulphonyl-1-methyl-1H-benzimidazol-2-yl)-methyl]-benzamidine, (f) 4-[(5-(N-Cyclopentyl-methanesulphonylamino)-1-methyl-1H-benzimidazol-2-yl)-methyl]-benzamidine, (g) 4-[(5-(N-Cyclopentyl-3-carboxypropionylamino)-1-methyl-1H-benzimidazol-2-yl)-methyl]-benzamidine, (h) 4-[(5-Pyrrolidinocarbonylcyclopropyl-1-methyl-1H-benzimidazol-2-yl)-methyl]-benzamidine and (i) 4-[(5-(N-Carboxymethyl-quinolin-8-yl-sulphonylamino-benzothiazol-2-yl)-methyl]-benzamidine and the salts thereof.

According to the invention the compounds of general formula I are obtained using known methods, e.g. the following processes:

a) In order to prepare a compound of general formula I wherein $R_c$ denotes a cyano group and X denotes a nitrogen atom:

cyclising a compound of general formula

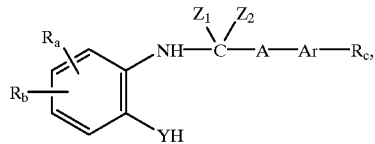

(II)

optionally formed in the reaction mixture
wherein
$R_a$, $R_b$, A, Ar and Y are as hereinbefore defined, $Z_1$ and $Z_2$, which may be identical or different, denote amino, hydroxy or mercapto groups optionally substituted by alkyl groups having 1 to 6 carbon atoms or $Z_1$ and $Z_2$ together denote an oxygen or sulphur atom, an imino group optionally substituted by an alkyl group having 1 to 3 carbon atoms, an alkylenedioxy or alkylenedithio group each having 2 or 3 carbon atoms.

The cyclisation is appropriately carried out in a solvent or mixture of solvents such as ethanol, isopropanol, glacial acetic acid, benzene, chlorobenzene, toluene, xylene, glycol, glycolmonomethylether, diethylenglycol dimethylether, sulpholane, dimethylformamide, tetraline or in an excess of the acylating agent used to prepare the compound of general formula II, e.g. in the corresponding nitrile, anhydride, acid halide, ester or amide, for example at temperatures between 0 and 250° C., but preferably at the boiling temperature of the reaction mixture, optionally in the presence of a condensing agent such as phosphorus oxychloride, thionylchloride, sulphurylchloride, sulphuric acid, p-toluenesulphonic acid, methanesulphonic acid, hydrochloric acid, phosphoric acid, polyphosphoric acid, acetic anhydride or optionally also in the presence of a base such as potassium ethoxide or potassium tert.butoxide. The cyclising may also, however, be carried out without a solvent and/or condensing agent.

However, it is particularly advantageous to carry out the reaction by preparing a compound of general formula II in the reaction mixture by reduction of a corresponding o-nitro compound optionally in the presence of a carboxylic acid of general formula

wherein
A and Ar are as hereinbefore defined, by acylating a corresponding amino compound formed in the reaction mixture.

b) In order to prepare a compound of general formula I wherein $R_b$ denotes a $R_3$—$SO_2$—$NR_4$, $R_3$—CO—$NR_4$ or ($R_5NR_6$)CO—$NR_4$ group and $R_c$ denotes a cyano group:

acylating a compound of general formula

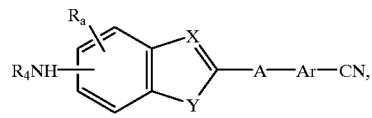

(IV)

wherein
$R_a$, $R_4$, A, Ar, X and Y are as hereinbefore defined, with an acid of general formula

wherein
$R_{10}$ has the meanings given for $R_3$ to $R_6$ hereinbefore and W denotes a carbonyl or sulphonyl group, or with the reactive derivatives thereof.

The reaction of an acid of general formula V is optionally carried out in a solvent or mixture of solvents such as methylene chloride, dimethylformamide, benzene, toluene, chlorobenzene, tetrahydrofuran, benzene/tetrahydrofuran or dioxan, optionally in the presence of a dehydrating agent, e.g. in the presence of isobutyl chloroformate, tetraethyl orthocarbonate, trimethyl orthoacetate, 2,2-dimethoxypropane, tetramethoxysilane, thionylchloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxy-benzotriazole, 2-(1H-benzotriazol-1-yl)-1,1,3,3-tetramethyluronium-tetrafluoroborate, 2-(1H-benzotriazol-1-yl)-1,1,3,3-tetramethyluronium-tetrafluoroborate/1-hydroxy-benzotriazole, N,N'-carbonyldiimidazole or triphenylphosphine/carbon tetrachloride, and optionally with the addition of a base such as pyridine, 4-dimethylaminopyridine, N-methyl-morpholine or triethylamine appropriately at temperatures between 0 and 150° C., preferably at temperatures between 0 and 100° C.

The reaction of a corresponding reactive compound of general formula V such as an ester, imidazolide or halide thereof is preferably carried out in a solvent such as methylene chloride or ether and preferably in the presence of a tertiary organic base such as triethylamine, N-ethyl-diisopropylamine or N-methyl-morpholine at temperatures between 0 and 150° C., preferably at temperatures between 50 and 100° C.

c) In order to prepare a compound of general formula I wherein $R_b$ denotes a $R_3$—$SO_2$—$NR_4$ group and $R_c$ denotes a cyano group:

reacting a compound of general formula

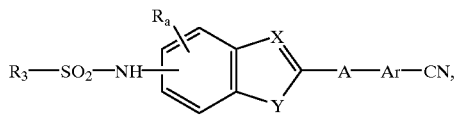

(VI)

wherein $R_a$, $R_3$, A, Ar, X and Y are as hereinbefore defined, with a compound of general formula $R_4$—$Z_3$, (VII)

wherein $R_4$ is as hereinbefore defined and $Z_3$ denotes a nucleofugic leaving group such as a halogen atom, e.g. a chlorine, bromine or iodine atom, or a sulphonic acid ester group, e.g. a trifluoromethane-sulphonyloxy, methanesulphonyloxy or p-toluenesulphonyloxy group.

The reaction is preferably carried out in a solvent such as methanol, ethanol, methylene chloride, tetrahydrofuran, toluene, dioxan, dimethylsulphoxide or dimethylformamide optionally in the presence of an inorganic or tertiary organic base such as sodium hydride, potassium carbonate, potassium tert.butoxide or N-ethyl-diisopropylamine at temperatures between 20° C. and the boiling temperature of the solvent used, preferably at temperatures between 0 and 60° C.

d) In order to prepare a compound of general formula I wherein $R_b$ denotes one of the groups mentioned for $R_b$ hereinbefore, which contains an alkylated phosphinyl and sulphimidoyl group, and $R_c$ denotes a cyano group:

reacting a compound of general formula

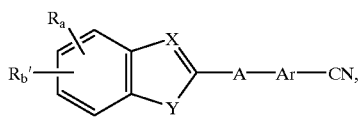

(VIII)

wherein $R_a$, $R_3$, A, Ar, X and Y are as hereinbefore defined and $R_b'$ denotes one of the groups mentioned for $R_b$ hereinbefore which contains a phosphinyl and sulphimidoyl group, with a compound of general formula $Z_4$—$R^{11}$ (IX)

wherein $Z_4$ denotes a nucleofugic leaving group such as a halogen atom, e.g. a chlorine, bromine or iodine atom, and $R_{11}$ denotes one of the alkyl moieties which were mentioned in the definition of the alkylated phosphinyl and sulphimidoyl groups mentioned for the group $R_b$ hereinbefore.

The reaction is preferably carried out in a solvent such as methanol, ethanol, methylene chloride, tetrahydrofuran, toluene, dioxan, dimethylsulphoxide or dimethylformamide, optionally in the presence of an inorganic or tertiary organic base such as sodium hydride, potassium carbonate, potassium-tert.butoxide or N-ethyl-diisopropylamine at temperatures between 20° C. and the boiling temperature of the solvent used, preferably at temperatures between 0 and 60° C.

e) In order to prepare a compound of general formula I wherein $R_b$ denotes one of the groups given for $R_b$ hereinbefore which contains an acylated sulphimidoyl group:

reacting a compound of general formula

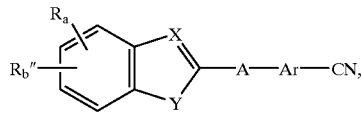

(X)

wherein $R_a$, $R_c$, A, Ar, X and Y are as hereinbefore defined and $R_b''$ denotes one of the groups given for $R_b$ hereinbefore, which contains a sulphimidoyl group, with a compound of general formula

HO—$R_{12}$, (XI)

wherein $R_{12}$ denotes one of the acyl moieties which were mentioned in the definition of the acylated sulphimidoyl groups given for the group $R_b$ hereinbefore, or with the reactive derivatives thereof.

The reaction of an acid of general formula XI is optionally carried out in a solvent or mixture of solvents such as methylene chloride, dimethylformamide, benzene, toluene, chlorobenzene, tetrahydrofuran, benzene/tetrahydrofuran or dioxan optionally in the presence of a dehydrating agent, e.g. in the presence of isobutyl chloroformate, tetraethyl orthocarbonate, trimethyl orthoacetate, 2,2-dimethoxypropane, tetramethoxysilane, thionyl chloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxy-benzotriazole, 2-(1H-benzotriazol-1-yl)-1,1,3,3-tetramethyluronium-tetrafluoroborate, 2-(1H-benzotriazol-1-yl)-1,1,3,3-tetramethyluronium-tetrafluoroborate/1-hydroxy-benzotriazole, N,N'-carbonyldiimidazole or triphenylphosphine/carbon tetrachloride, and optionally with the addition of a base such as pyridine, 4-dimethylaminopyridine, N-methyl-morpholine or triethylamine appropriately at temperatures between 0 and 150° C., preferably at temperatures between 0 and 100° C.

The reaction of a corresponding reactive compound of general formula XI such as an ester, imidazolide or halide thereof is preferably carried out in a solvent such as methylene chloride or ether and preferably in the presence of a tertiary organic base such as triethylamine, N-ethyl-diisopropylamine or N-methyl-morpholine at temperatures between 0 and 150° C., preferably at temperatures between 50 and 100° C.

f) In order to prepare a compound of general formula I wherein $R_b$ denotes a $R_5NR_6$—CO, $R_5NR_6$—$SO_2$, $R_5NR_6$—CO—$C_{3-5}$-cycloalkylene or $R_5NR_6$—CO—$NR_4$ group and $R_c$ denotes a cyano group:

reacting a compound of general formula

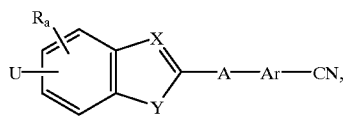

(XII)

wherein $R_a$, A, Ar, X and Y are as hereinbefore defined and U denotes a HO—CO—$C_{3-5}$-cycloalkylene, HO—CO or HO—$SO_2$, or with the reactive derivatives thereof, with an amine of general formula

 (XIII)

wherein $R_5$ and $R_6$ are as hereinbefore defined.

The reaction of an acid of general formula XII is optionally carried out in a solvent or mixture of solvents such as methylene chloride, dimethylformamide, benzene, toluene, chlorobenzene, tetrahydrofuran, benzene/tetrahydrofuran or dioxan, optionally in the presence of a dehydrating agent, e.g. in the presence of isobutyl chloroformate, tetraethyl orthocarbonate, trimethyl orthoacetate, 2,2-dimethoxypropane, tetramethoxysilane, thionylchloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxy-benzotriazole, 2-(1H-benzotriazol-1-yl)-1,1,3,3-tetramethyluronium-tetrafluoroborate, 2-(1H-benzotriazol-1-yl)-1,1,3,3-tetramethyluronium tetrafluoroborate/1-hydroxy-benzotriazole, N,N'-carbonyldiimidazole or triphenylphosphine/carbon tetrachloride, and optionally with the addition of a base such as pyridine, 4-dimethylaminopyridine, N-methyl-morpholine or triethylamine appropriately at temperatures between 0 and 150° C., preferably at temperatures between 0 and 100° C.

The reaction of a corresponding reactive compound of general formula XII such as an ester, imidazolide or halide thereof is preferably carried out in a solvent such as methylene chloride or ether and preferably in the presence of a tertiary organic base such as triethylamine, N-ethyl-diisopropylamine or N-methyl-morpholine at temperatures between 0 and 150° C., preferably at temperatures between 50 and 100° C.

g) In order to prepare a compound of general formula I wherein $R_b$ denotes a $R_3$—CO—$C_{3-5}$-cycloalkylene group and $R_c$ denotes a cyano group:

Oxidising a compound of general formula

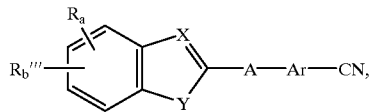

(XIV)

wherein $R_a$, A, Ar, X and Y are as hereinbefore defined and $R_b''$ denotes a $R_3$—(HCOH)—$C_{3-5}$-cycloalkylene group.

The oxidation is preferably carried out in a solvent such as ether, tetrahydrofuran, methylene chloride, glacial acetic acid or acetonitrile in the presence of an oxidising agent such as manganese dioxide, potassium permanganate, potassium dichromate, dimethylsulphoxide/oxalyl chloride or dimethylsulphoxide/dicyclohexylcarbodiimide at temperatures between 0 and 50° C., preferably at temperatures between 15 and 25° C.

h) In order to prepare a compound of general formula I wherein $R_b$ denotes one of the groups mentioned for $R_b$ hereinbefore which contains a methyl group linked to the adjacent bicyclic moiety substituted with an optionally substituted amino group:

Reductive amination of a ketone of general formula

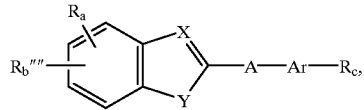

(XV)

wherein $R_a$, $R_c$, A, Ar, X and Y are as hereinbefore defined and $R_b''''$ denotes one of the groups mentioned for $R_b$ hereinbefore which is linked via a carbonyl group to the adjacent bicyclic moiety, with an amine of general formula

 (XVI)

wherein $R_{13}$ denotes an optionally substituted amino group, such as the one mentioned for $R_b$ hereinbefore, if $R_b$ is linked to the adjacent bicyclic moiety via a methyl group optionally substituted by an amino group.

The reductive amination is carried out in the presence of a solvent such as methanol, methanol/water, diethylether, tetrahydrofuran or dioxan in the presence of a reducing agent such as a complex metal hydride, e.g. with sodium borohydride, lithium borohydride or sodium cyanoborohydride, preferably at a pH of between 6 and 7 or with catalytically activated hydrogen, e.g. with hydrogen in the presence of palladium, at temperatures between 0 and 50° C., preferably at temperatures between 15 and 30° C., i) In order to prepare a compound of general formula I wherein $R_b$ denotes one of the optionally substituted phenyl groups mentioned for $R_b$ hereinbefore and $R_c$ denotes a cyano group:

reacting a compound of general formula

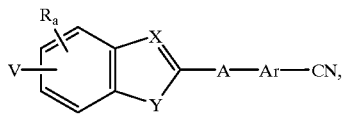

(XVII)

wherein $R_a$, A, Ar, X and Y are as hereinbefore defined and V denotes a trifluoromethanesulphonyloxy group, a bromine or iodine atom, with a compound of general formula $R_{14}$—$Z_5$ (XVIII)

wherein $R_{14}$ denotes one of the optionally substituted phenyl groups mentioned for $R_b$ hereinbefore and $Z_5$ denotes a boric acid group or a tri-($C_{1-3}$-alkyl)-tin group.

The reaction is preferably carried out in a solvent such as toluene/water, dimethoxyethane or dimethylformamide in the presence of a phosphine such as bis(triphenyl-phosphine)-palladium(II)choride or tetrakis-(triphenyl-phosphine)-palladium(O) in the presence of a base such as sodium carbonate at temperatures between 20 and 100° C., preferably at temperatures between 40 and 80° C.

j) In order to prepare a compound of general formula I wherein $R_c$ denotes an amidino group, which may be substituted by one or two $C_{1-3}$-alkyl groups:

Reacting a compound of general formula

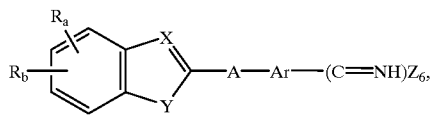

(XIX)

optionally formed in the reaction mixture
wherein $R_a$, $R_b$, A, Ar, X and Y are as hereinbefore defined and $Z_6$ denotes an alkoxy or aralkoxy group such as the methoxy, ethoxy, n-propoxy, isopropoxy or benzyloxy group or an alkylthio or aralkylthio group such as the methylthio, ethylthio, n-propylthio or benzylthio group, with an amine of general formula

H—$R_{15}NR_{16}$, (XX)

wherein $R_{15}$ and $R_{16}$, which may be identical or different, each denote a hydrogen atom or a $C_{1-3}$-alkyl group, or with a salt thereof.

The reaction is appropriately carried out in a solvent such as methanol, ethanol, n-propanol, tetrahydrofuran or dioxan at temperatures between 0 and 150° C., preferably at temperatures between 0 and 80° C., with an amine of general formula XX or with a corresponding acid addition salt such as for example ammonium carbonate or ammonium acetate.

A compound of general formula XIX is obtained for example by reacting a corresponding cyano compound with a corresponding alcohol such as methanol, ethanol, n-propanol, isopropanol or benzylalcohol in the presence of an acid such as hydrochloric acid or by reacting a corresponding amide with a trialkyloxonium salt such as triethyloxonium-tetrafluoroborate in a solvent such as methylene chloride, tetrahydrofuran or dioxan at temperatures between 0 and 50° C., but preferably at 20° C., or a corresponding nitrile with hydrogen sulphide appropriately in a solvent such as pyridine or dimethylformamide and in the presence of a base such as triethylamine and subsequent alkylation of the resulting thioamide with a corresponding alkyl or aralkylhalide.

k) In order to prepare a compound of general formula I wherein $R_c$ denotes an amidino group which is substituted by a hydroxy group:

reacting a nitrile of general formula

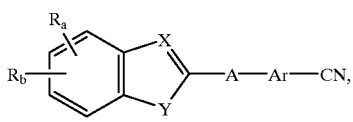

(XXI)

wherein $R_a$, $R_b$, A, Ar, X and Y are as hereinbefore defined, with hydroxylamine or the salts thereof.

The reaction is appropriately carried out in a solvent such as methanol, ethanol, n-propanol, water, methanol/water, tetrahydrofuran, tetrahydrofuran/water, dioxan or dioxan/water at temperatures between 0 and 150° C., preferably at temperatures between 0 and 80° C.

l) In order to prepare a compound of general formula I wherein $R_b$ contains a carboxy group and $R_c$ is as hereinbefore defined or $R_b$ is as hereinbefore defined and $R_c$ denotes an amidino group optionally substituted by a hydroxy group or by one or two $C_{1-3}$-alkyl groups:

Converting a compound of general formula

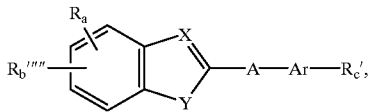

(XIV)

wherein $R_a$, A, Ar, X and Y are as hereinbefore defined and $R_b''''$ and $R_c'$ have the meanings given for $R_b$ and $R_c$ hereinbefore with the proviso that $R_b$ contains a group which can be converted into a carboxy group by hydrolysis, treatment with an acid or base, thermolysis or hydrogenolysis and $R_c$ is as hereinbefore defined or $R_c$ denotes a group which can be converted into an amidino group optionally substituted by a hydroxy group or by one or two $C_{1-3}$-alkyl groups by hydrolysis, treatment with an acid or base, thermolysis or hydrogenolysis and $R_b$ is as hereinbefore defined, is converted, by hydrolysis, treatment with an acid or base, thermolysis or hydrogenolysis, into a compound of general formula I wherein $R_b$ contains a carboxy group and $R_c$ is as hereinbefore defined or $R_b$ is as hereinbefore defined and $R_c$ denotes an amidino group optionally substituted by a hydroxy group or by one or two $C_{1-3}$-alkyl groups.

An example of a group which may be converted into a carboxy group might be, for example, a carboxyl group protected by a protecting group, such as a functional derivative thereof, e.g. an unsubstituted or substituted amide, ester, thioester, trimethylsilylester, orthoester or iminoester thereof, which are appropriately converted into a carboxyl group by hydrolysis, the esters thereof with tertiary alcohols, e.g. the tert. butyl ester, which are appropriately converted into a carboxyl group by treatment with an acid or thermolysis, and the esters thereof with aralkanols, e.g. the benzyl ester, which are appropriately converted into a carboxyl group by hydrogenolysis.

The hydrolysis is appropriately carried out either in the presence of an acid such as hydrochloric acid, sulphuric acid, phosphoric acid, acetic acid, trichloracetic acid, trifluoracetic acid or mixtures thereof or in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxan at temperatures between −10 and 120° C., e.g. at temperatures between ambient temperature and the boiling temperature of the reaction mixture.

If, for example, a compound of formula XXII contains the tert.butyl or tert.butyloxycarbonyl group, this may also by cleaved by treating with an acid such as trifluoracetic acid, formic acid, p-toluenesulphonic acid, sulphuric acid, hydrochloric acid, phosphoric acid or polyphosphoric acid, optionally in an inert solvent such as methylene chloride, chloroform, benzene, toluene, diethylether, tetrahydrofuran or dioxan preferably at temperatures between −10 and 120° C., e.g. at temperatures between 0 and 60° C., or also thermally, optionally in an inert solve nt such as methylene chloride, chloroform, benzene, toluene, tetrahydrofuran or dioxan and preferably in the presence of a ca taly tic amount of an acid such as p-toluenesulphonic acid, sulphuric acid, phosphoric acid or polyphosphoric acid preferably at the boiling temperature of the solvent used, e.g. at temperatures between 40 and 120° C.

If, for example, a compound of formula XXII for example contains the benzyloxy or benzyloxycarbonyl group, these may also be cleaved hydrogenolytically in the presence of a hydrogenation catalyst such as palladium/charcoal in a suitable solvent such as methanol, ethanol, ethanol/water, glacial acetic acid, ethyl acetate, dioxan or dimethylformamide, preferably at temperatures between 0 and 50° C., e.g. at ambient temperature, and at a hydrogen pressure of 1 to 5 bar.

m) In order to prepare a compound of general formula I wherein $R_c$ denotes an amidino group which is substituted by one or two $C_{1-8}$-alkoxycarbonyl groups or by a group which can be cleaved in vivo:

reacting a compound of general formula I

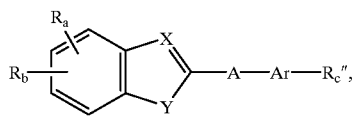

(XXIII)

wherein $R_a$, $R_b$, A, Ar, X and Y are as hereinbefore defined and $R_c''$ denotes an amidino group, with a compound of general formula $$Z_7\text{—}R_{17},$$ (XXIV)

wherein $R_{17}$ denotes a $C_{1-8}$-alkoxycarbonyl group or the acyl group of one of the groups which can be cleaved in vivo mentioned hereinbefore and $Z_7$ denotes a nucleofugic leaving group such as a halogen atom, e.g. a chlorine, bromine or iodine atom, or a p-nitrophenyl group.

The reaction is preferably carried out in a solvent such as methanol, ethanol, methylene chloride, tetrahydrofuran, toluene, dioxan, dimethylsulphoxide or dimethylformamide optionally in the presence of an inorganic or tertiary organic base, preferably at temperatures between 20° C. and the boiling temperature of the solvent used.

In the case of a compound of general formula XXIV wherein $Z_3$ denotes a nucleofugic leaving group, the reaction is preferably carried out in a solvent such as methylene chloride, acetonitrile, tetrahydrofuran, toluene, dimethylformamide or dimethylsulphoxide, optionally in the presence of a base such as sodium hydride, potassium carbonate, potassium-tert.butoxide or N-ethyl-diisopropylamine at temperatures between 0 and 60° C.

If according to the invention a compound of general formula I is obtained wherein $R_c$ denotes an amidino group, this may be converted, by reacting with a haloacetic acid derivative, by subsequent hydrolysis and decarboxylation, into a corresponding amidino compound substituted by one or two methyl groups, and/or if a compound of general formula I is obtained wherein $R_c$ denotes a hydroxyamidino group, this can be converted by catalytic hydrogenation into a corresponding amidino compound and/or if a compound of general formula I is obtained wherein $R_b$ contains a carboxy group, this can be converted by esterification into a corresponding ester and/or if a compound of general formula I is obtained wherein $R_b$ contains an O-alkyl-phosphinyl group, this can be converted by ether splitting into a corresponding phosphinyl compound and/or if a compound of general formula I is obtained wherein $R_b$ contains a halogen atom, this can be converted by dehalogenation into a corresponding dehalogenated compound and/or if a compound of general formula I is obtained wherein $R_b$ contains a quinolyl group, this may be converted by catalytic hydrogenation into a corresponding tetrahydroquinolyl compound.

The subsequent alkylation is appropriately carried out in a solvent such as methylene chloride, tetrahydrofuran, dioxan, dimethylsulphoxide, dimethylformamide or acetone optionally in the presence of a reaction accelerator such as sodium or potassium iodide and preferably in the presence of a base such as sodium carbonate or potassium carbonate or in the presence of a tertiary organic base such as N-ethyl-diisopropylamine or N-methyl-morpholine, which may simultaneously serve as the solvent, or optionally in the presence of silver carbonate or silver oxide at temperatures between −30 and 100° C., but preferably at temperatures between −10 and 80° C.

The subsequent hydrolyse is appropriately carried out either in the presence of an acid such as hydrochloric acid, sulphuric acid, phosphoric acid, acetic acid, trichloracetic acid, trifluoracetic acid or mixtures thereof or in the presence of a base such as lithium hydroxide, sodium hydroxide or potassium hydroxide in a suitable solvent such as water, water/methanol, water/ethanol, water/isopropanol, methanol, ethanol, water/tetrahydro or water/dioxan and the subsequent decarboxylation is performed in the presence of an acid as described hereinbefore at temperatures between −10 and 120° C., e.g. at temperatures between ambient temperature and the boiling temperature of the reaction mixture.

The subsequent esterification is carried out with a corresponding alcohol appropriately in a solvent or mixture of solvents such as methylene chloride, benzene, toluene, chlorobenzene, tetrahydrofuran, benzene/tetrahydrofuran or dioxan, but preferably in an excess of the alcohol used, optionally in the presence of an acid such as hydrochloric acid or in the presence of a dehydrating agent, e.g. in the presence of isobutyl chloroformate, thionyl chloride, trimethylchlorosilane, hydrochloric acid, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole or N,N'-thionyldiimidazole, triphenylphosphine/carbon tetrachloride or triphenylphosphine/diethyl azodicarboxylate, optionally in the presence of a base such as potassium carbonate, N-ethyl-diisopropylamine or N,N-dimethylaminopyridine appropriately at temperatures between 0 and 150° C., preferably at temperatures between 0 and 80° C., or with a corresponding halide in a solvent such as methylene chloride, tetrahydrofuran, dioxan, dimethylsulphoxide, dimethylformamide or acetone, optionally in the presence of a reaction accelerator such as sodium or potassium iodide and preferably in the presence of a base such as sodium carbonate or potassium carbonate or in the presence of a tertiary organic base such as N-ethyl-diisopropylamine or N-methyl-morpholine, which may simultaneously serve as the solvent, or optionally in the presence of silver carbonate or silver oxide at temperatures between −30 and 100° C., but preferably at temperatures between −10 and 80° C.

The subsequent dehalogenation and catalytic hydrogenation is carried out with hydrogen in the presence of a catalyst such as palladium/charcoal or platinum in a solvent such as methanol, ethanol, ethyl acetate, dimethylformamide, dimethylformamide/acetone or glacial acetic acid optionally with the addition of an acid such as hydrochloric acid at temperatures between 0 and 50° C., but preferably at ambient temperature, and at a hydrogen pressure of 1 to 7 bar, but preferably 3 to 5 bar.

The subsequent ether splitting is carried out for example with iodotrimethylsilane, bromotrimethylsilane or chloromethylsilane/sodium iodide in a solvent such as methylene chloride, chloroform or acetonitrile at temperatures between 0° C. and the boiling temperature of the reaction mixture, but preferably at temperatures between 20 and 60° C.

In the reactions described hereinbefore, any reactive groups present such as hydroxy, carboxy, amino, alkylamino or imino groups may be protected during the reaction by conventional protecting groups which are cleaved again after the reaction.

For example, the protecting group for a hydroxy group may be the trimethylsilyl, acetyl, benzoyl, tert.butyl, trityl, benzyl or tetrahydropyranyl group, the protecting groups for a carboxyl group may be the trimethylsilyl, methyl, ethyl, tert.butyl, benzyl or tetrahydropyranyl group and the protecting group for an amino, alkylamino or imino group may be the acetyl, trifluoracetyl, benzoyl, ethoxycarbonyl, tert.butoxycarbonyl, benzyloxycarbonyl, benzyl, methoxybenzyl or 2,4-dimethoxybenzyl group and for the amino group the phthalyl group is another possibility.

The optional subsequent cleaving of any protecting group used is carried out for example by hydrolysis in an aqueous solvent, e.g. in water, isopropanol/water, tetrahydrofuran/water or dioxan/water, in the presence of an acid such as trifluoracetic acid, hydrochloric acid or sulphuric acid or in the presence of an alkali metal base such as lithium hydroxide, sodium hydroxide or potassium hydroxide or by means of ether splitting, e.g. in the presence of iodotrimethylsilane, at temperatures between 0 and 100° C., preferably at temperatures between 10 and 5° C.

A benzyl, methoxybenzyl or benzyloxycarbonyl group may, however, be cleaved hydrogenolytically for example, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, but preferably 3 to 5 bar.

A methoxybenzyl group can also be cleaved in the presence of an oxidising agent such as cerium(IV) ammonium nitrate in a solvent such as methylene chloride, acetonitrile or acetonitrile/water at temperatures between 0 and 5° C., but preferably at ambient temperature.

A 2,4-dimethoxybenzyl group, however, is preferably cleaved in trifluoracetic acid in the presence of anisole.

A tert.butyl or tert.butyloxycarbonyl group is preferably cleaved by treating with an acid such as trifluoracetic acid or hydrochloric acid, optionally using a solvent such as methylene chloride, dioxan or ether.

A phthalyl group is preferably cleaved in the presence of hydrazine or a primary amine such as methylamine, ethylamine or n-butylamine in a solvent such as methanol, ethanol, isopropanol, toluene/water or dioxan at temperatures between 20 and 50° C.

An allyloxycarbonyl group is cleaved by treating with a catalytic amount of tetrakis-(triphenylphosphine)-palladium (O), preferably in a solvent such as tetrahydrofuran and preferably in the presence of an excess of a base such as morpholine or 1,3-dimedone at temperatures between 0 and 100° C., preferably at ambient temperature and under an inert gas, or by treating with a catalytic amount of tris-(triphenylphosphine)-rhodium(I)chloride in a solvent such as aqueous ethanol and optionally in the presence of a base such as 1,4-diazabicyclo[2.2.2]octane at temperatures between 20 and 70° C.

The compounds of general formulae II to XXIV used as starting materials, some of which are known from the literature, are obtained by methods known from the literature, and furthermore their preparation is described in the Examples.

The chemistry of the compounds of general formula III is described, for example, by Jack Robinson in J. Chem. Soc. 1941, 744, that of the benzimidazoles is described by Katritzky and Rees in Comprehensive Heterocyclic Chemistry, Oxford, Pergamon Press, 1984, that of the benzothiazoles and benzoxazoles is described by Schaumann in Hetarene III, Methoden der organischen Chemie (Houben-Weyl), 4$^{th}$ Edition, Verlag Thieme, Stuttgart 1993, that of the benzofurans by Mustafa in Chemistry of Heterocyclic Compounds, Vol. 29, New York, Wiley 1974, that of the sulphoximides by Johnson in Accounts in Chemical Research 6, 341 (1973), that of the phosphinic acids by Regitz in Phosphor-Verbindungen 1 und 2, Methoden der organischen Chemie (Houben-Weyl), Vol. 12, Verlag Thieme, Stuttgart 1993, and that of the boric acids by Sieckus in Pure and Applied Chemistry 66, 2155 (1994).

Thus, for example, a compound of general formula II is obtained by acylating a corresponding o-diamino compound with a corresponding reactive derivative of a compound of general formula III, a compound of general formulae IV, XV, VIII, X, XII, XIV and XVII is obtained by cyclising a corresponding substituted compound and if necessary subsequently reducing a nitro group present in the phenyl moiety, acylation, amidation and/or halogenation, a compound of general formula VI is obtained by sulphonylation of a compound of general formula IV, a compound of general formulae XIX, XXI, XXII and XXIII is appropriately obtained by one of the methods described above.

Furthermore the compounds of general formula I obtained may be resolved into their enantiomers and/or diastereomers.

Thus, for example, the compounds of general formula I obtained which occur in the form of racemates may be resolved into their optical antipodes by methods known per se (cf. Allinger N. L. and Eliel E. L. in "Topics in Stereochemistry", Vol. 6, Wiley Interscience, 1971) and compounds of general formula I with at least 2 asymmetric carbon atoms may be separated into their diastereomers on the basis of their physico-chemical differences using methods known per se, e.g. by chromatography and/or fractional crystallisation, and if they occur in racemic form they may subsequently be separated into their enantiomers, as mentioned above.

Enantiomer separation is preferably carried out by column separation on chiral phases or by recrystallisation from an optically active solvent or by reacting with an optically active substance which forms salts or derivatives, such as e.g. esters or amides, with the racemic compound, particularly acids and the activated derivatives or alcohols thereof, and separating the diastereomeric salt mixture or derivative thus obtained, e.g. on the basis of their different solubilities, whilst the free antipodes can be released from the pure diastereomeric salts or derivatives by the action of suitable agents. Particularly common, optically active acids include e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol might be, for example, (+) or (−)-menthol and an optically active acyl group in amides might be, for example, the (+) or (−)-menthyloxycarbonyl group.

In addition the compounds of formula I obtained may be converted into the salts thereof, particularly for pharmaceutical use into the physiologically acceptable salts thereof with inorganic or organic acids. Examples of suitable acids for this purpose include hydrochloric acid, hydrobromic acid, sulphuric acid, phosphoric acid, fumaric acid, succinic acid, lactic acid, citric acid, tartaric acid or maleic acid.

Furthermore, the new compounds of formula I thus obtained, if they contain a carboxy group, may subsequently, if desired, be converted into the salts thereof with inorganic or organic bases, particularly into the physiologically acceptable salts thereof for pharmaceutical use. Examples of suitable bases include sodium hydroxide, potassium hydroxide, cyclohexylamine, ethanolamine, diethanolamine and triethanolamine.

As already mentioned hereinbefore, the new compounds of general formula I and the salts thereof have valuable properties. Thus, the compounds of general formula I wherein $R_c$ denotes a cyano group are valuable intermediate products for preparing the other compounds of general formula I, and the compounds of general formula I wherein $R_c$ denotes one of the amidino groups mentioned hereinbefore, as well as the tautomers, stereoisomers and the physiologically acceptable salts thereof, have valuable pharmacological properties, particularly an antithrombotic effect which is preferably based on a thrombin- or factor Xa-influencing activity, for example a thrombin-inhibiting or factor Xa-inhibiting activity, an aPTT-time-extending activity and an inhibitory effect on related serine proteases such as e.g. trypsin, urokinase factor VIIa, factor IX, factor XI and factor XII.

For example, the following compounds

A=4-[(5-(N-Carboxymethyl-quinolin-8-yl-sulphonylamino)-1-methyl-1H-benzimidazol-2-yl)-methyl]-benzamidine-hydrochloride, B=4-[(5-(N-Carboxymethylaminoacetyl-quinolin-8-yl-sulphonylamino)-1-methyl-1H-benzimidazol-2-yl)-methyl]-benzamidine-hydrochloride, C=4-[(5-(N-(2-Dimethylamino-ethyl)-benzenesulphonylamino)-1-benzyl-1H-benzimidazol-2-yl)-methyl]-benzamidine-dihydrochloride, D=4-[(5-(N-(2-Diethylamino-ethyl)-benzenesulphonylamino-1-(carboxymethylaminocarbonylmethyl)-1H-benzimidazol-2-yl)-methyl]-benzamidine-dihydrochloride, E=4-[(5-Pyrrolidinosulphonyl-1-methyl-1H-benzimidazol-2-yl)-methyl]-benzamidine-hydrochloride, F=4-[(5-(N-Cyclopentyl-methanesulphonylamino)-1-methyl-1H-benzimidazol-2-yl)-methyl]-benzamidine-hydrochloride, G=4-[(5-(N-Cyclopentyl-3-carboxypropionylamino)-1-methyl-1H-benzimidazol-2-yl)-methyl]-benzamidine-hydrochloride, H=4-[(5-(1-Pyrrolidinocarbonylcyclopropyl)-1-methyl-1H-benzimidazol-2-yl)-methyl]-benzamidine-hydrochloride and I=4-[(5-(N-Carboxymethyl-quinolin-8-yl-sulphonylamino)-benzothiazol-2-yl)-methyl]-benzamidine-hydrochloride were investigated for their effect on extending the aPTT time as follows:

Material:-Plasma, from human citrated blood,
PTT-reagent, Boehringer Mannheim (524298),
Calcium solution (0.025 mol/l), Behring Werke, Marburg (ORH 056/57),
diethylbarbiturate acetate buffer, Behring Werke, Marburg (ORWH 60/61),
Biomatic B10 coagulometer, Desaga, Wiesloch.

Method:

The aTTP [sic] time is determined with a Biomatic B10-coagulometer made by Messrs Desaga.

The test substance was placed in the test tubes prescribed by the manufacturer with 0.1 ml of human citrated plasma and 0.1 ml of PTT-reagent. The mixture was incubated for three minutes at 37° C. The coagulation reaction was started by the addition of 0.1 ml of calcium solution. The time taken for the mixture to coagulate from the addition of the calcium solution is measured using the equipment. Mixtures to which 0.1 ml of DBA buffer had been added were used as the control.

The effective concentration of substance with which the aPTT time was double that of the control was defined by means of a dosage/activity curve.

The following Table contains the results obtained:

| Substance | aTTP time (ED$_{200}$ in $\mu$M) |
|---|---|
| A | 0.92 |
| B | 0.55 |
| C | 5.60 |
| D | 3.80 |
| E | 0.25 |
| F | 0.35 |
| G | 0.82 |
| H | 0.50 |
| I | 1.00 |

The compounds prepared according to the invention are well tolerated as no toxic side effects can be observed at therapeutic doses.

In view of their pharmacological properties the new compounds and the physiologically acceptable salts thereof are suitable for the prevention and treatment of venous and arterial thrombotic diseases, such as for example the treatment of deep leg vein thrombosis, the prevention of reocclusions after bypass operations or angioplasty (PT(C)A), and occlusion in peripheral arterial diseases such as pulmonary embolism, disseminated intravascular clotting, the prevention of coronary thrombosis, stroke prevention and the preventing the occlusion of shunts. In addition the compounds according to the invention are suitable for antithrombotic support in thrombolytic treatment, such as for example with rt-PA or streptokinase, to prevent long-term restenosis after PT(C)A, to prevent metastasis and the growth of clot-dependent tumours and fibrin-dependent inflammatory processes.

The dosage required to achieve a corresponding activity is appropriately 0.1 to 30 mg/kg, preferably 0.3 to 10 mg/kg, by intravenous route and 0.1 to 50 mg/kg, preferably 0.3 to 30 mg/kg, by oral route, 1 to 4 times a day. For this purpose the compounds of formula I prepared according to the invention, optionally in conjunction with other active substances, may be formulated together with one or more conventional inert carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, cetylstearyl alcohol, carboxymethylcellulose or fatty substances such as hard fat or suitable mixtures thereof, into conventional galenic preparations such as plain or coated tablets, capsules, powders, suspensions or suppositories.

The following Examples are intended to illustrate the invention more fully:

EXAMPLE 1

4-[(5-benzenesulphonylamino-1-methyl-1H-benzimidazol-2-yl)-methyl]-benzamidine-hydrochloride a. 4-[(5-nitro-1H-benzimidazol-2-yl)-methyl]-benzonitrile 3.1 g (0.02 mol) of 4-nitro-o-phenylenediamine and 3.7 g (0.023 mol) of 4-cyanophenylacetic acid are refluxed for 2 hours in 30 ml of phosphorus oxychloride. After cooling the mixture is neutralised with concentrated ammonia and extracted with ethyl acetate. The combined organic extracts are dried over sodium sulphate and concentrated by evaporation. The residue is chromatographed on silica gel, eluting with methylene chloride/methanol (50:1). The desired fractions are concentrated by evaporation, the residue is triturated with ethyl acetate/ether, suction filtered and dried.

Yield: 2.1 g (38% of theory), R$_f$ value: 0.25 (Silica gel; methylene chloride/methanol=19:1) C$_{15}$H$_{10}$N$_4$O$_2$ (278.3); Mass spectrum: M$^+$=278.

b. 4-[(5-nitro-1-methyl-1H-benzimidazol-2-yl)-methyl]-benzonitrile and 4-[(6-nitro-1-methyl-1H-benzimidazol-2-yl)-methyl]-benzonitrile 1.4 g (5.0 mmol) of 4-[(5-nitro-1H-benzimidazol-2-yl)-methyl]-benzonitrile, 2.6 g (15 mmol) of potassium carbonate×2 H$_2$O and 0.84 g (6.0 mmol) of methyl iodide are dissolved in 60 ml acetone and stirred for 1 hour at ambient temperature. The solvent is evaporated off, the residue is mixed with water, the product precipitated is suction filtered and dried.

Yield: 1.1 g (75% of theory), R$_f$ value: 0.2 (Silica gel; methylene chloride/methanol=19:1).

c. 4-[(5-amino-1-methyl-1H-benzimidazol-2-yl)-methyl]-benzonitrile 1.1 g (37.6 mmol) of 4-[(5-nitro-1-methyl-1H-benzimidazol-2-yl)-methyl]-benzonitrile and 4-[(6-nitro-1-methyl-1H-benzimidazol-2-yl)-methyl]-benzonitrile are dissolved in 30 ml methanol and 40 ml methylene chloride and after the addition of 0.2 g palladium on activated charcoal (10%) hydrogenated for 60 minutes at ambient temperature. Then the catalyst is filtered off and the filtrate is concentrated by evaporation. The residue is chromatographed on silica gel and eluted with methylene chloride/methanol (30:1).

Yield: 0.3 g (30% of theory), R$_f$ value: 0.4 (silica gel; methylene chloride/methanol=9:1) C$_{16}$H$_{14}$N$_4$ (262.3); Mass spectrum: M$^+$=262.

d. 4-[(5-benzenesulphonylamino-1-methyl-1H-benzimidazol-2-yl)-methyl-benzonitrile 300 mg (11.4 mmol) of 4-[(5-amino-1-methyl-1H-benzimidazol-2-yl)-methyl]-benzonitrile and 200 mg (11.4 mmol) of benzenesulphonic acid chloride are stirred into 10 ml pyridine for one hour at ambient temperature. Then 1 ml water is added and the mixture is concentrated by evaporation. The residue is combined with water and ethyl acetate and stirred for one hour at ambient temperature, whilst the substance slowly crystallises. The ethyl acetate is evaporated off and the crystalline residue is suction filtered.

Yield: 380 mg (83% of theory), R$_f$ value: 0.5 (silica gel; methylene chloride/methanol=9:1).

e. 4-[(5-benzenesulphonylamino-1-methyl-1H-benzimidazol-2-yl)-methyl]-benzamidine-hydrochloride 430 mg (1.07 mmol) of 4-[(5-benzenesulphonylamino-1-methyl-1H-benzimidazol-2-yl)-methyl]-benzonitrile are dissolved in 30 ml saturated ethanolic hydrochloric acid and stirred for 5 hours at ambient temperature. The solvent is distilled off, the residue is dissolved in 30 ml absolute ethanol and combined with 1.0 g (10.7 mmol) of ammonium carbonate. After 60 hours at ambient temperature the mixture is evaporated to dryness. The residue is chromatographed on silica gel and eluted with methylene chloride/methanol (5:1). Corresponding fractions are evaporated down, triturated with ether and suction filtered.

Yield: 170 mg (29% of theory), R$_f$ value: 0.2 (silica gel; methylene chloride/methanol=5:1) C$_{22}$H$_{21}$N$_5$O$_2$S×HCl (419.50/455.96); Mass spectrum: (M+H)+=420.

EXAMPLE 2

4-[(5-benzenesulphonylamino-1H-benzimidazol-2-yl)-methyl]-benzamidine-hydrochloride Prepared analogously to Example 1e from 4-[(5-benzenesulphonylamino-1H-benzimidazol-2-yl)-methyl]-benzonitrile and hydrochloric acid/ammonium carbonate in ethanol.

Yield: 59% of theory, $C_{21}H_{19}N_5O_2S \times HCl$ (405.48/441.95); Mass spectrum: (M+H)+=406.

EXAMPLE 3

4-[(6-benzenesulphonylamino-4-methyl-1H-benzimidazol-2-yl)-methyl]-benzamidine-hydrochloride Prepared analogously to Example 1e from 4-[(6-benzenesulphonylamino-4-methyl-1H-benzimidazol-2-yl)-methyl]-benzonitrile and hydrochloric acid/ammonium carbonate in ethanol.

Yield: 38% of theory. $C_{22}H_{21}N_5O_2S \times HCl$ (419.50/455.96); Mass spectrum: (M+H)+=420.

EXAMPLE 4

4-[(6-benzenesulphonylamino-1-methyl-1H-benzimidazol-2-yl)-methyl]-benzamidine-hydrochloride Prepared analogously to Example 1e from 4-[(6-benzenesulphonylamino-1-methyl-1H-benzimidazol-2-yl)-methyl]-benzonitrile and hydrochloric acid/ammonium carbonate in ethanol.

Yield: 23% of theory; $R_f$ value: 0.25 (silica gel; methylene chloride/methanol 5:1) $C_{22}H_{21}N_5O_2S \times HCl$ (419.50/455.96); Mass spectrum: (M+H)$^+$=420.

EXAMPLE 5

4-[(5-benzenesulphonylamino-1-n-propyl-1H-benzimidazol-2-yl)-methyl]-benzamidine-hydrochloride Prepared analogously to Example 1e from 4-[(5-benzenesulphonylamino-1-n-propyl-1H-benzimidazol-2-yl)-methyl]-benzonitrile and hydrochloric acid/ammonium carbonate in ethanol.

Yield: 43% of theory, $C_{24}H_{25}N_5O_2S \times HCl$ (447.55/484.02); Mass spectrum: (M+H)$^+$=448.

EXAMPLE 6

4-[(6-benzenesulphonylamino-1-n-propyl-1H-benzimidazol-2-yl)-methyl]-benzamidine-hydrochloride Prepared analogously to Example 1e from 4-[(6-benzenesulphonylamino-1-n-propyl-1H-benzimidazol-2-yl)-methyl]-benzonitrile and hydrochloric acid/ammonium carbonate in ethanol.

Yield: 39% of theory, $C_{24}H_{25}N_5O_2S \times HCl$ (447.55/484.02); Mass spectrum: (M+H)$^+$=448.

EXAMPLE 7

4-[(5-phenylaminosulphonyl-1-methyl-1H-benzimidazol-2-yl)-methyl]-benzamidine-hydrochloride a. 4-phenylaminosulphonyl-2-nitro-chlorobenzene Prepared analogously to Example 1d from aniline and 4-chlorine-3-nitro-benzenesulphonic acid chloride in pyridine.

Yield: 97% of theory, $R_f$ value: 0.5 (silica gel; methylene chloride/ethanol=19:1).

b. 4-phenylaminosulphonyl-2-nitro-N-methyl-aniline 6.0 g (0.019 mol) of 4-phenylaminosulphonyl-2-nitro-chlorobenzene and 40 ml methylamine solution (40% in $H_2O$) are heated to 130° C. in a bomb for two hours. The contents are diluted with water and neutralised with hydrochloric acid. The precipitated product is suction filtered and dried.

Yield: 5.0 g (86% of theory), $R_f$ value: 0.45 (silica gel; methylene chloride/ethanol 19:1).

c. 4-phenylaminosulphonyl-2-amino-N-methyl-aniline 5.0 g (0.016 mol) of 4-phenylaminosulphonyl-2-nitro-N-methylaniline are dissolved in 300 ml ethyl acetate and 30 ml methanol and after the addition of 1.0 g Raney nickel hydrogenated with hydrogen at 60° C. The catalyst is removed by suction filtering, 40 ml methanolic hydrochloric acid are added and the solution is evaporated down. The residue is crystallised with ether/ethyl acetate, suction filtered and dried.

Yield: 5.0 g (89% of theory), $R_f$ value: 0.41 (silica gel; methylene chloride/ethanol=9:1).

d. 4-[(5-phenylaminosulphonyl-1-methyl-1H-benzimidazol-2-yl)-methyl]-benzonitrile Prepared analogously to Example 1a from 4-phenylaminosulphonyl-2-amino-N-methyl-aniline-hydrochloride and 4-cyano-phenylacetic acid in phosphorus oxychloride.

Yield: 36% of theory.

e. 4-[(5-phenylaminosulphonyl-1-methyl-1H-benzimidazol-2-yl)-methyl]-benzamidine-hydrochloride Prepared analogously to Example 1e from 4-[(5-phenylaminosulphonyl-1-methyl-1H-benzimidazol-2-yl)-methyl]-benzonitrile and hydrochloric acid/ammonium carbonate in ethanol.

Yield: 11% of theory, $C_{22}H_{21}N_5O_2S \times HCl$ (419.5/456.0); Mass spectrum: (M+H)$^+$=420.

EXAMPLE 8

4-[(5-benzenesulphonylamino-1-ethyl-1H-benzimidazol-2-yl)-methyl]-benzamidine-hydrochloride Prepared analogously to Example 1e from 4-[(5-benzenesulphonylamino-1-ethyl-1H-benzimidazol-2-yl)-methyl]-benzonitrile and hydrochloric acid/ammonium carbonate in ethanol.

Yield: 35% of theory, $C_{23}H_{23}N_5O_2S \times HCl$ (433.53/469.99); Mass spectrum: (M+H)$^+$=434.

EXAMPLE 9

4-[(5-(N-methyl-benzenesulphonylamino)-1-methyl-1H-benzimidazol-2-yl)-methyl]-benzamidine-hydrochloride Prepared analogously to Example 1e from 4-[(5-(N-methyl-benzenesulphonylamino)-1-methyl-1H-benzimidazol-2-yl)-methyl]-benzonitrile and hydrochloric acid/ammonium carbonate in ethanol.

Yield: 27% of theory, $C_{23}H_{23}N_5O_2S \times HCl$ (433.53/469.99); Mass spectrum: (M+H)$^+$=434.

EXAMPLE 10

4-[(5-benzenesulphonylamino-1-ethoxycarbonylmethyl-1H-benzimidazol-2-yl)-methyl]-benzamidine-hydrochloride Prepared analogously to Example 1e from 4-[(5-benzenesulphonylamino-1-ethoxycarbonylmethyl-1H-benzimidazol-2-yl)-methyl]-benzonitrile and hydrochloric acid/ammonium carbonate in ethanol.

Yield: 68% of theory, $C_{25}H_{25}N_5O_4S \times HCl$ (491.58/528.05); Mass spectrum: $(M+H)^+ = 492$.

EXAMPLE 11

4-[(5-benzenesulphonylamino-1-carboxymethyl-1H-benzimidazol-2-yl)-methyl]-benzamidine 200 mg (0.379 mmol) of 4-[(5-benzenesulphonylamino-1-ethoxycarbonylmethyl-1H-benzimidazol-2-yl)-methyl]-benzamidine-hydrochloride are dissolved in 10 ml ethanol and stirred at 40° C. for 90 minutes after the addition of 1 ml 2N sodium hydroxide solution. The solvent is distilled off, the residue diluted with 20 ml water and acidified with glacial acetic acid. The precipitated product is suction filtered and dried.

Yield: 160 mg (91% of theory), $C_{23}H_{21}N_5O_4S$ (463.53); Mass spectrum: $(M+H)^+ = 464$.

EXAMPLE 12

4-[(5-(N-ethoxycarbonylmethyl-benzenesulphonylamino)-1-methyl-1H-benzimidazol-2-yl)-methyl]-benzamidine-hydrochloride a. 4-[(5-(N-ethoxycarbonylmethyl-benzenesulphonylamino)-1-methyl-1H-benzimidazol-2-yl)-methyl]-benzonitrile Prepared analogously to Example 1b from 4-[(5-benzenesulphonylamino-1-methyl-1H-benzimidazol-2-yl)-methyl]-benzonitrile and ethyl bromoacetate in potassium carbonate/acetone.

Yield: 99% of theory, $R_f$ value: 0.3 (silica gel; methylene chloride/methanol=9:1).

b. 4-[(5-(N-ethoxycarbonylmethyl-benzenesulphonylamino)-1-methyl-1H-benzimidazol-2-yl)-methyl]-benzamidine-hydrochloride Prepared analogously to Example 1e from 4-[(5-(N-ethoxycarbonylmethyl-benzenesulphonylamino)-1-methyl-1H-benzimidazol-2-yl)-methyl]-benzonitrile and hydrochloric acid/ammonium carbonate in ethanol.

Yield: 41% of theory, $C_{24}H_{23}N_5O_4S \times HCl$ (505.62/542.06); Mass spectrum: $(M+H)^+ = 506$; $(3M+2H)^{++} = 758.8$.

EXAMPLE 13

4-[(5-(N-carboxymethyl-benzenesulphonylamino)-1-methyl-1H-benzimidazol-2-yl)-methyl]-benzamidine-hydrochloride 0.6 g (1.1 mmol) of 4-[(5-(N-ethoxycarbonylmethyl-benzenesulphonylamino)-1-methyl-1H-benzimidazol-2-yl)-methyl]-benzamidine-hydrochloride and 0.22 g (5.5 mmol) of sodium hydroxide are stirred in 15 ml water and 10 ml ethanol for two hours at ambient temperature. The mixture is diluted with water and adjusted to pH 4 with hydrochloric acid. The solvent is concentrated by evaporation, the residue is triturated with ether, suction filtered and dried.

Yield: 0.3 g (53% of theory), $C_{24}H_{23}N_5O_4S \times HCl$ (477.54/514.00); Mass spectrum: $(M+H)^+ = 478$.

EXAMPLE 14

4-[(5-(N-benzyl-methanesulphonylamino)-1-methyl-1H-benzimidazol-2-yl)-methyl]-benzamidine-hydrochloride a. 4-[(5-methanesulphonylamino-1-methyl-1H-benzimidazol-2-yl)-methyl]-benzonitrile Prepared analogously to Example 1d from 4-[(5-amino-1-methyl-1H-benzimidazol-2-yl)-methyl]-benzonitrile and methanesulphonic acid chloride in pyridine.

Yield: 62% of theory, $R_f$ value: 0.6 (silica gel; methylene chloride/methanol=9:1).

b. 4-[(5-(N-benzyl-methanesulphonylamino)-1-methyl-1H-benzimidazol-2-yl)-methyl]-benzonitrile Prepared analogously to Example 1b from 4-[(5-methanesulphonylamino-1-methyl-1H-benzimidazol-2-yl)-methyl]-benzonitrile, benzylchloride and potassium carbonate in acetone.

Yield: 79% of theory, $R_f$ value: 0.7 (silica gel; methylene chloride/methanol 9:1).

c. 4-[(5-(N-benzyl-methanesulphonylamino)-1-methyl-1H-benzimidazol-2-yl)-methyl]-benzamidine-hydrochloride Prepared analogously to Example 1e from 4-[(5-(N-benzyl-methanesulphonylamino)-1-methyl-1H-benzimidazol-2-yl)-methyl]-benzonitrile and hydrochloric acid/ammonium carbonate in ethanol.

Yield: 54% of theory, $C_{24}H_{25}N_5O_2S \times HCl$ (447.55/484.01); Mass spectrum: $(M+H)^+ 448$.

EXAMPLE 15

4-[(5-(N-(naphthalen-1-yl-methyl)-methanesulphonylamino)-1-methyl-1H-benzimidazol-2-yl)-methyl]-benzamidine-hydrochloride Prepared analogously to Example 1e from 4-[(5-(N-(naphthalen-1-yl-methyl)-methanesulphonylamino)-1-methyl-1H-benzimidazol-2-yl)-methyl]-benzonitrile and hydrochloric acid/ammonium carbonate in ethanol.

Yield: 11% of theory, $C_{28}H_{27}N_5O_2S \times HCl$ (497.62/534.08); Mass spectrum: $(M+H)^+ = 498$.

EXAMPLE 16

4-[(5-(naphthalen-1-yl-sulphonylamino)-1-methyl-1H-benzimidazol-2-yl)-methyl]-benzamidine-hydrochloride Prepared analogously to Example 1e from 4-[(5-(naphthalen-1-yl-sulphonylamino)-1-methyl-1H-benzimidazol-2-yl)-methyl]-benzonitrile and hydrochloric acid/ammonium carbonate in ethanol.

Yield: 66% of theory, $C_{26}H_{23}N_5O_2S \times HCl$ (469.57/506.03); Mass spectrum: $(M+H)^+ 470$.

EXAMPLE 17

4-[(5-(naphthalen-2-yl-sulphonylamino)-1-methyl-1H-benzimidazol-2-yl)-methyl]-benzamidine-hydrochloride Prepared analogously to Example 1e from 4-[(5-(naphthalen-2-yl-sulphonylamino)-1-methyl-1H-benzimidazol-2-yl)-methyl]-benzonitrile and hydrochloric acid/ammonium carbonate in ethanol.

Yield: 74% of theory, $C_{26}H_{23}N_5O_2S \times HCl$ (469.57/506.03); Mass spectrum: $(M+H)^+ = 470$.

EXAMPLE 18

4-[(5-benzylsulphonylamino-1-methyl-1H-benzimidazol-2-yl)-methyl]-benzamidine-hydrochloride Prepared analogously to Example 1e from 4-[(5-benzylsulphonylamino-1-methyl-1H-benzimidazol-2-yl)-methyl]-benzonitrile and hydrochloric acid/ammonium carbonate in ethanol.

Yield: 68% of theory, $C_{23}H_{23}N_5O_2S\times HCl$ (433.53/469.99); Mass spectrum: $(M+H)^+=434$.

EXAMPLE 19

4-[(5-(Quinolin-8-yl-sulphonylamino)-1-methyl-1H-benzimidazol-2-yl)-methyl]-benzamidine-hydrochloride Prepared analogously to Example 1e from 4-[(5-(quinolin-8-yl-sulphonylamino)-1-methyl-1H-benzimidazol-2-yl)-methyl]-benzonitrile and hydrochloric acid/ammonium carbonate in ethanol.

Yield: 65% of theory, $C_{25}H_{22}N_6O_2S\times HCl$ (470.55/507.01); Mass spectrum: $(M+H)^+=471$.

EXAMPLE 20

4-[(5-(3,5-Bis-trifluoromethylphenylsulphonylamino)-1-methyl-1H-benzimidazol-2-yl)-methyl]-benzamidine-hydrochloride Prepared analogously to Example 1e from 4-[(5-(3,5-Bis-trifluoromethylphenylsulphonylamino)-1-methyl-1H-benzimidazol- 2-yl)-methyl]-benzonitrile and hydrochloric acid/ammonium carbonate in ethanol.

Yield: 63% of theory, $C_{24}H_{19}F_6N_5O_2S\times HCl$ (555.51/591.97); Mass spectrum: $(M+H)^+=556$.

EXAMPLE 21

4-[(5-(2,5-dimethoxyphenylsulphonylamino)-1-methyl-1H-benzimidazol-2-yl)-methyl]-benzamidine-hydrochloride Prepared analogously to Example 1e from 4-[(5-(2,5-dimethoxyphenylsulphonylamino)-1-methyl-1H-benzimidazol-2-yl)-methyl]-benzonitrile and hydrochloric acid/ammonium carbonate in ethanol.

Yield: 83% of theory, $C_{24}H_{25}N_5O_4S\times HCl$ (479.55/516.01); Mass spectrum: $(M+H)^+=480$.

EXAMPLE 22

4-[(5-(2,3,5,6-tetramethylphenylsulphonylamino)-1-methyl-1H-benzimidazol-2-yl)-methyl]-benzamidine-hydrochloride Prepared analogously to Example 1e from 4-[(5-(2,3,5,6-tetramethylphenylsulphonylamino)-1-methyl-1H-benzimidazol-2-yl)-methyl]-benzonitrile and hydrochloric acid/ammonium carbonate in ethanol.

Yield: 17% of theory, $C_{26}H_{29}N_5O_2S\times HCl$ (475.61/512.08); Mass spectrum: $(M+H)^+=476$.

EXAMPLE 23

4-[(5-phenylsulphonylaminoacetylamino-1-methyl-1H-benzimidazol-2-yl)-methyl]-benzamidine-hydrochloride Prepared analogously to Example 1e from 4-[(5-phenylsulphonylaminoacetylamino-1-methyl-1H-benzimidazol-2-yl)-methyl]-benzonitrile and hydrochloric acid/ammonium carbonate in ethanol.

Yield: 65% of theory, $C_{24}H_{24}N_6O_3S\times HCl$ (476.56/513.03); Mass spectrum: $(M+H)^+=477$.

EXAMPLE 24

4-[(5-(N-methyl-naphthalen-1-yl-aminocarbonyl)-1-methyl-1H-benzimidazol-2-yl)-methyl]-benzamidine-hydrochloride a. 4-chloro-3-nitro-benzoic acid chloride 20.1 g (0.1 mol) of 4-chloro-3-nitro-benzoic acid, 11 ml thionyl chloride and 1 drop of dimethylformamide are mixed together and refluxed for two hours. The thionyl chloride is evaporated off.

Yield: 21.9 9 (100% of theory).

b. 4-chloro-3-nitro-N-(naphthalen-1-yl)-benzamide

To a solution of 2.8 g (0.02 mol) of 1-naphthylamine and 2.0 g (0.02 mol) of triethylamine in 50 ml tetrahydrofuran is added dropwise at 15–20° C. a solution of 4.4 g (0.02 mol) of 4-chloro-3-nitro-benzoic acid chloride in 20 ml tetrahydrofuran. The solution is stirred for 30 minutes at ambient temperature. Then the solvent is evaporated off and the residue is chromatographed on silica gel, eluting with methylene chloride. The desired fractions are concentrated by evaporation, triturated with ether, suction filtered and dried.

Yield: 5.9 g (90% of theory).

c. 4-chloro-3-nitro-N-methyl-N-(naphthalen-1-yl)-benzamide 3.2 g (0.01 mol) of 4-chloro-3-nitro-N-(naphthalen-1-yl)-benzamide and 1.1 g (0.01 mol) of potassium-tert.-butoxide are dissolved in 50 ml dimethylsulphoxide and stirred for 30 minutes at ambient temperature. Then 1 ml methyl iodide is added thereto and the mixture is stirred for a further 3 hours at ambient temperature. The solution is poured onto saturated sodium chloride solution and extracted with ethyl acetate. The combined organic extracts are dried over sodium sulphate and concentrated by evaporation. The residue is chromatographed on silica gel and eluted with methylene chloride.

Yield: 3.2 g (94% of theory), Melting point: 118–120° C.

d. 4-methylamino-3-nitro-N-methyl-N-(naphthalen-1-yl)-benzamide 3.0 g (8.83 mmol) of 4-chloro-3-nitro-N-methyl-N-(naphthalen-1-yl)-benzamide and 30 ml methylamine solution (40% in $H_2O$) are heated to 130° C. in a bomb for 14 hours. After cooling the solution is poured onto water, the residue is suction filtered and chromatographed on silica gel, eluting with methylene chloride.

Yield: 2.9 g (98% of theory), $R_f$ value: 0.3 (silica gel; methylene chloride/ethanol=50:1).

e. 4-methylamino-3-amino-N-methyl-N-(naphthalen-1-yl)-benzamide 2.9 g (8.6 mmol) of 4-methylamino-3-nitro-N-methyl-N-(naphthalen-1-yl)-benzamide are dissolved in 100 ml methanol and after the addition of 0.5 g palladium on activated charcoal (20%) hydrogenated for two hours at ambient temperature. Then the catalyst is filtered off and the filtrate is concentrated by evaporation.

Yield: 2.6 g (98% of theory), $R_f$ value: 0.15 (silica gel; methylene chloride/ethanol=50:1).

f. 4-[(5-(N-methyl-naphthalen-1-yl-aminocarbonyl)-1-methyl-1H-benzimidazol-2-yl)-methyl]-benzonitrile 483 mg (3.0 mmol) of 4-cyanophenylacetic acid and 486 mg (3.0 mmol) of carbonyldiimidazole are dissolved in 20 ml tetrahydrofuran and stirred for 1 hour at 50° C. Then 916 mg 5-(naphthalen-1-yl-methylaminocarbonyl)-2-methylamino-aniline are added thereto and stirring is continued for a further 3 hours at 50° C. The solvent is concentrated by evaporation, the residue is combined with 30 ml glacial acetic acid and refluxed for 1 hour. After evaporation of the solvent the filtrate is chromatographed on silica gel, eluting with methylene chloride/ethanol 99:1, 98:1 and 97:1. The desired fractions are concentrated by evaporation, the residue is triturated with acetone/ether, suction filtered and dried.

Yield: 970 mg (75% of theory), Melting point: 266–268° C.

g. 4-[(5-(N-methyl-naphthalen-1-yl-aminocarbonyl)-1-methyl-1H-benzimidazol-2-yl)-methyl]-benzamidine-hydrochloride Prepared analogously to Example 1e from 4-[(5-(N-methyl-naphthalen-1-yl-aminocarbonyl)-1-methyl-1H-benzimidazol-2-yl)-methyl]-benzonitrile and hydrochloric acid/ammonium carbonate in ethanol.

Yield: 82% of theory, $C_{28}H_{25}N_5O \times HCl$ (447.55/484.01); Mass spectrum: $M^+=447$.

EXAMPLE 25

4-[(5-phenylmethylaminocarbonyl-1-methyl-1H-benzimidazol-2-yl)-methyl]-benzamidine-hydrochloride Prepared analogously to Example 1e from 4-[(5-phenylmethylaminocarbonyl-1-methyl-1H-benzimidazol-2-yl)-methyl]-benzonitrile and hydrochloric acid/ammonium carbonate in ethanol.

Yield: 95.5% of theory, $C_{24}H_{23}N_5O \times HCl$ (397.49/433.96); Mass spectrum: $M^+=397$.

EXAMPLE 26

4-[(5-(N-phenyl-n-butylaminocarbonyl)-1-methyl-1H-benzimidazol-2-yl)-methyl]-benzamidine-hydrochloride Prepared analogously to Example 1e from 4-[(5-(N-phenyl-n-butylaminocarbonyl)-1-methyl-1H-benzimidazol-2-yl)-methyl]-benzonitrile and hydrochloric acid/ammonium carbonate in ethanol.

Yield: 95% of theory, $C_{27}H_{29}N_5O \times HCl$ (439.57/476.03); Mass spectrum: $(M+H)^+=440$.

EXAMPLE 27

4-[(4-benzenesulphonylamino-1-methyl-1H-benzimidazol-2-yl)-methyl]-benzamidine-hydrochloride Prepared analogously to Example 1e from 4-[(4-benzenesulphonylamino-1-methyl-1H-benzimidazol-2-yl)-methyl]-benzonitrile and hydrochloric acid/ammonium carbonate in ethanol.

Yield: 63% of theory, $C_{22}H_{21}N_5O_2S \times HCl$ (419.50/455.96); Mass spectrum: $(M+H)^+=420$.

EXAMPLE 28

4-[(5-(N-methylaminocarbonyl-N-phenyl-aminocarbonyl)-1-methyl-1H-benzimidazol-2-yl)-methyl]-benzamidine-mesylate 700 mg (1.6 mmol) of 4-[(5-(N-methylaminocarbonyl-N-phenylaminocarbonyl)-1-methyl-1H-benzimidazol-2-yl)-methyl]-benzonitrile, 222 mg (3.2 mmol) of hydroxylamine-hydrochloride and 170 mg (1.6 mmol) of sodium carbonate are refluxed in 100 ml methanol and 4 ml water for 16 hours. After the addition of 150 mg methanesulphonic acid and 500 mg Raney nickel the mixture is hydrogenated at ambient temperature and with 5 atm. hydrogen. The catalyst is filtered off, the residue is concentrated by evaporation and chromatographed on silica gel, eluting with methylene chloride/ethanol (8:2).

Yield: 680 mg (77% of theory), $C_{26}H_{26}N_6O_2 \times CH_3SO_3H$ (454.54/550.64); Mass spectrum: $(M+H)^+=455$.

EXAMPLE 29

4-[(6-(naphthalen-2-yl-sulphonylamino)-1-ethoxycarbonylmethyl-1H-benzimidazol-2-yl)-methyl]-benzamidine-hydrochloride Prepared analogously to Example 1e from 4-[(6-(naphthalen-2-yl-sulphonylamino)-1-ethoxycarbonylmethyl-1H-benzimidazol-2-yl)-methyl]-benzonitrile and hydrochloric acid/ammonium carbonate in ethanol.

Yield: 63% of theory, $C_{29}H_{27}N_5O_4S \times HCl$ (541.64/578.1); Mass spectrum: $(M+H)^+=542$.

EXAMPLE 30

4-[(4-(naphthalen-2-yl-sulphonylamino)-1-methyl-1H-benzimidazol-2-yl)-methyl]-benzamidine-hydrochloride Prepared analogously to Example 1e from 4-[(4-(naphthalen-2-yl-sulphonylamino)-1-methyl-1H-benzimidazol-2-yl)-methyl]-benzonitrile and hydrochloric acid/ammonium carbonate in ethanol.

Yield: 66% of theory, $C_{26}H_{23}N_5O_2S \times HCl$ (469.57/506.03); Mass spectrum: $(M+H)^+=470$.

EXAMPLE 31

4-[(5-(N-(2-morpholino-ethyl)-quinolin-8-yl-sulphonylamino)-1-methyl-1H-benzimidazol-2-yl)-methyl]-benzamidine-dihydrochloride Prepared analogously to Example 1e from 4-[(5-(N-(2-morpholino-ethyl)-quinolin-8-yl-sulphonylamino)-1-methyl-1H-benzimidazol-2-yl)-methyl]-benzonitrile and hydrochloric acid/ammonium carbonate in ethanol.

Yield: 66% of theory, $C_{31}H_{33}N_7O_3S \times 2\ HCl$ (583.72/656.63); Mass spectrum: $(M+H)^+=584$.

EXAMPLE 32

4-[(5-(N-(2-morpholino-ethyl)-quinolin-8-yl-amino)-1-methyl-1H-benzimidazol-2-yl)-methyl]-benzamidine-hydrochloride Prepared analogously to Example 1e from 4-[(5-(N-(2-morpholino-ethyl)-quinolin-8-yl-sulphonylamino)-1-methyl-1H-benzimidazol-2-yl)-methyl]-benzonitrile and hydrochloric acid/ammonium carbonate in ethanol.

Yield: 96% of theory, $C_{31}H_{31}N_7O_4S \times HCl$ (597.70/634.17); Mass spectrum: $(M+H)^+=598$.

EXAMPLE 33

4-[(5-(N-(3-ethoxycarbonyl-n-propyl)-quinolin-8-yl-sulphonylamino)-1-methyl-1H-benzimidazol-2-yl)-methyl]-benzamidine-hydrochloride Prepared analogously to Example 1e from 4-[(5-(N-(3-ethoxycarbonyl-n-propyl)-quinolin-8-yl)-sulphonylamino)-1-methyl-1H-benzimidazol-2-yl)-methyl]-benzonitrile and hydrochloric acid/ammonium carbonate in ethanol.

Yield: 58% of theory, $C_{31}H_{32}N_6O_4S \times HCl$ (584.71/621.17); Mass spectrum: $(M+H)^+=585$.

EXAMPLE 34

4-[(5-(N-ethoxycarbonylmethyl-quinolin-8-yl-sulphonylamino)-1-methyl-1H-benzimidazol-2-yl)-methyl]-benzamidine-hydrochloride Prepared analogously to Example 1e from 4-[(5-(N-ethoxycarbonylmethyl-quinolin-8-yl-sulphonylamino-1-methyl-1H-benzimidazol-2-yl)-methyl]-benzonitrile and hydrochloric acid/ammonium carbonate in ethanol.

Yield: 68% of theory, $C_{29}H_{28}N_6O_4S \times HCl$ (556.65/593.12); Mass spectrum: $(M+H)^+557$; $(M+Na)^+=579$; $(M+2H)^{++}=279$.

EXAMPLE 35

4-[(5-(N-ethoxycarbonylmethyl-benzoylamino)-1-methyl-1H-benzimidazol-2-yl)-methyl]-benzamidine-hydrochloride Prepared analogously to Example 1e from 4-[(5-(N-ethoxycarbonylmethyl-benzoylamino)-1-methyl-1H-benzimidazol-2-yl)-methyl]-benzonitrile and hydrochloric acid/ammonium carbonate in ethanol.

Yield: 47% of theory, $C_{27}H_{27}N_5O_3 \times HCl$ (469.55/506.0); Mass spectrum: $(M+H)^+=470$.

EXAMPLE 36

4-[(5-(N-(3-ethoxycarbonyl)-phenylsulphonylamino)-1-methyl-1H-benzimidazol-2-yl)-methyl]-benzamidine-hydrochloride Prepared analogously to Example 1e from 4-[(5-(N-(3-ethoxycarbonyl)-phenylsulphonylamino-1-methyl-1H-benzimidazol-2-yl)-methyl]-benzonitrile and hydrochloric acid/ammonium carbonate in ethanol.

Yield: 24% of theory, $C_{25}H_{25}N_5O_4S \times HCl$ (491.6/528.0); Mass spectrum: $(M+H)^+=492$.

EXAMPLE 37

4-[(5-(N-methyl-pyridine-3-ylaminocarbonyl)-1-methyl-1H-benzimidazol-2-yl)-methyl]-benzamidine-hydrochloride Prepared analogously to Example 1e from 4-[(5-(N-methyl-pyridine-3-ylaminocarbonyl)-1-methyl-1H-benzimidazol-2-yl)-methyl]-benzonitrile and hydrochloric acid/ammonium carbonate in ethanol.

Yield: 49% of theory, $C_{23}H_{22}N_6O \times HCl$ (398.48/434.94); Mass spectrum: $(M+H)^+=399$.

EXAMPLE 38

4-[(5-(N-methyl-pyridine-2-ylaminocarbonyl)-1-methyl-1H-benzimidazol-2-yl)-methyl]-benzamidine-hydrochloride Prepared analogously to Example 1e from 4-[(5-(N-methyl-pyridine-2-yl-aminocarbonyl)-1-methyl-1H-benzimidazol-2-yl)-methyl]-benzonitrile and hydrochloric acid/ammonium carbonate in ethanol.

Yield: 49% of theory, $C_{23}H_{22}N_6O \times HCl$ (398.48/434.94); Mass spectrum: $(M+H)^+=399$.

EXAMPLE 39

4-[(5-(N-phenyl-N-ethoxycarbonylmethyl-aminocarbonyl)-1-methyl-1H-benzimidazol-2-yl)-methyl]-benzamidine-hydrochloride Prepared analogously to Example 1e from 4-[(5-(N-phenyl-N-ethoxycarbonylmethyl-aminocarbonyl)-1-methyl-1H-benzimidazol-2-yl)-methyl]-benzonitrile and hydrochloric acid/ammonium carbonate in ethanol.

Yield: 65% of theory, $C_{27}H_{27}N_5O_3 \times HCl$ (469.55/506.02); Mass spectrum: $(M+H)^+=470$.

EXAMPLE 40

4-[(5-(N-phenyl-N-(2-dimethylamino-ethyl)-aminocarbonyl)-1-methyl-1H-benzimidazol-2-yl)-methyl]-benzamidine-dihydrochloride Prepared analogously to Example 1e from 4-[(5-(N-phenyl-N-(2-dimethylamino-ethyl)-aminocarbonyl)-1-methyl-1H-benzimidazol-2-yl)-methyl]-benzonitrile and hydrochloric acid/ammonium carbonate in ethanol.

Yield: 24% of theory, $C_{27}H_{30}N_6O \times 2\ HCl$ (454.59/527.50); Mass spectrum: $(M+H)^+=455$.

EXAMPLE 41

4-[(5-(N-carboxymethyl-quinolin-8-yl-sulphonylamino)-1-methyl-1H-benzimidazol-2-yl)-methyl]-benzamidine-hydrochloride Prepared analogously to Example 13 from 4-[(5-(N-carboxymethyl-quinolin-8-yl-sulphonylamino)-1-methyl-1H-benzimidazol-2-yl)-methyl]-benzamidine-hydrochloride and sodium hydroxide in ethanol/water.

Yield: 56% of theory, $C_{27}H_{24}N_6O_4S \times HCl$ (528.60/565.05); Mass spectrum: $(M+H)^+=529$; $(M+Na)^+=551$.

EXAMPLE 42

4-[(5-(N-(3-carboxy-n-propyl)-quinolin-8-yl-sulphonylamino)-1-methyl-1H-benzimidazol-2-yl)-methyl]-benzamidine-hydrochloride Prepared analogously to Example 13 from 4-[(5-(N-(3-carboxy-n-propyl)-quinolin-8-yl-sulphonylamino)-1-methyl-1H-benzimidazol-2-yl)-methyl]-benzamidine-hydrochloride and sodium hydroxide in ethanol/water.

Yield: 46% of theory, $C_{29}H_{28}N_6O_4S \times HCl$ (556.65/593.10); Mass spectrum: $(M+H)^+=557$; $(M+Na)^+=579$.

EXAMPLE 43

4-[(5-(N-(2-morpholino-ethyl)-quinolin-8-yl-sulphonylamino)-1-methyl-1H-benzimidazol-2-yl)-carbonyl]-benzamidine-dihydrochloride Prepared analogously to Example 1e from 4-[(5-(N-(2-morpholino-ethyl)-quinolin-8-yl-sulphonylamino)-1-methyl-1H-benzimidazol-2-yl)-carbonyl]-benzonitrile and hydrochloric acid/ammonium carbonate in ethanol.

Yield: 37% of theory, $C_{31}H_{31}N_7O_4S \times 2\ HCl$ (597.7/670.62); Mass spectrum: $(M+H)^+=598$.

EXAMPLE 44

4-[(5-(N-(3-dimethylamino-n-propyl)-quinolin-8-yl-sulphonylamino)-1-methyl-1H-benzimidazol-2-yl)-methyl]-benzamidine-dihydrochloride Prepared analogously to Example 1e from 4-[(5-(N-(3-dimethylamino-n-propyl)-quinolin-8-yl-sulphonylamino)-1-methyl-1H-benzimidazol-2-yl)-methyl]-benzonitrile and hydrochloric acid/ammonium carbonate in ethanol.

Yield: 78% of theory, $C_{30}H_{33}N_7O_2S \times 2\ HCl$ (555.71/663.07); Mass spectrum: $(M+H)^+=556$; $(M+2H)^{++}=278.8$.

EXAMPLE 45

4-[(5-(N-(2-dimethylamino-ethyl)-quinolin-8-yl-sulphonylamino)-1-methyl-1H-benzimidazol-2-yl)-methyl]-benzamidine-dihydrochloride Prepared analogously to Example 1e from 4-[(5-(N-(2-dimethylamino-ethyl)-quinolin-8-yl-sulphonylamino)-1-methyl-1H-benzimidazol-2-yl)-methyl]-benzonitrile and hydrochloric acid/ammonium carbonate in ethanol.

Yield: 81% of theory, $C_{29}H_{31}N_7O_2S \times 2HCl$ (541.68/612.59); Mass spectrum: $(M+H)^+=542$.

EXAMPLE 46

4-[(5-(N-benzoyl-N-carboxymethyl-amino)-1-methyl-1H-benzimidazol-2-yl)-methyl]-benzamidine-hydrochloride Prepared analogously to Example 13 from 4-[(5-(N-benzoyl-N-ethoxycarbonylmethyl-amino)-1-methyl-1H-benzimidazol-2-yl)-methyl]-benzamidine-hydrochloride and sodium hydroxide in ethanol/water.

Yield: 98% of theory, $C_{25}H_{23}N_5O_3 \times HCl$ (441.50/447.95); Mass spectrum: $(M+H)^+=442$; $(M+Na)^+=464$.

EXAMPLE 47

4-[(5-(3-carboxyphenylsulphonylamino)-1-methyl-1H-benzimidazol2-yl)-methyl]-benzamidine-hydrochloride Prepared analogously to Example 13 from 4-[(5-(3-ethoxycarbonylphenylsulphonylamino)-1-methyl-1H-benzimidazol-2-yl)-methyl]-benzamidine-hydrochloride and sodium hydroxide in ethanol/water.

Yield: 82% of theory, $C_{23}H_{21}N_5O_4S \times HCl$ (463.50/499.95); Mass spectrum: $(M+H)^+=464$.

EXAMPLE 48

4-[(5-(N-phenyl-N-carboxymethyl-aminocarbonyl)-1-methyl-1H-benzimidazol-2-yl)-methyl]-benzamidine-hydrochloride Prepared analogously to Example 13 from 4-[(5-(N-phenyl-N-ethoxycarbonylmethyl-aminocarbonyl)-1-methyl-1H-benzimidazol-2-yl)-methyl]-benzamidine-hydrochloride and sodium hydroxide in ethanol/water.

Yield: 68% of theory, $C_{25}H_{23}N_5O_3$ (441.50/477.95); Mass spectrum: $(M+H)^+=442$.

EXAMPLE 49

4-[(5-benzenesulphonylamino-1-n-propyl-1H-benzimidazol-2-yl)-methyl]-benzamidine-hydrochloride Prepared analogously to Example 1e from 4-[(5-benzenesulphonylamino-1-n-propyl-1H-benzimidazol-2-yl)-methyl]-benzonitrile and hydrochloric acid/ammonium carbonate in ethanol.

Yield: 62% of theory, $C_{25}H_{27}N_5O_2S \times HCl$ (461.58/498.04); Mass spectrum: $(M+H)^+=462$.

EXAMPLE 50

4-[(5-(N-ethoxycarbonylmethyl-benzenesulphonylamino)-1-n-propyl-1H-benzimidazol-2-yl)-methyl]-benzamidine-hydrochloride Prepared analogously to Example 1e from 4-[(5-(N-ethoxycarbonylmethyl-benzenesulphonylamino)-1-n-propyl-1H-benzimidazol- 2-yl)-methyl]-benzonitrile and hydrochloric acid/ammonium carbonate in ethanol.

Yield: 45% of theory, $C_{29}H_{33}N_5O_4S \times HCl$ (547.68/584.14); Mass spectrum: $(M+H)^+=548$.

EXAMPLE 51

4-[(5-(N-methyl-benzenesulphonylamino)-1-n-propyl-1H-benzimidazol-2-yl)-methyl]-benzamidine-hydrochloride Prepared analogously to Example 1e from 4-[(5-(N-methyl-benzenesulphonylamino)-1-n-propyl-1H-benzimidazol-2-yl)-methyl]-benzonitrile and hydrochloric acid/ammonium carbonate in ethanol.

Yield: 45% of theory, $C_{26}H_{29}N_5O_2S \times HCl$ (475.62/512.08); Mass spectrum: $(M+H)^+=476$.

EXAMPLE 52

4-[(5-(N-carboxymethyl-benzenesulphonylamino)-1-n-propyl-1H-benzimidazol-2-yl)-methyl]-benzamidine-hydrochloride Prepared analogously to Example 13 from 4-[(5-(N-ethoxycarbonylmethyl-benzenesulphonylamino)-1-n-propyl-1H-benzimidazol-2-yl)-methyl]-benzamidine-hydrochloride and sodium hydroxide in ethanol/water.

Yield: 62% of theory, $C_{27}H_{29}N_5O_4S \times HCl$ (519.63/556.08); Mass spectrum: $(M+H)^+=520$.

EXAMPLE 53

4-[(5-(N-phenyl-N-(3-ethoxycarbonyl-n-propyl)-aminocarbonyl)-1-methyl-1H-benzimidazol-2-yl)-methyl]-benzamidine-hydrochloride Prepared analogously to Example 1e from 4-[(5-(N-phenyl-N-(3-ethoxycarbonyl-n-propyl)-aminocarbonyl)-1-methyl-1H-benzimidazol-2-yl)-methyl]-benzonitrile and hydrochloric acid/ammonium carbonate in ethanol.

Yield: 70% of theory, $C_{29}H_{31}N_5O_3 \times HCl$ (497.61/534.07); Mass spectrum: $(M+H)^+=498$.

EXAMPLE 54

4-[(5-((N-pyridin-3-yl-carbonyl)-N-methyl-amino)-1-methyl-1H-benzimidazol-2-yl)-methyl]-benzamidine-hydrochloride Prepared analogously to Example 1e from 4-[(5-((N-pyridin-3-yl-carbonyl)-N-methyl-amino)-1-methyl-1H-benzimidazol-2-yl)-methyl]-benzonitrile and hydrochloric acid/ammonium carbonate in ethanol.

Yield: 54% of theory, $C_{23}H_{22}N_6O \times HCl$ (398.5/434.95); Mass spectrum: $M^+=398$.

EXAMPLE 55

4-[(5-((N-pyridin-4-yl-carbonyl)-N-methyl-amino)-1-methyl-1H-benzimidazol-2-yl)-methyl]-benzamidine-hydrochloride Prepared analogously to Example 1e from 4-[(5-((N-pyridin-4-yl-carbonyl)-N-methyl-amino)-1-methyl-1H-benzimidazol-2-yl)-methyl]-benzonitrile and hydrochloric acid/ammonium carbonate in ethanol.

Yield: 53% of theory, $C_{23}H_{22}N_6O \times HCl$ (398.5/434.95); Mass spectrum: $(M+H)^+=399$.

EXAMPLE 56

4-[(5-(pyridin-3-yl-sulphonylamino)-1-methyl-1H-benzimidazol-2-yl)-methyl]-benzamidine-hydrochloride Prepared analogously to Example 1e from 4-[(5-(pyridin-3-yl-sulphonylamino)-1-methyl-1H-benzimidazol-2-yl)-methyl]-benzonitrile and hydrochloric acid/ammonium carbonate in ethanol.

Yield: 48% of theory, $C_{21}H_{20}N_6O_2S \times HCl$ (420.5/456.95); Mass spectrum: $(M+H)^+=421$.

EXAMPLE 57

4-[(5-(N-ethoxycarbonylmethyl-
benzenesulphonylamino)-1-ethoxycarbonylmethyl-
1H-benzimidazol-2-yl)-methyl]-benzamidine-
hydrochloride Prepared analogously to Example 1e from 4-[(5-(N-ethoxycarbonylmethyl-benzenesulphonylamino)-1-ethoxycarbonylmethyl-1H-benzimidazol-2-yl)-methyl]-benzonitrile and hydrochloric acid/ammonium carbonate in ethanol.

Yield: 64.5% of theory, $C_{29}H_{31}N_5O_6S \times HCl$ (577.67/614.14); Mass spectrum: $(M+H)^+=578$.

EXAMPLE 58

4-[(5-(N-(2-dimethylamino-ethyl)-
benzenesulphonylamino)-1-ethoxycarbonylmethyl-
1H-benzimidazol-2-yl)-methyl]-benzamidine-
dihydrochloride Prepared analogously to Example 1e from 4-[(5-(N-(2-dimethylamino-ethyl)-benzenesulphonylamino)-1-ethoxycarbonylmethyl-1H-benzimidazol-2-yl)-methyl]-benzonitrile and hydrochloric acid/ammonium carbonate in ethanol.

Yield: 11.1% of theory, $C_{28}H_{32}N_6O_4S \times 2$ HCl (548.68/621.6); Mass spectrum: $(M+H)^+549$; $(M+2H)^{++}=275.1$.

EXAMPLE 59

4-[(6-benzenesulphonylamino-1-
ethoxycarbonylmethyl-1H-benzimidazol-2-yl)-
methyl]-benzamidine-hydrochloride Prepared analogously to Example 1e from 4-[(6-benzenesulphonylamino-1-ethoxycarbonylmethyl-1H-benzimidazol-2-yl)-methyl]-benzonitrile and hydrochloric acid/ammonium carbonate in ethanol.

Yield: 90% of theory, $C_{25}H_{25}N_5O_4S \times HCl$ (491.58/528.05); Mass spectrum: $(M+H)^+=492$.

EXAMPLE 60

4-[(5-(3-ethoxycarbonyl-n-propylamino)-1-
ethoxycarbonylmethyl-1H-benzimidazol-2-yl)-
methyl]-benzamidine-hydrochloride Prepared analogously to Example 1e from 4-[(5-(3-ethoxycarbonyl-n-propylamino)-1-ethoxycarbonylmethyl-1H-benzimidazol-2-yl)-methyl]-benzonitrile and hydrochloric acid/ammonium carbonate in ethanol.

Yield: 41.7% of theory, $C_{25}H_{31}N_5O_4 \times HCl$ (465.56/502.03); Mass spectrum: $(M+H)^+=466$.

EXAMPLE 61

4-[(5-(ethoxycarbonylmethylamino)-1-
ethoxycarbonylmethyl-1H-benzimidazol-2-yl)-
methyl]-benzamidine-hydrochloride Prepared analogously to Example 1e from 4-[(5-(ethoxycarbonylmethylamino)-1-ethoxycarbonylmethyl-1H-benzimidazol-2-yl)-methyl]-benzonitrile and hydrochloric acid/ammonium carbonate in ethanol.

Yield: 56.4% of theory, $C_{23}H_{27}N_5O_4 \times HCl$ (437.51/473.98); Mass spectrum: $(M+H)^+=438$.

EXAMPLE 62

4-[(5-(N-methyl-piperidin-1-yl-carbonylamino)-1-
methyl-1H-benzimidazol-2-yl)-methyl]-
benzamidine-hydrochloride Prepared analogously to Example 1e from 4-[(5-(N-methyl-piperidin-1-yl-carbonylamino)-1-methyl-1H-benzimidazol-2-yl)-methyl]-benzonitrile and hydrochloric acid/ammonium carbonate in ethanol.

Yield: 55% of theory, $C_{23}H_{28}N_6O \times HCl$ (404.52/440.98); Mass spectrum: $M^+=404$.

EXAMPLE 63

4-[(5-(N-methyl-2,3-dihydroindol-1-yl-
carbonylamino)-1-methyl-1H-benzimidazol-2-yl)-
methyl]-benzamidine-hydrochloride Prepared analogously to Example 1e from 4-[(5-(N-methyl-2,3-dihydroindol-1-yl-carbonylamino)-1-methyl-1H-benzimidazol-2-yl)-methyl]-benzonitrile and hydrochloric acid/ammonium carbonate in ethanol.

Yield: 78% of theory, $C_{26}H_{26}N_6O \times HCl$ (438.54/475.00); Mass spectrum: $M^+=438$.

EXAMPLE 64

4-[(5-(N-(3-ethoxycarbonyl-n-propyl)-
benzenesulphonylamino)-1-ethoxycarbonylmethyl-
1H-benzimidazol-2-yl)-methyl]-benzamidine-
hydrochloride Prepared analogously to Example 1e from 4-[(5-(N-(3-ethoxycarbonyl-n-propyl)-benzenesulphonylamino)-1-ethoxycarbonylmethyl-1H-benzimidazol-2-yl)-methyl]-benzonitrile and hydrochloric acid/ammonium carbonate in ethanol.

Yield: 59.5% of theory, $C_{31}H_{35}N_5O_6S \times HCl$ (605.9/641.4); Mass spectrum: $(M+H)^+=606$.

EXAMPLE 65

4-[(6-(N-methyl-benzenesulphonylamino)-1-
ethoxycarbonylmethyl-1H-benzimidazol-2-yl)-
methyl]-benzamidine-hydrochloride Prepared analogously to Example 1e from 4-[(6-(N-methyl-benzenesulphonylamino)-1-ethoxycarbonylmethyl-1H-benzimidazol-2-yl)-methyl]-benzonitrile and hydrochloric acid/ammonium carbonate in ethanol.

Yield: 45% of theory, $C_{26}H_{27}N_5O_4S \times HCl$ (505.61/542.07); Mass spectrum: $(M+H)^+=506$.

EXAMPLE 66

4-[(5-benzenesulphonylamino-1-(3-ethoxycarbonyl)-
n-propyl-1H-benzimidazol-2-yl)-methyl]-
benzamidine-hydrochloride Prepared analogously to Example 1e from 4-[(5-benzenesulphonylamino-1-(3-ethoxycarbonyl)-n-propyl-1H-benzimidazol-2-yl)-methyl]-benzonitrile and hydrochloric acid/ammonium carbonate in ethanol.

Yield: 58% of theory, $C_{27}H_{29}N_5O_4S \times HCl$ (519.6/556.1); Mass spectrum: $(M+H)^+=520$.

EXAMPLE 67

4-[(5-benzenesulphonylamino-1-benzyl-1H-
benzimidazol-2-yl)-methyl]-benzamidine-
hydrochloride Prepared analogously to Example 1e from 4-[(5-benzenesulphonylamino-1-benzyl-1H-benzimidazol-2-yl)-methyl]-benzonitrile and hydrochloric acid/ammonium carbonate in ethanol.

Yield: 63% of theory, $C_{28}H_{25}N_5O_2S \times HCl$ (495.6/532.1); Mass spectrum: $(M+H)^+=496$.

EXAMPLE 68

4-[(5-benzenesulphonylamino-1-(2-morpholino-ethyl)-1H-benzimidazol-2-yl)-methyl]-benzamidine-dihydrochloride Prepared analogously to Example 1e from 4-[(5-benzenesulphonylamino-1-(2-morpholino-ethyl)-1H-benzimidazol-2-yl)-methyl]-benzonitrile and hydrochloric acid/ammonium carbonate in ethanol.

Yield: 96% of theory, $C_{27}H_{30}N_6O_3S \times 2$ HCl (518.65/591.56); Mass spectrum: $(M+H)^+=519$.

EXAMPLE 69

4-[(5-benzenesulphonylamino-1-(2-dimethylamino-ethyl)-1H-benzimidazol-2-yl)-methyl]-benzamidine-dihydrochloride Prepared analogously to Example 1e from 4-[(5-benzenesulphonylamino-1-(2-dimethylamino-ethyl)-1H-benzimidazol-2-yl)-methyl]-benzonitrile and hydrochloric acid/ammonium carbonate in ethanol.

Yield: 38% of theory, $C_{25}H_{28}N_6O_2S \times 2$ HCl (476.6/549.56); Mass spectrum: $(M+H)^+=477$.

EXAMPLE 70

4-[(5-(N-ethoxycarbonylmethyl-benzenesulphonylamino)-1-(3-ethoxycarbonyl-n-propyl)-1H-benzimidazol-2-yl)-methyl]-benzamidine-hydrochloride Prepared analogously to Example 1e from 4-[(5-(N-ethoxycarbonylmethyl-benzenesulphonylamino)-1-(3-ethoxycarbonyl-n-propyl)-1H-benzimidazol-2-yl)-methyl]-benzonitrile and hydrochloric acid/ammonium carbonate in ethanol.

Yield: 61% of theory, $C_{31}H_{35}N_5O_6S \times HCl$ (605.7/642.2); Mass spectrum: $(M+H)^+=606$.

EXAMPLE 71

4-[(5-(N-ethoxycarbonylmethyl-benzenesulphonylamino)-1-benzyl-1H-benzimidazol-2-yl)-methyl]-benzamidine-hydrochloride Prepared analogously to Example 1e from 4-[(5-(N-ethoxycarbonylmethyl-benzenesulphonylamino)-1-benzyl-1H-benzimidazol-2-yl)-methyl]-benzonitrile and hydrochloric acid/ammonium carbonate in ethanol.

Yield: 43% of theory, $C_{32}H_{31}N_5O_4S \times HCl$ (581.7/618.2); Mass spectrum: $(M+H)^+=582$.

EXAMPLE 72

4-[(5-(N-(N'-phenyl-methylaminocarbonyl)-methylamino)-1-methyl-1H-benzimidazol-2-yl)-methyl]-benzamidine-hydrochloride Prepared analogously to Example 1e from 4-[(5-(N-(N'-phenylmethylaminocarbonyl)-methylamino)-1-methyl-1H-benzimidazol-2-yl)-methyl]-benzonitrile and hydrochloric acid/ammonium carbonate in ethanol.

Yield: 43% of theory, $C_{25}H_{26}N_6O \times HCl$ (426.52/462.98); Mass spectrum: $(M+H)^+=427$.

EXAMPLE 73

4-[(5-(N-(ethoxycarbonylmethylaminoacetyl)-quinolin-8-yl-sulphonylamino)-1-methyl-1H-benzimidazol-2-yl)-methyl]-benzamidine-hydrochloride Prepared analogously to Example 1e from 4-[(5-(N-(ethoxycarbonylmethylaminoacetyl)-quinolin-8-yl-sulphonylamino)-1-methyl-1H-benzonitrile and hydrochloric acid/ammonium carbonate in ethanol.

Yield: 80% of theory, $C_{31}H_{31}N_7O_5S \times HCl$ (613.70/650.16); Mass spectrum: $(M+H)^+=614$.

EXAMPLE 74

4-[(5-(N-(4-dimethylaminopiperidinocarbonylmethyl)-quinolin-8-yl-sulphonylamino)-1-methyl-1H-benzimidazol-2-yl)-methyl]-benzamidine-dihydrochloride Prepared analogously to Example 1e from 4-[(5-(N-(4-dimethylaminopiperidinocarbonylmethyl)-quinolin-8-yl-sulphonylamino)-1-methyl-1H-benzimidazol-2-yl)-methyl]-benzonitrile and hydrochloric acid/ammonium carbonate in ethanol.

Yield: 78% of theory, $C_{34}H_{38}N_8O_3S \times 2$ HCl (638.8/711.73); Mass spectrum: $(M+H)^+=639$.

EXAMPLE 75

4-[(5-(N-ethoxycarbonylmethyl-benzenesulphonylamino)-1-(2-morpholino-ethyl)-1H-benzimidazol-2-yl)-methyl]-benzamidine-dihydrochloride Prepared analogously to Example 1e from 4-[(5-(N-ethoxycarbonylmethyl-benzenesulphonylamino)-1-(2-morpholino-ethyl)-1H-benzonitrile and hydrochloric acid/ammonium carbonate in ethanol.

Yield: 68% of theory, $C_{31}H_{36}N_6O_5S \times 2$ HCl (604.7/677.66); Mass spectrum: $(M+H)^+=605$.

EXAMPLE 76

4-[(5-(N-aminocarbonylmethyl-benzenesulphonylamino)-1-(3-ethoxycarbonyl-n-propyl)-1H-benzimidazol-2-yl)-methyl]-benzamidine-hydrochloride Prepared analogously to Example 1e from 4-[(5-(N-aminocarbonylmethyl-benzenesulphonylamino)-1-(3-ethoxycarbonyl-n-propyl)-1H-benzonitrile and hydrochloric acid/ammonium carbonate in ethanol.

Yield: 49% of theory, $C_{29}H_{32}N_6O_5S \times HCl$ (576.7/613.1); Mass spectrum: $(M+H)^+=577$.

EXAMPLE 77

4-[(5-(N-aminocarbonylmethyl-benzenesulphonylamino)-1-benzyl-1H-benzimidazol-2-yl)-methyl]-benzamidine-hydrochloride Prepared analogously to Example 1e from 4-[(5-(N-aminocarbonylmethyl-benzenesulphonylamino)-1-benzyl-1H-benzimidazol-2-yl)-methyl]-benzonitrile and hydrochloric acid/ammonium carbonate in ethanol.

Yield: 61% of theory, $C_{30}H_{28}N_6O_3S \times HCl$ (552.7/588.2); Mass spectrum: $(M+H)^+=553$.

EXAMPLE 78

4-[(5-(N-aminocarbonylmethyl-
benzenesulphonylamino)-1-(2-morpholino-ethyl)-
1H-benzimidazol-2-yl)-methyl]-benzamidine-
dihydrochloride Prepared analogously to Example 1e from 4-[(5-(N-aminocarbonylmethyl-benzenesulphonylamino)-1-(2-morpholino-ethyl)-1H-benzonitrile and hydrochloric acid/ammonium carbonate in ethanol.

Yield: 78% of theory, $C_{29}H_{33}N_7O_4S \times HCl$ (575.7/648.6); Mass spectrum: $(M+H)^+=576$.

EXAMPLE 79

4-[(5-(N-carboxymethyl-benzenesulphonylamino)-1-
(2-morpholinoethyl)-1H-benzimidazol-2-yl)-
methyl]-benzamidine-dihydrochloride Prepared analogously to Example 13 from 4-[(5-N-(ethoxycarbonylmethyl-benzenesulphonylamino)-1-(2-morpholino-ethyl)-1H-benzimidazol-2-yl)-methyl]-benzamidine-di-hydrochloride and sodium hydroxide in ethanol/water.

Yield: 87% of theory, $C_{29}H_{32}N_6O_5S \times 2$ HCl (576.7/649.62); Mass spectrum: $(M+H)^+=577$.

EXAMPLE 80

4-[(5-(N-ethoxycarbonylmethyl-
benzenesulphonylamino-1-(2-dimethylamino-ethyl)-
1H-benzimidazol-2-yl)-methyl]-benzamidine-
dihydrochloride Prepared analogously to Example 1e from 4-[(5-(N-ethoxycarbonylmethyl-benzenesulphonylamino)-1-(2-dimethylamino-ethyl)-1H-benzimidazol-2-yl)-methyl]-benzonitrile and hydrochloric acid/ammonium carbonate in ethanol.

Yield: 60% of theory, $C_{29}H_{34}N_6O_4S \times 2$ HCl (562.7/635.66); Mass spectrum: $(M+H)^+=563$; $(M+2H)^{++}=282$.

EXAMPLE 81

4-[(5-(N-carboxymethyl-benzenesulphonylamino)-1-
benzyl-1H-benzimidazol-2-yl)-methyl]-
benzamidine-hydrochloride Prepared analogously to Example 13 from 4-[(5-(N-ethoxycarbonylmethyl-benzenesulphonylamino)-1-benzyl-1H-benzimidazol-2-yl)-methyl]-benzamidine-hydrochloride and sodium hydroxide in ethanol/water.

Yield: 84% of theory, $C_{30}H_{27}N_5O_4S \times HCl$ (553.65/590.11); Mass spectrum: $(M+H)^+=554$.

EXAMPLE 82

4-[(5-(N-(carboxymethylaminoacetyl)-quinolin-8-yl-
sulphonylamino)-1-methyl-1H-benzimidazol-2-yl)-
methyl]-benzamidine-hydrochloride Prepared analogously to Example 13 from 4-[(5-(N-(ethoxycarbonylmethylaminoacetyl)-quinolin-8-yl-sulphonylamino)-1-methyl-1H-benzimidazol-2-yl)-methyl]-benzamidine-hydrochloride and sodium hydroxide in ethanol/water.

Yield: 74% of theory, $C_{29}H_{27}N_7O_5S \times HCl$ (585.65/622.11); Mass spectrum: $(M+H)^+=586$; $(M+Na)^+=608$.

EXAMPLE 83

4-[(5-(N-carboxymethyl-benzenesulphonylamino)-1-
(2-dimethylamino-ethyl)-1H-benzimidazol-2-yl)-
methyl]-benzamidine-dihydrochloride Prepared analogously to Example 13 from 4-[(5-(N-ethoxycarbonylmethyl-benzenesulphonylamino)-1-(2-dimethylamino-ethyl)-1H-benzimidazol-2-yl)-methyl]-benzamidine-dihydrochloride and sodium hydroxide in ethanol/water.

Yield: 62% of theory, $C_{27}H_{30}N_6O_4S \times 2$ HCl (534.65/607.56); Mass spectrum: $(M+H)^+=535$.

EXAMPLE 84

4-[(5-(N-(4-methylpiperazinocarbonylmethyl)-
quinolin-8-yl-sulphonylamino)-1-methyl-1H-
benzimidazol-2-yl)-methyl]-benzamidine-
dihydrochloride Prepared analogously to Example 1e from 4-[(5-(N-(4-methylpiperazinocarbonylmethyl)-quinolin-8-yl-sulphonylamino)-1-methyl-1H-benzimidazol-2-yl)-methyl]-benzonitrile and hydrochloric acid/ammonium carbonate in ethanol.

Yield: 86% of theory, $C_{32}H_{34}N_8O_3S \times 2$ HCl (610.74/683.67); Mass spectrum: $(M+H)^+=611$.

EXAMPLE 85

4-[(5-(N-(N'-(2-dimethylaminoethyl)-
ethylaminocarbonylmethyl)-quinolin-8-yl-
sulphonylamino)-1-methyl-1H-benzimidazol-2-yl)-
methyl]-benzamidine-dihydrochloride Prepared analogously to Example 1e from 5-(N-(N'-(2-dimethylaminoethyl)-ethylaminocarbonylmethyl)-quinolin-8-yl-sulphonylamino)-1-methyl-1H-benzimidazol-2-yl)-methyl]-benzonitrile and hydrochloric acid/ammonium carbonate in ethanol.

Yield: 95% of theory, $C_{33}H_{38}N_8O_3S \times 2$ HCl (626.79/699.71); Mass spectrum: $(M+H)^+=627$.

EXAMPLE 86

4-[(5-[(1-ethoxycarbonyl-2-aminocarbonyl-
ethylamino)-carbonylmethyl]-quinolin-8-yl-
sulphonylamino)-1-methyl-1H-benzimidazol-2-yl)-
methyl]-benzamidine-hydrochloride Prepared analogously to Example 1e from 4-[(5-[(1-ethoxycarbonyl-2-aminocarbonyl-ethylamino)-carbonylmethyl]-quinolin-8-yl-sulphonylamino)-1-methyl-1H-benzimidazol-2-yl)-methyl]-benzonitrile and hydrochloric acid/ammonium carbonate in ethanol.

Yield: 63% of theory, $C_{33}H_{34}N_8O_6S \times HCl$ (670.75/707.21); Mass spectrum: $(M+H)^+=671$.

EXAMPLE 87

4-[(5-(N-(4-(2-morpholino-2-oxo-ethyl)-
piperazinocarbonylmethyl)-quinolin-8-yl-
sulphonylamino)-1-methyl-1H-benzimidazol-2-yl)-
methyl]-benzamidine-dihydrochloride Prepared analogously to Example 1e from 4-[(5-(N-(4-(2-morpholino-2-oxo-ethyl)-piperazinocarbonylmethyl)-quinolin-8-yl-sulphonylamino)-1-methyl-1H-benzimidazol-2-yl)-methyl]-benzonitrile and hydrochloric acid/ammonium carbonate in ethanol.

Yield: 81% of theory, $C_{37}H_{41}N_9O_5S \times 2$ HCl (723.87/796.79); Mass spectrum: $(M+H)^+=724$.

EXAMPLE 88

4-[(5-(N-(2-dimethylamino-ethyl)-benzenesulphonylamino)-1-ethoxycarbonylmethyl-1H-benzimidazol-2-yl)-methyl]-benzamidine-dihydrochloride Prepared analogously to Example 1e from 4-[(5-(N-(2-dimethylamino-ethyl)-benzenesulphonylamino)-1-ethoxycarbonylmethyl-1H-benzimidazol-2-yl)-methyl]-benzonitrile and hydrochloric acid/ammonium carbonate in ethanol.

Yield: 84% of theory, $C_{29}H_{34}N_6O_4S \times 2$ HCl (562.71/635.63); Mass spectrum: $(M+H)^+=563$.

EXAMPLE 89

4-[(5-(N-(2-dimethylamino-ethyl)-quinolin-8-yl-sulphonylamino-1-ethoxycarbonylmethyl-1H-benzimidazol-2-yl)-methyl]-benzamidine-dihydrochloride Prepared analogously to Example 1e from 4-[(5-(N-(2-dimethylamino-ethyl)-quinolin-8-yl-sulphonylamino)-1-ethoxycarbonylmethyl-1H-benzimidazol-2-yl)-methyl]-benzonitrile and hydrochloric acid/ammonium carbonate in ethanol.

Yield: 86% of theory, $C_{32}H_{35}N_7O_4S \times 2$ HCl (613.75/686.68); Mass spectrum: $(M+H)^+=614$.

EXAMPLE 90

4-[(5-(N-aminocarbonylmethyl-benzenesulphonylamino)-1-(2-dimethylamino-ethyl)-1H-benzimidazol-2-yl)-methyl]-benzamidine-dihydrochloride Prepared analogously to Example 1e from 4-[(5-(N-aminocarbonylmethyl-benzenesulphonylamino)-1-(2-dimethylamino-ethyl)-1H-benzimidazol-2-yl)-methyl]-benzonitrile and hydrochloric acid/ammonium carbonate in ethanol.

Yield: 83% of theory, $C_{27}H_{31}N_7O_3S \times 2$ HCl (533.7/606.56); Mass spectrum: $(M+H)^+=534$.

EXAMPLE 91

4-[(5-(N-(2-dimethylamino-ethyl)-benzenesulphonylamino-1-(2-morpholino-ethyl)-1H-benzimidazol-2-yl)-methyl]-benzamidine-trihydrochloride Prepared analogously to Example 1e from 4-[(5-(N-(2-dimethylamino-ethyl)-benzenesulphonylamino)-1-(2-morpholino-ethyl)-1H-benzimidazol-2-yl)-methyl]-benzonitrile and hydrochloric acid/ammonium carbonate in ethanol.

Yield: 76% of theory, $C_{31}H_{39}N_7O_3S \times 3$ HCl (589.8/699.18); Mass spectrum: $(M+H)^+=590$; $(M+2H)^{++}=295.8$.

EXAMPLE 92

4-[(5-(N-(2-dimethylamino-ethyl)-benzenesulphonylamino)-1-(3-ethoxycarbonyl-n-propyl)-1H-benzimidazol-2-yl)-methyl]-benzamidine-dihydrochloride Prepared analogously to Example 1e from 4-[(5-(N-(2-dimethylamino-ethyl)-benzenesulphonylamino)-1-(3-ethoxycarbonyl-n-propyl)-1H-benzimidazol-2-yl)-methyl]-benzonitrile and hydrochloric acid/ammonium carbonate in ethanol.

Yield: 70% of theory, $C_{31}H_{38}N_6O_4S \times 2$ HCl (590.7/663.62); Mass spectrum: $(M+H)^+=591$.

EXAMPLE 93

4-[(5-(N-(2-dimethylamino-ethyl)-benzenesulphonylamino)-1-benzyl-1H-benzimidazol-2-yl)-methyl]-benzamidine-dihydrochloride Prepared analogously to Example 1e from 4-[(5-(N-(2-dimethylamino-ethyl)-benzenesulphonylamino)-1-benzyl-1H-benzimidazol-2-yl)-methyl]-benzonitrile and hydrochloric acid/ammonium carbonate in ethanol.

Yield: 55% of theory, $C_{32}H_{34}N_6O_2S \times 2$ HCl (566.7/639.62); Mass spectrum: $(M+H)^+=567$.

EXAMPLE 94

4-[(5-(N-[(1-carboxy-2-aminocarbonyl-ethylamino)-carbonylmethyl]-quinolin-8-yl-sulphonylamino)-1-methyl-1H-benzimidazol-2-yl)-methyl]-benzamidine-hydrochloride Prepared analogously to Example 13 from 4-[(5-(N-[(1-ethoxycarbonyl-2-aminocarbonyl-ethylamino)-carbonylmethyl]-quinolin-8-yl-sulphonylamino)-1-methyl-1H-benzimidazol-2-yl)-methyl]-benzamidine-hydrochloride and sodium hydroxide in ethanol/water.

Yield: 55% of theory, $C_{31}H_{30}N_8O_6S \times HCl$ (642.70/679.16); Mass spectrum: $(M+H)^+=643$.

EXAMPLE 95

4-[(5-(N-(2-dimethylamino-ethyl)-n-butanesulphonylamino)-1-ethoxycarbonylmethyl-1H-benzimidazol-2-yl)-methyl]-benzamidine-dihydrochloride Prepared analogously to Example 1e from 4-[(5-(N-(2-dimethylamino-ethyl)-n-butanesulphonylamino)-1-ethoxycarbonylmethyl-1H-benzimidazol-2-yl)-methyl]-benzonitrile and hydrochloric acid/ammonium carbonate in ethanol.

Yield: 77% of theory, $C_{27}H_{38}N_6O_4S \times 2$ HCl (542.72/615.64); Mass spectrum: $(M+H)^+=543$.

EXAMPLE 96

4-[(5-(N-methoxycarbonylmethyl-quinolin-8-yl-sulphonylamino)-1-methyl-1H-benzimidazol-2-yl)-methyl]-benzamidine-hydrochloride Prepared analogously to Example 1e from 4-[(5-(N-methoxycarbonylmethyl-quinolin-8-yl-sulphonylamino)-1-methyl-1H-benzimidazol-2-yl)-methyl]-benzonitrile and hydrochloric acid/ammonium carbonate in methanol.

Yield: 67% of theory, $C_{28}H_{26}N_6O_4S \times HCl$ (542.63/579.09); Mass spectrum: $(M+H)^+=543$; $(M+2H)^{++}272$; $(M+H+Na)^{2+}=283$.

EXAMPLE 97

4-[(5-(N-methoxycarbonylmethyl-quinolin-8-yl-sulphonylamino)-1-methyl-1H-benzimidazol-2-yl)-methyl]-N'-methoxycarbonyl-benzamidine 0.7 g (1.2 mmol) of 4-[(5-(N-methoxycarbonylmethyl-quinolin-8-yl-sulphonylamino)-1-methyl-1H-benzimidazol- 2-yl)-methyl]-benzamidine-hydrochloride and 0.66 g (4.8 mmol) of potassium carbonate are dissolved in 5 ml water and 20 ml acetone and after the addition of 0.12 9 (1.3 mmol) of methylchloroformate the mixture is stirred for 30 minutes at ambient temperature. The solvent is evaporated off, the residue chromatographed on silica gel and eluted with methylene chloride/methanol 40:1. The desired fractions are concentrated by evaporation, the residue is triturated with ether and suction filtered.

Yield: 0.26 g (36% of theory), $C_{30}H_{28}N_6O_6S$ (600.66); Mass spectrum: $(M+H)^+=601$; $(M+Na)^+=623$.

EXAMPLE 98

4-[(5-(N-(2-dimethylamino-ethyl)-quinolin-8-yl-sulphonylamino)-1-carboxymethyl-1H-benzimidazol-2-yl)-methyl]-benzamidine-hydrochloride Prepared analogously to Example 13 from 4-[(5-(N-(2-dimethylamino-ethyl)-quinolin-8-yl-sulphoamino)-1-ethoxycarbonylmethyl-1H-benzimidazol-2-yl)-methyl]-benzamidine-hydrochloride and soium hydroxide in ethanol/water.

Yield: 60% of theory, $C_{30}H_{31}N_7O_4S\times HCl$ (585.67/622.13); Mass spectrum: $(M+H)^+=586$.

EXAMPLE 99

4-[(5-(N-(2-dimethylamino-ethyl)-benzenesulphonylamino)-1-(ethoxycarbonylmethylaminocarbonylmethyl)-1H-benzimidazol-2-yl]-methyl-benzamidine-dihydrochloride Prepared analogously to Example 1e from 4-[(5-(N-(2-dimethylamino-ethyl)-benzenesulphonylamino-1-(ethoxycarbonylmethylaminocarbonylmethyl)-1H-benzimidazol-2-yl)-methyl]-benzonitrile and hydrochloric acid/ammonium carbonate in ethanol.

Yield: 85% of theory, $C_{31}H_{37}N_7O_5S\times 2$ HCl (619.76/692.68); Mass spectrum: $(M+H)^+=620$; $(M+2H)^{++}=310.8$.

EXAMPLE 100

4-[(5-(N-(3-dimethylamino-n-propyl)-benzenesulphonylamino)-1-benzyl-1H-benzimidazol-2-yl)-methyl]-benzamidine-dihydrochloride Prepared analogously to Example 1e from 4-[(5-(N-(3-dimethylamino-n-propyl)-benzenesulphonylamino)-1-benzyl-1H-benzimidazol-2-yl)-methyl]-benzonitrile and hydrochloric acid/ammonium carbonate in ethanol.

Yield: 83% of theory, $C_{33}H_{36}N_6O_2S\times 2$ HCl (580.8/653.7); Mass spectrum: $(M+H)^+=581$; $(M+2H)^{++}=291$.

EXAMPLE 101

4-[(5-(N-(2-dimethylamino-ethyl)-benzenesulphonylamino)-1-(carboxymethylaminocarbonylmethyl)-1H-benzimidazol-2-yl)-methyl]-benzamidine-dihydrochloride Prepared analogously to Example 13 from 4-[(5-(N-(2-dimethylamino-ethyl)-benzenesulphonylamino)-1-(ethoxycarbonylmethylaminocarbonylmethyl)-1H-benzimidazol-2-yl)-methyl]-benzamidine-dihydrochloride and sodium hydroxide in ethanol/water.

Yield: 94% of theory, $C_{29}H_{33}N_7O_5S\times 2$ HCl (591.71/664.64); Mass spectrum: $(M+H)^+=592$.

EXAMPLE 102

4-[(5-(N-(2-methyl-propyloxycarbonylmethyl)-quinolin-8-yl-sulphonylamino)-1-methyl-1H-benzimidazol-2-yl)-methyl]-N'-methoxycarbonyl-benzamidine Prepared analogously to Example 97 from 4-[(5-(N-(2-methylpropyloxycarbonylmethyl)-quinolin-8-yl-sulphonylamino)-1-methyl-1H-benzimidazol-2-yl)-methyl]-benzamidine-hydrochloride and methyl chloroformate in acetone/water.

Yield: 25% of theory, $C_{33}H_{34}N_6O_6S$ (642.74); Mass spectrum: $(M+H)^+=643$; $(M+Na)^+=665$.

EXAMPLE 103

4-[(5-(N-ethoxycarbonylmethyl-isoquinolin-5-yl-sulphonylamino)-1-methyl-1H-benzimidazol-2-yl)-methyl]-benzamidine-hydrochloride Prepared analogously to Example 1e from 4-[(5-(N-ethoxycarbonylmethyl-isoquinolin-5-yl-sulphonylamino)-1-methyl-1H-benzimidazol-2-yl)-methyl]-benzonitrile and hydrochloric acid/ammonium carbonate in ethanol.

Yield: 98% of theory, $C_{29}H_{28}N_6O_4S\times HCl$ (556.65/593.11); Mass spectrum: $(M+H)^+=557$.

EXAMPLE 104

4-[(5-(isoquinolin-5-yl-sulphonylamino)-1-methyl-1H-benzimidazol-2-yl)-methyl]-benzamidine-hydrochloride Prepared analogously to Example 1e from 4-[(5-(isoquinolin-5-yl-sulphonylamino)-1-methyl-1H-benzimidazol-2-yl)-methyl]-benzonitrile and hydrochloric acid/ammonium carbonate in ethanol.

Yield: 48% of theory, $C_{25}H_{22}N_6O_2S\times HCl$ (470.55/507.02); Mass spectrum: $(M+H)^+=471$.

EXAMPLE 105

4-[(5-(N-(2-pyrrolidino-ethyl)-benzenesulphonylamino-1-benzyl-1H-benzimidazol-2-yl)-methyl]-benzamidine-dihydrochloride Prepared analogously to Example 1e from 4-[(5-(N-(2-pyrrolidino-ethyl)-benzenesulphonylamino)-1-benzyl-1H-benzimidazolyl)-methyl]-benzonitrile and hydrochloric acid/ammonium carbonate in ethanol.

Yield: 53% of theory, $C_{34}H_{36}N_6O_2S\times 2$ HCl (592.8/665.7); Mass spectrum: $(M+H)^+=593$; $(M+2H)^{++}=297$.

EXAMPLE 106

4-[(5-(N-(2-pyrrolidino-ethyl)-benzenesulphonylamino-1-(3-ethoxycarbonyl-n-propyl)-1H-benzimidazol-2-yl)-methyl]-benzamidine-dihydrochloride Prepared analogously to Example 1e from 4-[(5-(N-(2-pyrrolidino-ethyl)-benzenesulphonylamino)-1-(3-ethoxycarbonyl-n-propyl)-1H-benzonitrile and hydrochloric acid/ammonium carbonate in ethanol.

Yield: 33% of theory, $C_{33}H_{40}N_6O_4S\times 2$ HCl (616.8/689.7); Mass spectrum: $(M+H)^+=617$; $(M+2H)^{++}=309$.

EXAMPLE 107

4-[(5-(N-(3-piperidino-n-propyl)-
benzenesulphonylamino)-1-benzyl-1H-
benzimidazol-2-yl)-methyl]-benzamidine-
dihydrochloride Prepared analogously to Example 1e from 4-[(5-(N-(3-piperidino-n-propyl)-benzenesulphonylamino)-1-benzyl-1H-benzimidazol-2-yl)-methyl]-benzonitrile and hydrochloric acid/ammonium carbonate in ethanol.

Yield: 56% of theory, $C_{36}H_{40}N_6O_2S\times 2$ HCl (620.8/693.7); Mass spectrum: $(M+H)^+=621$.

EXAMPLE 108

4-[(5-benzenesulphonylamino-1-(2-ethoxycarbonyl-
ethyl)-1H-benzimidazol-2-yl)-methyl]-benzamidine-
hydrochloride Prepared analogously to Example 1e from 4-[(5-benzenesulphonylamino-1-(2-ethoxycarbonyl-ethyl)-1H-benzimidazol-2-yl)-methyl]-benzonitrile and hydrochloric acid/ammonium carbonate in ethanol.

Yield: 67% of theory, $C_{26}H_{27}N_5O_4S\times HCl$ (505.60/542.06); Mass spectrum: $(M+H)^+=506$.

EXAMPLE 109

4-[(5-(N-carboxymethyl-isoquinolin-5-yl-
sulphonylamino)-1-methyl-1H-benzimidazol-2-yl)-
methyl]-benzamidine-hydrochloride Prepared analogously to Example 13 from 4-[(5-(N-ethoxycarbonylmethyl-isoquinolin-5-yl-sulphonylamino)-1-methyl-1H-benzimidazol-2-yl)-methyl]-benzamidine-hydrochloride and sodium hydroxide in ethanol/water.

Yield: 90% of theory, $C_{27}H_{24}N_6O_4S\times HCl$ (528.60/565.06); Mass spectrum: $(M+H)^+=529$.

EXAMPLE 110

4-[(5-(N-(3-dimethylamino-n-propyl)-
benzenesulphonylamino)-1-(3-ethoxycarbonyl-n-
propyl)-1H-benzimidazol-2-yl)-methyl]-
benzamidine-dihydrochloride Prepared analogously to Example 1e from 4-[(5-(N-(3-dimethylamino-n-propyl)-benzenesulphonylamino)-1-(3-ethoxycarbonyl-n-propyl)-1H-benzimidazol-2-yl)-methyl]-benzonitrile and hydrochloric acid/ammonium carbonate in ethanol.

Yield: 78% of theory, $C_{32}H_{40}N_6O_4S\times 2$ HCl (604.8/677.7); Mass spectrum: $(M+H)^+=605$.

EXAMPLE 111

4-[(5-(N-(3-piperidino-n-propyl)-
benzenesulphonylamino)-1-(3-ethoxycarbonyl-n-
propyl)-1H-benzimidazol-2-yl)-methyl]-
benzamidine-dihydrochloride Prepared analogously to Example 1e from 4-[(5-(N-(3-piperidino-n-propyl)-benzenesulphonylamino)-1-(3-ethoxycarbonyl-n-propyl)-1H-benzimidazol-2-yl)-methyl]-benzonitrile and hydrochloric acid/ammonium carbonate in ethanol.

Yield: 72% of theory, $C_{35}H_{44}N_6O_4S\times 2$ HCl (644.8/717.7); Mass spectrum: $(M+H)^+=645$.

EXAMPLE 112

4-[(5-(N-(3-dimethylamino-n-propyl)-
benzenesulphonylamino)-1-(3-carboxy-n-propyl)-
1H-benzimidazol-2-yl)-methyl]-benzamidine-
dihydrochloride Prepared analogously to Example 13 from 4-[(5-(N-(3-dimethylamino-n-propyl)-benzenesulphonylamino)-1-(3-ethoxycarbonyl-n-propyl)-1H-benzimidazol-2-yl)-methyl]-benzamidine-dihydrochloride and sodium hydroxide in ethanol/water.

Yield: 79% of theory, $C_{30}H_{36}N_6O_4S\times 2$ HCl (576.7/649.6); Mass spectrum: $(M+H)^+=577$.

EXAMPLE 113

4-[(5-(N-(3-piperidino-n-propyl)-
benzenesulphonylamino)-1-(3-carboxy-propyl)-1H-
benzimidazol-2-yl)-methyl]-benzamidine-
dihydrochloride Prepared analogously to Example 13 from 4-[(5-(N-(3-piperidino-n-propyl)-benzenesulphonylamino)-1-(3-ethoxycarbonyl-propyl)-1H-benzimidazol-2-yl)-methyl]-benzamidine-dihydrochloride and sodium hydroxide in ethanol/water.

Yield: 64% of theory, $C_{33}H_{40}N_6O_4S\times 2$ HCl (616.8/689.7); Mass spectrum: $(M+H)^+=617$.

EXAMPLE 114

4-[(5-(N-(2-dimethylamino-ethyl)-
benzenesulphonylamino)-1-(4-methoxycarbonyl-
benzyl)-1H-benzimidazol-2-yl)-methyl]-
benzamidine-dihydrochloride Prepared analogously to Example 1e from 4-[(5-(N-(2-dimethylamino-ethyl-benzenesulphonylamino)-1-(4-methoxycarbonyl-benzyl)-1H-benzimidazol-2-yl)-methyl]-benzonitrile and hydrochloric acid/ammonium carbonate in ethanol.

Yield: 78% of theory, $C_{34}H_{36}N_6O_4S\times 2$ HCl (624.8/697.7); Mass spectrum: $(M+H)^+=625$.

EXAMPLE 115

4-[(5-(N-(2-dimethylamino-ethyl)-
benzenesulphonylamino)-1-(2-ethoxycarbonyl-ethyl)-
1H-benzimidazol-2-yl)-methyl]-benzamidine-
dihydrochloride Prepared analogously to Example 1e from 4-[(5-(N-(2-dimethylamino-ethyl)-benzenesulphonylamino)-1-(2-ethoxycarbonylethyl)-1H-benzimidazol-2-yl)-methyl]-benzonitrile and hydrochloric acid/ammonium carbonate in ethanol.

Yield: 84% of theory, $C_{30}H_{36}N_6O_4S\times 2$ HCl (576.73/651.65); Mass spectrum: $(M+H)^+=577$.

EXAMPLE 116

4-[(5-(N-(3-dimethylamino-n-propyl)-
benzenesulphonylamino)-1-(2-ethoxycarbonyl-
ethyl)-1H-benzimidazol-2-yl)-methyl]-benzamidine-
dihydrochloride Prepared analogously to Example 1e from 4-[(5-(N-(3-dimethylamino-n-propyl)-benzenesulphonylamino)-1-(2-ethoxycarbonylethyl-1H-benzimidazol-2-yl)-methyl]-benzonitrile and hydrochloric acid/ammonium carbonate in ethanol.

Yield: 81% of theory, $C_{31}H_{38}N_6O_4S \times 2$ HCl (590.75/663.67); Mass spectrum: $(M+H)^+=591$; $(M+2H)^{++}=296$.

EXAMPLE 117

4-[(5-(N-(2-dimethylamino-ethyl)-benzenesulphonylamino)-1-(2-carboxy-ethyl)-1H-benzimidazol-2-yl)-methyl]-benzamidine-dihydrochloride Prepared analogously to Example 13 from 4-[(5-(N-(2-dimethylamino-ethyl)-benzenesulphonylamino)-1-(2-ethoxycarbonylethyl)-1H-benzimidazol-2-yl)-methyl]-benzamidine-dihydrochloride and sodium hydroxide in ethanol/water.

Yield: 92% of theory, $C_{28}H_{32}N_6O_4S \times 2$ HCl (548.67/621.59); Mass spectrum: $(M+H)^+=549$.

EXAMPLE 118

4-[(5-(N-(3-dimethylamino-n-propyl)-benzenesulphonylamino)-1-(2-carboxy-ethyl)-1H-benzimidazol-2-yl)-methyl]-benzamidine-dihydrochloride Prepared analogously to Example 13 from 4-[(5-(N-(3-dimethylamino-n-propyl)-benzenesulphonylamino)-1-(2-ethoxycarbonylethyl)-1H-benzimidazol-2-yl)-methyl]-benzamidine-dihydrochloride and sodium hydroxide in ethanol/water.

Yield: 42% of theory, $C_{29}H_{34}N_6O_4S \times 2$ HCl (548.67/621.59); Mass spectrum: $(M+H)^+=549$.

EXAMPLE 119

4-[(5-(N-phenyl-N-(3-carboxy-n-propyl)-aminocarbonyl)-1-methyl-1H-benzimidazol-2-yl)-methyl]-benzamidine-hydrochloride Prepared analogously to Example 13 from 4-[(5-(N-phenyl-N-(3-ethoxycarbonyl-n-propyl)-aminocarbonyl)-1-methyl-1H-benzimidazol-2-yl)-methyl]-benzamidine-hydrochloride and sodium hydroxide in ethanol/water.

Yield: 78% of theory, $C_{27}H_{27}N_5O_3 \times HCl$ (469.55/506.02); Mass spectrum: $(M+H)^+=470$.

EXAMPLE 120

4-[(5-(N-(3-dimethylamino-n-propyl)-methanesulphonylamino-1-(2-ethoxycarbonyl-ethyl)-1H-benzimidazol-2-yl)-methyl]-benzamidine-dihydrochloride Prepared analogously to Example 1e from 4-[(5-(N-(3-dimethylamino-n-propyl)-methanesulphonylamino)-1-(2-ethoxycarbonylethyl-1H-benzimidazol-2-yl)-methyl]-benzonitrile and hydrochloric acid/ammonium carbonate in ethanol.

Yield: 90% of theory, $C_{26}H_{36}N_6O_4S \times 2$ HCl (528.68/601.61); Mass spectrum: $(M+H)^+=529$.

EXAMPLE 121

4-[(5-(N-(2-dimethylamino-ethyl)-methanesulphonylamino)-1-(2-ethoxycarbonyl-ethyl)-1H-benzimidazol-2-yl)-methyl]-benzamidine-dihydrochloride Prepared analogously to Example 1e from 4-[(5-(N-(2-dimethylamino-ethyl)-methanesulphonylamino)-1-(2-ethoxycarbonylethyl)-1H-benzimidazol-2-yl)-methyl]-benzonitrile and hydrochloric acid/ammonium carbonate in ethanol.

Yield: 94% of theory, $C_{25}H_{34}N_6O_4S \times 2$ HCl (514.65/587.57); Mass spectrum: $(M+H)^+=515$.

EXAMPLE 122

4-[(5-(2-dimethylamino-ethylaminosulphonyl)-1-benzyl-1H-benzimidazol-2-yl)-methyl]-benzamidine-dihydrochloride Prepared analogously to Example 1e from 4-[(5-(2-dimethylamino-ethylaminosulphonyl)-1-benzyl-1H-benzimidazol-2-yl)-methyl]-benzonitrile and hydrochloric acid/ammonium carbonate in ethanol.

Yield: 84% of theory, $C_{26}H_{30}N_6O_2S \times 2$ HCl (490.6/563.6); Mass spectrum: $(M+H)^+=491$.

EXAMPLE 123

4-[(5-(N-methyloxycarbonylmethyl-quinolin-8-yl-sulphonylamino)-methyl-1H-benzimidazol-2-yl)-metehyl]-N'-isobutyloxycarbonyl-benzamidine Prepared analogously to Example 97 from 4-[(5-(N-methyloxycarbonylmethyl-quinolin-8-yl-sulphonylamino)-1-methyl-1H-benzimidazol-2-yl)-methyl]-benzamidine-hydrochloride and isobutyl chloroformate in acetone/water.

Yield: 41% of theory, $C_{33}H_{34}N_6O_6S$ (642.75); Mass spectrum: $(M+H)^+=643$; $(M+Na)^+=665$.

EXAMPLE 124

4-[(5-(N-(3-dimethylamino-n-propyl)-methanesulphonylamino)-1-(2-carboxy-ethyl)-1H-benzimidazol-2-yl)-methyl]-benzamidine-dihydrochloride Prepared analogously to Example 13 from 4-[(5-(N-(3-dimethylamino-n-propyl)-methanesulphonylamino)-1-(2-ethoxycarbonylethyl)-1H-benzimidazol-2-yl)-methyl]-benzamidine-dihydrochloride and sodium hydroxide in ethanol/water.

Yield: 63% of theory, $C_{24}H_{32}N_6O_4S \times 2$ HCl (500.62/573.54); Mass spectrum: $(M+H)^+=501$.

EXAMPLE 125

4-[(5-(N-(2-dimethylamino-ethyl)-methanesulphonylamino)-1-(2-carboxy-ethyl))-1H-benzimidazol-2-yl)-methyl]-benzamidine-dihydrochloride Prepared analogously to Example 13 from 4-[(5-(N-(2-dimethylamino-ethyl)-methanesulphonylamino)-1-(2-ethoxycarbonylethyl)-1H-benzimidazol-2-yl)-methyl]-benzamidine-dihydrochloride and sodium hydroxide in ethanol/water.

Yield: 72% of theory, $C_{23}H_{30}N_6O_4S \times 2$ HCl (486.6/559.52); Mass spectrum: $(M+H)^+=487$.

EXAMPLE 126

4-[(5-(N-ethyloxycarbonylmethyl-quinolin-8-yl-sulphonylamino)-1-methyl-1H-benzimidazol-2-yl)-methyl]-N'-cyclohexyloxycarbonyl-benzamidine Prepared analogously to Example 97 from 4-[(5-(N-ethyloxycarbonylmethyl-quinolin-8-yl-sulphonylamino-1- methyl-1H-benzimidazol-2-yl)-methyl]-benzamidine-hydrochloride and cyclohexyl chloroformate in acetone/water.

Yield: 61% of theory, $C_{36}H_{38}N_6O_6S$ (682.81); Mass spectrum: $(M+H)^+=683$; $(M+Na)^+=705$.

EXAMPLE 127

4-[(5-(N-ethyloxycarbonylmethyl-quinolin-8-yl-sulphonylamino)-1-methyl-1H-benzimidazol-2-yl)-methyl]-N'-benzyloxycarbonylbenzamidine Prepared analogously to Example 97 from 4-[(5-(N-ethyloxycarbonylmethyl-quinolin-8-yl-sulphonylamino)-1-methyl-1H-benzimidazol-2-yl)-methyl]-benzamidine-hydrochloride and benzyl chloroformate in acetone/water.

Yield: 65% of theory, $C_{37}H_{34}N_6O_6S$ (690.79); Mass spectrum: $(M+H)^+=691$; $(M+Na)^+=713$.

EXAMPLE 128

4-[(5-(4-dimethylamino-piperidino)-1H-benzimidazol-2-yl)-methyl]-benzamidine-dihydrochloride Prepared analogously to Example 1e from 4-[(5-(4-dimethylamino-piperidino)-1H-benzimidazol-2-yl)-methyl]-benzonitrile and hydrochloric acid/ammonium carbonate in ethanol.

Yield: 100% of theory, $C_{22}H_{28}N_6 \times 2$ HCl (376.51/449.42); Mass spectrum: $(M+H)^+377$.

EXAMPLE 129

4-[(5-(4-dimethylamino-piperidino)-1-(2-ethoxycarbonyl-ethyl)-1H-benzimidazol-2-yl)-methyl]-benzamidine-dihydrochloride Prepared analogously to Example 1e from 4-[(5-(4-dimethylamino-piperidino)-1-(2-ethoxycarbonyl-ethyl)-1H-benzimidazol-2-yl)-methyl]-benzonitrile and hydrochloric acid/ammonium carbonate in ethanol.

Yield: 100% of theory, $C_{27}H_{36}N_6O_2 \times 2$ HCl (476.63/549.56); Mass spectrum: $(M+H)^+=477$.

EXAMPLE 130

4-[(5-(N-(2-dimethylamino-ethyl)-methanesulphonylamino)-1-(3-ethoxycarbonylmethylaminocarbonyl-n-propyl)-1H-benzimidazol-2-yl)-methyl]-benzamidine-dihydrochloride Prepared analogously to Example 1e from 4-[(5-(N-(2-dimethylamino-ethyl)-methanesulphonylamino)-1-(3-ethoxycarbonylmethylaminocarbonyl-n-propyl)-1H-benzimidazol-2-yl)-methyl]-benzonitrile and hydrochloric acid/ammonium carbonate in ethanol.

Yield: 98% of theory, $C_{28}H_{39}N_7O_5S \times 2$ HCl (585.74/658.67); Mass spectrum: $(M+H)^+=586$.

EXAMPLE 131

4-[(5-(N-(2-dimethylamino-ethyl)-methanesulphonylamino)-1-(3-ethoxycarbonyl-n-propyl)-1H-benzimidazol-2-yl)-methyl]-benzamidine-dihydrochloride Prepared analogously to Example 1e from 4-[(5-(N-(2-dimethylamino-ethyl)-methanesulphonylamino)-1-(3-ethoxycarbonyl-n-propyl)-1H-benzonitrile and hydrochloric acid/ammonium carbonate in ethanol.

Yield: 94% of theory, $C_{26}H_{36}N_6O_4S \times 2$ HCl (528.69/601.62); Mass spectrum: $(M+H)^+=529$.

EXAMPLE 132

4-[(5-(N-ethyloxycarbonylmethyl-quinolin-8-yl-sulphonylamino)-1-methyl-1H-benzimidazol-2-yl)-methyl]-N'-ethyloxycarbonyl-benzamidine Prepared analogously to Example 97 from 4-[(5-(N-ethyloxycarbonylmethyl-quinolin-8-yl-sulphonylamino)-1-methyl-1H-benzimidazol-2-yl)-methyl]-benzamidine-hydrochloride and ethyl chloroformate in acetone/water.

Yield: 63% of theory, $C_{32}H_{32}N_6O_6S$ (628.71); Mass spectrum: $(M+H)^+=629$.

EXAMPLE 133

4-[(5-(N-methyl-piperidinocarbonylamino)-1-(3-ethoxycarbonyl-n-propyl)-1H-benzimidazol-2-yl)-methyl]-benzamidine-hydrochloride Prepared analogously to Example 1e from 4-[(5-(N-methyl-piperidinocarbonylamino)-1-(3-ethoxycarbonyl-n-propyl)-1H-benzimidazol-2-yl)-methyl]-benzonitrile and hydrochloric acid/ammonium carbonate in ethanol.

Yield: 21% of theory, $C_{28}H_{36}N_6O_3 \times HCl$ (504.64/541.11); Mass spectrum: $(M+H)^+=505$; $(M+2H)^{++}=253$.

EXAMPLE 134

4-[(5-(N-carboxymethyl-quinolin-8-yl-sulphonylamino)-1-methyl-1H-benzimidazol-2-yl)-methyl]-N'-ethyloxycarbonyl-benzamidine Prepared analogously to Example 13 from 4-[(5-(N-ethoxycarbonylmethyl-quinolin-8-yl-sulphonylamino)-1-methyl-1H-benzimidazol-2-yl)-methyl]-N'-ethyloxycarbonyl-benzamidine-hydrochloride and sodium hydroxide in ethanol/water.

Yield: 70% of theory, $C_{30}H_{28}N_6O_6S$ (600.66); Mass spectrum: $(M+H)^+=601$; $(M-H)^-=599$; $(M+Na)^+=623$.

EXAMPLE 135

4-[(5-(N-methyl-piperidinocarbonylamino)-1-(3-carboxy-n-propyl)-1H-benzimidazol-2-yl)-methyl]-benzamidine-hydrochloride Prepared analogously to Example 13 from 4-[(5-(N-methyl-piperidinocarbonylamino)-1-(3-ethoxycarbonyl-n-propyl)-1H-benzimidazol-2-yl)-methyl]-benzamidine-hydrochloride and sodium hydroxide in ethanol/water.

Yield: 63% of theory, $C_{26}H_{32}N_6O_3 \times HCl$ (476.59/513.05); Mass spectrum: $(M+H)^+=477$.

EXAMPLE 136

4-[(5-(N-(2-diethylamino-ethyl)-benzenesulphonylamino)-1-(ethoxycarbonylmethylaminocarbonylmethyl)-1H-benzimidazol-2-yl)-methyl]-benzamidine-dihydrochloride Prepared analogously to Example 1e from 4-[(5-(N-(2-diethylamino-ethyl)-benzenesulphonylamino)-1-(ethoxycarbonylmethylaminocarbonylmethyl)-1H- benzimidazol-2-yl)-methyl]-benzonitrile and hydrochloric acid/ammonium carbonate in ethanol.

Yield: 76% of theory, $C_{33}H_{41}N_7O_5S \times 2$ HCl (647.81/720.74); Mass spectrum: $(M+H)^+=648$; $(M+2H)^{++}=324.8$.

EXAMPLE 137

4-[(5-(N-(2-dimethylamino-ethyl)-N-ethyl-aminosulphonyl)-1-(3-ethoxycarbonyl-n-propyl)-1H-benzimidazol-2-yl)-methyl]-benzamidine-dihydrochloride Prepared analogously to Example 1e from 4-[(5-(N-(2-dimethylamino-ethyl)-N-ethyl-aminosulphonyl)-1-(3-ethoxycarbonyl-n-propyl)-1H-benzimidazol-2-yl)-methyl]-benzonitrile and hydrochloric acid/ammonium carbonate in ethanol.

Yield: 64% of theory, $C_{27}H_{38}N_6O_4S \times 2$ HCl (542.7/615.6); Mass spectrum: $(M+H)^+=543$.

EXAMPLE 138

4-[(5-(N-(2-dimethylamino-ethyl)-aminosulphonyl)-1-(3-ethoxycarbonyl-n-propyl-1H-benzimidazol-2-yl)-methyl]-benzamidine-dihydrochloride Prepared analogously to Example 1e from 4-[(5-(N-(2-dimethylamino-ethyl)-aminosulphonyl)-1-(3-ethoxycarbonyl-n-propyl)-1H-benzimidazol-2-yl)-methyl]-benzonitrile and hydrochloric acid/ammonium carbonate in ethanol.

Yield: 93% of theory, $C_{25}H_{34}N_6O_4S \times 2$ HCl (514.7/587.6); Mass spectrum: $(M+H)^+=515$.

EXAMPLE 139

4-[(5-(N-(2-diethylamino-ethyl)-benzenesulphonylamino)-1-(carboxymethylaminocarbonylmethyl)-1H-benzimidazol-2-yl)-methyl]-benzamidine-dihydrochloride Prepared analogously to Example 13 from 4-[(5-(N-(2-diethylamino-ethyl)-benzenesulphonylamino)-1-(ethoxycarbonylmethylaminocarbonylmethyl)-1H-benzimidazol-2-yl)-methyl]-benzamidine-dihydrochloride and sodium hydroxide in ethanol/water.

Yield: 78% of theory, $C_{31}H_{37}N_7O_5S \times 2$ HCl (619.76/692.69); Mass spectrum: $(M+H)^+620$; $(M+2H)^{++}311$; $(M+H+Na)^{++}=322$.

EXAMPLE 140

4-[(5-(N-(2-dimethylamino-ethyl)-ethylaminosulphonyl)-1-(3-carboxy-n-propyl)-1H-benzimidazol-2-yl)-methyl]-benzamidine-dihydrochloride Prepared analogously to Example 13 from 4-[(5-(N-(2-dimethylamino-ethyl)-ethylaminosulphonyl)-1-(3-ethoxycarbonyl-n-propyl)-1H-benzimidazol-2-yl)-methyl]-benzamidine-dihydrochloride and sodium hydroxide in ethanol/water.

Yield: 86% of theory, $C_{25}H_{34}N_6O_4S \times 2$ HCl (514.7/587.6); Mass spectrum: $(M+H)^+=515$.

EXAMPLE 141

4-[(5-(N-(ethoxycarbonylmethylaminocarbonylmethyl)-phenylaminocarbonyl)-1-methyl-1H-benzimidazol-2-yl)-methyl]-benzamidine-hydrochloride Prepared analogously to Example 1 from 4-[(5-(N-(ethoxycarbonylmethylaminocarbonylmethyl)-phenylaminocarbonyl)-1-methyl-1H-benzimidazol-2-yl)-methyl]-benzonitrile and hydrochloric acid/ammonium carbonate in ethanol.

Yield: 88% of theory, $C_{28}H_{30}N_6O_4 \times HCl$ (514.6/551.05); Mass spectrum: $(M+H)^+=515$.

EXAMPLE 142

4-[(5-(N-(carboxymethylaminocarbonylmethyl)phenylaminocarbonyl)-1-methyl-1H-benzimidazol-2-yl)-methyl]-benzamidine-hydrochloride Prepared analogously to Example 13 from 4-[(5-(N-(ethoxycarbonylmethylaminocarbonylmethyl)-phenylaminocarbonyl)-1-methyl-1H-benzimidazol-2-yl)-methyl]-benzamidine-hydrochloride and sodium hydroxide in ethanol/water.

Yield: 33% of theory, $C_{27}H_{26}N_6O_4 \times HCl$ (498.55/535.13); Mass spectrum: $(M+H)^+=499$.

EXAMPLE 143

4-[(5-(2-dimethylamino-ethylaminosulphonyl)-1-(3-carboxy-n-propyl)-1H-benzimidazol-2-yl)-methyl]-benzamidine-dihydrochloride Prepared analogously to Example 13 from 4-[(5-(2-dimethylamino-ethylaminosulphonyl)-1-(3-ethoxycarbonyl-n-propyl)-1H-benzimidazol-2-yl)-methyl]-benzamidine-dihydrochloride and sodium hydroxide in ethanol/water.

Yield: 75% of theory, $C_{23}H_{30}N_6O_4S \times 2$ HCl (486.6/559.5); Mass spectrum: $(M+H)^+=487$.

EXAMPLE 144

4-[(5-(N-(1-methyl-piperidin-2-yl-methyl)-benzenesulphonylamino)-1-(ethoxycarbonylmethylaminocarbonylmethyl)-1H-benzimidazol-2-yl)-methyl]-benzamidine-dihydrochloride a. 4-[(5-benzenesulphonylamino-1-(ethoxycarbonylmethylaminocarbonylmethyl)-1H-benzimidazol-2-yl)-methyl]-benzonitrile 2.7 g (6.1 mmol) of 4-[(5-benzenesulphonylamino-1-carboxymethyl-1H-benzimidazol-2-yl)-methyl]-benzonitrile, 0.85 g (6.1 mmol) of glycine-ethyl ester-hydrochloride and 1.5 g (15 mmol) of triethylamine are dissolved in 80 ml dimethylformamide and after the addition of 2.4 g (7.5 mmol) of O-(benzotriazol-1-yl)-N,N,N',N'-tetramethyluroniumtetrafluoroborate the mixture is stirred for 16 hours at ambient temperature. The solvent is evaporated off, the residue chromatographed on silica gel and eluted with methylene chloride/ethanol 99:1 and 98:2. The desired fractions are concentrated by evaporation, the residue is triturated with ether, suction filtered and dried.

Yield: 1.9 g (59% of theory), Melting point: 166–168 C.

b. 4-[(5-(N-(1-methyl-piperidin-2-yl-methyl)-benzenesulphonylamino)-1-(ethoxycarbonylmethylaminocarbonylmethyl)-1H-benzimidazol-2-yl)-methyl]-benzonitrile Prepared analogously to Example 1b from 4-[(5-benzenesulphonyl-amino-1-(ethoxycarbonylmethylaminocarbonylmethyl)-1H-benzimidazol-2-yl)-methyl]-benzonitrile, 2-(chloromethyl)-N-methyl-piperidine and potassium carbonate in acetone.

Yield: 38% of theory, $C_{34}H_{38}N_6O_5S$ (642.79); Mass spectrum: $(M+H)^+=643$.

c. 4-[(S-(N-(1-methyl-piperidin-2-yl-methyl)-benzenesulphonylamino)-1-(ethoxycarbonylmethylaminocarbonylmethyl)-1H-benzimidazol-2-yl)-methyl]-benzamidine-dihydrochloride Prepared analogously to Example 1e from 4-[(5-(N-(1-methylpiperidin-2-yl-methyl)-benzenesulphonylamino)-1-(ethoxycarbonylmethylaminocarbonylmethyl)-1H-benzimidazol-2-yl)-methyl]-benzonitrile and hydrochloric acid/ammonium carbonate in ethanol.

Yield: 100% of theory, $C_{34}H_{41}N_7O_5S \times 2$ HCl (659.82/732.75); Mass spectrum: $(M+H)^+=660$; $(M+2H)^{++}=330.7$.

EXAMPLE 145

4-[(5-(N-(N'-ethoxycarbonylmethyl-N'-methyl-aminocarbonylmethyl)-quinolin-8-yl-sulphonylamino)-1-methyl-1H-benzimidazol-2-yl)-methyl]-benzamidine-hydrochloride Prepared analogously to Example 1e from 4-[(5-(N-(N'-ethoxycarbonylmethyl-N'-methyl-aminocarbonylmethyl)-quinolin-8-yl-sulphonylamino)-1-methyl-1H-benzimidazol-2-yl)-methyl]-benzonitrile and hydrochloric acid/ammonium carbonate in ethanol.

Yield: 52% of theory, $C_{32}H_{33}N_7O_5S \times HCl$ (627.73/664.19); Mass spectrum: $(M+H)^+=628$.

EXAMPLE 146

4-[(5-(N-methyl-piperidinocarbonylamino)-1-benzyl-1H-benzimidazol-2-yl)-methyl]-benzamidine-hydrochloride Prepared analogously to Example 1e from 4-[(5-(N-methyl-piperidinocarboamino)-1-benzyl-1H-benzimidazol-2-yl)-methyl]-benzonitrile and hydrochloric acid/ammonium carbonate in ethanol.

Yield: 57% of theory, $C_{29}H_{32}N_6 0 \times HCl$ (480.62./517.08); Mass spectrum: $(M+H)^+ 481$.

EXAMPLE 147

4-[(5-(N-(N'-carboxymethyl-N'-methyl-aminocarbonylmethyl)-quinolin-8-yl-sulphonylamino)-1-methyl-1H-benzimidazol-2-yl)-methyl]-benzamidine-hydrochloride Prepared analogously to Example 13 from 4-[(5-(N-(N'-ethoxycarbonylmethyl-N'-methyl-aminocarbonylmethyl)-quinolin-8-yl-sulphonylamino)-1-methyl-1H-benzimidazol-2-yl)-methyl]-benzamidine-hydrochloride and sodium hydroxide in ethanol/water.

Yield: 69% of theory, $C_{30}H_{29}N_7O_5S \times HCl$ (599.67/636.13); Mass spectrum: $(M+H)^+=600$.

EXAMPLE 148

4-[(5-(N-ethoxycarbonylmethylaminocarbonylmethyl-quinolin-8-yl-sulphonylamino)-1-methyl-1H-benzimidazol-2-yl)-methyl]-N'-cyclohexyloxycarbonyl-benzamidine Prepared analogously to Example 97 from 4-[(5-(N-ethoxycarbonylmethylaminocarbonylmethyl-quinolin-8-yl-sulphonylamino)-1-methyl-1H-benzimidazol-2-yl)-methyl]-benzamidine-hydrochloride and cyclohexyl chloroformate in tetrahydrofuran/water.

Yield: 48% of theory, $C_{38}H_{41}N_7O_7S$ (739.86); Mass spectrum: $(M+H)^+=740$; $(M+2H)^{++}=370.8$; $(M+H+Na)^{++}=381.6$.

EXAMPLE 149

4-[(5-(N-ethoxycarbonylmethylaminocarbonylmethyl-quinolin-8-yl-sulphonylamino)-1-methyl-1H-benzimidazol-2-yl)-methyl]-N'-benzyloxycarbonyl-benzamidine Prepared analogously to Example 97 from 4-[(5-(N-ethoxycarbonylmethylaminocarbonylmethyl-quinolin-8-yl-sulphonylamino)-1-methyl-1H-benzimidazol-2-yl)-methyl]-benzamidine-hydrochloride and benzyl chloroformate in tetrahydrofuran/water.

Yield: 38% of theory, $C_{39}H_{37}N_7O_7S$ (747.85); Mass spectrum: $(M+H)^+=748$; $(M+Na)^+=770$; $(M+H+Na)^{++}=385.2$.

EXAMPLE 150

4-[(5-(N-(1-methyl-piperidin-2-yl-methyl)-benzenesulphonylamino-1-(carboxymethylaminocarbonylmethyl)-1H-benzimidazol-2-yl)-methyl]-benzamidine-dihydrochloride Prepared analogously to Example 13 from 4-[(5-(N-(1-methylpiperidin-2-yl-methyl)-benzenesulphonylamino)-1-(ethoxycarbonylmethylaminocarbonylmethyl)-1H-benzimidazol-2-yl)-methyl]-benzamidine-dihydrochloride and sodium hydroxide in ethanol.

Yield: 83% of theory, $C_{32}H_{37}N_7O_5S \times 2$ HCl (631.77/704.7); Mass spectrum: $(M+H)^+ 632$; $(M+2H)^{++}=316.8$.

EXAMPLE 151

4-[(5-(2-dimethylamino-ethyl)-aminocarbonyl)-1-(ethoxycarbonylmethylaminocarbonylmethyl)-1H-benzimidazol-2-yl)-methyl]-benzamidine-dihydrochloride Prepared analogously to Example 1e from 4-[(5-(2-dimethylamino-ethyl)-aminocarbonyl)-1-(ethoxycarbonylmethylaminocarbonylmethyl)-1H-benzimidazol-2-yl)-methyl]-benzonitrile and hydrochloric acid/ammonium carbonate in ethanol.

Yield: 95% of theory, $C_{26}H_{33}N_7O_4 \times 2$ HCl (507.61/580.54); Mass spectrum: $(M+H)^+=508$.

EXAMPLE 152

4-[(5-(N-(2-dimethylamino-ethyl)-ethylaminosulphonyl)-1-methyl-1H-benzimidazol-2-yl)-methyl]-benzamidine-dihydrochloride Prepared analogously to Example 1e from 4-[(5-(N-(2-dimethylamino-ethyl)-ethylaminosulphonyl)-1-methyl-1H-benzimidazol-2-yl)-methyl-benzonitrile and hydrochloric acid/ammonium carbonate in ethanol.

Yield: 82% of theory, $C_{22}H_{30}N_6O_2S \times 2$ HCl (442.6/515.5); Mass spectrum: $(M+H)^+=443$.

EXAMPLE 153

4-[(5-cyclohexylcarbonylamino-1-(3-ethoxycarbonyl-n-propyl)-1H-benzimidazol-2-yl)-methyl]-benzamidine-hydrochloride a. 4-cyclohexylcarbonylamino-2-nitro-fluorobenzene 15.6 g (0.1 mol) of 4-fluoro-3-nitro-aniline and 17.9 g (0.11 mol) of cyclohexylcarboxylic acid chloride are dissolved in 250 ml tetrahydrofuran and after the addition of 12.1 g (0.12 mol) of triethylamine the mixture is stirred for 3 hours at ambient temperature. The solvent is distilled off, the residue is mixed with water and extracted with ethyl acetate. The combined organic extracts are dried over sodium sulphate and concentrated by evaporation.

Yield:17.1 g (64% of theory), $R_f$ value: 0.2 (silica gel; methylene chloride/petroleum ether 9:1).

b. tert.butyl 4-[4-(cyclohexylcarbonylamino)-2-nitro-phenylamino]butyrate

Prepared analogously to Example 7b from 4-cyclohexylcarbonylamino-2-nitro-fluorobenzene, tert.butyl aminobutyrate and potassium carbonate in dimethylsulphoxide.

Yield: 49% of theory, $R_f$ value: 0.3 (silica gel; methylene chloride/methanol 50:1).

c. tert.butyl 4-[4-(cyclohexylcarbonylamino)-2-aminophenyl aminol butyrate

Prepared analogously to Example 7c from tert.butyl 4-[4-(cyclohexylcarbonylamino)-2-nitro-phenylamino]butyrate and palladium on activated charcoal/hydrogen in methanol.

Yield: 94% of theory, $R_f$ value: 0.5 (silica gel; methylene chloride/methanol=9:1).

d. 4-[(5-cyclohexylcarbonylamino-1-(3-tert.butyloxycarbonyl-n-propyl)-1H-benzimidazol-2-yl)-methyl]-benzonitrile 0.65 g (4.0 mmol) of 4-cyanophenylacetic acid and 0.65 g (4.0 mmol) of N,N'-carbonyldiimidazole are dissolved in 50 ml tetrahydrofuran and refluxed for 30 minutes. After the addition of 1.3 g (3.5 mmol) of tert.butyl 4-[4-(cyclohexylcarbonylamino)-2-amino-phenylamino]butyrate the mixture is refluxed for a further 3 hours. The solvent is concentrated by evaporation and the residue refluxed for 1 hour with 30 ml glacial acetic acid. Then it is evaporated down in vacuo, the residue is poured onto water, made basic with ammonia and extracted with ethyl acetate. The combined organic extracts are dried and evaporated down. The residue is chromatographed on silica gel and eluted with methylene chloride/methanol 50:1. The desired fractions are combined and concentrated by evaporation.

Yield: 0.9 g (52% of theory), $R_f$ value: 0.4 (silica gel; methylene chloride/methanol=9:1).

e. 4-[(5-cyclohexylcarbonylamino-1-(3-ethoxycarbonyl-n-propyl)-1H-benzimidazol-2-yl)-methyl]-benzamidine-hydrochloride Prepared analogously to Example 1e from 4-[(5-cyclohexylcarbonylamino-1-(3-tert.butyloxycarbonyl-n-propyl)- 1H-benzimidazol-2-yl)-methyl]-benzonitrile and hydrochloric acid/ammonium carbonate in ethanol.

Yield: 95% of theory, $C_{28}H_{35}N_5O_3 \times HCl$ (489.62/526.08); Mass spectrum: $(M+H)^+=490$.

EXAMPLE 154

4-[(5-cyclohexylcarbonylamino-1-(4-ethoxycarbonyl-n-butyl)-1H-benzimidazol-2-yl)-methyl]-benzamidine-hydrochloride Prepared analogously to Example 1e from 4-[(5-cyclohexylcarbonylamino-1-(4-ethoxycarbonyl-n-butyl)-1H-benzimidazol-2-yl)-methyl]-benzonitrile and hydrochloric acid/ammonium carbonate in ethanol.

Yield: 79% of theory, $C_{29}H_{37}N_5O_3 \times HCl$ (503.64/540.11); Mass spectrum: $(M+H)^+=504$.

EXAMPLE 155

4-[(5-cyclohexylcarbonylamino-1-(3-carboxy-n-propyl)-1H-benzimidazol-2-yl)-methyl]-benzamidine-hydrochloride Prepared analogously to Example 13 from 4-[(5-cyclohexylcarbonylamino-1-(3-ethoxycarbonyl-n-propyl)-1H-benzimidazol-2-yl)-methyl]-benzamidine-hydrochloride and sodium hydroxide in ethanol/water.

Yield: 100% of theory, $C_{26}H_{31}N_5O_3 \times HCl$ (461.57/498.03); Mass spectrum: $(M+H)^+462$.

EXAMPLE 156

4-[(5-cyclohexylcarbonylamino-1-(4-carboxy-n-butyl)-1H-benzimidazol-2-yl)-methyl]-benzamidine-hydrochloride Prepared analogously to Example 13 from 4-[(5-cyclohexylcarbonylamino-1-(4-ethoxycarbonyl-n-butyl)-1H-benzimidazol-2-yl)-methyl]-benzamidine-hydrochloride and sodium hydroxide in ethanol/water.

Yield: 98% of theory, $C_{27}H_{33}N_5O_3 \times HCl$ (475.59/512.05); Mass spectrum: $(M+H)^+=476$.

EXAMPLE 157

4-((5-cyclohexylmethylaminocarbonyl-1-(3-ethoxycarbonyl-n-propyl)-1H-benzimidazol-2-yl)-methyl]-benzamidine-hydrochloride Prepared analogously to Example 1e from 4-[(5-cyclohexylmethylaminocarbonyl-1-(3-ethoxycarbonyl-n-propyl)-1H-benzimidazol-2-yl)-methyl]-benzonitrile and hydrochloric acid/ammonium carbonate in ethanol.

Yield: 67% of theory, $C_{29}H_{37}N_5O_3 \times HCl$ (503.66/540.12); Mass spectrum: $(M+H)^+=504$.

EXAMPLE 158

4-[(5-(N-cyclohexyl-methylaminocarbonyl)-1-(3-ethoxycarbonyl-n-propyl)-1H-benzimidazol-2-yl)-methyl]-benzamidine-hydrochloride Prepared analogously to Example 1e from 4-[(5-(N-cyclohexylmethylaminocarbonyl)-1-(3-ethoxycarbonyl-n-propyl)-1H-benzimidazol-2-yl)-methyl]-benzonitrile and hydrochloric acid/ammonium carbonate in ethanol.

Yield: 64% of theory, $C_{29}H_{37}N_5O_3 \times HCl$ (503.66/540.12); Mass spectrum: $(M+H)^+=504$.

EXAMPLE 159

4-[(5-(N-methyl-cyclohexylcarbonylamino)-1-(3-ethoxycarbonyl-n-propyl)-1H-benzimidazol-2-yl)-methyl]-benzamidine-hydrochloride Prepared analogously to Example 1e from 4-[(5-(N-methyl-cyclohexylcarbonylamino)-1-(3-ethoxycarbonyl-n-propyl)-1H-benzimidazol-2-yl)-methyl]-benzonitrile and hydrochloric acid/ammonium carbonate in ethanol.

Yield: 74% of theory, $C_{29}H_{37}N_5O_3 \times HCl$ (503.65/540.11); Mass spectrum: $(M+H)^+504$.

EXAMPLE 160

4-[(5-(N-methyl-cyclohexylcarbonylamino)-1-(4-ethoxycarbonyl-n-butyl)-1H-benzimidazol-2-yl)-methyl]-benzamidine-hydrochloride Prepared analogously to Example 1e from 4-[(5-(N-methyl-cyclohexylcarbonylamino)-1-(4-ethoxycarbonyl-n-butyl)-1H-benzimidazol-2-yl)-methyl]-benzonitrile and hydrochloric acid/ammonium carbonate in ethanol.

Yield: 87% of theory, $C_{30}H_{39}N_5O_3 \times HCl$ (517.68/554.15); Mass spectrum: $(M+H)^+=518$.

EXAMPLE 161

4-[(5-(N-methyl-cyclohexylcarbonylamino)-1-(3-carboxy-n-propyl)-1H-benzimidazol-2-yl)-methyl]-benzamidine-hydrochloride Prepared analogously to Example 13 from 4-[(5-(N-methyl-cyclohexylcarbonylamino)-1-(3-ethoxycarbonyl-n-propyl)-1H-benzimidazol-2-yl)-methyl]-benzamidine-hydrochloride and sodium hydroxide in ethanol/water.

Yield: 44% of theory, $C_{27}H_{33}N_5O_3 \times HCl$ (475.59/512.06); Mass spectrum: $(M+H)^+=476$.

EXAMPLE 162

4-[(5-(N-methyl-cyclohexylcarbonylamino)-1-(4-carboxy-n-butyl)-1H-benzimidazol-2-yl)-methyl]-benzamidine-hydrochloride Prepared analogously to Example 13 from 4-[(5-(N-methyl-cyclohexylcarbonylamino)-1-(4-ethoxycarbonyl-n-butyl)-1H-benzimidazol-2-yl)-methyl]-benzamidine-hydrochloride and sodium hydroxide in ethanol/water.

Yield: 47% of theory, $C_{28}H_{35}N_5O_3 \times HCl$ (489.62/526.08); Mass spectrum: $(M+H)^+=490$.

EXAMPLE 163

4-[(5-(N-(3-ethoxycarbonyl-n-propyl)-ethylaminosulphonyl)-1-methyl-1H-benzimidazol-2-yl)-methyl]-benzamidine-hydrochloride Prepared analogously to Example 1e from 4-[(5-(N-(3-ethoxycarbonyl-n-propyl)-ethylaminosulphonyl)-1-methyl-1H-benzimidazol-2-yl)-methyl]-benzonitrile and hydrochloric acid/ammonium carbonate in ethanol.

Yield: 61% of theory, $C_{24}H_{31}N_5O_4S \times HCl$ (485.6/522.1); Mass spectrum: $(M+H)^+=486$.

EXAMPLE 164

4-[(5-(N-(4-ethoxycarbonyl-n-butyl)-ethylaminosulphonyl)-1-methyl-1H-benzimidazol-2-yl)-methyl]-benzamidine-hydrochloride Prepared analogously to Example 1e from 4-[(5-(N-(4-ethoxycarbonyl-n-butyl)-ethylaminosulphonyl)-1-methyl-1H-benzimidazol-2-yl)-methyl]-benzonitrile and hydrochloric acid/ammonium carbonate in ethanol.

Yield: 63% of theory, $C_{25}H_{33}N_5O_4S \times HCl$ (499.6/536.1); Mass spectrum: $(M+H)^+=500$.

EXAMPLE 165

4-[(5-(N-(3-carboxy-n-propyl)-ethylaminosulphonyl)-1-methyl-1H-benzimidazol-2-yl)-methyl]-benzamidine-hydrochloride Prepared analogously to Example 13 from 4-[(5-(N-(3-ethoxycarbonyl-n-propyl)-ethylaminosulphonyl)-1-methyl-1H-benzimidazol-2-yl)-methyl]-benzamidine-hydrochloride and sodium hydroxide in ethanol.

Yield: 66% of theory, $C_{22}H_{27}N_5O_4S \times HCl$ (457.6/494.1); Mass spectrum: $(M+H)^+=458$.

EXAMPLE 166

4-[(5-(N-(4-carboxy-n-butyl)-ethylaminosulphonyl)-1-methyl-1H-benzimidazol-2-yl)-methyl]-benzamidine-hydrochloride Prepared analogously to Example 13 from 4-[(5-(N-(4-ethoxycarbonyl-n-butyl)-ethylaminosulphonyl)-1-methyl-1H-benzimidazol-2-yl)-methyl]-benzamidine-hydrochloride and sodium hydroxide in ethanol.

Yield: 66% of theory, $C_{23}H_{29}N_5O_4S \times HCl$ (471.6/508.1); Mass spectrum: $(M+H)^+=472$.

EXAMPLE 167

4-[(5-(N-(2-ethoxycarbonyl-ethyl)-ethylaminosulphonyl)-1-methyl-1H-benzimidazol-2-yl)-methyl]-benzamidine-hydrochloride Prepared analogously to Example 1e from 4-[(5-(N-(2-ethoxycarbonyl-ethyl)-ethylaminosulphonyl)-1-methyl-1H-benzimidazol-2-yl)-methyl]-benzonitrile and hydrochloric acid/ammonium carbonate in ethanol.

Yield: 18% of theory, $C_{23}H_{29}N_5O_4S \times HCl$ (471.6/508.1); Mass spectrum: $(M+H)^+=472$.

EXAMPLE 168

4-[(5-(N-ethoxycarbonylmethyl-quinolin-8-yl)-sulphonylamino)-1-methyl-1H-benzimidazol-2-yl)-amino]-benzamidine-hydrochloride a. 2-methylamino-5-nitro-aniline 12.5 g (0.079 mol) of 2-fluoro-5-nitroaniline and 100 ml methylamine (40% in water) are stirred for 48 hours at ambient temperature. The precipitated product is diluted with water, suction filtered, washed and dried.

Yield: 12.0 g (91% of theory), $R_f$ value: 0.5 (silica gel; ethyl acetate/petroleum ether=6:4).

b. 5-nitro-1-methyl-benzimidazol-2-one 3.4 g (0.02 mol) of 2-methylamino-5-nitro-aniline and 3.9 g (0.024 mol) of N,N'-carbonyldiimidazole are dissolved in 100 ml tetrahydrofuran and refluxed for two hours. The solvent is concentrated by evaporation, the residue is mixed with water, the product precipitated is suction filtered and dried.

Yield: 3.1 g (86% of theory), $C_8H_7N_3O_3 \times HCl$ (193.17); Mass spectrum: $M^+=193$.

c. 5-nitro-2-chloro-1-methyl-benzimidazole 2.1 g (0.01 mol) of phosphorus pentachloride are dissolved in 2.5 ml phosphorus oxychloride and after the addition of 1.9 g (0.01 mol) of 5-nitro-1-methyl-benzimidazol-2-one the mixture is stirred for two hours at 125° C. The solvent is evaporated off, the residue is poured onto ice water and neutralised with ammonia. The precipitate formed is suction filtered and dried.

Yield: 1.6 g (76% of theory), $R_f$ value: 0.66 (silica gel; ethyl acetate/petroleum ether=4:1).

d. 4-r5-nitro-1-methyl-1H-benzimidazol-2-yl]-amino-benzonitrile 1.5 g (7.1 mmol) of $^5$-nitro-2-chloro-1-methyl-benzimidazole and 2.1 g (17.5 mmol) of 4-aminobenzonitrile are melted for two hours at 150° C. The reaction mixture is cooled and diluted with ethyl acetate. The precipitate is suction filtered and dried.

Yield: 2.0 g (95% of theory), $R_f$ value: 0.6 (silica gel; ethyl acetate/ethanol/ammonia=90:10:1).

e. 4-[5-amino-1-methyl-1H-benzimidazol-2-yl]-amino-benzonitrile

Prepared analogously to Example 1c from 4-[5-nitro-1-methyl-1H-benzimidazol-2-yl]-amino-benzonitrile and palladium on activated charcoal/hydrogen in dimethylformamide.

Yield: 55% of theory, $R_f$ value: 0.5 (silica gel; ethyl acetate/ethanol/ammonia=90:10:1).

f. 4-[(5-(quinolin-8-yl-sulphonylamino)-1-methyl-1H-benzimidazol-2-yl)-amino]-benzonitrile Prepared analogously to Example 1d from 4-[5-amino-1-methyl-1H-benzimidazol-2-yl]-amino-benzonitrile and 8-quinolinesulphonic acid chloride in pyridine.

Yield: 91% of theory, $R_f$ value: 0.6 (silica gel; ethyl acetate/ethanol/ammonia=90:10:1).

g. 4-[(5-(N-ethoxycarbonylmethyl-quinolin-8-yl-sulphonylamino)-1-methyl-1H-benzimidazol-2-yl)-amino]-benzonitrile 1.0 g (2.2 mmol) of 4-[(5-(quinolin-8-yl-sulphonylamino)-1-methyl-1H-benzimidazol-2-yl)-amino]-benzonitrile and 0.8 g (2.5 mmol) of caesium carbonate are dissolved in 15 ml dimethylformamide and after the addition of 0.4 g (2.5 mmol) of ethyl bromoacetate stirred for 30 minutes at ambient temperature. The solvent is concentrated by evaporation, the residue is taken up in water and extracted with ethyl acetate. The combined organic extracts are dried and evaporated down.

Yield: 0.8 g (70% of theory), $R_f$ value: 0.7 (silica gel; ethyl acetate/ethanol/ammonia=90:10:1).

h. 4-[(5-(N-ethoxycarbonylmethyl-quinolin-8-yl-sulphonylamino)-1-methyl-1H-benzimidazol-2-yl)-amino]-benzamidine-hydrochloride Prepared analogously to Example 1e from 4-[(5-(N-ethoxycarbonylmethyl-quinolin-8-yl-sulphonylamino)-1-methyl-1H-benzimidazol-2-yl)-amino]-benzonitrile and hydrochloric acid/ammonium carbonate in ethanol.

Yield: 86% of theory, $C_{28}H_{27}N_7O_4S \times HCl$ (557.64/594.11); Mass spectrum: $(M+H)^+=558$.

EXAMPLE 169

4-[(5-(N-carboxymethyl-quinolin-8-yl-sulphonylamino)-1-methyl-1H-benzimidazol-2-yl)-amino]-benzamidine-hydrochloride Prepared analogously to Example 13 from 4-[(5-(N-ethoxycarbonylmethyl-quinolin-8-yl-sulphonylamino)-1-methyl-1H-benzimidazol-2-yl)-amino]-benzamidine-hydrochloride and sodium hydroxide in ethanol.

Yield: 78% of theory, $C_{26}H_{23}N_7O_4S \times HCl$ (529.52/565.98); Mass spectrum: $(M+H)^+=530$.

EXAMPLE 170

4-[(5-(N-carboxymethyl-quinolin-8-yl-sulphonylamino)-1-methyl-1H-benzimidazol-2-yl)-methyl]-N'-tert.butyloxycarbonyl-benzamidine Prepared analogously to Example 13 from 4-[(5-(N-ethoxycarbonylmethylquinolin-8-yl-sulphonylamino)-1-methyl-1H-benzimidazol-2-yl)-methyl]-N'-tert.butyloxycarbonyl-benzamidine and sodium hydroxide in ethanol.

Yield: 64% of theory, $C_{32}H_{32}N_6O_6S$ (628.71); Mass spectrum: (M+H)+629.

EXAMPLE 171

4-[(5-(4-methyl-piperazino)-1H-benzimidazol-2-yl)-methyl]-benzamidine-dihydrochloride Prepared analogously to Example 1e from 4-[(5-(4-methyl-piperazino)-1H-benzimidazol-2-yl)-methyl]-benzonitrile and hydrochloric acid/ammonium carbonate in ethanol.

Yield: 72% of theory, $C_{20}H_{24}N_6 \times 2\ HCl$ (348.46/421.39); Mass spectrum: $(M+H)^+=349$.

EXAMPLE 172

4-[(5-(N-(5-ethoxycarbonyl-n-pentyl)-ethylaminosulphonyl)-1-methyl-1H-benzimidazol-2-yl)-methyl]-benzamidine-hydrochloride Prepared analogously to Example 1e from 4-[(5-(N-(5-ethoxycarbonyl-n-pentyl)ethylaminosulphonyl)-1-methyl-1H-benzimidazol-2-yl)-methyl]-benzonitrile and hydrochloric acid/ammonium carbonate in ethanol.

Yield: 60% of theory, $C_{26}H_{35}N_5O_4S \times HCl$ (513.7/550.1); Mass spectrum: $(M+H)^+=514$.

EXAMPLE 173

4-[(5-pyrrolidinosulphonyl-1-methyl-1H-benzimidazol-2-yl)-methyl]-benzamidine-hydrochloride Prepared analogously to Example 1e from 4-[(5-pyrrolidinosulphonyl-1-methyl-1H-benzimidazol-2-yl)-methyl]-benzonitrile and hydrochloric acid/ammonium carbonate in ethanol.

Yield: 43% of theory, $C_{20}H_{23}N_5O_2S \times HCl$ (397.5/434.0); Mass spectrum: $(M+H)^+=398$.

EXAMPLE 174

4-[(5-(quinolin-8-yl-sulphonylamino)-1-methyl-1H-benzimidazol-2-yl)-amino]-benzamidine-hydrochloride Prepared analogously to Example 1e from 4-[(5-(quinolin-8-yl-sulphonylamino)-1-methyl-1H-benzimidazol-2-yl)-amino]-benzonitrile and hydrochloric acid/ammonium carbonate in ethanol.

Yield: 90% of theory, $C_{24}H_{21}N_7O_2S \times 2HCl$ (471.54/544.48); Mass spectrum: $(M+H)^+=472$.

EXAMPLE 175

4-[(5-(N-(3-ethoxycarbonyl-n-propyl)-phenylaminosulphonyl)-1-methyl-1H-benzimidazol-2-yl)-methyl]-benzamidine-hydrochloride Prepared analogously to Example 1e from 4-[(5-(N-(3-ethoxycarbonyl-n-propyl)-phenylaminosulphonyl)-1-methyl-1H-benzimidazol-2-yl)-methyl]-benzonitrile and hydrochloric acid/ammonium carbonate in ethanol.

Yield: 41% of theory, $C_{28}H_{31}N_5O_4S \times HCl$ (533.7/570.1); Mass spectrum: $(M+H)^+=534$.

EXAMPLE 176

4-[(5-(N-(4-ethoxycarbonyl-n-butyl)-isobutylaminosulphonyl)-1-methyl-1H-benzimidazol-2-yl)-methyl]-benzamidine-hydrochloride Prepared analogously to Example 1e from 4-[(5-(N-(4-ethoxycarbonyl-n-butyl)-isobutylaminosulphonyl)-1-methyl-1H-benzimidazol-2-yl)-methyl]-benzonitrile and hydrochloric acid/ammonium carbonate in ethanol.

Yield: 41% of theory, $C_{27}H_{37}N_5O_4S \times HCl$ (527.7/564.2); Mass spectrum: $(M+H)^+=528$.

EXAMPLE 177

4-[(5-(2-dimethylamino-ethylsulphonyl)-1-methyl-1H-benzimidazol-2-yl)-methyl]-benzamidine-dihydrochloride Prepared analogously to Example 1e from 4-[(5-(2-dimethylamino-ethylsulphonyl)-1-methyl-1H-benzimidazol-2-yl)-methyl]-benzonitrile and hydrochloric acid/ammonium carbonate in ethanol.

Yield: 78% of theory, $C_{20}H_{25}N_5O_2S \times HCl$ (399.52/472.44); Mass spectrum: $(M+H)^+=400$.

EXAMPLE 178

4-[(5-(2-ethoxycarbonyl-pyrrolidinosulphonyl)-1-methyl-1H-benzimidazol-2-yl)-methyl]-benzamidine-hydrochloride Prepared analogously to Example 1e from 4-[(5-(2-ethoxycarbonyl-pyrrolidinosulphonyl)-1-methyl-1H-benzimidazol-2-yl)-methyl]-benzonitrile and hydrochloric acid/ammonium carbonate in ethanol.

Yield: 64% of theory, $C_{23}H_{27}N_5O_4S \times HCl$ (469.6/506.0); Mass spectrum: $(M+H)^+=470$.

EXAMPLE 179

4-[(5-(4-oxo-3,4-dihydro-phthalazin-1-yl)-1-methyl-1H-benzimidazol-2-yl)-methyl]-benzamidine-hydrochloride Prepared analogously to Example 1e from 4-[(5-(4-oxo-3,4-dihydro-phthalazin-1-yl)-1-methyl-1H-benzimidazol-2-yl)-methyl]-benzonitrile and hydrochloric acid/ammonium carbonate in ethanol.

Yield: 90% of theory, $C_{24}H_{20}N_6O \times HCl$ (408.5/444.9); Mass spectrum: $(M+H)^+=409$.

EXAMPLE 180

4-[(5-(2-carboxy-pyrrolidinosulphonyl)-1-methyl-1H-benzimidazol-2-yl)-methyl]-benzamidine-hydrochloride Prepared analogously to Example 13 from 4-[(5-(2-ethoxycarbonyl-pyrrolidinosulphonyl)-1-methyl-1H-benzimidazol-2-yl)-methyl]-benzamidine-hydrochloride and sodium hydroxide in ethanol.

Yield: 85% of theory, $C_{21}H_{23}N_5O_4S \times HCl$ (441.5/477.96); Mass spectrum: $(M+H)^+=442$.

EXAMPLE 181

4-[(5-benzylaminocarbonyl-1-methyl-1H-benzimidazol-2-yl)-methyl]-benzamidine-hydrochloride Prepared analogously to Example 1e from 4-[(5-benzylaminocarbonyl-1-methyl-1H-benzimidazol-2-yl)-methyl]-benzonitrile and hydrochloric acid/ammonium carbonate in ethanol.

Yield: 72% of theory, $C_{24}H_{23}N_6O \times HCl$ (397.49/470.42); Mass spectrum: $(M+H)^+=398$.

EXAMPLE 182

4-[(5-pyrrolidinosulphonyl-1-methyl-1H-benzimidazol-2-yl)-(ethoxycarbonylmethyl)methyl]-benzamidine-hydrochloride a. Methyl 2-(4-cyanophenyl)-tert.butyl malonate 1.7 g (0.01 mol) of methyl 4-cyanophenylacetate are dissolved in 30 ml tetrahydrofuran, 0.48 g (0.01 mol) of sodium hydride (60% in oil) are added in batches thereto and stirred for 15 minutes at 60° C. Then 1.5 ml (0.01 mol) of tert.butyl bromoacetate are added dropwise at ambient temperature. The reaction mixture is refluxed for 5 hours, cooled and poured onto water and extracted with methylene chloride. The combined organic extracts are dried and evaporated down. The residue is chromatographed on silica gel and eluted with petroleum ether/ethyl acetate (4:1).

Yield: 1.5 g (52% of theory), $R_f$ value: 0.7 (silica gel; petroleum ether/ethyl acetate=7:3).

b. mono-tert.butyl 2-(4-cyanophenyl)-malonate 1.5 g (5.2 mmol) of methyl 2-(4-cyanophenyl)-tert.butyl malonate and 0.6 g (15 mmol) of sodium hydroxide are stirred in 25 ml ethanol and 5 ml water for two hours at ambient temperature. Then the mixture is acidified with hydrochloric acid and concentrated by evaporation. The residue is extracted with methylene chloride and water, the combined organic extracts are dried and evaporated down. The crude product is chromatographed on silica gel and eluted with methylene chloride+1–5% ethanol.

Yield: 950 mg (67% of theory), $R_f$ value: 0.40 (silica gel; methylene chloride/ethanol=19:1).

c. 4-[(5-pyrrolidinosulphonyl-1-methyl-1H-benzimidazol-2-yl)-(tert.butoxycarbonylmethyl)methyl]-benzonitrile Prepared analogously to Example 24f from mono-tert.butyl 2-(4-cyanophenyl)-malonate and 4-pyrrolidinosulphonyl-2-amino-N-methylaniline in N,N'-carbonyldiimidazole/tetrahydrofuran and glacial acetic acid.

Yield: 47% of theory, $R_f$ value: 0.6 (silica gel; methylene chloride/ethanol=19:1).

d. 4-[(5-pyrrolidinosulphonyl-1-methyl-1H-benzimidazol-2-yl)-(ethoxycarbonylmethyl)methyl]-benzamidine-hydrochloride Prepared analogously to Example 1e from 4-[(5-pyrrolidinosulphonyl-1-methyl-1H-benzimidazol-2-yl)-(tert.butoxycarbonylmethyl)methyl]-benzonitrile and hydrochloric acid/ammonium carbonate in ethanol.

Yield: 63% of theory, $C_{24}H_{29}N_5O_4S \times HCl$ (483.6/520.1); Mass spectrum: $(M+H)^+=484$.

EXAMPLE 183

4-[(5-(N-(2-ethoxycarbonyl-ethyl)-quinolin-8-yl-sulphonylamino)-1-methyl-1H-benzimidazol-2-yl)-methyl]-benzamidine-hydrochloride Prepared analogously to Example 1e from 4-[(5-(N-(2-ethoxycarbonyl-ethyl)-quinolin-8-yl-sulphonylamino)-1-methyl-1H-benzimidazol-2-yl)-methyl]-benzonitrile and hydrochloric acid/ammonium carbonate in ethanol.

Yield: 92% of theory, $C_{30}H_{30}N_6O_4S \times HCl$ (570.68/607.14); Mass spectrum: $(M+H)^+=571$.

EXAMPLE 184

4-[(5-(N-(2-ethoxycarbonyl-ethyl)-quinolin-8-yl-sulphonylamino)-1-methyl-1H-benzimidazol-2-yl)-methyl]-benzamidine-hydrochloride Prepared analogously to Example 13 from 4-[(5-(N-(2-ethoxycarbonyl-ethyl)-quinolin-8-yl-sulphonylamino)-1-methyl-1H-benzimidazol-2-yl)-methyl]-benzamidine-hydrochloride and sodium hydroxide in ethanol.

Yield: 67% of theory, $C_{28}H_{26}N_6O_4S \times HCl$ (542.63/585.09); Mass spectrum: $(M+H)^+=543$.

EXAMPLE 185

4-[(5-cyclohexylcarbonyl-1-methyl-1H-benzimidazol-2-yl)-methyl]-benzamidine-hydrochloride Prepared analogously to Example 1e from 4-[(5-cyclohexylcarbonyl-1-methyl-1H-benzimidazol-2-yl)-methyl]-benzonitrile and hydrochloric acid/ammonium carbonate in ethanol.

Yield: 95% of theory, $C_{23}H_{26}N_4O \times HCl$ (374.49/410.95); Mass spectrum: $(M+H)^+=375$.

EXAMPLE 186

4-[(5-(α-ethoxycarbonyl)benzylaminocarbonyl-1-methyl-1H-benzimidazol-2-yl)-methyl]-benzamidine-hydrochloride Prepared analogously to Example 1e from 4-[(5-(α-ethoxycarbonyl)benzylaminocarbonyl-1-methyl-1H- benzimidazol-2-yl)-methyl]-benzonitrile and hydrochloric acid/ammonium carbonate in ethanol.

Yield: 69% of theory, $C_{27}H_{27}N_5O_3 \times HCl$ (469.55/506.01); Mass spectrum: $(M+H)^+=470$.

EXAMPLE 187

4-[(5-(α-carboxy)benzylaminocarbonyl-1-methyl-1H-benzimidazol-2-yl)-methyl]-benzamidine-hydrochloride Prepared analogously to Example 13 from 4-[(5-(α-ethoxycarbonyl)benzylaminocarbonyl-1-methyl-1H-benzimidazol-2-yl)-methyl]-benzamidine-hydrochloride and sodium hydroxide.

Yield: 91% of theory, $C_{25}H_{23}N_5O_3 \times HCl$ (441.5/477.96); Mass spectrum: $(M+H)^+=442$.

EXAMPLE 188

4-[(5-pyrrolidinosulphonyl-1-methyl-1H-benzimidazol-2-yl)-(carboxymethyl)methyl]-benzamidine-hydrochloride Prepared analogously to Example 13 from 4-[(5-pyrrolidinosulphonyl-1-methyl-1H-benzimidazol-2-yl)-(ethoxycarbonylmethyl)methyl]-benzamidine-hydrochloride and sodium hydroxide in ethanol.

Yield: 76% of theory, $C_{22}H_{25}N_5O_4S \times HCl$ (455.5/491.96); Mass spectrum: $(M+H)^+=456$.

EXAMPLE 189

4-[(5-cyclohexyl-(α-n-propylamino)methyl-1-methyl-1H-benzimidazol-2-yl)-methyl]-benzamidine-dihydrochloride a. 4-(cyclohexylcarbonyl)-chlorobenzene To a mixture of 80 ml (0.78 mol) of chlorobenzene and 30 g (0.22 mol) of aluminium chloride are added dropwise at 15–20° C. 24 ml (0.18 mol) of cyclohexanecarboxylic acid chloride. After one hour at ambient temperature the reaction mixture is heated for 5 hours to 50° C. After cooling, the mixture is then decomposed with ice water/conc. hydrochloric acid and the aqueous phase is extracted with methylene chloride. The combined organic extracts are dried and evaporated down. The residue is distilled under high vacuum (2 mm, 105–115° C.). The desired fraction is combined with water, the precipitate formed is suction filtered and dried.

Yield: 6.6 g (16% of theory), $C_{13}H_{15}ClO$ (222.72); Mass spectrum: $M^+=222$.

b. 4-(cyclohexylcarbonyl)-2-nitro-chlorobenzene

To 50 ml fuming nitric acid are added batchwise at −25° C. 6.4 g (28.8 mmol) of 4-(cyclohexylcarbonyl)-chlorobenzene. The solution is stirred for 10 minutes at −25° C. and then poured onto ice water. The precipitated product is suction filtered, washed with water and dried.

Yield: 7.3 g (95% of theory), $R_f$ value: 0.2 (silica gel, petroleum ether/methylene chloride=2:1).

c. 4-(cyclohexylcarbonyl)-2-nitro-N-methyl-aniline

Prepared analogously to Example 7b from 4-(cyclohexylcarbonyl)-2-nitro-chlorobenzene and methylamine solution.

Yield: 96.5% of theory, $C_{14}H_{18}N_2O_3$ (262.31); Mass spectrum: $M^+=262$.

d. 4-(cyclohexylcarbonyl)-2-amino-N-methyl-aniline 2.6 g (0.01 mol) of 4-(cyclohexylcarbonyl)-2-nitro-N-methylaniline are dissolved in 100 ml ethyl acetate and 30 ml methanol and after the addition of 0.5 g Raney nickel hydrogenated with hydrogen at ambient temperature. Then the catalyst is filtered off and the filtrate is concentrated by evaporation.

Yield: 2.2 g (100% of theory), $R_f$ value: 0.55 (silica gel; methylene chloride/ethanol=19:1).

e. 4-[(5-cyclohexylcarbonyl-1-methyl-1H-benzimidazol-2-yl)-methyl]-benzonitrile

Prepared analogously to Example 24f from 4-(cyclohexylcarbonyl)-2-amino-N-methyl-aniline, 4-cyanophenylacetic acid and N,N'-carbonyldiimidazole in tetrahydrofuran, and glacial acetic acid.

Yield: 74% of theory, $R_f$ value: 0.3 (silica gel; methylene chloride/ethanol=50:1).

f. 4-[(5-cyclohexyl-(α-n-propylamino)methyl-1-methyl-1H-benzimidazol-2-yl)-methyl]-benzonitrile and 4-[(5-cyclohexyl-(hydroxy)methyl-1-methyl-1H-benzimidazol-2-yl)-methyl]-benzonitrile 715 mg (2.0 mmol) of 4-[(5-cyclohexylcarbonyl-1H-benzimidazol-2-yl)-methyl]-benzonitrile, 1.0 ml n-propylamine and 1.0 g sodium acetate are dissolved in 30 ml methanol, 2 ml water and 2 ml glacial acetic acid and combined batchwise with 1.5 g (39.6 mmol) of sodium borohydride. After 1 hour at ambient temperature the mixture is poured onto water and extracted with ethyl acetate. The combined organic extracts are washed with common salt solution and dried over sodium sulphate. After evaporation of the solvent in vacuo the residue is chromatographed on silica gel and eluted with methylene chloride+1–10% ethanol.

Yield: 100 mg (12% of theory), $R_f$ value: 0.1 and 0.4 (silica gel; methylene chloride/ethanol=19:1).

g. 4-[(5-cyclohexyl-(α-n-propylamino)methyl-1-methyl-1H-benzimidazol-2-yl)-methyl]-benzamidine-dihydrochloride Prepared analogously to Example 1e from 4-[(5-cyclohexyl-(α-n-propylamino)methyl-1-methyl-1H-benzimidazol-2-yl)-methyl]-benzonitrile and hydrochloric acid/ammonium carbonate in ethanol.

Yield: 100% of theory, $C_{26}H_{35}N_5 \times 2$ HCl (417.61/490.54); Mass spectrum: $(M+H)^+=418$.

EXAMPLE 190

4-[(5-(cyclohexyl-(methoxy)methyl)-1-methyl-1H-benzimidazol-2-yl)-methyl]-benzamidine-hydrochloride Prepared analogously to Example 1e from 4-[(5) cyclohexyl-(hydroxy)methyl)-1-methyl-1H-benzimidazol-2-yl)-methyl]-benzonitrile and hydrochloric acid/ammonium carbonate in methanol.

Yield: 75% of theory, $C_{24}H_{30}N_4O \times HCl$ (390.54/427.0); Mass spectrum: $(M+H)^+=391$.

EXAMPLE 191

4-[(5-(4-oxo-2,3-diaza-spiro[5.5]undec-1-en-1-yl)-1-methyl-1H-benzimidazol-2-yl)-methyl]-benzamidine-hydrochloride a. [1-(4-chloro-benzoyl)-cyclohexyl]-acetic acid 8.4 g (0.04 mol) of 4-(4-chlorophenyl)-4-oxo-butyric acid are dissolved in 300 ml tetrahydrofuran, combined batchwise with 5.8 g (0.12 mol) of sodium hydride (50% in oil) and refluxed for 90 minutes. After the addition of 8.9 ml (0.06 mol) of 1,5-diiodopentane the reaction mixture is refluxed for a further 3 hours. After cooling the reaction mixture is stirred into ice water, the tetrahydrofuran is distilled off and the residue is extracted with methylene chloride. The aqueous phase is acidified with hydrochloric acid and extracted with methylene chloride. The combined organic extracts are dried and evaporated down. The residue is chromatographed on silica gel and eluted with methylene chloride+ethanol (1 to 2%).

Yield: 6.2 g (55% of theory).

b. [1-(4-chloro-3-nitro-benzoyl)-cyclohexyl]-acetic acid

Prepared analogously to Example 189b from [1-(4-chloro-benzoyl)-cyclohexyl]-acetic acid and fuming nitric acid.

Yield: 96% of theory.

c. [1-(4-N-methylamino-3-nitro-benzoyl)-cyclohexyl]-acetic acid

Prepared analogously to Example 7b from [1-(4-chloro-benzoyl)-cyclohexyl]-acetic acid and methylamine solution.

Yield: 93% of theory.

d. 4-[(5-(4-oxo-2,3-diaza-spiro[5.5]undec-1-en-1-yl)-3-nitro-N-methylaniline 2.5 ml hydrazine hydrate are slowly added dropwise to 25 ml glacial acetic acid and then 2.4 g (7.5 mmol) of [1-(4-N-methylamino-3-nitro-benzoyl)-cyclohexyl]-acetic acid are added. The reaction mixture is refluxed for 3 hours, then cooled and diluted with water. The precipitate formed is suction filtered and dried.

Yield: 2.0 g (85% of theory).

e. 4-[(5-(4-oxo-2,3-diaza-spiro[5.5]undec-1-en-1-yl)-3-amino-N-methylaniline

Prepared analogously to Example 1c from 4-[(5-(4-oxo-2,3-diaza-spiro[5.5]undec-1-en-1-yl)-3-nitro-N-methylaniline and palladium on activated charcoal/hydrogen in dimethylformamide.

Yield: 80% of theory.

f. 4-[(5-(4-oxo-2,3-diaza-spiro[5.5]undec-1-en-1-yl)-1-methyl-1H-benzimidazol-2-yl)-methyl]-benzonitrile Prepared analogously to Example 24f from 4-[(5-(4-oxo-2,3-diaza-spiro[5.5]undec-1-en-1-yl)-3-amino-N-methylaniline, 4-cyanophenylacetic acid and N,N'-carbonyldiimidazole in tetrahydrofuran, glacial acetic acid.

Yield: 49% of theory, $R_f$ value: 0.4 (silica gel; methylene chloride/ethanol=19:1).

g. 4-[(5-(4-oxo-2,3-diaza-spiro[5.5]undec-1-en-1-yl)-1-methyl-1H-benzimidazol-2-yl)-methyl]-benzamidine-hydrochloride Prepared analogously to Example 1e from 4-[(5-(4-oxo-2,3-diaza-spiro[5.5]undec-1-en-1-yl)-1-methyl-1H-benzimidazol-2-yl)-methyl]-benzonitrile and hydrochloric acid/ammonium carbonate in ethanol.

Yield: 70% of theory, $C_{25}H_{28}N_6O \times HCl$ (428.5/465.0); Mass spectrum: $(M+H)^+=429$.

EXAMPLE 192

4-[(5-(1-ethoxycarbonylmethyl-cyclohexan-1-yl-carbonyl)-1-methyl-1H-benzimidazol-2-yl)-methyl]-benzamidine-hydrochloride a. Methyl[1-(4-methylamino-3-nitro-benzoyl)-cyclohexyl]-acetate 4.9 g (0.015 mol) of [1-(4-methylamino-3-nitro-benzoyl)-cyclohexyl]-acetic acid are dissolved in 100 ml tetrahydrofuran and after the addition of 2.4 g (0.015 mol) of N,N'-carbonyldiimidazole the mixture is refluxed for 15 minutes. After concentration of the solution and addition of 30 ml methanol the mixture is refluxed for 3 hours. The solvent is distilled off, the residue chromatographed on silica gel and eluted with methylene chloride+methanol (1–5%). The desired fractions are combined and concentrated by evaporation.

Yield: 2.4 g (48% of theory).

b. methyl [1-(4-methylamino-3-amino-benzoyl)-cyclohexyl]-acetate

Prepared analogously to Example 1c from methyl [1-(4-methylamino-3-nitro-benzoyl)-cyclohexyl]-acetate and palladium on activated charcoal/hydrogen in methanol.

Yield: 96% of theory.

c. 4-[(5-(1-ethoxycarbonylmethyl-cyclohexan-1-yl-carbonyl)-1-methyl-1H-benzimidazol-2-yl)-methyl]-benzonitrile Prepared analogously to Example 24f from methyl [1-(4-methylamino-3-amino-benzoyl)-cyclohexyl]-acetate, 4-cyanophenylacetic acid and N,N'-carbonyldiimidazole in tetrahydrofuran/glacial acetic acid.

Yield: 66% of theory, $R_f$ value: 0.5 (silica gel; methylene chloride/ethanol=50:1).

d. 4-[(5-(1-ethoxycarbonylmethyl-cyclohexan-1-yl-carbonyl)-1-methyl-1H-benzimidazol-2-yl)-methyl]-benzamidine-hydrochloride Prepared analogously to Example 1e from 4-[(5-(1-ethoxycarbonylmethyl-cyclohexan-1-yl-carbonyl)-1-methyl-1H-benzimidazol-2-yl)-methyl]-benzonitrile and hydrochloric acid/ammonium carbonate in ethanol.

Yield: 55% of theory, $C_{27}H_{32}N_4O_3 \times HCl$ (460.6/497.0); Mass spectrum: $(M+H)^+=461$.

EXAMPLE 193

4-[(5-(n-pentyl-o-ethyl-phosphinyl)-1-methyl-1H-benzimidazol-2-yl)-methyl]-benzamidine-hydrochloride a. dichloro-(4-chlorphenyl)-phosphine To a suspension of 53.3 g (0.4 mol) of aluminium chloride in 40 ml (0.39 mol) of chlorobenzene, 104.8 ml (1.2 mol) of phosphorus trichloride are added dropwise at ambient temperature. The reaction mixture is refluxed for three hours. Then within 30 minutes 37.2 ml (0.4 mol) of phosphorus oxychloride are added dropwise at 83° C. After 12 hours at ambient temperature the residue is stirred with petroleum ether and decanted off. The combined organic extracts are distilled under high vacuum at 57–61° C. and 0.048–0.035 mbar.

Yield: 45.6 g (55% of theory).

b. Diethyl (4-chlorophenyl)-phosphonate

To a solution of 14.9 ml (0.184 mol) of pyridine and 10.8 ml (0.184 mol) of ethanol in 50 ml tetrahydrofuran is added dropwise, within one hour, with cooling, a solution of 17.9 g (0.083 mol) of dichloro-(4-chlorophenyl)-phosphine in 20 ml tetrahydrofuran. The suspension is stirred for 72 hours at ambient temperature, suction filtered and concentrated by evaporation. The residue is distilled at 80–83° C. and 0.19 mbar.

Yield: 11.7 g (61% of theory), $R_f$ value: 0.4 (silica gel; methylene chloride/ethanol=50:1).

c. ethyl(4-chlorophenyl)-n-pentyl-phosphinate 3.5 g (15 mmol) of diethyl(4-chlorophenyl)-phosphonate and 3 ml (24.7 mmol) of n-pentylbromide are heated to 150° C. for 90 minutes with stirring. The cooled clear solution is chromatographed on silica gel and eluted with cyclohexane/ethyl acetate (7:3 to 1:1).

Yield: 2.7 g (66% of theory), $C_{13}H_{20}ClO_2P$ (274.74); Mass spectrum: $M^+=274$.

d. ethyl(4-chloro-3-nitro-phenyl)-n-pentyl-phosphinate

Prepared analogously to Example 189b from ethyl(4-chlorophenyl)-n-pentyl-phosphinate and fuming nitric acid.

Yield: 56% of theory.

e. ethyl(4-methylamino-3-nitro-phenyl)-n-pentyl-phosphinate

Prepared analogously to Example 7b from ethyl(4-chloro-3-nitro-phenyl)-n-pentyl-phosphinate and methylamine solution.

Yield: 100% of theory.

f. ethyl(4-methylamino-3-amino-phenyl)-n-pentyl-phosphinate

Prepared analogously to Example 1c from ethyl(4-methylamino-3-nitro-phenyl)-n-pentyl-phosphinate and palladium on activated charcoal/hydrogen in ethanol.

Yield: 100% of theory.

g. 4-[(5-(n-pentyl-O-ethyl-phosphinyl)-1-methyl-1H-benzimidazol-2-yl)-methyl]-benzonitrile Prepared analogously to Example 24f from ethyl(4-methylamino-3-amino-phenyl)-n-pentyl-phosphinate, 4-cyanophenylacetic acid and N,N'-carbonyldiimidazole in tetrahydrofuran and glacial acetic acid.

Yield: 43.7% of theory.

h. 4-[(5-(n-pentyl-O-ethyl-phosphinyl)-1-methyl-1H-benzimidazol-2-yl)-methyl]-benzamidine-hydrochloride Prepared analogously to Example 1e from 4-[(5-(n-pentyl-O-ethyl-phosphinyl)-1-methyl-1H-benzimidazol-2-yl)-methyl]-benzonitrile and hydrochloric acid/ammonium carbonate in ethanol.

Yield: 78% of theory, $C_{23}H_{31}N_4O_2P \times HCl$ (426.51/462.97); Mass spectrum: $(M+H)^+=427$.

EXAMPLE 194

4-[(5-(N-(2-dimethylamino-ethyl)-benzenesulphonylamino-1-methyl-1H-benzimidazol-2-yl)-methyl]-benzamidine-dihydrochloride Prepared analogously to Example 1e from 4-[(5-(N-(2-dimethylamino-ethyl)-benzenesulphonylamino)-1-methyl-1H-benzimidazol-2-yl)-methyl]-benzonitrile and hydrochloric acid/ammonium carbonate in ethanol.

Yield: 83% of theory, $C_{26}H_{30}N_6O_2S \times 2\ HCl$ (490.64/563.57); Mass spectrum: $(M+H)^+=491$.

EXAMPLE 195

4-[(5-(n-pentyl-phosphinyl)-1-methyl-1H-benzimidazol-2-yl)-methyl]-benzamidine-hydrochloride To a solution of 100 mg (0.2 mmol) of 4-[(5-(n-pentyl-O-ethyl-phosphinyl)-1-methyl-1H-benzimidazol-2-yl)-methyl]-benzamidine-hydrochloride in 5 ml methylene chloride are added 1.8 ml (14 mmol) of trimethylsilylbromide. After the addition of 20 ml methylene chloride the reaction mixture is stirred for 6 days at ambient temperature. After evaporation of the solvent the residue is triturated with water/2N hydrochloric acid. The solid formed is suction filtered, the filtrate is concentrated by evaporation, mixed several times with ethanol and concentrated by evaporation. The residue is triturated with methanol/acetone, suction filtered and dried.

Yield: 70 mg (74% of theory) $C_{21}H_{27}N_4O_2P \times HCl$ (398.45/434.91); Mass spectrum: $(M+H)^+=399$.

EXAMPLE 196

4-[(5-(n-pentyl-O-ethoxycarbonylmethyl-phosphinyl)-1-methyl-1H-benzimidazol-2-yl)-methyl]-benzamidine-hydrochloride a. [(5-(n-pentyl-phosphinyl)-1-methyl-1H-benzimidazol-2-yl)-methyl]-benzonitrile 0.6 g (1.5 mmol) of 4-[(5-(n-pentyl-O-ethyl-phosphinyl)-1-methyl-1H-benzimidazol-2-yl)-methyl]-benzonitrile are dissolved in 45 ml methylene chloride, combined with 2 ml (15.4 mmol) of trimethylbromosilane and stirred for 22 hours at ambient temperature. After evaporation of the solvent the residue is combined with ice water and adjusted to pH 6 with sodium acetate. After two hours the precipitate formed is suction filtered and dried.

Yield: 0.37 g (66% of theory), $R_f$ value: 0.35 (Reversed Phase, 5% sodium chloride solution/methanol=1:2).

b. 4-[(5-n-pentyl-O-ethoxycarbonylmethyl-phosphinyl)-1-methyl-1H-benzimidazol-2-yl)-methyl]-benzonitrile To a solution of 370 mg (0.97 mmol) of 4-[(5-(n-pentyl-phosphinyl)-1-methyl-1H-benzimidazol-2-yl)-methyl]-benzonitrile in 7 ml dimethylformamide are added 170 mg (1.2 mmol) of potassium carbonate and 130 mg (1.2 mmol) of ethyl bromoacetate. The reaction mixture is heated to 5° C. for 20 minutes, cooled and then poured onto ice water and extracted with ethyl acetate. The organic extracts are washed with citric acid and sodium carbonate solution, dried over sodium sulphate and evaporated down. The residue is chromatographed on silica gel and eluted with ethyl acetate/ethanol (25:1 and 10:1).

Yield: 0.4 g (88% of theory), $R_f$ value: 0.4 (silica gel; methylene chloride/ethanol=50:1).

c. 4-[(5-n-pentyl-O-ethoxycarbonylmethyl-phosphinyl)-1-methyl-1H-benzimidazol-2-yl)-methyl]-benzamidine-hydrochloride Prepared analogously to Example 1e from 4-[(5-n-pentyl-O-ethoxycarbonylmethyl-phosphinyl)-1-methyl-1H-benzimidazol-2-yl)-methyl]-benzonitrile and hydrochloric acid/ammonium carbonate in ethanol.

Yield: 76% of theory, $C_{25}H_{33}N_4O_4P \times HCl$ (484.55/521.01); Mass spectrum: $(M+H)^+=485$.

EXAMPLE 197

4-[(5-(n-pentyl-O-carboxymethyl-phosphinyl)-1-methyl-1H-benzimidazol-2-yl)-methyl]-benzamidine-hydrochloride Prepared analogously to Example 13 from 4-[(5-(n-pentyl-O-ethoxycarbonylmethyl-phosphinyl)-1-methyl-1H-benzimidazol-2-yl)-methyl]-benzamidine-hydrochloride and sodium hydroxide in ethanol.

Yield: 74% of theory, $C_{23}H_{29}N_4O_4P \times HCl$ (456.49/492.95); Mass spectrum: $(M+H)^+=457$.

EXAMPLE 198

4-[(5-(1-carboxymethyl-cyclohexan-1-yl-carbonyl)-1-methyl-1H-benzimidazol-2-yl)-methyl]-benzamidine To a solution of 160 mg (4 mmol) of sodium hydroxide in 5 ml water and 20 ml ethanol are added 400 mg (0.8 mmol) of 4-[(5-(1-ethoxycarbonylmethyl-cyclohexan-1-yl-carbonyl)-1-methyl-1H-benzimidazol-2-yl)-methyl]-benzamidine-hydrochloride. After two hours at ambient temperature the solution is evaporated down, the residue is dissolved in water and acidified with glacial acetic acid. The precipitate is suction filtered and dried.

Yield: 250 mg (72% of theory), $C_{25}H_{28}N_4O_3$ (432.5); Mass spectrum: $(M+H)^+=433$.

EXAMPLE 199

4-[(5-(2-oxo-piperidin-1-yl)-1-methyl-1H-benzimidazol-2-yl)-methyl]-benzamidine-hydrochloride a. 4-fluoro-3-nitro-N-(5-bromobutyloxy)-aniline After the addition of 3 ml triethylamine to a solution of 3.7 g (0.024 mol) of 4-fluoro-3-nitro-aniline in 100 ml tetrahydrofuran at ambient temperature, 4.8 g (0.024 mol) of 5-bromovaleric acid chloride are added dropwise. Then the mixture is stirred for two hours at ambient temperature and concentrated by evaporation. The residue is chromatographed on silica gel and eluted with methylene chloride. The desired fractions are combined and evaporated down.

Yield: 7.0 g (92% of theory), $R_f$ value: 0.6 (silica gel; petroleum ether/ethyl acetate=3:7).

b. 4-(2-oxo-piperidin-1-yl)-2-nitro-fluorobenzene

To a suspension of 1.0 g (21.9 mmol) of sodium hydride (50% in oil) in 200 ml tetrahydrofuran is added dropwise at ambient temperature a solution of 7.0 g (21.9 mmol) of 4-fluoro-3-nitro-N-(5-brombutyloxy)-aniline in 50 ml tetrahydrofuran. After 30 minutes it is poured onto ice water, the tetrahydrofuran is distilled off and the aqueous phase is extracted with methylene chloride. The combined organic extracts are dried and evaporated down. The residue is chromatographed on silica gel and eluted with petroleum ether/ethyl acetate (7:3).

Yield: 4.1 g (79% of theory), $R_f$ value: 0.4 (silica gel; petroleum ether/ethyl acetate=3:7).

c. 4-(2-oxo-piperidin-1-yl)-2-nitro-N-methyl-aniline

Prepared analogously to Example 7b from 4-(2-oxo-piperidin-1-yl)-2-nitro-fluorobenzene and aqueous methylamine solution.

Yield: 92% of theory, $R_f$ value: 0.35 (silica gel; petroleum ether/ethyl acetate=1:9).

d. 4-(2-oxo-piperidin-1-yl)-2-amino-N-methyl-aniline

Prepared analogously to Example 1c from 4-(2-oxo-piperidin-1-yl)-2-nitro-N-methyl-aniline and palladium on activated charcoal/hydrogen in methanol.

Yield: 97% of theory, $R_f$ value: 0.25 (silica gel; methylene chloride/ethanol=19:1).

e. 4-[(5-(2-oxo-piperidin-1-yl)-1-methyl-1H-benzimidazol-2-yl)-methyl]-benzonitrile Prepared analogously to Example 24f from 4-(2-oxo-piperidin-1-yl)-2-amino-N-methyl-aniline, 4-cyanophenylacetic acid and N,N'-carbonyldiimidazole in tetrahydrofuran/glacial acetic acid.

Yield: 35% of theory, $R_f$ value: 0.23 (silica gel, methylene chloride/ethanol=19:1).

f. 4-[(5-(2-oxo-piperidin-1-yl)-1-methyl-1H-benzimidazol-2-yl)-methyl]-benzamidine-hydrochloride Prepared analogously to Example 1e from 4-[(5-(2-oxo)piperidin-1-yl-1-methyl-1H-benzimidazol-2-yl)-methyl]-benzonitrile and hydrochloric acid/ammonium carbonate in ethanol.

Yield: 87% of theory, $C_{21}H_{23}N_5O \times HCl$ (361.5/397.9); Mass spectrum: $(M+H)^+=362$.

EXAMPLE 200

4-[(5-(n-butane-sultam-2-yl)-1-methyl-1H-benzimidazol-2-yl)-methyl]-benzamidine-hydrochloride Prepared analogously to Example 1e from 4-[(5-(n-butane-sultam-2-yl)-1-methyl-1H-benzimidazol-2-yl)-methyl]-benzonitrile and hydrochloric acid/ammonium carbonate in ethanol.

Yield: 77% of theory, $C_{20}H_{23}N_5O_2S \times HCl$ (397.5/434.0); Mass spectrum: $(M+H)^+=398$.

EXAMPLE 201

4-[(5-(N-cyclohexyl-methanesulphonylamino)-1-methyl-1H-benzimidazol-2-yl)-methyl]-benzamidine-hydrochloride Prepared analogously to Example 1e from 4-[(5-N-cyclohexyl-methanesulphonylamino)-1-methyl-1H-benzimidazol-2-yl)-methyl]-benzonitrile and hydrochloric acid/ammonium carbonate in ethanol.

Yield: 52% of theory, $C_{23}H_{29}N_5O_2S \times HCl$ (439.59/476.06); Mass spectrum: $(M+H)^+=440$.

EXAMPLE 202

4-[(5-(1-methyl-cyclohexan-1-yl-carbonyl)-1-methyl-1H-benzimidazol-2-yl)-methyl]-benzamidine-hydrochloride Prepared analogously to Example 1e from 4-[(5-(1-methyl-cyclohexan-1-yl-carbonyl)-1-methyl-1H-benzimidazol-2-yl)-methyl]-benzonitrile and hydrochloric acid/ammonium carbonate in ethanol.

Yield: 63% of theory, $C_{24}H_{28}N_4O \times HCl$ (388.5/425.0); Mass spectrum: $(M+H)^+=389$.

EXAMPLE 203

4-[(5-(1-isobutyl-tetrazol-5-yl)-1-methyl-1H-benzimidazol-2-yl)-methyl]-benzamidine-hydrochloride a. 4-chloro-3-nitro-benzoic acid-isobutylamide Prepared analogously to Example 24b from 4-chloro-3-nitro-benzoylchloride, isobutylamine and triethylamine in tetrahydrofuran.

Yield: 88% of theory.

b. 4-[(5-(1-isobutyl-tetrazol-5-yl)-2-nitro-chlorobenzene 10.3 g (0.04 mol) of 4-chloro-3-nitro-benzoic acid-isobutylamide are dissolved in 200 ml methylene chloride and combined with 2.6 g (0.04 mol) of sodium azide. Then 6.7 ml (0.04 mol) of trifluoromethanesulphonic acid anhydride are added dropwise at 0° C. The reaction is then stirred for 40 hours at ambient temperature and combined with 5% sodium carbonate solution. The organic phase is separated off, dried and evaporated down. The residue is chromatographed on silica gel and eluted with methylene chloride+ethanol (0–1%). The desired fractions are combined and evaporated down.

Yield: 3.6 g (32% of theory), $C_{11}H_{12}ClN_5O_2$ (281.7); Mass spectrum: $M^+=281$.

c. 4-[(5-(1-isobutyl-tetrazol-5-yl)-2-nitro-N-methyl-aniline

Prepared analogously to Example 7b from 4-[(5-(1-isobutyl-tetrazol-5-yl)-2-nitro-chlorobenzene and methylamine solution.

Yield: 100% of theory, $R_f$ value: 0.3 (silica gel; methylene chloride/ethanol=50:1).

d. 4-F(5-(1-isobutyl-tetrazol-5-yl)-2-amino-N-methyl-aniline

Prepared analogously to Example 24e from 4-[(5-(1-isobutyltetrazol-5-yl)-2-nitro-N-methyl-aniline and palladium on activated charcoal/hydrogen in methanol.

Yield: 100% of theory, $R_f$ value: 0.3 (silica gel; methylene chloride/ethanol=19:1).

e. 4-[(5-(1-isobutyl-tetrazol-5-yl-1-methyl-1H-benzimidazol-2-yl)-methyl]-benzonitrile Prepared analogously to Example 24f from 4-[(5-(1-isobutyltetrazol-5-yl)-2-amino-N-methyl-aniline, 4-cyanophenylacetic acid and N,N'-carbonyldiimidazole in tetrahydrofuran, glacial acetic acid.

Yield: 86% of theory, $R_f$ value: 0.4 (silica gel; methylene chloride/ethanol=19:1).

f. 4-[(5-(1-isobutyl-tetrazol-5-yl-1-methyl-1H-benzimidazol-2-yl)-methyl]-benzamidine-hydrochloride Prepared analogously to Example 1e from 4-[(5-(1-isobutyltetrazol-5-yl-1-methyl-1H-benzimidazol-2-yl)-methyl]-benzonitrile and hydrochloric acid/ammonium carbonate in ethanol.

Yield: 44% of theory, $C_{21}H_{24}N_8 \times HCl$ (388.5/425.0); Mass spectrum: $(M+H)^+=389$.

EXAMPLE 204

4-[(5-phenyl-1-methyl-1H-benzimidazol-2-yl)-methyl]-benzamidine-hydrochloride a. 2-nitro-4-phenyl-N-methyl-acetanilide 3.0 g (11.7 mmol) of 2-nitro-4-phenylacetanilide are dissolved in 70 ml dimethylformamide and combined batchwise with 576 mg (12 mmol) of sodium hydride (50% in oil) at ambient temperature. After 30 minutes at 65° C. the reaction mixture is cooled to ambient temperature, combined with 3 ml methyl iodide and stirred for 30 minutes. The mixture is stirred into saturated sodium chloride solution and extracted with ethyl acetate. The combined organic extracts are washed with water, dried and evaporated down. The residue is chromatographed on silica gel and eluted with methylene chloride+ethanol (0–5%). The desired fractions are combined and evaporated down.

Yield: 3.2 g (100% of theory), $R_f$ value: 0.43 (silica gel; methylene chloride/ethanol=19:1).

b. 2-nitro-4-phenyl-N-methyl-aniline 3.2 g (11.7 mmol) of 2-nitro-4-phenyl-N-methyl-acetanilide are refluxed in 99 ml semiconcentrated hydrochloric acid for 7 hours. The solution is cooled and extracted with methylene chloride. The organic phase is washed with water and sodium hydrogen carbonate solution, dried over sodium sulphate and evaporated down. The residue is chromatographed on silica gel and eluted with methylene chloride. The desired fractions are combined and evaporated down.

Yield: 2.0 g (75% of theory), $R_f$ value: 0.8 (silica gel; methylene chloride).

c. 2-amino-4-phenyl-N-methyl-aniline

Prepared analogously to Example 1c from 2-nitro-4-phenyl-N-methyl-aniline and palladium on activated charcoal/hydrogen in methanol.

Yield: 91% of theory, $R_f$ value: 0.4 (silica gel; methylene chloride/ethanol=19:1).

d. 4-[(5-phenyl-1-methyl-1H-benzimidazol-2-yl)-methyl]-benzonitrile

Prepared analogously to Example 24f from 2-amino-4-phenyl-N-methyl-aniline, 4-cyanophenylacetic acid and N,N'-carbonyldiimidazole in tetrahydrofuran and glacial acetic acid.

Yield: 100% of theory, e. 4-[(5-phenyl-1-methyl-1H-benzimidazol-2-yl)-methyl]-benzamidine-hydrochloride Prepared analogously to Example 1e from 4-[(5-phenyl-1-methyl-1H-benzimidazol-2-yl)-methyl]-benzonitrile and hydrochloric acid/ammonium carbonate in ethanol.

Yield: 60% of theory, $C_{22}H_{20}N_4 \times HCl$ (340.4/376.9); Mass spectrum: $(M+H)^+=341$.

EXAMPLE 205

4-[(5-((1-methyl-cyclohexan-1-yl)-ethoxycarbonylmethyloxyimino-methylene)-1-methyl-1H-benzimidazol-2-yl)-methyl]-benzamidine-hydrochloride a. 4-[(5-((1-methyl-cyclohexan-1-yl)-ethoxycarbonylmethyloxyimino-methylene)-1-methyl-1H-benzimidazol-2-yl)-methyl]-benzonitrile 750 mg (2 mmol) of 4-[(5-(1-methyl-cyclohexan-1-yl-carbonyl)-1-methyl-1H-benzimidazol-2-yl)-methyl]-benzonitrile (prepared analogously to Example 194) and 645 mg (3 mmol) of carboxymethoxyamine are refluxed for two hours in 10 ml methanol and 1 ml water. The solvent is distilled off, the residue is chromatographed on silica gel and eluted with methylene chloride+ethanol (5–10%). The desired fractions are combined and evaporated down.

Yield: 450 mg (54% of theory), $R_f$ value: 0.5 (silica gel; methylene chloride/ethanol=9:1).

b. 4-[(5-((1-methyl-cyclohexan-1-yl)-ethoxycarbonylmethyloxyimino-methylene)-1-methyl-1H-benzimidazol-2-yl)-methyl]-benzamidine-hydrochloride Prepared analogously to Example 1e from 4-[(5-((1-methylcyclohexan-1-yl)-ethoxycarbonylmethyloxyimino-methylene)-1-methyl-1H-benzimidazol-2-yl)-methyl]-benzonitrile and hydrochloric acid/ammonium carbonate in ethanol.

Yield: 41% of theory, $C_{28}H_{35}N_5O_3 \times HCl$ (489.6/526.1); Mass spectrum: $(M+H)^+=490$.

EXAMPLE 206

4-[(5-(N-cyclopentyl-methanesulphonylamino)-1-methyl-1H-benzimidazol-2-yl)-methyl]-benzamidine-hydrochloride Prepared analogously to Example 1e from 4-[(5-(N-cyclopentyl-methanesulphonylamino)-1-methyl-1H-benzimidazol-2-yl)-methyl]-benzonitrile and hydrochloric acid/ammonium carbonate in ethanol.

Yield: 65% of theory, $C_{22}H_{27}N_5O_2S \times HCl$ (425.56/462.02); Mass spectrum: $(M+H)^+=426$.

EXAMPLE 207

4-[(5-(N-(2-ethoxycarbonyl-ethyl)-isobutylaminocarbonyl)-1-methyl-1H-benzimidazol-2-yl)-methyl]-benzamidine-hydrochloride Prepared analogously to Example 1e from 4-[(5-(N-(2-ethoxycarbonyl-ethyl)-isobutylaminocarbonyl)-1-methyl-1H-benzimidazol-2-yl)-methyl]-benzonitrile and hydrochloric acid/ammonium carbonate in ethanol.

Yield: 54% of theory, $C_{26}H_{33}N_5O_3 \times HCl$ (463.59/500.06); Mass spectrum: $(M+H)^+=464$.

EXAMPLE 208

4-[(5-(N-(2-carboxy-ethyl)-isobutylaminocarbonyl)-1-methyl-1H-benzimidazol-2-yl)-methyl]-benzamidine Prepared analogously to Example 198 from 4-[(5-(N-(2-ethoxycarbonyl-ethyl)-isobutylaminocarbonyl-1-methyl-1H-benzimidazol-2-yl)-methyl]-benzamidine-hydrochloride) and sodium hydroxide in ethanol.

Yield: 72% of theory, $C_{24}H_{29}N_5O_3$ (435.5); Mass spectrum: $(M+H)^+=436$.

EXAMPLE 209

4-[(5-tert.butylcarbonyl-1-methyl-1H-benzimidazol-2-yl)-methyl]-benzamidine-hydrochloride Prepared analogously to Example 1e from 4-[(5-tert.butylcarbonyl-1-methyl-1H-benzimidazol-2-yl)-methyl]-benzonitrile and hydrochloric acid/ammonium carbonate in ethanol.

Yield: 50% of theory, $C_{21}H_{24}N_4O \times HCl$ (348.5/384.9); Mass spectrum: $(M+H)^+=349$.

EXAMPLE 210

4-[(5-(1-methyl-cyclopentan-1-yl-carbonyl)-1-methyl-1H-benzimidazol-2-yl)-methyl]-benzamidine-hydrochloride Prepared analogously to Example 1e from 4-[(5-(1-methyl-cyclopentan-1-yl-carbonyl)-1-methyl-1H- benzimidazol-2-yl)-methyl]-benzonitrile and hydrochloric acid/ammonium carbonate in ethanol.

Yield: 55% of theory, $C_{23}H_{26}N_4O \times HCl$ (374.5/411.0); Mass spectrum: $(M+H)^+=375$.

EXAMPLE 211

4-[(5-(S-cyclohexyl-sulphimidoyl)-1-methyl-1H-benzimidazol-2-yl)-methyl]-benzamidine-hydrochloride a. 1-chloro-4-cyclohexanesulphanyl-2-nitrobenzene 16.4 g (0.095 mol) of 4-chloro-3-nitroaniline are suspended in 150 ml hydrochloric acid (12%) and at 2–5° C. combined with a solution of 6.55 g (0.095 mol) of sodium nitrite in 12 ml water. The reaction mixture is added dropwise to a suspension of 11.6 ml (0.095 mol) of cyclohexylmercaptan in 175 ml sodium hydroxide solution (15%), combined with 10 g of copper powder and then heated to 80° C. for 1 hour. After cooling to ambient temperature the mixture is extracted with methylene chloride, the organic extracts are washed with hydrochloric acid and water, dried and evaporated down. The residue is chromatographed on aluminium oxide and eluted with cyclohexane/ethyl acetate (9:1 and 4:1). The desired fractions are combined and concentrated by evaporation.

Yield: 15.7 g (61% of theory), $R_f$ value: 0.3 (aluminium oxide, petroleum ether).

b. 1-chloro-4-cyclohexansulphinyl-2-nitrobenzene 11.6 g (0.043 mol) of 1-chloro-4-cyclohexanesulphanyl-2-nitrobenzene are dissolved in 200 ml acetic anhydride and at 10° C. combined with 4.4 g (0.038 mol) of perhydrol. The solution is stirred for 48 hours at ambient temperature and concentrated by evaporation. The residue is combined with ice and ammonia and extracted with ethyl acetate. The organic extracts are washed with sodium chloride solution, dried and concentrated by evaporation. The residue is chromatographed on silica gel and eluted with cyclohexane/ethyl acetate 7:3 and 1:2.

Yield: 6.7 g (54% of theory), $R_f$ value: 0.9 (silica gel; cyclohexane/ethyl acetate 2:1).

c. 1-chloro-4-cyclohexylsulphimidoyl-2-nitrobenzene 8.4 g (0.029 mol) of 1-chloro-4-cyclohexansulphinyl-2-nitrobenzene, 24.8 g (0.086 mol) of ethyl O-mesitylene-sulphonyl-acetohydroxamate and 28.6 g (0.15 mol) of p-toluenesulphonic acid are dissolved in 160 ml dimethylformamide and stirred for 90 hours at ambient temperature. Then the mixture is diluted with ice water and combined with sodium carbonate. After extraction with ethyl acetate the combined organic phases are washed with sodium chloride, dried and evaporated down. The residue is chromatographed on silica gel and eluted with methylene chloride/ethanol (50:1 and 30:1). The desired fractions are combined and concentrated by evaporation.

Yield: 7.1 g (81% of theory), $R_f$ value: 0.3 (silica gel; cyclohexane/ethyl acetate=2:1).

d. 1-chloro-4-cyclohexyl-N-tert.butoxycarbonyl-sulphimidoyl-2-nitrobenzene

To a solution of 3.1 g (0.01 mol) of 1-chloro-4-cyclohexylsulphimidoyl-2-nitrobenzene in 10 ml tetrahydrofuran is added dropwise at 5° C. a solution of 1.4 g (0.012 mol) of potassium-tert.butoxide in 5 ml tetrahydrofuran. After 20 minutes a solution of 4.4 g (0.02 mol) of di-tert.butyldicarbonate in 30 ml tetrahydrofuran is added. After 3 hours at ambient temperature the mixture is stirred with ammonium chloride solution and extracted with ethyl acetate. The organic extracts are washed with water and sodium chloride solution, dried over sodium sulphate and concentrated by evaporation. The residue is chromatographed on silica gel and eluted with ethyl acetate/cyclohexane (9:1 and 4:1).

Yield: 2.7 g (65% of theory), $R_f$ value: 0.5 (silica gel; petroleum ether/ethyl acetate=4:1).

e. 1-methylamino-4-cyclohexyl-N-tert.butoxycarbonylsulphimidoyl-2-nitrobenzene

Prepared analogously to Example 7b from 1-chloro-4-cyclohexyl-N-tert.butoxycarbonyl-sulphimidoyl-2-nitrobenzene and methylamine solution.

Yield: 92% of theory, $R_f$ value: 0.6 (silica gel; cyclohexane/ethyl acetate=1:1).

f. 1-methylamino-2-amino-4-cyclohexyl-N-tert.butoxycarbonylsulphimidoyl-benzene

Prepared analogously to Example 1c from 1-methylamino-4-cyclohexyl-N-tert.butoxycarbonyl-sulphimidoyl-2-nitrobenzene and palladium on activated charcoal/hydrogen in methanol. The crude product is further reacted without being purified.

g. 4-[(5-(cyclohexyl-N-tert.butoxycarbonyl-sulphimidoyl)-1-methyl-1H-benzimidazol-2-yl)-methyl]-benzonitrile Prepared analogously to Example 24f from 1-methylamino-2-amino-4-cyclohexyl-N-tert.butoxycarbonylsulphimidoyl-benzene, 4-cyanophenylacetic acid and N,N'-carbonyldiimidazole in tetrahydrofuran/glacial acetic acid.

Yield: 40.6% of theory, $R_f$ value: 0.5 (silica gel; ethyl acetate).

h. 4-[(5-(cyclohexyl-sulphimidoyl)-1-methyl-1H-benzimidazol-2-yl)-methyl]-benzonitrile 1.3 g (2.6 mmol) of 4-[(5-(cyclohexyl-N-tert.butoxycarbonylsulphimidoyl)-1-methyl-1H-benzimidazol-2-yl)-methyl]-benzonitrile are dissolved in 15 ml dioxan and after the addition of 10 ml 6N hydrochloric acid the mixture is stirred for 8 hours at ambient temperature. The solution is diluted with ice, combined with ammonia and extracted with ethyl acetate. The organic phase is washed with water and sodium chloride solution, dried and concentrated by evaporation.

Yield: 1.0 g (98% of theory), $R_f$ value: 0.65 (silica gel; methylene chloride/ethanol=9:1).

i. 4-[(5-(cyclohexyl-sulphimidoyl)-1-methyl-1H-benzimidazol-2-yl)-methyl]-benzamidine-hydrochloride Prepared analogously to Example 1e from 4-[(5-(cyclohexylsulphimidoyl)-1-methyl-1H-benzimidazol-2-yl)-methyl]-benzonitrile and hydrochloric acid/ammonium carbonate in ethanol.

Yield: 90% of theory, $C_{22}H_{27}N_5O_5S \times HCl$ (409.56/446.02); Mass spectrum: $(M+H)^+=410$.

EXAMPLE 212

4-[(5-(N-ethoxycarbonylmethyl-cyclohexylsulphimidoyl)-1-methyl-1H-benzimidazol-2-yl)-(ethoxycarbonylmethyl)-methylene]-benzamidine-hydrochloride a. 4-[(5-(N-ethoxycarbonylmethyl-cyclohexylsulphimidoyl)-1-methyl-1H-benzimidazol-2-yl)-(ethoxycarbonylmethyl)-methylene]-benzonitrile and 4-[(5-(cyclohexyl-sulphimidoyl)-1-methyl-1H-benzimidazol-2-yl)-(ethoxycarbonylmethyl)methylene]-benzonitrile 0.7 g (1.78 mmol) of 4-[(5-(cyclohexylsulphimidoyl)-1-methyl-1H-benzimidazol-2-yl)-methyl]-benzonitrile and 1 g (7.25 mmol) of potassium carbonate are dissolved in 100 ml acetone and after the addition of 0.45 ml (4.0 mmol) of ethyl bromoacetate the mixture is refluxed for 95 hours. The precipitate formed is suction filtered, the mother liquor concentrated by evaporation and the residue chromatographed on silica gel, eluting with ethyl acetate/ethanol (1:0 and 9:1).

Yield: 0.2 g (20% of theory) 4-[(5-(N-ethoxycarbonylmethyl-cyclohexylsulphimidoyl)-1-methyl-1H-benzimidazol-2-yl)-(ethoxycarbonylmethyl)methylene]-benzonitrile, $C_{30}H_{36}N_4O_5S$ (564), Mass spectrum: $M^+=564$; and 0.2 g (20% of theory), 4-[(5-(cyclohexylsulphimidoyl)-1-methyl-1H-benzimidazol-2-yl)-(ethoxycarbonylmethyl)methylene]-benzonitrile, $C_{26}H_{30}N_5O_3S$ (478.6), Mass spectrum: $M^+=478$.

b. 4-[(5-(N-ethoxycarbonylmethyl-cyclohexylsulphimidoyl)-1-methyl-1H-benzimidazol-2-yl)-(ethoxycarbonylmethyl)-methylene]-benzamidine-hydrochloride Prepared analogously to Example 1e from 4-[(5-(N-ethoxycarbonylmethyl-cyclohexylsulphimidoyl)-1-methyl-1H-benzimidazol-2-yl)-(ethoxycarbonylmethyl)methylene]-benzonitrile and hydrochloric acid/ammonium carbonate in ethanol.

Yield: 31% of theory, $C_{30}H_{39}N_5O_5S\times HCl$ (581.75/618.21); Mass spectrum: $(M+H)^+=582$.

EXAMPLE 213

4-[(5-(cyclohexyl-sulphimidoyl)-1-methyl-1H-benzimidazol-2-yl)-(ethoxycarbonylmethyl)methylene]-benzamidine-hydrochloride Prepared analogously to Example 1e from 4-[(5-(cyclohexyl-sulphimidoyl)-1-methyl-1H-benzimidazol-2-yl)-(ethoxycarbonylmethyl)methylene]-benzonitrile and hydrochloric acid/ammonium carbonate in ethanol.

Yield: 70% of theory, $C_{26}H_{33}N_5O_3S\times HCl$ (495.66/532.12); Mass spectrum: $(M+H)^+=496$.

EXAMPLE 214

4-[(5-(N-cyclopentyl-3-methoxycarbonylpropionylamino)-1-methyl-1H-benzimidazol-2-yl)-methyl]-benzamidine-hydrochloride Prepared analogously to Example 1e from 4-[(5-(N-cyclopentyl-3-methoxycarbonylpropionylamino)-1-methyl-1H-benzimidazol-2-yl)-methyl]-benzonitrile and hydrochloric acid/ammonium carbonate in ethanol.

Yield: 81% of theory, $C_{26}H_{31}N_5O_3\times HCl$ (461.57/498.04); Mass spectrum: (M+H)+462; $(M+2H)^{++}=231.7$; $(M+H+Na)^{++}=242.8$.

EXAMPLE 215

4-[(5-(N-acetyl-cyclohexylsulphimidoyl)-1-methyl-1H-benzimidazol-2-yl)-methyl]-benzamidine-hydrochloride 150 mg (0.29 mmol) of 4-[(5-(N-acetyl-cyclohexylsulphimidoyl)-1-methyl-1H-benzimidazol-2-yl)-methyl]-benzamidine-hydrochloride are suspended in 5 ml glacial acetic acid and after the addition of 3 ml acetic anhydride stirred for 75 minutes at 40° C. The reaction mixture is concentrated by evaporation at 70° C., the residue is triturated with ether, suction filtered and dried.

Yield: 150 mg (100% of theory), $C_{24}H_{29}N_5O_2S\times HCl$ (451.6/488.06); Mass spectrum: $(M+H)^+=452$.

EXAMPLE 216

4-[(5-(N-(3-carboxypropionyl)-cyclohexylsulphimidoyl)-1-methyl-1H-benzimidazol-2-yl)-methyl]-benzamidine-hydrochloride 210 mg (0.4 mmol) of 4-[(5-(cyclohexylsulphimidoyl)-1-methyl-1H-benzimidazol-2-yl)-methyl]-benzamidirie-hydrochloride are dissolved in 5 ml glacial acetic acid and after the addition of 61 mg (0.6 mmol) of succinic anhydride stirred at 70° C. for 1 hour. The glacial acetic acid is distilled off, the residue triturated with ether and acetone, suction filtered and dried.

Yield: 200 mg (86% of theory), $C_{26}H_{31}N_5O_4S\times HCl$ (509.64/546.1); Mass spectrum: $(M+H)^+=510$.

EXAMPLE 217

4-[(5-phenylsulphonyl-1-methyl-1H-benzimidazol-2-yl)-methyl]-benzamidine-hydrochloride a. 4-benzenesulphonyl-phenylamine Prepared analogously to Example 1c from 4-nitrodiphenylsulphone and hydrogen/palladium on activated charcoal in methylene chloride/methanol.

Yield: 99% of theory, $R_f$ value: 0.6 (silica gel; methylene chloride/ethanol=19:1).

b. N-(4-benzenesulphonyl-phenyl)-methanesulphonamide

Prepared analogously to Example 1d from 4-benzenesulphonylphenylamine and methanesulphonic acid chloride in pyridine.

Yield: 81% of theory, $R_f$ value: 0.45 (silica gel; methylene chloride/ethanol=19:1).

c. N-(4-benzenesulphonyl-2-nitro-phenyl)-methanesulphonamide

Prepared analogously to Example 189b from N-(4-benzenesulphonyl-phenyl)-methanesulphonamide and fuming nitric acid.

Yield: 90% of theory, $R_f$ value: 0.62 (silica gel; methylene chloride/ethanol=19:1).

d. N-(4-benzenesulphonyl-2-nitro-phenyl)-N-methyl-methanesulphonamide

Prepared analogously to Example 204a from N-(4-benzenesulphonyl-2-nitro-phenyl)-methanesulphonamide, methyl iodide and sodium hydride in dimethylformamide.

Yield: 50% of theory, $R_f$ value: 0.63 (silica gel; ethyl acetate).

e. (4-benzenesulphonyl-2-nitro-phenyl)-N-methylamine 7.2 g (19.4 mmol) of N-(4-benzenesulphonyl-2-nitro-phenyl)-N-methyl-methanesulphonamide are heated to 130° C. in 70 ml conc. sulphuric acid for 15 minutes. Then the mixture is poured onto ice water, the precipitate formed is suction filtered, washed with water and dried.

Yield: 5.5 g (97% of theory), $R_f$ value: 0.73 (silica gel; ethyl acetate/petroleum ether=3:1).

f. (4-benzenesulphonyl-2-amino-phenyl)-N-methylamine

Prepared analogously to Example 1c from (4-benzenesulphonyl-2-nitro-phenyl)-methyl-amine and palladium on activated charcoal/hydrogen in methylene chloride/methanol.

Yield: 100% of theory.

g. 4-(5-benzenesulphonyl-1-methyl-1H-benzimidazol-2-ylmethyl)-benzonitrile

Prepared analogously to Example 24f from (4-benzenesulphonyl-2-amino-phenyl)-methyl-amine, 4-cyanophenylacetic acid and N,N'-carbonyldiimidazole in tetrahydrofuran/glacial acetic acid.

Yield: 80% of theory, $R_f$ value: 0.54 (silica gel; methylene chloride/ethanol=19:1).

h. 4-(5-benzenesulphonyl-1-methyl-1H-benzimidazol-2-ylmethyl)-benzamidine-hydrochloride Prepared analogously to Example 1e from 4-(5-benzenesulphonyl-1-methyl-1H-benzimidazol-2-ylmethyl)-benzonitrile and hydrochloric acid/ammonium carbonate in ethanol.

Yield: 57% of theory, $C_{22}H_{20}N_4O_2S\times HCl$ (404.5/441.0); Mass spectrum: $(M+H)^+=405$.

EXAMPLE 218

4-[(5-(N-cyclopentyl-N-(2-ethoxycarbonyl-ethylsulphonyl)-amino-1-methyl-1H-benzimidazol-2-yl)-methyl]-benzamidine-hydrochloride a. Cyclopentyl-(4-fluoro-3-nitro-phenyl)-amine 6.7 g (0.08 mol) of cyclopentanone, 12.5 g (0.08 mol) of 4-fluoro-3-nitro-aniline and 30 ml titanium-IV-isopropoxide (0.1 mol) are stirred for 30 minutes at 40° C. and for one hour at ambient temperature. After the addition of 150 ml ethanol the reaction mixture is stirred for 30 minutes and then combined batchwise with 2.4 g (0.066 mol) of sodium borohydride. After 4 hours the reaction mixture is poured onto ice water and combined with ethyl acetate. After filtration the organic phase is separated off, dried and concentrated by evaporation. The residue is chromatographed on silica gel and eluted with petroleum ether/ethyl acetate (9:1). The desired fractions are combined and concentrated by evaporation.

Yield: 8.8 g (49% of theory), $R_f$ value: 0.68 (silica gel; petroleum ether/ethyl acetate=4:1).

b. N-cyclopentyl-(4-methylamino-2-nitro-pheny)1-amine

Prepared analogously to Example 168a from cyclopentyl-(4-fluoro-3-nitrophenyl)-amine and methylamine solution.

Yield: 100% of theory, $R_f$ value: 0.44 (silica gel; methylene chloride).

c. Methyl 3-[cyclopentyl-(4-methylamino-3-nitro-phenyl)-sulphamoyl]-propionate

Prepared analogously to Example 1d from cyclopentyl-(4-methylamino-2-nitro-phenyl)-amine and methyl chlorosulphonyl-propionate in pyridine.

Yield: 36% of theory, $R_f$ value: 0.45 (silica gel; methylene chloride/ethanol 50:1).

d. Methyl 3-[cyclopentyl-(3-amino-4-methylamino-phenyl)-sulphamoyl]-propionate

Prepared analogously to Example 1c from methyl 3-[cyclopentyl-(4-methylamino-3-nitro-phenyl)-sulphamoyl]-propionate and palladium on activated charcoal/hydrogen in methylene chloride/methanol.

Yield: 100% of theory, $R_f$ value: 0.52 (silica gel; methylene chloride/ethanol 50:1).

e. 4-[(5-(N-cyclopentyl-N-(2-ethoxycarbonyl-ethylsulphonyl)-amino)-1-methyl-1H-benzimidazol-2-yl)-methyl]-benzonitrile Prepared analogously to Example 24f from methyl 3-[(3-amino-4-methylamino-phenyl)-cyclopentyl-sulphamoyl]-propionate, 4-cyanophenylacetic acid and N,N'-carbonyldiimidazole in tetrahydrofuran/glacial acetic acid.

Yield: 72% of theory, $R_f$ value: 0.41 (silica gel; methylene chloride/ethanol=50:1).

f. 4-[(5-(N-cyclopentyl-N-(2-ethoxycarbonyl-ethylsulphonyl)-amino)-1-methyl-1H-benzimidazol-2-yl)-methyl]-benzamidine-hydrochloride Prepared analogously to Example 1e from 4-[(5-(N-cyclopentyl-N-(2-ethoxycarbonyl-ethylsulphonyl)-amino)-1-methyl-1H-benzimidazol-2-yl)-methyl]-benzonitrile and hydrochloric acid/ammonium carbonate in ethanol.

Yield: 76% of theory, $C_{26}H_{33}N_5O_4S \times HCl$ (511.66/548.12); Mass spectrum: $(M+H)^+=512$.

EXAMPLE 219

4-[(5-(1-methoxycarbonylmethyl-4-isobutyl-imidazol-5-yl)-1-methyl-1H-benzimidazol-2-yl)-methyl]-benzamidine-hydrochloride a. 1-(4-Chlorophenyl)-4-methyl-pentan-1-one To a suspension of 66.7 g (0.5 mol) of aluminium chloride in 300 ml chlorobenzene is added a solution of 56 g (0.42 mol) of isocaproic acid chloride in 20 ml chlorobenzene dropwise. The solution is stirred for 3 hours at 50° C. and then concentrated by evaporation. The residue is carefully poured onto ice water, acidified with hydrochloric acid and extracted with ethyl acetate. The organic phases are washed with water, dried, concentrated by evaporation and the residue obtained is chromatographed on silica gel with petroleum ether/methylene chloride (2:8).

Yield: 72.5 g (83% of theory), $R_f$ value: 0.6 (silica gel; methylene chloride).

b. 2-Bromo-1-(4-chloro-phenyl)-4-methyl-pentan-1-one 55 g (0.344 mol) of bromine are added dropwise to a solution of 72.5 g (0.344 mol) of 1-(4-chloro-phenyl)-4-methyl-pentan-1-one in 300 ml dioxan and 300 ml methylene chloride until decolorisation is just starting. After 10 minutes at ambient temperature the solvent is evaporated off.

Yield: 99 g (100% of theory), $R_f$ value: 0.76 (silica gel; methylene chloride).

c. 5-(4-Chloro-phenyl)-4-isobutyl-1H-imidazole 38 g (0.43 mol) of 2-bromo-1-(4-chloro-p)henyl)-4-methylpentan-1-one are heated to 160° C. in 400 ml formamide for 10 hours. After 12 hours at ambient temperature the mixture is diluted with water and combined with ammonia. The precipitate formed is filtered off, washed with water and ether.

Yield: 19 g (66% of theory), $R_f$ value: 0.5 (silica gel; methylene chloride/methanol=9:1).

d. Ethyl [5-(4-chloro-phenyl)-4-isobutyl-imidazol-1-yl]-acetate 19 g (0.085 mol) of 5-(4-chloro-phenyl)-4-isobutyl-1H-imidazole are dissolved in 500 ml acetone and after the addition of 41.5 g (0.3 mol) of potassium carbonate and 16.7 g (0.13 mol) of ethyl bromoacetate the mixture is refluxed for 16 hours. Then it is filtered to remove the insoluble matter and the mother liquor is concentrated by evaporation. The residue is chromatographed on silica gel and eluted with methylene chloride/methanol (80:1). The desired fractions are combined and concentrated by evaporation.

Yield: 5.4 g (20% of theory), $R_f$ value: 0.54 (silica gel; methylene chloride/methanol=9:1).

e. [5-(4-chloro-phenyl)-4-isobutyl-imidazol-1-yl]-acetic acid 4.8 g (0.015 mol) of ethyl [5-(4-chloro-phenyl)-4-isobutyl-imidazol-1-yl]-acetate are dissolved in 15 ml ethanol and 40 ml water and after the addition of 2.0 g (0.05 mol) of sodium hydroxide stirred for 2 hours at ambient temperature. The alcohol is distilled off, the residue diluted with water and adjusted to pH 5 with hydrochloric acid. The precipitate formed is filtered off, washed with water and dried.

Yield: 3.9 g (89% of theory), $R_f$ value: 0.38 (silica gel; methylene chloride/methanol=5:1).

f. [5-(4-chloro-3-nitro-phenyl)-4-isobutyl-imidazol-1-yl]-acetic acid

Prepared analogously to Example 189b from [5-(4-chlorophenyl)-4-isobutyl-imidazol-1-yl]-acetic acid and fuming nitric acid.

Yield: 75% of theory, $R_f$ value: 0.4 (silica gel; methylene chloride/methanol=5:1).

g. [4-isobutyl-5-(4-methylamino-3-nitro-phenyl)-imidazol-1-yl-acetic acid

Prepared analogously to Example 7b from [5-(4-chloro-3-nitrophenyl)-4-isobutyl-imidazol-1-yl]-acetic acid and methylamine solution (40%).

Yield: 99% of theory, $R_f$ value: 0.42 (Reversed phase, RP 18, methanol/5% sodium chloride solution=6:4).

h. ethyl [4-isobutyl-5-(4-methylamino-3-nitro-phenyl)-imidazol-1-yl]-acetate 100 ml absolute ethanol is saturated with hydrochloric acid gas and after the addition of 3.6 g (0.011 mol) of [4-isobutyl-5-(4-methylamino-3-nitro-phenyl)-imidazol-1-yl]-acetic acid stirred for 3 hours at ambient temperature. The solution is concentrated in vacuo by evaporation, the residue is dissolved in water, made basic with ammonia and extracted with ethyl acetate. The combined organic extracts are dried and concentrated by evaporation.

Yield: 2.9 g (73% of theory), $R_f$ value: 0.64 (silica gel; methylene chloride/methanol=9:1).

i. 4-[(5-(1-methoxycarbonylmethyl-4-isobutyl-imidazol-5-yl)-1-methyl-1H-benzimidazol-2-yl)-methyl]-benzonitrile Prepared analogously to Example 24f from [4-isobutyl-5-(4-methylamino-3-nitro-phenyl)-imidazol-1-yl]-acetic acid, N,N'-carbonyldiimidazole and 4-cyanophenylacetic acid in tetrahydrofuran/glacial acetic acid.

Yield: 37% of theory, $R_f$ value: 0.67 (silica gel; methylene chloride/methanol=9:1).

k. 4-[(5-(1-methoxycarbonylmethyl-4-isobutyl-imidazol-5-yl)-1-methyl-1H-benzimidazol-2-yl)-methyl]-benzamidine-hydrochloride Prepared analogously to Example 1e from 4-[(5-(1-methoxycarbonylmethyl-4-isobutyl-imidazol-5-yl)-1-methyl-1H-benzimidazol-2-yl)-methyl]-benzonitrile and hydrochloric acid/ammonium carbonate in methanol.

Yield: 29% of theory, $C_{26}H_{30}N_6O_2 \times HCl$ (458.57/495.038); Mass spectrum: $(M+H)^+ = 459$; $(M+2H)^{++} = 230$.

EXAMPLE 220

4-[(5-(N-cyclopentyl-tetrazol-5-yl-methylcarbonylamino)-1-methyl-1H-benzimidazol-2-yl)-methyl]-benza-midine-hydrochloride Prepared analogously to Example 1e from 4-[(5-(N-cyclopentyltetrazol-5-yl-methylcarbonylamino)-1-methyl-1H-benzimidazol-2-yl)-methyl]-benzonitrile and hydrochloric acid/ammonium carbonate in ethanol.

Yield: 63% of theory, $C_{24}H_{27}N_9O \times HCl$ (457.55/494.01); Mass spectrum: $(M+H)^+ = 458$.

EXAMPLE 221

4-[(5-(N-cyclohexyl-methanesulphonylamiino)-1-methyl-1H-benzimidazol-2-yl)-methyl]-benzamidine-hydrochloride Prepared analogously to Example 1e from 4-[(5-(N-cyclohexyl-methanesulphonylamino)-1-methyl-1H-benzmidazol-2-yl)-methyl]-benzonitrile and hydrochloric acid/ammonium carbonate in ethanol.

Yield: 89% of theory, $C_{23}H_{29}N_5O_2S \times HCl$ (439.59/476.06); Mass spectrum: $(M+H)^+ = 440$.

EXAMPLE 222

4-[(5-(N-cyclopentyl-3-carboxypropionylamino)-1-methyl-1H-benzimidazol-2-yl)-methyl]-benzanidine-hydrochloride Prepared analogously to Example 13 from 4-[(5-(N-cyclopentyl-3-ethoxycarbonylpropionylamino)-1-methyl-1H-benzimidazol-2-yl)-methyl]-benzamidine-hydrochloride and sodium hydroxide in ethanol.

Yield: 52% of theory, $C_{25}H_{29}N_6O \times HCl$ (447.55/484.02); Mass spectrum: $(M+H)^+ = 448$; $(M+Na)^+ = 470$; $(M+H+Na)^{++} = 235.6$.

EXAMPLE 223

4-[(5-(N-phenyl-methylaminocarbonyl)-1,7-dimethyl-1H-benzimidazol-2-yl)-methyl]-benzamidine-hydrochloride Prepared analogously to Example 1e from 4-[(5-(N-phenylmethylaminocarbonyl)-1,7-dimethyl-1H-benzimidazol-2-yl)-methyl]-benzonitrile and hydrochloric acid/ammonium carbonate in ethanol.

Yield: 56% of theory, $C_{25}H_{25}N_5O \times HCl$ (411.5/448.0); Mass spectrum: $M^+ = 411$.

EXAMPLE 224

4-[(5-(N-cyclopentyl-ethoxycarbonylmethyloxyacetylamino)-1-methyl-1H-benzimidazol-2-yl)-methyl]-benzalmidine-hydrochloride Prepared analogously to Example 1e from 4-[(5-(N-cyclopentyl-ethoxycarbonylmethyloxyacetylamino)-1-methyl-1H-benzimidazol-2-yl)-methyl]-benzonitrile and hydrochloric acid/ammonium carbonate in ethanol.

Yield: 68% of theory, $C_{27}H_{33}N_5O_4 \times HCl$ (491.60/528.07); Mass spectrum: $M^+ = 492$; $(M+2H)^{++} = 246.6$; $(M+H+Na)^{++} = 235.6$.

EXAMPLE 225

4-[(5-(N-cyclopentyl-carboxymethyloxyacetylamino)-1-methyl-1H-benzimidazol-2-yl)-methyl]-benzamidine-hydrochloride Prepared analogously to Example 13 from 4-[(5-(N-cyclopentyl-ethoxycarbonylmethyloxyacetylamino)-1-Methyl-1H-benzimidazol-2-yl)-methyl-benzamidine-hydrochloride and sodium hydroxide in ethanol.

Yield: 98% of theory, $C_{25}H_{29}N_5O_4 \times HCl$ (463.55/500.02); Mass spectrum: $(M+H)^+ = 464$; $(M+2H)^{++} = 232.7$; $(M+H+Na)^{++} = 243.7$.

EXAMPLE 226

4-[(5-(2,3-dihydroindol-1-yl-sulphonyl)-1-methyl-1H-benzimidazol-2-yl)-methyl]-benzamidine-hydrochloride Prepared analogously to Example 1e from 4-[(5-(2,3-dihydroindol-1-yl-sulphonyl)-1-methyl-1H-benzimidazol-2-yl)-methyl]-benzonitrile and hydrochloric acid/ammonium carbonate in ethanol.

Yield: 32% of theory, $C_{24}H_{23}N_5O_2S \times HCl$ (445.545/482.00); Mass spectrum: $(M+H)^+ = 446$.

EXAMPLE 227

4-[(5-(1,3-dihydro-isoindol-2-yl-sulphonyl)-1-methyl-1H-benzimidazol-2-yl)-methyl]-benzamidine-hydrochloride Prepared analogously to Example 1e from 4-[(5-(1,3-dihydro-isoindol-2-yl-sulphonyl)-1-methyl-1H-benzimidazol-2-yl)-methyl]-benzonitrile and hydrochloric acid/ammonium carbonate in ethanol.

Yield: 32% of theory, $C_{24}H_{23}N_5O_2S \times HCl$ (445.545/482.00); Mass spectrum: $(M+H)^+ = 446$.

EXAMPLE 228

4-[[5-(1-(N-ethoxycarbonylmethyl-methylaminocarbonyl)-cyclopropan-1-yl)-1-methyl-1H-benzimidazol-2-yl]-methyl]-benzamidine-hydrochloride a. Diethyl 2-acetylamino-2-(4-cyano-benzyl)-malonate 3 g sodium are dissolved in 100 ml ethanol and then combined with a solution of 27.7 g (0.127 mol) of diethyl acetamidomalonate and 6.4 g (0.04 mol) of potassium iodide in 200 ml dioxan. Then a solution of 25 g (0.127 mol) of 4-cyanobenzylbromide in 200 ml dioxan is added dropwise and the reaction mixture is refluxed for 3 hours. After 12 hours at ambient temperature it is filtered, the filtrate is concentrated by evaporation, the residue is crystallised with petroleum ether and suction filtered.

Yield: 41.1 g (97% of theory), $R_f$ value: 0.62 (silica gel; methylethylketone/xylene 1:1); Melting point: 177–178° C.

b. 2-amino-3-(4-cyano-phenyl)-propionic acid 40 g (0.12 mol) of diethyl 2-acetylamino-2-(4-cyanobenzyl)-malonate are dissolved in 110 ml glacial acetic acid, 50 ml concentrated hydrochloric acid and 135 ml water and refluxed for 8 hours. The solution is concentrated by evaporation in vacuo, the residue is crystallised with isopropanol/ether, suction filtered and dried.

Yield: 18.6 g (68% of theory), $R_f$ value: 0.37 (silica gel; methylethylketone/xylene 1:1).

c. 4-(5-oxo-2-trifluoromethyl-4,5-dihydro-oxazol-4-yl) methyl-benzonitrile 5.7 g (2.5 mmol) of 2-amino-3-(4-cyano-phenyl)-propionic acid are dissolved in 26.3 g (12.5 mmol) of trifluoracetic anhydride and refluxed for 24 hours. Then the solution is concentrated by evaporation in vacuo, the residue is chromatographed on silica gel and eluted with methylene chloride. The desired fractions are combined and concentrated by evaporation.

Yield: 3.6 g (53% of theory), $R_f$ value: 0.71 (silica gel; methylethylketone/xylene=1:1).

d. 4-(2-oxo-propionic acid)-benzonitrile 3.5 g (0.013 mol) of 4-(5-oxo-2-trifluoromethyl-4,5-dihydro-oxazol-4-ylmethyl)-benzonitrile are dissolved in 20 ml of 70% trifluoracetic acid and stirred for 24 hours at ambient temperature. The solid formed is suction filtered, washed with water and dried.

Yield: 1.8 g (75% of theory), $R_f$ value: 0.2 (silica gel; methylene chloride/ethanol=9:1).

e. 1-(4-Chloro-3-nitrophenyl)-cyclopropanecarboxylic acid 350 ml fuming nitric acid are combined batchwise at –25 to –30° C. with 50.0 g (0.21 mol) of 1-(4-chloro-phenyl)-cyclopropanecarboxylic acid. After it has all been added the mixture is stirred for a further 15 minutes at –25° C. and then poured onto ice. The substance precipitated is suction filtered, washed with water and dried.

Yield: 58.5 g (95% of theory), $R_f$ value: 0.43 (silica gel; methylene chloride/methanol=9.5:0.5);

f. 1-(4-methylamino-3-nitro-phenyl)-cyclopropanecarboxylic acid 20.0 g (0.083 mol) of 1-(4-chloro-3-nitro-phenyl)-cyclopropanecarboxylic acid are heated to 180° C. with 100 ml methylamine solution (40%) in a glass bomb for 5 hours. The solution is concentrated by evaporation in vacuo, the residue is taken up in water and acidified with glacial acetic acid. The substance precipitated is suction filtered, washed with water and dried.

Yield: 16.9 g (93% of theory), $R_f$ value: 0.59 (silica gel; methylene chloride/methanol 9:1).

g. 1-(3-amino-4-methylamino-phenyl)-cyclopropanecarboxylic acid 3.2 g (13.5 mmol) of 1-(4-methylamino-3-nitro-phenyl)-cyclopropanecarboxylic acid are dissolved in 120 ml ethanol and after the addition of 0.5 g palladium on activated charcoal hydrogenated with hydrogen for 90 minutes. The catalyst is filtered off, the solution is evaporated down.

Yield: 2.8 g (100% of theory), $R_f$ value: 0.41 (silica gel; methylene chloride/methanol=9:1).

h. 4-[(5-(1-carboxy-cyclopropan-1-yl)-1-methyl-1H-benzimidazol-2-yl)-methyl]-benzonitrile and 4-[(6-(1-carboxy-cyclopropan-1-yl)-1-methyl-2-oxo-1,2-dihydroquinoxalin-3-yl)-methyl]-benzonitrile 2.6 g (13.5 mmol) of 4-(2-oxo-propionic acid)-benzonitrile and 2.8 g (13.5 mmol) of 1-(3-amino-4-methylamino-phenyl)-cyclopropanecarboxylic acid are placed in 100 ml ethanol and refluxed for 5 hours under a nitrogen current. The reaction mixture is stirred for 72 hours at ambient temperature and then half the solvent is distilled off. The substance precipitated is suction filtered and dried.

Yield: 1.3 g (28% of theory) of 4-[(5-(1-carboxy-cyclopropan-1-yl)-1-methyl-1H-benzimidazol-2-yl)-methyl]-benzonitrile, $R_f$ value: 0.43 (silica gel; methylene chloride/ethanol=9:1); $C_{20}H_{17}N_3O_2$ (331.38); Mass spectrum: $M^+$=331.

The filtrate is evaporated down and combined with ether. The precipitate formed is suction filtered and dried.

Yield: 1.0 g (21% of theory), 4-[(6-(1-carboxy-cyclopropan-1-yl)-1-methyl-2-oxo-1,2-dihydroquinoxalin-3-yl)-methyl]-benzonitrile; $R_f$ value: 0.50 (silica gel; methylene chloride/ethanol=9:1); $C_{21}H_{17}N_3O_3$ (359.38); Mass spectrum: $M^+$=359.

i. 4-[[5-(1-(N-ethoxycarbonylmethyl-methylaminocarbonyl)-cyclopropan-1-yl)-1-methyl-1H-benzimidazol-2-yl]-methyl]-benzonitrile 0.5 g (1.5 mmol) of 4-[(5-(1-carboxy-cyclopropyl)-1-methyl-1H-benzimidazol-2-yl)-methyl]-benzonitrile are dissolved in 5 ml dimethylformamide and after the addition of 0.48 g (1.5 mmol) of O-(benzotriazol-1-yl)-N,N,N'N'-tetramethyluroniumtetrafluoroborate, 0.46 ml N-methylmorpholine and 0.3 g sarcosine ethylester hydrochloride the mixture is stirred for 20 hours at ambient temperature. The suspension is diluted with water and extracted with ethyl acetate. The combined organic extracts are washed with sodium hydrogen carbonate solution and sodium chloride solution, dried and concentrated by evaporation. The residue is chromatographed on silica gel and eluted with ethyl acetate/1% ammonia. The desired fractions are combined and concentrated by evaporation.

Yield: 370 mg (58% of theory), $R_f$ value: 0.61 (silica gel; methylene chloride/ethanol=9:1).

k. 4-[[5-(1-(N-ethoxycarbonylmethyl-methylaminocarbonyl)-cyclopropan-1-yl)-1-methyl-1H-benzimidazol-2-yl]-methyl]-benzamidine-hydrochloride Prepared analogously to Example 1e from 4-[[5-(1-(N-ethoxycarbonylmethyl-methylaminocarbonyl)-cyclopropan-1-yl)-1-methyl-1H-benzimidazol-2-yl]-methyl]-benzonitrile and hydrochloric acid/ammonium carbonate in ethanol.

Yield: 93% of theory, $C_{25}H_{29}N_5O_3 \times HCl$ (447.55/484.02); Mass spectrum: $(M+H)^+$=448.

EXAMPLE 229

4-[(5-(1-(pyrrolidin-1-yl-carbonyl)-cyclopropan-1-yl)-1-methyl-1H-benzimidazol-2-yl)-methyl]-benzamidine-hydrochloride Prepared analogously to Example 1e from 4-[(5-(1-(pyrrolidin-1-yl-carbonyl)-cyclopropan-1-yl)-1-methyl-1H-benzimidazo-2-yl)-methyl]-benzonitrile and hydrochloric acid/ammonium carbonate in ethanol.

Yield: 96% of theory, $C_{24}H_{27}N_5O \times HCl$ (401.52/437.99); Mass spectrum: $(M+H)^+$=402.

EXAMPLE 230

4-[(5-(1-(N-carboxymethyl-methylaminocarbonyl)-cyclopropan-1-yl)-1-methyl-1H-benzimidazol-2-yl)-methyl]-benzamidine-hydrochloride Prepared analogously to Example 13 from 4-[(S-(1-(N-ethoxycarbonylmethyl-methylaminocarbonyl)- cyclopropan-1-yl)-1-methyl-1H-benzimidazol-2-yl)-methyl]-benzamidine-hydrochloride and sodium hydroxide solution in ethanol.

Yield: 86% of theory, $C_{23}H_{25}N_5O_3 \times HCl$ (419.49/455.96); Mass spectrum: $(M+H)^+=420$; $(M+Na)^+=442$.

EXAMPLE 231

4-[(5-(pyrrolidin-1-yl-carbonyl-(ethoxycarbonylmethyl)-methylene)-1-methyl-1H-benzimidazol-2-yl)-methyl]-benzamidine-hydrochloride a. 2-(4-chloro-phenyl)-1-pyrrolidin-1-yl-ethanone Prepared analogously to Example 230i from p-chlorophenylacetic acid, pyrrolidine, O-(benzotriazol-1-yl)-N,N,N'N'-tetramethyl-uranium tetrafluoroborate and N-methylmorpholine in dimethyl-formamide.

Yield: 75% of theory, $R_f$ value: 0.5 (silica gel; methylene chloride/ethanol 19:1).

b. ethyl 3-(4-chloro-phenyl)-4-oxo-4-pyrrolidin-1-yl-butyrate 16.8 g (0.075 mol) of 2-(4-chloro-phenyl)-1-pyrrolidin-1-yl-ethanone are dissolved in 175 ml dimethylsulphoxide and after the addition of 8.9 g (0.08 mol) of potassium tert.butoxide stirred for 15 minutes at ambient temperature. After the addition of 18.1 ml (0.085 mol) of ethyl iodoacetate the reaction mixture is stirred for 45 hours at ambient temperature. The solution is poured onto ice water and extracted with ethyl acetate. The combined organic extracts are washed with sodium chloride solution, dried and concentrated by evaporation. The residue is chromatographed on silica gel, initially eluting with petroleum ether and later with petroleum ether/ethyl acetate (8:2 and 1:1). The desired fractions are combined and concentrated by evaporation.

Yield: 11.0 g (48% of theory), $R_f$ value: 0.73 (silica gel; ethyl acetate/petroleum ether=7:3).

c. Ethyl 3-(4-chloro-3-nitro-phenyl)-4-oxo-4-pyrrolidin-1-yl-butyrate and ethyl 3-(4-chloro-2-nitro-phenyl)-4-oxo-4-pyrrolidin-1-yl-butyrate To 40 ml fuming nitric acid, 7.8 g (0.025 mol) of ethyl 3-(4-chloro-phenyl)-4-oxo-4-pyrrolidin-1-yl-butyrate are added batchwise at −30° C. The solution is stirred for 15 minutes at −30° C. and then poured onto ice water. The supernatant water is decanted off, the residue is taken up in ethyl acetate and sodium hydrogen carbonate solution and extracted. The combined organic extracts are dried and concentrated by evaporation.

Yield: 7.9 g (89% of theory), ethyl 3-(4-chloro-3-nitro-phenyl)-4-oxo-4-pyrrolidin-1-yl-butyrate and ethyl 3-(4-chloro-2-nitro-phenyl)-4-oxo-4-pyrrolidin-1-yl-butyrate as a mixture of isomers in the ratio 1:9. $R_f$ value: 0.68 (silica gel; methylene chloride/ethanol=19:1).

d. Ethyl 3-(4-methylamino-3-nitro-phenyl)-4-oxo-4-pyrrolidin-1-yl-butyrate 7.9 g (23 mmol) of ethyl 3-(4-chloro-3-nitro-phenyl)-4-oxo-4-pyrrolidin-1-yl-butyrate and ethyl 3-(4-chloro-2-nitrophenyl)-4-oxo-4-pyrrolidin-1-yl-butyrate (isomer mixture) are dissolved in 65 ml ethanol and after the addition of 5 ml methylamine the mixture is heated to 80° C. for 1 hour in a pressure vessel. After cooling to ambient temperature and the addition of 5 g silica gel the mixture is evaporated to dryness. The residue is chromatographed on silica gel, eluting initially with petroleum ether and later with petroleum ether/ethyl acetate (9:1).

Yield: 330 mg (3.6% of theory), $R_f$ value: 0.58 (silica gel; methylene chloride/ethanol=19:1). $C_{17}H_{23}N_3O_5$ (349.4); Mass spectrum: $M^+=349$.

e. Ethyl 3-(4-methylamino-3-amino-phenyl)-4-oxo-4-pyrrolidin-1-yl-butyrate 300 mg (8.6 mmol) of ethyl 3-(4-methylamino-3-nitrophenyl)-4-oxo-4-pyrrolidin-1-yl-butyrate are dissolved in 60 ml ethyl acetate and 10 ml methanol and after the addition of 600 mg Raney nickel the mixture is hydrogenated with hydrogen for 2.5 hours at ambient temperature. The catalyst is filtered off and the filtrate is evaporated down.

Yield: 260 mg (94% of theory), $R_f$ value: 0.28 (silica gel; methylene chloride/ethanol=19:1).

f. 4-[(5-(pyrrolidin-1-yl-carbonyl-(ethoxycarbonylmethyl)-methylene)-1-methyl-1H-benzimidazol-2-yl)-methyl]-benzonitrile and
4-[(5-(pyrrolidin-1-yl-carbonyl-(ethoxycarbonylmethyl)-methylene)-1-methyl-2-oxo-1,2-dihydroquinoxalin-3-yl)-methyl]-benzonitrile 260 mg (0.81 mmol) of ethyl 3-(3-amino-4-methylamino-phenyl)-4-cyclopentyl-4-oxo-butyrate and 189 mg (1.0 mmol) of 3-(4-cyano-phenyl)-2-oxo-propionic acid are refluxed in 10 ml ethanol for 1 hour. The reaction solution is combined with 5 g silica gel and evaporated to dryness. The residue is chromatographed on silica gel, eluting initially with petroleum ether and later with petroleum ether/ethyl acetate 9:1 and 8:2. The desired fractions are combined and concentrated by evaporation.

Yield: 100 mg (28% of theory), 4-[(5-(pyrrolidin-1-yl-carbonyl-(ethoxycarbonylmethyl)methylene)-1-methyl-1H-benzimidazol-2-yl)-methyl]-benzonitrile: $R_f$ value: 0.28 (silica gel; methylene chloride/ethanol=19:1); $C_{26}H_{28}N_4O_3$ (444.5); Mass spectrum: $M^+=444$; and 200 mg (52% of theory) 4-[(5-(pyrrolidin-1-yl-carbonyl-(ethoxycarbonylmethyl)methylene)-1-methyl-2-oxo-1,2-dihydroquinoxalin-3-yl)-methyl]-benzonitrile, $C_{27}H_{28}N_4O_4$ (472.5); Mass spectrum: $M^+=472$.

g. 4-[(5-(pyrrolidin-1-yl-carbonyl-(ethoxycarbonylmethyl)-methylene)-1-methyl-1H-benzimidazol-2-yl)-methyl]-benzamidine-hydrochloride Prepared analogously to Example 1e from ethyl 3-[3-(4-cyanobenzyl)-1-methyl-2-oxo-1,2-dihydro-quinoxalin-6-yl]-4-cyclopentyl-4-oxo-butyrate and hydrochloric acid/ammonium carbonate in ethanol.

Yield: 21% of theory, $C_{26}H_{31}N_5O_3 \times HCl$ (461.6/498.05); Mass spectrum: $(M+H)^+=462$.

EXAMPLE 232

4-[(5-(1-(pyridine-2-yl-carbonyl)-cyclopropan-1-yl)-1-methyl-1H-benzimidazol-2-yl)-methyl]-benzamidine-hydrochloride a. [1-(4-chlorophenyl)-cyclopropan-1-yl]-pyridin-2-yl-methanone To a solution of 19.6 g (0.124 mol) of 2-bromopyridine in 200 ml tetrahydrofuran, a solution of 85 ml (0.141 mol) of n-butyllithium (15% in hexane) is added dropwise at −45° C. After 1 hour at −45° C. a solution of 21.2 g (0 119 mol) of 1-(4-chlorophenyl)-1-cyclopropanecarbonitrile in 50 ml tetrahydrofuran is added dropwise. After heating to ambient temperature the mixture is poured onto ice water, adjusted to pH 5 with formic acid and extracted with ethyl acetate. The organic extracts are washed with sodium chloride solution, dried and concentrated by evaporation. The residue is chromatographed on silica gel and eluted with petroleum ether/ethyl acetate (19:1). The desired fractions are combined and concentrated by evaporation.

Yield: 7.2 g (23% of theory), $R_f$ value: 0.71 (silica gel; methylene chloride/ethanol=19:1).

b. [1-(4-chloro-3-nitro-phenyl)-cyclopropan-1-yl]-pyridin-2-yl-methane

Prepared analogously to Example 231c from [1-(4-chlorophenyl)-cyclopropan-1-yl]-pyridin-2-yl-methanone and fuming nitric acid.

Yield: 28% of theory), $R_f$ value: 0.73 (silica gel; petroleum ether/ethyl acetate=1:1).

c. [1-(4-methylamino-3-nitro-phenyl)-cyclopropan-1-yl]-pyridin-2-yl-methanone

Prepared analogously to Example 231d from [1-(4-chloro-3-nitro-phenyl)-cyclopropan-1-yl]-pyridin-2-yl-methanone and methylamine in isopropanol.

Yield: 60% of theory.

d. 4-[5-(1-(hydroxy-pyridin-2-yl-methyl)-cyclopropan-1-yl)-1-methyl-1H-benzimidazol-2-yl)methyl]-benzonitrile Prepared analogously to Example 231f and Example 1c from [1-(4-methylamino-3-nitro-phenyl)-cyclopropan-1-yl]-pyridin-2-yl-methanone, hydrogen/palladium on activated charcoal and 3-(4-cyano-phenyl)-2-oxo-propionic acid in ethanol.

Yield: 10% of theory, $C_{25}H_{22}N_4O$ (394.5); Mass spectrum: $M^+$=394.

e. 4-[5-(1-(pyridin-2-yl-carbonyl)-cyclopropan-1-yl)-1-methyl-1H-benzimidazol-2-yl)methyl]-benzonitrile 415 mg (1.0 mmol) of 4-[5-(1-(hydroxy-pyridin-2-yl-methyl)-cyclopropan-1-yl]-1-methyl-1H-benzimidazol-2-yl)methyl]-benzonitrile are dissolved in 50 ml methylene chloride and after the addition of 2.5 g manganese dioxide stirred for 16 hours at ambient temperature. The precipitate is filtered off and the mother liquor is concentrated by evaporation. The residue is chromatographed on silica gel, eluting initially with methylene chloride and later with methylene chloride/ethanol (50:1 and 25:1). The desired fractions are combined and concentrated by evaporation.

Yield: 285 mg (69% of theory), $R_f$ value: 0.63 (silica gel; methylene chloride/ethanol=19:1).

f. 4-[(5-(1-(pyridin-2-yl-carbonyl)cyclopropan-1-yl-1-methyl-1H-benzimidazol-2-yl)-methyl]-benzamidine-hydrochloride Prepared analogously to Example 1e from 4-[5-(1-(pyridin-2-yl-carbonyl)-cyclopropan-1-yl)-1-methyl-1H-benzimidazol-2-yl)-methyl]-benzonitrile and hydrochloric acic/ammonium carbonate in ethanol.

Yield: 41% of theory, $C_{25}H_{23}N_5O$ (409.5/445.96); Mass spectrum: $(M+H)^+$=410.

EXAMPLE 233

4-[(5-benzenesulphonylamino-benzoxazol-2-yl)-methyl]-benzamidine-hydrochloride a. 4-benzenesulphonylamino-2-nitrophenol Prepared analogously to Example 1d from 4-hydroxy-3-nitroaniline and benzenesulphonic acid chloride in pyridine.

Yield: 45% of theory, $R_f$ value: 0.47 (silica gel; methylene chloride/ethanol=19:1).

b. 4-benzenesulphonylamino-2-amino-phenol

Prepared analogously to Example 1c from 4-benzenesulphonylamino-2-nitrophenol, palladium on activated charcoal in methanol and hydrogen.

Yield: 80% of theory, $R_f$ value: 0.26 (silica gel; methylene chloride/ethanol=19:1).

c. 4-[(5-benzenesulphonylamino-benzoxazol-2-yl)-methyl]-benzonitrile

Prepared analogously to Example 24f from 4-benzenesulphonylamino-2-amino-phenol, N,N'-carbonyldiimidazole in tetrahydrofuran and sulpholane.

Yield: 9.8% of theory, $R_f$ value: 0.38 (silica gel; methylene chloride/ethanol=19:1).

d. 4-[(5-benzenesulphonylamino-benzoxazol-2-yl)-methyl]-benzamidine-hydrochloride Prepared analogously to Example 1e from 4-[(5-benzenesulphonylamino-benzoxazol-2-yl)-methyl]-benzonitrile and hydrochloric acid/ammonium carbonate in ethanol.

Yield: 56% of theory, $C_{21}H_{18}N_4O_3S \times HCl$ (406.5/442.9); Mass spectrum: $(M+H)^+$=407; $(M+Na)^+$=439; $(2\ M+H)^+$=813.

EXAMPLE 234

4-[(5-(N-ethoxycarbonylmethyl-quinolin-8-yl-sulphonylamino)-benzothiazol-2-yl)-methyl]-benzamidine-hydrochloride a. 4-nitro-2-(4-cyanophenylmethylcarbonilamino)-fluorobenzene 7.0 g (44.8 mmol) of 4-cyanophenylacetic acid are dissolved in 200 ml methylene chloride and 4 drops of dimethylformamide and after the addition of 14 ml thionylchloride the mixture is refluxed for 30 minutes. The solvent is evaporated to dryness in vacuo, the residue is dissolved in 20 ml chlorobenzene and refluxed for 15 minutes with 7.0 g (44.8 mmol) of 2-fluoro-5-nitro-aniline. The solution is cooled, the precipitated substance is suction filtered and dried.

Yield: 10.9 g (81.5% of theory), $R_f$ value: 0.18 (silica gel; ethyl acetate/petroleum ether=3:7).

b. 4-(5-nitro-benzothiazol-2-yl)-methyl-benzonitrile 10.9 g (36.5 mmol) of 4-nitro-2-(4-cyancphenyl-methylcarbonylamino)-fluorobenzene, 7.6 9 2,4-bis-(4-methoxyphenyl)-1,3-di-thio-2,4-diphosphetan-2,4-disulphide and 300 ml toluene are refluxed for 18 hours. The solvent is distilled off, the residue is chromatographed on silica gel and extracted with methylene chloride. The desired fractions are combined and concentrated by evaporation.

Yield: 8.2 g (76% of theory), $R_f$ value: 0.44 (silica gel; ethyl acetate/petroleum ether=3:7).

c. 4-(5-amino-benzothiazol-2-yl)-methyl-benzonitrile 8.8 g (29.8 mmol) of 4-(5-nitro-benzothiazol-2-ylmethyl)-benzonitrile are dissolved in 300 ml pyridine, combined with 15.4 g sodium dithionite and 60 ml water at 50° C. and heated to 95° C. for 1 hour. The pyridine is distilled off, the residue is combined with ice water, the precipitated product is suction filtered and dried.

Yield: 6.9 g (87% of theory), Melting point: 178–180° C. $R_f$ value: 0.2 (silica gel; ethyl acetate/petroleum ether=1:1).

d. 4-[(5-(quinolin-8-yl-sulphonylamino)-benzothiazol-2-yl)-methyl]-benzonitrile

Prepared analogously to Example 1d from 4-(5-amino-benzothiazol-2-yl)-methyl-benzonitrile and quinolin-8-sulphonylchloride in pyridine.

Yield: 77% of theory, $R_f$ value: 0.25 (silica gel; ethyl acetate/petroleum ether/ammonia=1:1:0.01);

e. 4-[(5-(N-ethoxycarbonylmethyl-quinolin-8-yl-sulphonylamino)-benzthiazol-2-yl)-methyl]-benzonitrile-hydrochloride 3.8 g (8.3 mmol) of 4-[(5-(quinolin-8-yl-sulphonylamino)-benzothiazol-2-yl)-methyl]-benzonitrile, 5.7 g (41.6 mmol) of potassium carbonate, 2.3 ml (20.8 mmol) of ethyl bromoacetate and 1.4 ml (9.2 mmol) of 1,8-diazabicyclo[5.4.0]undec-7-ene are dissolved in 200 ml acetone and refluxed for 1 hour. The insoluble matter is filtered off and the mother liquor is concentrated by evaporation. The residue is chromatographed on silica gel and eluted with ethyl acetate/petroleum ether (1:9, 2:8 and 3:7). The desired fractions are combined and concentrated by evaporation.

Yield: 1.3 g (29% of theory), $R_f$ value: 0.45 (silica gel; ethyl acetate/petroleum ether/ammonia=1:1:0.01).

f. 4-[(5-(N-ethoxycarbonylmethyl-quinolin-8-yl-sulphonylamino)-benzthiazol-2-yl)-methyl]-benzamidine-hydrochloride Prepared analogously to Example 1e from 4-[(5-(N-ethoxycarbonylmethyl-quinolin-8-yl-sulphonylamino)-benzthiazol-2-yl)-methyl]-benzonitrile and hydrochloric acid/ammonium carbonate in ethanol.

Yield: 59% of theory, $C_{28}H_{25}N_5O_4S_2 \times HCl$ (559.67/596.13); Mass spectrum: $(M+H)^+=560$.

EXAMPLE 235

4-[(5-(N-carboxymethy-quinolin-8-yl-sulphonylamino)-benzothiazol-2-yl)-methyl]-benzamidine-hydrochloride Prepared analogously to Example 13 from 4-[(5-(N-ethoxycarbonylmethyl-quinolin-8-yl-sulphonylamino)-benzothiazol-2-yl)-methyl]-benzamidine-hydrochloride and sodium hydroxide solution in ethanol.

Yield: 88% of theory. $C_{26}H_{21}N_5O_4S \times HCl$ (531.62/568.08); Mass spectrum: $(M+H)^+=532$; $(M+Na)^+=554$.

EXAMPLE 236

4-[(5-(2-methylphenyl)-benzothiazol-2-yl)-methyl]-benzamidine-hydrochloride a. 4-[(5-(2-methylphenyl)-benzothiazol-2-yl)-methyl]-benzonitrile Under a nitrogen atmosphere 1.3 g (3.95 mmol) of 4-[(5-bromobenzothiazol-2-yl)-methyl]-benzonitrile and 1.3 g (1.1 mmol) of bis(triphenylphosphine)-palladium(II)-chloride are stirred into 40 ml toluene for 15 minutes at 40° C. Then 1.3 g (12.3 mmol) of sodium carbonate in 5.6 ml water and 0.84 g (6.1 mmol) of o-tolylboric acid in 5 ml methanol are added. The reaction mixture is refluxed for 10 hours. After cooling the reaction solution is diluted with ethyl acetate and extracted with water. The combined organic extracts are washed with sodium chloride solution and dried. The residue is chromatographed on silica gel and eluted with ethyl acetate/petroleum ether 5:95, 10:95 and 15:85. The desired fractions are combined and concentrated by evaporation.

Yield: 0.55 g (41% of theory), $R_f$ value: 0.51 (silica gel; ethyl acetate/petroleum ether=3:7).

b. 4-[(5-(2-methylphenyl)-benzothiazol-2-yl)-methyl]-benzamidine-hydrochloride

Prepared analogously to Example 1e from 4-[(5-(2-methylphenyl)-benzothiazol-2-yl)-methyl]-benzonitrile and hydrochloric acid/ammonium carbonate in ethanol.

Yield: 58% of theory, $C_{22}H_{19}N_3S \times HCl$ 357.48/393.94); Mass spectrum: $(M+H)^+=358$.

EXAMPLE 237

4-[(5-(Quinolin-8-yl-sulphonylamino)-indol-2-yl)-methyl]-benzamidine-hydrochloride a 1-methyl-2-tributyltin-1H-indole To a solution of 10.0 g (76.2 mmol) of N-methylindole in 100 ml tetrahydrofuran 30.5 ml (75 mmol) of n-butyllithium (2.5 molar in hexane) are added dropwise at 0 to 5° C. under a nitrogen atmosphere. After two hours at 0° C. the reaction mixture is cooled to −60° C., and 24.4 g (75 mmol) of tributyltin chloride are added dropwise. The reaction mixture is heated overnight to ambient temperature and extracted with ethyl acetate/sodium chloride solution. The combined organic extracts are dried and concentrated by evaporation. The residue is distilled in vacuo at 9 mbar and 196 to 200° C.

Yield: 20.9 g (65.3% of theory), $R_f$ value: 0.48 (aluminium oxide, petroleum ether); $C_{21}H_{35}NSn$ (420.219); Mass spectrum: $M^+=417/19/21$ (Sn).

b. 4-(1-methyl-1H-indol-2-yl)-methyl-benzonitrile 12.9 g (30.7 mmol) of 1-methyl-2-tributyltin-1H-indole, 5.7 g (29.2 mmol) of 4-(bromomethyl)-benzonitrile and 0.34 g bis-(triphenylphosphine)-palladium-dichloride are refluxed in 90 ml tetrahydrofuran for 2 hours under a nitrogen atmosphere. After cooling the mixture is diluted with ethyl acetate and 15% potassium fluoride solution and stirred overnight at ambient temperature. The precipitate formed is suction filtered and washed with ethyl acetate. The organic phase is washed with sodium chloride solution, dried and concentrated by evaporation. The residue is chromatographed on silica gel and eluted with ethyl acetate/petroleum ether (5:95). The desired fractions are combined and concentrated by evaporation.

Yield: 5.9 g (81.4% of theory), $R_f$ value: 0.41 (silica gel; ethyl acetate/petroleum ether=3:7).

c. 4-(1-methyl-5-nitro-1H-indol-2-yl)-methyl-benzonitrile 6.9 g (28 mmol) of 4-(1-methyl-1H-indol-2-yl)-methyl-benzonitrile are placed in 50 ml conc. sulphuric acid. At 2° C. 2.9 g (28 mmol) of potassium nitrate are added batchwise, whereupon the temperature rises to 10° C. After 30 minutes at 2° C. the mixture is poured onto ice and the product precipitated is suction filtered, washed with ice water, dried and recrystallised from acetone.

Yield: 5.2 g (63.7% of theory), $R_f$ value: 0.17 (silica gel; ethyl acetate/petroleum ether=3:7).

d. 4-(1-methyl-5-amino-1H-indol-2-yl)-methyl-benzonitrile

Prepared analogously to Example 1c from 4-(1-methyl-5-nitro-1H-indol-2-yl)-methyl-benzonitrile, palladium on activated charcoal in methylene chloride/methanol and hydrogen.

Yield: 90% of theory, $R_f$ value: 0.34 (silica gel; ethyl acetate/petroleum ether=5:5).

e. 4-[(5-(Quinolin-8-yl-sulphonylamino)-1-methyl-indol-2-yl)-methyl]-benzonitrile Prepared analogously to Example 1d from 4-(1-methyl-5-amino-1H-indol-2-yl)-methyl-benzonitrile and quinolin-8-sulphonic acid chloride.

Yield: 51% of theory, $R_f$ value: 0.49 (silica gel; methylene chloride/ethanol=19:1).

f. 4-[(5-(Quinolin-8-yl-sulphonylamino)-1-methyl-indol-2-yl)-methyl]-benzamidine-hydrochloride Prepared analogously to Example 1e from 4-[(5-(quinolin-8-yl-sulphonylamino)-1-methyl-indol-2-yl)-methyl]-benzonitrile and hydrochloric acid/ammonium carbonate in ethanol.

Yield: 30% of theory, $R_f$ value: 0.24 (silica gel; methylene chloride/ethanol/glacial acetic acid=4:1:0.01); $C_{26}H_{23}N_4O_2S \times HCl$ (469.57/506.03); Mass spectrum: $(M+H)^+=470$.

EXAMPLE 238

4-[(5-(N-ethoxycarbonylmethyl-quinolin-8-yl-sulphonylamino)-1-methyl-indol-2-yl)-methyl]-benzamidine-hydrochloride Prepared analogously to Example 1e from 4-[(5-(N-ethoxycarbonylmethyl-quinolin-8-yl-sulphonylamino)-1-methyl-indol-2-yl)-methyl]-benzonitrile and hydrochloric acid/ammonium carbonate in ethanol.

Yield: 71% of theory, $R_f$ value: 0.26 (silica gel; methylene chloride/ethanol/glacial acetic acid=4:1:0.01); $C_{30}H_{29}N_5O_4S \times HCl$ (555.66/592.12); Mass spectrum: $(M+H)^+=556$; $(M+2H)^{++}=278.8$; $(M+Na+H)^{++}=289.8$.

EXAMPLE 239

4-[(5-(N-carboxymethyl-quinolin-8-yl-sulphonylamino)-1-methylindol-2-yl)-methyl]-benzamidine-hydrochloride Prepared analogously to Example 13 from 4-[(5-(N-ethoxycarbonylmethyl-quinolin-8-yl-sulphonylamino)-1-methyl-indol-2-yl)-methyl]-benzamidine-hydrochloride and sodium hydroxide in ethanol.

Yield: 23% of theory, $R_f$ value: 0.14 (silica gel; methylene chloride/ethanol/glacial acetic acid=4:1:0.01); $C_{28}H_{25}N_5O_4S \times HCl$ (527.61/564.07); Mass spectrum: $(M+H)^+=528$; $(M+Na)^+=550$.

EXAMPLE 240

4-[(5-benzenesulphonylamino-1-methyl-indol-2-yl)-methyl]-benzamidine-hydrochloride Prepared analogously to Example 1e from 4-[(5-benzenesulphonylamino-1-methyl-indol-2-yl)-methyl]-benzonitrile and hydrochloric acid/ammonium carbonate in ethanol.

Yield: 20% of theory, $R_f$ value: 0.26 (silica gel; methylene chloride/ethanol/glacial acetic acid=4:1:0.01); $C_{23}H_{22}N_4O_2S \times HCl$ (418.52/454.98); Mass spectrum: $(M+H)^+=419$.

EXAMPLE 241

4-[(5-(N-(ethoxycarbonylmethylaminocarbonylmethyl)-quinolin-8-yl-sulphonylamino)-1-methyl-indol-2-yl)-methyl]-benzamidine-hydrochloride Prepared analogously to Example 1e from 4-[(5-(N-(ethoxycarbonylmethylaminocarbonylmethyl)-quinolin-8-yl-sulphonylamino-1-methyl-indol-2-yl)-methyl]-benzonitrile and hydrochloric acid/ammonium carbonate in ethanol.

Yield: 52% of theory, $R_f$ value: 0.22 (silica gel; methylene chloride/ethanol=4:1); $C_{32}H_{32}N_6O_5S \times HCl$ (612.71/649.17); Mass spectrum: $(M+H)^+=613$.

EXAMPLE 242

4-[(5-n-propanesulphonylamino-1-methyl-indol-2-yl)-methyl]-benzamidine-hydrochloride Prepared analogously to Example 1e from 4-[(5-n-propanesulphonylamino-1-methyl-indol-2-yl)-methyl]-benzonitrile and hydrochloric acid/ammonium carbonate in ethanol.

Yield: 71% of theory, $R_f$ value: 0.21 (silica gel; methylene chloride/ethanol=4:1); $C_{20}H_{24}N_4O_2S \times HCl$ (384.51/420.97); Mass spectrum: $(M+H)^+=385$.

EXAMPLE 243

4-[(5-(N-ethoxycarbonylmethyl-n-propanesulphonylamino)-1-methyl-indol-2-yl)-methyl]-benzamidine-hydrochloride Prepared analogously to Example 1e from 1-[(5-(N-ethoxycarbonylmethyl-n-propanesulphonylamino)-1-methyl-indol-2-yl)-methyl]-benzonitrile and hydrochloric acid/ammonium carbonate in ethanol.

Yield: 66% of theory, $R_f$ value: 0.52 (silica gel; methylene chloride/ethanol 4:1); $C_{24}H_{30}N_4O_4S \times HCl$ (470.60/507.06); Mass spectrum: $(M+H)^+=471$.

EXAMPLE 244

4-[(5-(N-carboxymethylaminocarbonylmethyl-quinolin-8-yl-sulphonylamino)-1-methyl-indol-2-yl)-methyl]-benzamidine-hydrochloride Prepared analogously to Example 13 from 4-[(5-(N-ethoxycarbonylmethylaminocarbonylmethyl-quinolin-8-yl-sulphonylamino-1-methyl-indol-2-yl)-methyl]-benzamidine hydrochloride and sodium hydroxide in ethanol.

Yield: 93% of theory, $C_{30}H_{28}N_6O_5S \times HCl$ (584.66/621.12); Mass spectrum: $(M+H)^+=585$.

EXAMPLE 245

4-[(5-(N-carboxymethyl-n-propanesulphonylamino)-1-methyl-indol-2-yl)-methyl]-benzamidine-hydrochloride Prepared analogously to Example 13 from 4-[(5-(N-ethoxycarbonylmethyl-n-propanesulphonylamino)-1-methyl-indol-2-yl)-methyl]-benzamidine-hydrochloride and sodium hydroxide in ethanol.

Yield: 86% of theory, $R_f$ value: 0.17 (silica gel; methylene chloride/ethanol=4:1); $C_{22}H_{26}N_4O_4S \times HCl$ (442.54/479.60); Mass spectrum: $(M+H)^+=443$; $(M+Na)^+=465$.

EXAMPLE 246

4-[(5-(N-ethoxycarbonylmethyl-n-butanesulphonylamino)-1-methylindol-2-yl)-methyl]-benzamidine-hydrochloride Prepared analogously to Example 1e from 4-[(5-(N-ethoxycarbonylmethyl-n-butanesulphonylamino)-1-methyl-indol-2-yl)-methyl]-benzonitrile and hydrochloric acid/ammonium carbonate in ethanol.

Yield: 71% of theory, $R_f$ value: 0.25 (silica gel; methylene chloride/ethanol=4:1); $C_{25}H_{32}N_4O_4S \times HCl$ (484.62/521.08); Mass spectrum: $(M+H)^+=485$.

EXAMPLE 247

4-[(5-(N-carboxymethyl-n-butanesulphonylamino)-1-methyl-indol-2-yl)-methyl]-benzamidine-hydrochloride Prepared analogously to Example 13 from 4-[(5-(N-ethoxycarbonylmethyl-n-butanesulphonylamino)-1-methyl-indol-2-yl)-methyl]-benzamidine-hydrochloride and sodium hydroxide in ethanol.

Yield: 68% of theory, $R_f$ value: 0.25 (silica gel; methylene chloride/ethanol=4:1); $C_{23}H_{28}N_4O_4S \times HCl$ (456.57/493.03); Mass spectrum: $(M+H)^+=457$; $(M+Na)^+=479$.

EXAMPLE 248

4-[(5-(N-ethoxycarbonylmethyl-quinolin-8-yl-sulphonylamino)-1-methyl-indol-2-yl)-methyl]-N'-(methoxycarbonyl)benzamidine Prepared analogously to Example 97 from 4-[(5-(N-ethoxycarbonylmethyl-quinolin-8-yl-sulphonylamino)-1-methyl-indol-2-yl)-methyl]-benzamidine-hydrochloride, methyl chloroformate and potassium carbonate in tetrahydrofuran.

Yield: 85% of theory, $C_{32}H_{31}N_5O_6S$ (613.70); Mass spectrum: $(M+H)^+=614$; $(M+Na)^+=636$.

EXAMPLE 249

4-[(5-(N-ethoxycarbonylmethyl-quinolin-8-yl-sulphonylamino)-1-methyl-indol-2-yl)-methyl]-N'-(2-methanesulphonyl-ethyloxycarbonyl)benzamidine 300 mg (0.5 mmol) of 4-[(5-(N-ethoxycarbonylmethyl-quinolin-8-yl-sulphonylamino)-1-methyl-indol-2-yl)- methyl]-benzamidine-hydrochloride, 170 mg (0.6 mmol) of 2-(methylsulphonyl)-ethyl-4-nitrophenylcarbonate and 210 mg (1.5 mmol) of potassium carbonate are stirred in 30 ml tetrahydrofuran for 5 hours at ambient temperature. Then the reaction mixture is filtered and the mother liquor is concentrated by evaporation. The residue is taken up in methylene chloride and washed with sodium hydrogen carbonate solution. The combined organic extracts are dried and concentrated by evaporation. The residue is chromatographed on aluminium oxide and eluted with methylene chloride/ethanol (99:1).

Yield: 150 mg (43% of theory), $C_{34}H_{35}N_5O_8S_2$ (705.81); Mass spectrum: $(M+H)^+=706$; $(M+Na)^+=728$;

EXAMPLE 250

4-[(5-(N-ethoxycarbonylmethyl-quinolin-8-yl-sulphonylamino-1-methyl-indol-2-yl)-methyl]-N,N-dimethylbenzamidine 450 mg (0.76 mmol) of 4-[(5-(N-ethoxycarbonylmethyl-quinolin-8-yl-sulphonylamino)-1-methyl-indol-2-yl)-methyl]-benzamidine are suspended in 15 ml tetrahydrofuran and at 5° C. combined with 0.11 ml (1.0 mmol) of 2-bromoethyl chlioroformate. After 10 minutes the mixture is extracted with ethyl acetate and sodium chloride solution, and the combined organic extracts are dried and concentrated by evaporation. The residue is taken up in 10 ml tetrahydrofuran and stirred with 5 ml dimethylamine for 18 hours at ambient temperature. After evaporation of the solvent the residue is chromatographed on aluminium oxide, eluting with methylene chloride+1–2% ethyl acetate.

Yield: 150 mg (34% of theory), $C_{32}H_{33}N_5O_4S$ (583.71); Mass spectrum: (M+H)+584.

EXAMPLE 251

4-[(5-(N-ethoxycarbonylmethyl-quinolin-8-yl-sulphonylamino)-1-methyl-indol-2-yl)-methyl]-(methylcarbonyloxy-(methyl)methyleneoxycarbonyl)-benzamidine a. Carbonic acid-(1-chloroethyl-4-nitrophenyl)-ester To a solution of 12.6 g (90 mmol) of p-nitrophenol in 300 ml methylene chloride and 7.2 g (91 mmol) of pyridine, 14.2 g (99 mmol) of 1-chloroethyl chloroformate are added dropwise at −10° C. The solution is stirred for 72 hours at ambient temperature and then extracted with water and 0.5% sodium hydroxide solution. The combined organic extracts are dried and concentrated by evaporation. The residue is chromatographed on aluminium oxide and eluted with methylene chloride. The combined fractions are concentrated by evaporation, triturated with petroleum ether and suction filtered.

Yield: 7.3 g (33% of theory), $R_f$ value: 0.58 (silica gel; ethyl acetate/petroleum ether=3:7).

b. 1-(4-nitro-phenoxycarbonyloxy)-ethyl acetate 7.2 g (29.3 mmol) of carbonic acid-(1-chloroethyl-4-nitrophenyl)-ester and 10.9 g (34.2 mmol) of mercury(II)-acetate are stirred in 200 ml glacial acetic acid for 16 hours at ambient temperature. Then the mixture is evaporated to dryness, the residue chromatographed on silica gel and extracted with methylene chloride.

Yield: 4.2 g (53% of theory), $R_f$ value: 0.48 (silica gel; methylene chloride).

c. 4-[(5-(N-ethoxycarbonylmethyl-quinolin-8-yl)-sulphonylamino)-1-methyl-indol-2-yl)-methyl]-N-(methylcarbonyloxy-(methyl)methylene-oxycarbonyl)-benzamidine 300 mg (0.5 mmol) of 4-[(5-(N-ethoxycarbonylmethyl-quinolin-8-yl)-sulphonylamino)-1-methyl-indol-2-yl)-methyl]-benzamidine-hydrochloride, 25 ml methylene chloride, 150 mg (0.55 mmol) of 1-(4-nitro-phenoxycarbonyloxy)-ethyl acetate and 0.18 ml (1 mmol) of N-ethyldiisopropylamine are stirred for 18 hours at ambient temperature. The solvent is distilled off, the residue chromatographed on aluminium oxide and eluted with methylene chloride/ethanol (99:1). The desired fractions are combined and concentrated by evaporation.

Yield: 220 mg (65% of theory), $C_{35}H_{35}N_5O_8S$ (685.76); Mass spectrum: $(M+H)^+=686$; $(M+Na)^+=708$.

EXAMPLE 252

4-[(5-(N-hydroxyaminocarbonylmethyl-quinolin-8-yl-sulphonylamino)-1-methyl-indol-2-yl)-methyl]-N-hydroxybenzamidine 540 mg (1 mmol) of 4-[(5-(N-ethoxycarbonylmethyl-quinolin-8-yl)-sulphonylamino-1-methyl-indol-2-yl)-methyl]-benzonitrile are refluxed for 5 hours with 278 mg (4 mmol) of hydroxylamine hydrochloride, 205 mg (4 mmol) of sodium carbonate, 14 ml methanol and 2 ml water. The solvent is distilled off, the residue chromatographed on silica gel and eluted with methylene chloride/1 to 5% ethanol. The desired fractions are combined and concentrated by evaporation.

Yield: 250 mg (44.6% of theory), $C_{28}H_{26}N_6O_5S$ (558.61); Mass spectrum: $(M+H)^+=559$; $(M+Na)^+=581$.

EXAMPLE 253

4-[(5-(N-isopropyloxycarbonylmethyl-quinolin-8-yl-sulphonylamino)-1-methyl-indol-2-yl)-methyl]-benzamidine-hydrochloride 420 mg (0.75 mmol) of 4-[(5-(N-carboxymethyl-quinolin-8-yl)-sulphonylamino)-1-methyl-indol-2-yl)-methyl]-benzamidine-hydrochloride are dissolved in 10 ml isopropanol and refluxed. Then hydrogen chloride gas is introduced for 30 minutes. The reaction mixture is concentrated by evaporation, the residue is triturated with ether and washed with acetone.

Yield: 450 mg (100% of theory), $C_{31}H_{31}N_5O_4S \times HCl$ (569.70/606.16); Mass spectrum: $(M+H)^+=570$.

EXAMPLE 254

4-[(5-(N-(2-hydroxyethyloxycarbonylmethyl)-quinolin-8-yl)-sulphonylamino)-1-methyl-indol-2-yl)-methyl]-benzamidine-hydrochloride Prepared analogously to Example 253 from 4-[(5-(N-carboxymethylquinolin-8-yl-sulphonylamino)-1-methyl-indol-2-yl)-methyl]-benzamidine-hydrochloride, ethylene glycol monobenzylether and hydrogen chloride gas.

Yield: 11% of theory, $C_{30}H_{29}N_5O_5S \times HCl$ (571.66/608.12); Mass spectrum: $(M+H)^+=572$.

EXAMPLE 255

4-[(5-(N-carboxymethyl-quinolin-8-yl-sulphonylamino)-1-methylindol-2-yl)-methyl]-N-hydroxybenzamidine 260 mg (0.5 mmol) of 4-[(5-(N-carboxymethyl-quinolin-8-yl-sulphonylamino-1-methyl-indol-2-yl)-methyl]-benzonitrile are refluxed for 24 hours together with 14 ml methanol, 139 mg hydroxylamine hydrochloride, 105 mg sodium carbonate and 1 ml water. The solvent is distilled off, the residue is mixed with water and acidified with hydrochloric acid. The precipitated substance is suction filtered and dried. The crude product is chromatographed on silica gel and eluted with methylene chloride/6 to 30% ethanol. The desired fractions are combined and concentrated by evaporation.

Yield: 180 mg (67% of theory), $C_{28}H_{25}N_5O_5S$ (543.61); Mass spectrum: $(M+H)^+=544$; $(M+Na)^+=566$.

EXAMPLE 256

4-[(5-(N-ethoxycarbonylmethyl-quinolin-8-yl-sulphonylamino-1-methyl-indol-2-yl)-methyl]-N,N-bis-(n-octyloxycarbonyl)-benzamidine Prepared analogously to Example 97 from 4-[(5-(N-ethoxycarbonylmethyl-quinolin-8-yl-sulphonylamino)-1-methyl-indol-2-yl)-methyl]-benzamidine-hydrochloride, n-octyl chloroformate and potassium carbonate in tetrahydrofuran.

Yield: 19% of theory, $C_{48}H_{61}N_5O_8S$ (868.11); Mass spectrum: $(M)^+=868$.

EXAMPLE 257

4-[(5-(N-ethoxycarbonylmethyl-quinolin-8-yl-sulphonylamino)-1-methyl-indol-2-yl)-methyl]-N-(n-octyloxycarbonyl)-benzamidine Prepared analogously to Example 97 from 4-[(5-(N-ethoxycarbonylmethyl-quinolin-8-yl-sulphonylamino-1-methyl-indol-2-yl)-methyl]-benzamidine-hydrochloride, n-octyl chloroformate and potassium carbonate in tetrahydrofuran.

Yield: 16% of theory, $C_{39}H_{45}N_5O_6S$ (711.89); Mass spectrum: $(M+H)^+=712$; $(M+H+Na)^{++}=367.7$.

EXAMPLE 258

4-[(5-(N-cyclopentyl-methoxycarbonylmethyloxymethylcarbonylamino)-1-methyl-indol-2-yl)-methyl]-benzamidine-hydrochloride Prepared analogously to Example 1e from 4-[(5-(N-cyclopentylmethoxycarbonylmethyloxymethylcarbonyl-amino)-1-methyl-indol-2-yl)-methyl]-benzonitrile and hydrochloric acid/ammonium carbonate in methanol.

Yield: 49% of theory, $C_{27}H_{32}N_4O_4 \times HCl$ (476.58/513.04); Mass spectrum: $(M+H)^+=477$; $(M+2H)^{++}=239$; $(M+H+Na)^{++}=250$.

EXAMPLE 259

4-[(5-(N-cyclopentyl-N-ethoxycarbonylmethylaminocarbonylamino)-1-methyl-indol-2-yl)-methyl]-benzamidine-hydrochloride Prepared analogously to Example 1e from 4-[(5-(N-cyclopentyl-N-ethoxycarbonylmethylaminocarbonylamino)-1-methyl-indol-2-yl)-methyl]-benzonitrile and hydrochloric acid/ammonium carbonate in ethanol.

Yield: 79% of theory, $C_{27}H_{33}N_5O_3 \times HCl$ (475.6/512.06); Mass spectrum: $(M+H)^+=476$; $(M+H+Na)^{++}=250$.

EXAMPLE 260

4-[(5-(N-cyclopentyl-N-carboxymethylaminocarbonylamino)-1-methyl-indol-2-yl)-methyl]-benzamidine-hydrochloride Prepared analogously to Example 13 from 4-[(5-(N-cyclopentyl-N-ethoxycarbonylmethylaminocarbonylamino)-1-methyl-indol-2-yl)-methyl]-benzamidine-hydrochloride and sodium hydroxide in ethanol.

Yield: 79% of theory, $C_{25}H_{29}N_5O_3 \times HCl$ (447.54/484.0); Mass spectrum: $(M+H)^+=448$; $(M+Na)^+=470$; $(M+H+Na)^{++}=235.6$.

EXAMPLE 261

4-[(5-(N-cyclopentyl-N-carboxymethyloxymethylcarbonylamino)-1-methyl-indol-2-yl)-methyl]-benzamidine-hydrochloride Prepared analogously to Example 13 from 4-[(5-(N-cyclopentyl-N-ethoxycarbonylmethyloxymethylcarbonylamino)-1-methyl-indol-2-yl)-methyl]-benzamidine-hydrochloride and sodium hydroxide in ethanol.

Yield: 43% of theory, $C_{26}H_{30}N_4O_4 \times HCl$ (462.55/499.01); Mass spectrum: $(M+H)^+=463$; $(M+2H)^{++}=232$; $(M+H+Na)^{++}=243$.

EXAMPLE 262

4-[(6-(Quinolin-8-yl-sulphonylamino)-3-methyl-benzofuran-2-yl)-methyl]-benzamidine-hydrochloride a. 3-methyl-2-tributyltin-benzofuran Prepared analogously to Example 237a from 3-methylbenzofuran, n-butyllithium in tetrahydrofuran and tributyltin chloride.

Yield: 100% of theory, $R_f$ value: 0.73 (silica gel; petroleum ether); $C_{21}H_{34}OSn$ (421.19); Mass spectrum: $M^+=422$.

b. 4-(3-methyl-benzofuran-2-yl)methyl-benzonitrile

Prepared analogously to Example 237b from 3-methyl-2-tributyltin-benzofuran, 4-(bromomethyl)-benzonitrile and bis(triphenylphosphine)-palladium(II)-chloride in tetrahydrofuran.

Yield: 49% of theory, $R_f$ value: 0.57 (silica gel; petroleum ether/ethyl acetate=4:1).

c. 4-(3-methyl-6-nitro-benzofuran-2-yl)methyl-benzonitrile 4.3 g (17.4 mmol) of 4-(3-methyl-benzofuran-2-yl)methyl-benzonitrile are dissolved in 50 ml methylene chloride and at −50° C. mixed within 30 minutes with a solution of 9.0 g (34.8 mmol) of tin(IV)chloride in 22 g (34.8 mmol) of fuming nitric acid. After 2 hours at −50° C. the mixture is extracted with methylene chloride and water. The combined organic extracts are dried and concentrated by evaporation. The residue is chromatographed on silica gel, eluted with methylene chloride, the desired fractions are combined and concentrated by evaporation.

Yield: 2.5 g (49% of theory), $R_f$ value: 0.79 (silica gel; methylene chloride).

d. 4-(3-methyl-6-amino-benzofuran-2-yl)methyl-benzonitrile

Prepared analogously to Example 189d from 4-(3-methyl-6-nitrobenzofuran-2-yl)methyl-benzonitrile and Raney nickel/hydrogen in methanol/methylene chloride.

Yield: 64% of theory, $R_f$ value: 0.25 (silica gel; methylene chloride).

e. 4-[(6-(Quinolin-8-yl-sulphonylamino)-3-methyl-benzofuran-2-yl)-methyl]-benzonitrile Prepared analogously to Example 1d from 4-(3-methyl-6-amino-benzofuran-2-yl)methyl-benzonitrile and quinoline-8-sulphonic acid chloride in pyridine.

Yield: 17% of theory, $R_f$ value: 0.66 (silica gel; methylene chloride/ethanol 95:5).

f. 4-[(6-(Quinolin-8-yl-sulphonylamino)-3-methyl-benzofuran-2-yl)-methyl]-benzamidine-hydrochloride Prepared analogously to Example 1e from 4-[(6-(quinolin-8-yl-sulphonylamino)-3-methyl-benzofuran-2-yl)-methyl]-benzonitrile and hydrochloric acid/ammonium carbonate in ethanol.

Yield: 59% of theory, $C_{26}H_{22}N_4O_3S \times HCl$ (470.56/507.03); Mass spectrum: $(M+H)^+=471$.

EXAMPLE 263

4-[(6-(N-ethoxycarbonylmethyl-quinolin-8-yl-sulphonylamino)-3-methyl-benzofuran-2-yl)-methyl]-benzamidine-hydrochloride Prepared analogously to Example 1e from 4-[(6-(N-ethoxycarbonylmethyl-quinolin-8-yl-sulphonylamino)-3-methyl-benzofuran-2-yl)-methyl]-benzonitrile and hydrochloric acid/ammonium carbonate in ethanol.

Yield: 41% of theory, $C_{30}H_{28}N_4O_5S \times HCl$ (556.65/593.12); Mass spectrum: $(M+H)^+=557$; $(M+2H)^{++}=279$; $(M+H+Na)^{++}=290$.

EXAMPLE 264

4-[(6-(N-carboxymethyl-quinolin-8-yl-sulphonylamino)-3-methyl-benzofuran-2-yl)-methyl]-benzamidine-hydrochloride Prepared analogously to Example 13 from 4-[(6-(N-ethoxycarbonylmethyl-quinolin-8-yl-sulphonylamino-3-methyl-benzofuran-2-yl)-methyl]-benzamidine-hydrochloride and sodium hydroxide in ethanol.

Yield: 83% of theory, $C_{28}H_{24}N_4O_5S \times HCl$ (528.6/565.06); Mass spectrum: $(M+H)^+=529$; $(M+Na)^+=551$; $(M+H+Na)^{++}=276$.

EXAMPLE 265

4-[(6-(Quinolin-8-yl-sulphonylamino)-3-bromo-benzofuran-2-yl)-methyl]-benzamidine-hydrochloride a. 4-(benzofuran-2-yl)methyl-benzonitrile 10.4 g (77.3 mmol) of 2-coumaranone are dissolved in 200 ml xylene and after the addition of 32 g (77.3 mmol) of 4-cyanobenzyl-triphenylphosphonium chloride and 8.7 g (77.3 mmol) of potassium-tert.butoxide the mixture is refluxed for 3 hours under a nitrogen atmosphere. The solvent is distilled off, the residue is taken up in ethyl acetate, combined with silica gel and concentrated by evaporation. Then it is chromatographed on silica gel and eluted with petroleum ether/ethyl acetate (8:2). The desired fractions are combined and concentrated by evaporation.

Yield: 17.0 g (94% of theory), $R_f$ value: 0.5 (silica gel; petroleum ether/ethyl acetate=4:1).

b. 4-(3-Bromo-benzofuran-2-yl)methyl-benzonitrile

To a solution of 1.2 g (5 mmol) of 4-(benzofuran-2-yl)methyl-benzonitrile in 25 ml methylene chloride, a solution of 0.8 g (5 mmol) of bromine in 5 ml carbon tetrachloride is added dropwise at 2° C. The solution is stirred for 90 minutes at 2° C., the precipitate formed is suction filtered, washed with a little methylene chloride and dried.

Yield: 1.1 g (70% of theory), $R_f$ value: 0.57 (silica gel; petroleum ether/ethyl acetate=4:1).

c. 4-(3-Bromo-6-nitro-benzofuran-2-yl)methyl-benzonitrile

Prepared analogously to Example 262c from 4-(3-bromo-benzofuran-2-yl)-methyl-benzonitrile and tin(IV)chloride/fuming nitric acid in methylene chloride.

Yield: 30% of theory, $R_f$ value: 0.71 (silica gel; methylene chloride).

d. 4-(6-amino-3-bromo-benzofuran-2-yl)methyl-benzonitrile

Prepared analogously to Example 189d from 4-(3-bromo-6-nitro-benzofuran-2-yl)methyl-benzonitrile and Raney nickel/hydrogen in methylene chloride/methanol.

Yield: 59% of theory, $R_f$ value: 0.25 (silica gel; methylene chloride).

e. 4-[(6-(Quinolin-8-yl-sulphonylamino)-3-bromo-benzofuran-2-yl)-methyl]-benzonitrile Prepared analogously to Example 1d from 4-(6-amino-3-bromo-benzofuran-2-yl)methyl-benzonitrile and quinolin-8-sulphonic acid chloride in pyridine.

Yield: 93% of theory, $R_f$ value: 0.7 (silica gel; methylene chloride/ethanol=95:5).

f. 4-[(6-(Quinolin-8-yl-sulphonylamino)-3-bromo-benzofuran-2-yl)-methyl]-benzamidine-hydrochloride Prepared analogously to Example 1e from 4-[(6-(quinolin-8-yl-sulphonylamino)-3-bromo-benzofuran-2-yl)-methyl]-benzonitrile and hydrochloric acid/ammonium carbonate in ethanol.

Yield: 42% of theory, $C_{25}H_{19}BrN_4O_3S \times HCl$ (535.44/571.9); Mass spectrum: $(M+H)^+=535/7$ (Cl).

EXAMPLE 266

4-[(6-(1,2,3,4-tetrahydroquinolin-8-yl-sulphonylamino)-3-bromo-benzofuran-2-yl)-methyl]-benzamidine and 4-[(6-(1,2,3,4-tetrahydroquinolin-8-yl-sulphonylamino)-benzofuran-2-yl)-methyl]-benzamidine 0.18 g (0.336 mmol) of 4-[(6-(quinolin-8-yl-sulphonylamino)-3-bromo-benzofuran-2-yl)-methyl]-benzamidine-hydrochloride are dissolved in 10 ml methanol and after the addition of 200 mg palladium on activated charcoal hydrogenated with hydrogen for 60 minutes. The catalyst is filtered off, the solvent concentrated by evaporation. The residue is chromatographed on silica gel and eluted with methylene chloride/ethanol/glacial acetic acid 95:5:0.1 and 90:10:0.1. The desired fractions are combined and concentrated by evaporation.

Yield: 30 mg (18% of theory), $C_{25}H_{23}BrN_4O_3S$ (539.47); Mass spectrum: $(M2+H)^+=539/41$ (Br); $C_{25}H_{24}N_4O_3S$ (460.57); Mass spectrum: $(M1+H)^+=461$; as a mixture in the ratio 1:1.

EXAMPLE 267

4-[(6-(N-ethoxycarbonylmethyl-quinolin-8-yl)-sulphonylamino)-3-bromo-benzofuran-2-yl)-methyl]-benzamidine-hydrochloride a. 4-[(6-(N-ethoxycarbonylmethyl-quinolin-8-yl)-sulphonylamino-3-bromo-benzofuran-2-yl)-methyl]-benzonitrile 1.0 g (2 mmol) of 4-[(6-(quinolin-8-yl-sulphonylamino)-3-bromo-benzofuran-2-yl)-methyl]-benzonitrile are dissolved in 20 ml absolute tetrahydrofuran and after the addition of 100 g (2 mmol) of sodium hydride (50% in oil) stirred for 20 minutes at ambient temperature. Then 0.22 ml (2 mmol) of ethyl bromoacetate are added under a nitrogen atmosphere. The reaction mixture is refluxed for 6 hours, cooled, diluted with ethyl acetate and washed with sodium chloride solution. The combined organic extracts are dried and concentrated by evaporation. The residue is chromatographed on silica gel and eluted with petroleum ether/ethyl acetate (90:10 and 75:25). The desired fractions are combined and concentrated by evaporation.

Yield: 420 mg (35% of theory), $R_f$ value: 0.55 (silica gel; petroleum ether/ethyl acetate=1:1).

b. 4-[(6-(N-ethoxycarbonylmethyl-quinolin-8-yl-sulphonylamino)-3-bromo-benzofuran-2-yl)-methyl]-benzamidine-hydrochloride Prepared analogously to Example 1e from 4-[(6-(N-ethoxycarbonylmethyl-quinolin-8-yl-sulphonylamino)-3-bromo-benzofuran-2-yl)-methyl]-benzonitrile and hydrochloric acid/ammonium carbonate in ethanol.

Yield: 43% of theory, $C_{29}H_{25}BrN_4O_5S \times HCl$ (621.53/658.0); Mass spectrum: $(M+H)^+=621/23$ (Br).

EXAMPLE 268

4-[(6-(N-carboxymethyl-quinolin-8-yl-sulphonylamino)-3-ethoxy-benzofuran-2-yl)-methyl]-benzamidine-hydrochloride Prepared analogously to Example 13 from 4-[(6-(N-ethoxycarbonylmethyl-quinolin-8-yl-sulphonylamino)-3-bromo-benzofuran-2-yl)-methyl]-benzamidine-hydrochloride and sodium hydroxide in ethanol.

Yield: 90% of theory, $C_{29}H_{26}N_4O_6S \times HCl$ (558.63/595.09); Mass spectrum: $(M+H)^+=559$; $(M+Na)^+=5816$.

EXAMPLE 269

4-[(5-(2-ethoxycarbonyl-ethyl-benzimidazol-1-yl)methyl-1-methyl-1H-benzimidazol-2-yl)-methyl]-benzamidine-hydrochloride a. Ethyl 3-(1H-benzimidazol-2-yl)-propionate Hydrogen chloride gas is introduced into a suspension of 10 g (52.5 mmol) of 2-benzimidazole-propionic acid refluxing in 250 ml absolute ethanol over 1 hour. Then the mixture is concentrated by evaporation, the residue is dissolved in water and made alkaline with concentrated ammonia. Then it is extracted with ethyl acetate, the combined organic extracts are washed with water, dried and concentrated by evaporation.

Yield: 10.2 g (89% of theory).

b. Ethyl 3-[1-(4-chloro-3-nitro-benzyl)-1H-benzimidazol-2-yl]-propionate

Prepared analogously to Example 231b from ethyl 3-(1H-benzmidazol-2-yl)-propionate, 4-chloro-3-nitro-benzylester methanesulphonate and potassium-tert.butoxide in dimethylsulphoxide.

Yield: 75% of theory, $R_f$ value: 0.54 (silica gel; methylene chloride/ethanol=19:1).

c. N-methyl-3-[1-(4-methylamino-3-nitro-benzyl)-1H-benzimidazol-2-yl]-propionamide Prepared analogously to Example 7b from ethyl 3-[1-(4-chloro-3-nitro-benzyl)-1H-benzimidazol-2-yl]-propionate and methylamine solution at 80° C.

Yield: 99% of theory, $R_f$ value: 0.21 (silica gel; methylene chloride/ethanol=19:1).

d. 3-[1-(4-methylamino-3-nitro-benzyl)-1H-benzimidazol-2-yl]-propionic acid 4.5 g (12.2 mmol) of N-methyl-3-[1-(4-methylamino-3-nitro-benzyl)-1H-benzimidazol-2-yl]-propionamide are stirred in 100 ml semiconc. hydrochloric acid for 3 hours at 100° C. Then the mixture is cooled, the precipitated product is suction filtered, washed with water and dried.

Yield: 4.1 g (95% of theory), $R_f$ value: 0.12 (silica gel; methylene chloride/ethanol=19:1).

e. Ethyl 3-[1-(4-methylamino-3-nitrobenz-yl)-1H-benzimidazol-2-yl]-propionate

Prepared from 3-[1-(4-methylamino-3-nitro-benzyl)-1H-benzimidazol-2-yl]-propionic acid and hydrochloric acid gas in ethanol.

Yield: 93% of theory, $R_f$ value: 0.33 (silica gel; methylene chloride/ethanol=19:1).

f. Ethyl 3-[1-(3-amino-4-methylamino-benzyl)-1H-benzimidazol-2-yl]-propionate

Prepared analogously to Example 1c from ethyl 3-[1-(4-methylamino-3-nitro-benzyl)-1H-benzimidazol-2-yl]-propionate and palladium on activated charcoal in methanol/methylene chloride.

Yield: 100% of theory.

g. 4-[(5-(2-ethoxycarbonyl-ethyl-benzimidazol-1-yl)methyl-1-methyl-1H-benzimidazol-2-yl)-methyl]-benzonitrile Prepared analogously to Example 24f from ethyl 3-[1-(3-amino-4-methylamino-benzyl)-1H-benzimidazol-2-yl]-propionate, 4-cyanophenylacetic acid and N,N'-carbonyldiimidazole in tetrahydrofuran, glacial acetic acid.

Yield: 100% of theory.

h. 4-[(5-(2-ethoxycarbonyl-ethyl-benzimidazol-1-yl)methyl-1-methyl-1H-benzimidazol-2-yl)-methyl]-benzamidine-hydrochloride Prepared analogously to Example 1e from 4-[(5-(2-ethoxycarbonyl-ethyl-benzimidazol-1-yl)methyl-1-methyl-1H-benzimidazol-2-yl)-methyl]-benzonitrile and hydrochloric acid/ammonium carbonate in ethanol.

Yield: 58% of theory, $C_{29}H_{30}N_6O_2 \times HCl$ (494.6/531.07); Mass spectrum: $(M+H)^+=495$; $(M+2H)^{++}=248$; $(2M+H)^+=989$.

EXAMPLE 270

4-[(5-(2-carboxy-ethyl-benzimidazol-1-yl)methyl-1-methyl-1H-benzimidazol-2-yl)-methyl]-benzamidine-hydrochloride Prepared analogously to Example 13 from 4-[(5-(2-ethoxycarbonyl-ethyl-benzimidazol-1-yl)methyl-1-methyl-1H-benzimidazol-2-yl)-methyl]-benzamidine-hydrochloride and sodium hydroxide in ethanol.

Yield: 78% of theory, $C_{27}H_{26}N_6O_2 \times HCl$ (466.55/503.01); Mass spectrum: $(M+H)^+=467$; $(M+Na)^+=489$.

EXAMPLE 271

4-[(5-(imidazol-1-yl-methyl)-1-methyl-1H-benzimidazol-2-yl)-methyl]-benzamidine-hydrochloride Prepared analogously to Example 1e from 4-[(5-(imidazol-1-yl-methyl-1-methyl-1H-benzimidazol-2-yl)-methyl]-benzonitrile and hydrochloric acid/ammonium carbonate in ethanol.

Yield: 52% of theory, $C_{20}H_{20}N_6 \times HCl$ (344.4/380.9); Mass spectrum: $(M+H)^+=345$; $(M+2H)^{++}=173$.

EXAMPLE 272

4-[(5-(2-ethyl-4-methyl-imidazol-1-yl-methyl)-1-methyl-1H-benzimidazol-2-yl)-methyl]-benzamidine-dihydrochloride Prepared analogously to Example 1e from 4-[(5-(2-ethyl-4-methyl-imidazol-1-yl-methyl)-1-methyl-1H-benzimidazol-2-yl)-methyl]-benzonitrile and hydrochloric acid/ammonium carbonate in ethanol.

Yield: 30% of theory, $C_{23}H_{26}N_6 \times 2$ HCl (386.5/459.42); Mass spectrum: $(M+H)^+=387$; $(M+2H)^{++}=194$.

EXAMPLE 273

4-[[5-(1-methyl-pyrazol-5-yl-carbonyl-cyclopropan-1-yl)-1-methyl-1H-benzimidazol-2-yl]-methyl]-benzamidine-hydrochloride Prepared analogously to Example 1e from 4-[[5-(1-methyl-pyrazol-5-yl-carbonyl-cyclopropan-1-yl)-1-methyl- 1H-benzimidazol-2-yl]-methyl]-benzonitrile and hydrochloric acid/ammonium carbonate in ethanol.

Yield: 14% of theory, $C_{24}H_{24}N_6O \times HCl$ (412.5/448.96); Mass spectrum: $(M+H)^+=413$.

EXAMPLE 274

4-[[5-(3-Methyl-5-(furan-2-yl)-pyrazol-1-yl)-1-methyl-1H-benzimidazol-2-yl]-methyl]-benzamidin-hydrochlorid Prepared analogously to Example 1e from 4-[[5-(3-methyl-5-(furan-2-yl)-pyrazol-1-yl)-1-methyl-1H-benzimidazol-2-yl]-methyl]-benzonitrile and hydrochloric acid/ammonium carbonate in ethanol.

Yield: 84% of theory, $C_{24}H_{22}N_6O \times HCl$ (410.48/446.94); Mass spectrum: $(M+H)^+=411$.

EXAMPLE 275

Dry ampoule containing 75 mg active substance per 10 ml
Composition:

| active substance | 75,0 mg |
|---|---|
| mannitol | 50,0 mg |
| water for injections | ad 10,0 ml |

Preparation:

The active substance and mannitol are dissolved in water. After decanting the solution is freeze-dried. The product is dissolved with water for injections to prepare the finished solution ready for use.

EXAMPLE 276

Dry ampoule containing 35 mg active substance per 2 ml
Composition:

| active substance | 35,0 mg |
|---|---|
| mannitol | 100,0 mg |
| water for injections | ad 2,0 ml |

Preparation:

The active substance and mannitol are dissolved in water. After decanting, the solution is freeze-dried. The product is dissolved with water for injections to prepare the finished solution ready for use.

EXAMPLE 277

Tablet containing 50 mg active substance
Composition:

| (1) | active substance | 50,0 mg |
|---|---|---|
| (2) | lactose | 98,0 mg |
| (3) | maize starch | 50,0 mg |
| (4) | polyvinylpyrrolidone | 15,0 mg |
| (5) | magnesium stearate | 2,0 mg |
| | | 215,0 mg |

Preparation:

(1), (2) and (3) are mixed together and granulated with an aqueous solution of (4). (5) is added to the dry granules. Tablets are compressed from this mixture, which are biplanar, facetted on both sides and have a dividing notch on one side. Diameter of tablets: 9 mm.

EXAMPLE 278

Tablet containing 350 mg active substance
Composition:

| (1) | active substance | 350,0 mg |
|---|---|---|
| (2) | lactose | 136,0 mg |
| (3) | maize starch | 80,0 mg |
| (4) | polyvinylpyrrolidone | 30,0 mg |
| (5) | magnesium stearate | 4,0 mg |
| | | 600,0 mg |

Preparation:

(1), (2) and (3) are mixed together and granulated with an aqueous solution of (4). (5) is added to the dry granules. Tablets are compressed from this mixture, which are biplanar, facetted on both sides and have a dividing notch on one side.

Diameter of tablets: 12 mm.

EXAMPLE 279

Capsules containing 50 mg active substance
Composition:

| (1) | active substance | 50,0 mg |
|---|---|---|
| (2) | dried maize starch | 58,0 mg |
| (3) | powdered lactose | 50,0 mg |
| (4) | magnesium stearate | 2,0 mg |
| | | 160,0 mg |

Preparation:

(1) is triturated with (3). This trituration is added to the mixture of (2) and (4) with thorough blending.

This powdered mixture is packed into size 3 hard gelatine capsules in a capsule filling machine.

EXAMPLE 280

Capsules containing 350 mg active substance
Composition:

| (1) | active substance | 350,0 mg |
|---|---|---|
| (2) | dried maize starch | 46,0 mg |
| (3) | powdered lactose | 30,0 mg |
| (4) | magnesium stearate | 4,0 mg |
| | | 430,0 mg |

Preparation:

(1) is triturated with (3). This trituration is added to the mixture of (2) and (4) with thorough blending.

This powdered mixture is packed into size 0 hard gelatine capsules in a capsule filling machine.

EXAMPLE 281

Suppositories containing 100 mg active substance

| 1 suppository contains: | |
|---|---|
| active substance | 100,0 mg |
| polyethyleneglycol (M.W. 1500) | 600,0 mg |
| polyethyleneglycol (M.W. 6000) | 460,0 mg |

-continued

| 1 suppository contains: | |
|---|---|
| polyethylenesorbitanmonostearate | 840,0 mg |
| | 2 000,0 mg |

Preparation:

The polyethyleneglycol is melted together with polyethylensor bitanmonostearate. At 40° C. the ground active substance is homogeneously dispersed in the melt. It is cooled to 38° C. and poured into slightly chilled suppository moulds.

What is claimed is:

1. A compound of the formula I

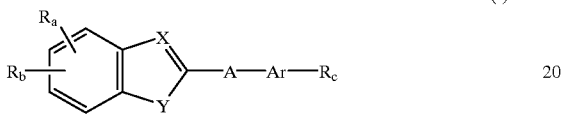

(I)

wherein

A is an oxygen or sulphur atom, a carbonyl, sulphinyl, or sulphonyl group, an imino group unsubstituted or substituted by a $C_{1-3}$-alkyl group, or a methylene group unsubstituted, mono-, or disubstituted by a carboxy-$C_{1-3}$-alkyl- or $C_{1-3}$-alkoxy-carbonyl-$C_{1-3}$-alkyl group;

Ar is a phenylene or naphthylene group, each unsubstituted or substituted by a fluorine, chlorine, or bromine atom, or by a trifluoromethyl, $C_{1-3}$-alkyl-, or $C_{1-3}$-alkoxy group, or a thienylene, thiazolylene, pyridinylene, pyrimidinylene, pyrazinylene, or pyridazinylene group each unsubstituted or substituted in the carbon skeleton by a $C_{1-3}$-alkyl group;

X is a nitrogen atom or an —$R_1C$═ group, wherein
    $R_1$ is a hydrogen, fluorine, chlorine, bromine, or iodine atom, or a $C_{1-3}$-alkyl or $C_{1-3}$-alkoxy group;

Y is an oxygen or sulphur atom, or an —$R_2N$— group, wherein
    $R_2$ is a hydrogen atom or a $C_{1-5}$-alkyl group,
    a $C_{1-3}$-alkyl group substituted by a phenyl group unsubstituted or substituted by a carboxy or $C_{1-3}$-alkoxycarbonyl group,
    a $C_{1-5}$-alkyl group substituted by a carboxy, $C_{1-3}$-alkoxycarbonyl, carboxy-$C_{1-3}$-alkoxycarbonyl, $C_{1-3}$-alkoxycarbonyl-$C_{1-3}$-alkoxycarbonyl, carboxy-$C_{1-3}$-alkylaminocarbonyl, or $C_{1-3}$-alkoxycarbonyl-$C_{1-3}$-alkylaminocarbonyl group, or
    an n-$C_{2-4}$-alkyl group terminally substituted by a di-($C_{1-3}$-alkyl)-amino, pyrrolidino, piperidino, morpholino, piperazino, or N—$C_{1-3}$-alkyl-piperazino group, wherein the abovementioned cyclic groups are unsubstituted or substituted by one or two $C_{1-3}$-alkyl groups;

$R_a$ is a hydrogen atom or a $C_{1-3}$-alkyl group;

$R_b$ is a $R_3$—CO—$C_{3-5}$-cycloalkylene, $R_3$—$SO_2$—$NR_4$, $R_3$—CO—$NR_4$, $R_5NR_6$—CO, $R_5NR_6$—$SO_2$—, or $R_5NR_6$—CO—$C_{3-5}$-cycloalkylene group, wherein
    $R_3$ is a $C_{1-6}$-alkyl- or $C_{5-7}$-cycloalkyl group,
    a $C_{1-3}$-alkyl group substituted by a $C_{5-7}$-cycloalkyl, phenyl, $C_{1-3}$-alkylamino, di-($C_{1-3}$-alkyl)-amino, carboxy-$C_{1-3}$-alkylamino, $C_{1-3}$-alkoxycarbonylamino, phenylsulphonylamino, or tetrazolyl group, a $C_{1-3}$-alkyl group substituted by a carboxy, $C_{1-3}$-alkoxycarbonyl, carboxy-$C_{1-3}$-alkoxy, or $C_{1-3}$-alkoxy-carbonyl-$C_{1-3}$-alkoxy group, a $C_{1-3}$-alkyl group substituted by an imidazolyl or benzimidazolyl group, wherein the imidazole moiety of the abovementioned groups is unsubstituted or substituted by one or two $C_{1-3}$-alkyl groups or by a carboxy-$C_{1-3}$-alkyl or $C_{1-3}$-alkoxycarbonyl-$C_{1-3}$-alkyl group, or a phenyl group unsubstituted, mono-, or disubstituted by $C_{1-3}$-alkyl, $C_{1-3}$-alkoxy, trifluoromethyl, carboxy, or $C_{1-3}$-alkoxycarbonyl groups, wherein the substituents are identical or different, a phenyl group substituted by 3 or 4 methyl groups, or a naphthyl, pyridinyl, pyrazolyl, quinolyl, or isoquinolyl group each unsubstituted or substituted by a $C_{1-3}$-alkyl group, $R_4$ is a hydrogen atom, or a $C_{1-5}$-alkyl or $C_{5-7}$-cycloalkyl group, a $C_{1-5}$-alkyl group substituted by a carboxy group or by a $C_{1-5}$-alkoxycarbonyl group, wherein the alkoxy moiety in the 2 or 3 position is unsubstituted or substituted by a hydroxy group, a $C_{1-3}$-alkyl group substituted by an aminocarbonyl, hydroxyaminocarbonyl, $C_{1-3}$-alkylaminocarbonyl, di-($C_{1-3}$-alkyl)-aminocarbonyl, or $C_{5-7}$-alkylene-iminocarbonyl group, wherein the $C_{6-7}$-alkylencimino moiety is unsubstituted or substituted in the 4 position by a di-($C_{1-3}$-alkyl)-amino group, a $C_{1-3}$-alkyl group unsubstituted or substituted by a phenyl group and substituted in the alkyl moiety by a carboxy-$C_{1-3}$-alkoxy-carbonyl, $C_{1-3}$-alkoxycarbonyl-$C_{1-3}$-alkoxycarbonyl, carboxy-$C_{1-3}$-alkylaminocarbonyl, N-($C_{1-3}$-alkyl)-carboxy-$C_{1-3}$-alkyl-aminocarbonyl, $C_{1-3}$-alkoxycarbonyl-$C_{1-3}$-alkylaminocarbonyl, N-($C_{1-3}$-alkyl)-$C_{1-3}$-alkoxycarbonyl-$C_{1-3}$-alkylaminocarbonyl, morpholinocarbonyl, or 4-($C_{1-3}$-alkyl)-piperazinocarbonyl group, a $C_{1-3}$-alkyl group substituted by a carboxy-$C_{1-3}$-alkylaminocarbonyl, N-($C_{1-3}$-alkyl)-carboxy-$C_{1-3}$- alkyl-aminocarbonyl, $C_{1-3}$-alkoxycarbonyl-$C_{1-3}$-alkylaminocarbonyl or N-($C_{1-3}$-alkyl)-$C_{1-3}$-alkoxycarbonyl-$C_{1-3}$-alkylamino-carbonyl group, which are additionally substituted at a carbon atom of the alkylamino moiety by a carboxy or $C_{1-3}$-alkoxycarbonyl group, a $C_{1-3}$-alkyl group substituted by a di-($C_{1-3}$-alkyl)-aminocarbonyl group, wherein an alkyl moiety is unsubstituted or substituted in the 2 or 3 position by a di-($C_{1-3}$-alkyl)-amino group, a $C_{1-3}$-alkyl group substituted by a 4-(morpholinocarbonyl-$C_{1-3}$-alkyl)-piperazinocarbonyl, N-($C_{1-3}$-alkyl)-pyrrolidinyl, or N-($C_{1-3}$-alkyl)-piperidinyl group, or an n-$C_{2-4}$-alkyl group terminally substituted by a di-($C_{1-3}$-alkyl)-amino, $C_{5-7}$-alkyleneimino, or morpholino group, $R_5$ is a $C_{1-5}$-alkyl or $C_{5-7}$-cycloalkyl group, a phenyl-$C_{1-3}$-alkyl group unsubstituted or substituted in the alkyl moiety by a carboxy or $C_{1-3}$-alkoxycarbonyl group, an n-$C_{2-4}$-alkyl group substituted in the 2, 3 or 4 position by a hydroxy, $C_{1-3}$-alkylamino, or di-($C_{1-3}$-alkyl)-amino group, or a phenyl group unsubstituted, mono-, or disubstituted by a $C_{1-3}$-alkyl, $C_{1-3}$-alkoxy, trifluoromethyl, carboxy, or $C_{1-3}$-alkoxycarbonyl group, wherein the substituents are identical or different, a phenyl group substituted by 3 or 4 methyl groups, or a naphthyl, pyridinyl, quinolyl, or isoquinolyl group, $R_6$ is a $C_{1-5}$-alkyl group unsubstituted or substituted by a carboxy or $C_{1-3}$-alkoxycarbonyl group,
 a $C_{1-3}$-alkyl group substituted in the alkyl moiety by a $C_{1-3}$-alkylaminocarbonyl, di-($C_{1-3}$-alkyl)-aminocarbonyl, carboxy-$C_{1-3}$-alkylaminocarbonyl, or $C_{1-3}$-alkyloxycarbonyl-$C_{1-3}$-alkylaminocarbonyl group, or
an n-$C_{2-4}$-alkyl group substituted in the 2, 3, or 4 position by a hydroxy, $C_{1-3}$-alkylamino, or di-($C_{1-3}$-alkyl)-amino group, or one of the groups $R_5$ or $R_6$ is a hydrogen atom and the other one of the groups has the meanings given for $R_5$ and $R_6$ hereinbefore, or $R_5$ and $R_6$ together with the nitrogen atom between them are a pyrrolidino or piperidino group unsubstituted or substituted by one or two $C_{1-3}$-alkyl groups, which are unsubstituted or substituted by a carboxy-$C_{1-3}$-alkyl or $C_{1-3}$-alkoxy-$C_{1-3}$-alkyl group or on to which a benzene ring is or is not condensed via two adjacent carbon atoms, or $R_b$ is an amino, $C_{1-3}$-alkylamino or $C_{5-7}$-cycloalkyl-amino group, which is unsubstituted or substituted at the nitrogen atom by a phenylaminocarbonyl, N-phenyl-$C_{1-3}$-alkylaminocarbonyl, phenylsulphonylamino-$C_{1-3}$-alkylcarbonyl, $C_{1-3}$-alkyloxy-carbonyl-$C_{1-3}$-alkyl, N-($C_{3-5}$-cycloalkyl)-$C_{1-3}$-alkylamino-carbonyl, N-(hydroxycarbonyl-$C_{1-3}$-alkyl)-aminocarbonyl, or N-($C_{1-3}$-alkoxycarbonyl-$C_{1-3}$-alkyl)-aminocarbonyl-$C_{3-5}$-cyclo-alkylamino group, a piperidino group substituted in the 4 position by a di-($C_{1-3}$-alkyl)-amino group, a piperazino group substituted in the 4 position by a $C_{1-3}$-alkyl group, a $C_{2-4}$-alkylsulphonyl group substituted in the 2, 3, or 4 position by a di-($C_{1-3}$-alkyl)-amino group, a 4-oxo-3,4-dihydro-phthalazinyl-1-yl or 4-oxo-2,3-diaza-spiro[5.5]undec-1-en-1-yl group, a methyl group substituted by a $C_{5-7}$-cycloalkyleneimino-carbonyl group, wherein the methyl group is substituted by a carboxy-$C_{1-3}$-alkyl or $C_{1-3}$-alkoxy-$C_{1-3}$-alkyl group, a carbonyl or methyl group substituted by a $C_{3-5}$-cycloalkyl or $C_{3-5}$-alkyl group, wherein the cycloalkyl moiety is unsubstituted or substituted by a $C_{1-3}$-alkyl, carboxy-$C_{1-3}$-alkyl, or $C_{1-3}$-alkoxycarbonyl-$C_{1-3}$-alkyl group, and the methyl moiety is substituted by a $C_{1-3}$-alkoxy or $C_{1-4}$-alkylamino group, a $C_{5-7}$-cycloalkyl-N-(carboxy-$C_{1-3}$-alkoxy)-iminomethylene or $C_{5-7}$-cycloalkyl-N-($C_{1-3}$-alkoxycarbonyl-$C_{1-3}$-alkoxy)-iminomethylene group, which is unsubstituted or substituted in the cycloalkyl moiety by a $C_{1-3}$ alkyl group, a phosphinyl group substituted by a $C_{1-6}$-alkyl or $C_{5-7}$-cycloalkyl group and by a hydroxy, $C_{1-3}$-alkoxy, carboxy-$C_{1-3}$-alkoxy, or $C_{1-3}$-alkoxycarbonyl-$C_{1-3}$-alkoxy group, a piperidino group, wherein in the 2 position a methylene group is replaced by a carbonyl or sulphonyl group, a tetrazolyl group unsubstituted or substituted by a $C_{1-5}$-alkyl group, a phenyl or phenylsulphonyl group unsubstituted, mono-, or disubstituted by a $C_{1-3}$-alkyl, $C_{1-3}$-alkoxy, trifluoromethyl, carboxy, or $C_{1-3}$-alkoxycarbonyl group, wherein the substituents are identical or different, a sulphimidoyl group substituted at the sulphur atom by a $C_{5-7}$-cycloalkyl group and unsubstituted or substituted at the nitrogen atom by a $C_{2-4}$-alkanoyl, carboxy-$C_{1-3}$-alkyl, $C_{1-3}$-alkoxycarbonyl-$C_{1-3}$-alkyl, carboxy-$C_{2-4}$-alkanoyl or $C_{1-3}$-alkoxycarbonyl-$C_{2-4}$-alkanoyl group, an imidazolyl group substituted in the 1 position by a carboxy-$C_{1-3}$-alkyl or $C_{1-3}$-alkoxycarbonyl-$C_{1-3}$-alkyl group, which is unsubstituted or substituted by a $C_{1-5}$-alkyl group, a $C_{1-3}$-alkoxycarbonyl-$C_{1-3}$-alkyl group substituted in the alkyl moiety by a $C_{5-7}$-cycloalkylaminocarbonyl group, a $C_{1-3}$-alkyl group substituted by a 1-imidazolyl group, wherein the imidazolyl moiety is unsubstituted or substituted by one or two $C_{1-3}$-alkyl groups, or in the 2 position by a 1-benzimidazolyl group substituted by a carboxy-$C_{1-3}$-alkyl or $C_{1-3}$-alkoxycarbonyl-$C_{1-3}$-alkyl group, or a furanyl-1-pyrazolyl group unsubstituted or substituted by a $C_{1-3}$-alkyl group; and $R_c$ is a cyano group or an amidino group, unsubstituted or substituted by a hydroxy group, by one or two $C_{1-3}$-alkyl groups, by one or two $C_{1-8}$-alkoxycarbonyl groups, or by a group which can be cleaved in vivo, or a tautomer or salt thereof.

2. The compound of the formula I according to claim 1, wherein

Ar is a 1,4-phenylene group;

$R_3$ does not represent a pyrazolyl group or a naphthyl, pyridinyl, pyrazolyl, quinolyl, or isoquinolyl group each substituted by a $C_{1-3}$-alkyl group; and $R_b$ does not represent a furanyl-1-pyrazolyl group unsubstituted or substituted by a $C_{1-3}$-alkyl group, or a tautomer or salt thereof.

3. The compound of the formula I according to claim 1, wherein Ar is a 1,4-phenylene group, or a tautomer or salt thereof.

4. The compound of the formula I according to claim 1, wherein

A is a methylene group unsubstituted or substituted by a carboxy-$C_{1-3}$-alkyl or $C_{1-3}$-alkoxycarbonyl-$C_{1-3}$-alkyl group, or a carbonyl or imino group;

Ar is a 1,4-phenylene group;

X is a nitrogen atom or an —$R_1C$= group, wherein $R_1$ is a hydrogen, fluorine, chlorine, or bromine atom, or a $C_{1-3}$-alkyl or $C_{1-3}$-alkoxy group;

Y is an oxygen or sulphur atom, or an —$R_2N$— group, wherein $R_2$ is a hydrogen atom or a $C_{1-5}$-alkyl group,
 a benzyl group, unsubstituted or substituted in the phenyl moiety by a carboxy or $C_{1-3}$-alkoxycarbonyl group,
 a $C_{1-5}$-alkyl group substituted by a carboxy or $C_{1-3}$-alkoxycarbonyl group,
 a $C_{1-3}$-alkyl group substituted by a carboxy-$C_{1-3}$-alkoxycarbonyl, carboxy-$C_{1-3}$-alkylaminocarbonyl, or $C_{1-3}$-alkoxycarbonyl-$C_{1-3}$-alkylaminocarbonyl group, or
an n-$C_{2-4}$-alkyl group terminally substituted by a di-($C_{1-3}$-alkyl)-amino or morpholino group, $R_a$ is a hydrogen atom or a methyl group;

$R_b$ is an $R_3$—CO—$C_{3-5}$-cycloalkylene, $R_3$—$SO_2$—$NR_4$, $R_3$—CO—$NR_4$, $R_5NR_6$—CO, $R_5NR_6$—$SO_2$, or $R_5NR_6$—CO—$C_{3-5}$-cycloalkylene group, wherein $R_3$ is a $C_{1-4}$-alkyl, cyclopentyl, cyclohexyl, or benzyl group, a $C_{1-3}$-alkyl group substituted by a tetrazolyl, carboxy, $C_{1-3}$-alkoxycarbonyl, carboxy-$C_{1-3}$-alkoxy, $C_{1-3}$-alkoxycarbonyl-$C_{1-3}$-alkoxy, carboxy-$C_{1-3}$-alkylamino, or $C_{1-3}$-alkoxycarbonylamino group, a phenyl group unsubstituted, mono-, or disubstituted by methyl, methoxy, trifluoromethyl, carboxy, or methoxycarbonyl groups, wherein the substituents are identical or different, a phenyl group substituted by 3 or 4 methyl groups, a 5-pyrazolyl group unsubstituted or substituted by a $C_{1-3}$-alkyl group, or a naphthyl, pyridinyl, quinolyl or isoquinolyl group, $R_4$ is a hydrogen atom, a $C_{1-5}$-alkyl or $C_{5-7}$-cycloalkyl group, a $C_{1-5}$-alkyl group substituted by a carboxy group or by a $C_{1-5}$-alkoxycarbonyl group, wherein the alkoxy moiety in the 2 or 3 position is unsubstituted or substituted by a hydroxy group, a $C_{1-3}$-alkyl group substituted by an aminocarbonyl, hydroxyaminocarbonyl, or piperidinocarbonyl group, wherein the piperidino moiety is unsubstituted or substituted in the 4 position by a dimethylamino group, a $C_{1-3}$-alkyl group substituted by a carboxy-$C_{1-3}$-alkylaminocarbonyl, N-($C_{1-3}$-alkyl)-carboxy-$C_{1-3}$-alkyl-aminocarbonyl, $C_{1-3}$-alkoxycarbonyl-$C_{1-3}$-alkylaminocarbonyl, N-($C_{1-3}$-alkyl)-$C_{1-3}$-alkoxycarbonyl-$C_{1-3}$-alkylaminocarbonyl, morpholinocarbonyl, or 4-($C_{1-3}$-alkyl)-piperazinocarbonyl group, a $C_{1-3}$-alkyl group substituted by a carboxy-$C_{1-3}$-alkylaminocarbonyl, N-($C_{1-3}$-alkyl)-carboxy-$C_{1-3}$-alkyl-aminocarbonyl, $C_{1-3}$-alkoxycarbonyl-$C_{1-3}$-alkylaminocarbonyl, or N-($C_{1-3}$-alkyl)-$C_{1-3}$-alkoxycarbonyl-$C_{1-3}$-alkylaminocarbonyl group, which are additionally substituted at a carbon atom of the alkylamino moiety by a carboxy or $C_{1-3}$-alkoxycarbonyl group, a $C_{1-3}$-alkyl group substituted in the alkyl moiety by a di-($C_{1-3}$-alkyl)-aminocarbonyl group, wherein an alkyl moiety is unsubstituted or substituted in the 2 or 3 position by a di-($C_{1-3}$-alkyl)-amino group, a $C_{1-3}$-alkyl group substituted in the alkyl moiety by a 4-(morpholinocarbonyl-$C_{1-3}$-alkyl)-piperazinocarbonyl or N-($C_{1-3}$-alkyl)-pyrrolidinyl group, or an n-$C_{2-3}$-alkyl group terminally substituted by a di-($C_{1-3}$-alkyl)-amino, $C_{5-7}$-alkyleneimino, or morpholino group, $R_5$ is a $C_{1-5}$-alkyl or $C_{5-7}$-cycloalkyl group, a phenyl-$C_{1-3}$-alkyl group unsubstituted or substituted in the alkyl moiety by a carboxy or $C_{1-3}$-alkoxycarbonyl group, or a phenyl, naphthyl, pyridinyl, quinolyl, or isoquinolyl group, and $R_6$ is a $C_{1-5}$-alkyl group unsubstituted or substituted by a carboxy or $C_{1-3}$-alkoxycarbonyl group, a $C_{1-3}$-alkyl group substituted in the alkyl moiety by a $C_{1-3}$-alkylaminocarbonyl, di-($C_{1-3}$-alkyl)-aminocarbonyl, carboxy-$C_{1-3}$-alkylaminocarbonyl, or $C_{1-3}$-alkyloxycarbonyl-$C_{1-3}$-alkylaminocarbonyl group, or an n-$C_{2-3}$-alkyl group substituted in the 2 or 3 position by a $C_{1-3}$-alkylamino or di-($C_{1-3}$-alkyl)-amino group, or one of the groups $R_5$ or $R_6$ is a hydrogen atom and the other one of the groups has the meanings given for $R_5$ and $R_6$ hereinbefore, or $R_5$ and $R_6$ together with the nitrogen atom between them are a pyrrolidino or piperidino group unsubstituted or substituted by a $C_{1-3}$-alkyl, carboxy-$C_{1-3}$-alkyl, or $C_{1-3}$-alkoxy-$C_{1-3}$-alkyl group, onto which a benzene ring is or is not condensed via two adjacent carbon atoms, or $R_b$ is an amino, methylamino, cyclopentylamino, or cyclohexylamino group, substituted at the nitrogen atom by a phenylaminocarbonyl, N-phenylmethylaminocarbonyl, phenylsulphonylaminomethylcarbonyl, hydroxycarbonylmethylaminocarbonyl, or $C_{1-3}$-alkyloxycarbonylmethylaminocarbonyl group, a piperidino group substituted in the 4 position by a di-($C_{1-3}$-alkyl)-amino group, a piperazino group substituted in the 4 position by a $C_{1-3}$-alkyl group, a $C_{2-3}$-alkylsulphonyl group substituted in the 2 or 3 position by a di-($C_{1-3}$-alkyl)-amino group, a 4-oxo-3,4-dihydro-phthalazinyl-1-yl or 4-oxo-2,3-diaza-spiro[5.5]undec-1-en-1-yl group, a carbonyl or methyl group substituted by a cyclopentyl, cyclohexyl, or $C_{3-5}$-alkyl group, wherein the methyl moiety is substituted by a $C_{1-3}$-alkoxy or $C_{1-4}$-alkylamino group and the cycloalkyl moiety is unsubstituted or substituted by a methyl, carboxymethyl, or $C_{1-3}$-alkoxycarbonylmethyl group, a cyclohexyl-N-(carboxymethoxy)-iminomethylene or cyclohexyl-N-($C_{1-3}$-alkoxycarbonylmethoxy)-iminomethylene group, unsubstituted or substituted by a methyl group in the cyclohexyl moiety, a phosphinyl group substituted by a $C_{3-6}$-alkyl group and by a hydroxy, $C_{1-3}$-alkoxy, carboxymethoxy, or $C_{1-3}$-alkoxycarbonylmethoxy group, a piperidino group wherein in the 2 position a methylene group is replaced by a carbonyl or sulphonyl group, a tetrazolyl group unsubstituted or substituted by a $C_{1-5}$-alkyl group, a phenyl or phenylsulphonyl group unsubstituted or substituted by a methyl group, a sulphimidoyl group substituted at the sulphur atom by a cyclohexyl group and unsubstituted or substituted at the nitrogen atom by a $C_{2-4}$-alkanoyl, carboxymethyl, $C_{1-3}$-alkoxycarbonylmethyl, carboxy-$C_{2-3}$-alkanoyl, or $C_{1-3}$-alkoxycarbonyl-$C_{2-3}$-alkanoyl group, an imidazolyl group substituted in the 1 position by a carboxymethyl or $C_{1-3}$-alkoxycarbonylmethyl group, which is unsubstituted or substituted by a $C_{1-5}$-alkyl group, a $C_{1-3}$-alkoxycarbonyl-$C_{1-3}$-alkyl group substituted in the alkyl moiety by a $C_{5-7}$-cycloalkylaminocarbonyl group, a $C_{1-3}$-alkyl group substituted by a 1-imidazolyl group, wherein the imidazolyl moiety is unsubstityed or substituted by one or two $C_{1-3}$-alkyl groups, or by a 1-benzimidazolyl group substituted in the 2 position by a carboxy-$C_{1-3}$-alkyl or $C_{1-3}$-alkoxycarbonyl-$C_{1-3}$-alkyl group, or a 5-furanyl-1-pyrazolyl group unsubstituted or substituted by a $C_{1-3}$-alkyl group, and $R_c$ is a cyano group or an amidino group, which is unsubstituted or substituted by one or two $C_{1-3}$-alkyl groups, by one or two $C_{1-8}$-alkoxycarbonyl groups, or by a hydroxy group, or a tautomer or salt thereof.

5. The compound of the formula I according to claim 1, wherein

A is a methylene or imino group;

Ar is a 1,4-phenylene group;

X is a nitrogen atom or an —$R_1C$= group, wherein
$R_1$ is a hydrogen, fluorine, chlorine, or bromine atom, or a methyl group;

Y is an oxygen or sulphur atom, or an —$R_2N$— group, wherein
$R_2$ is a hydrogen atom, or a methyl, benzyl, 4-carboxybenzyl, or 4-methoxycarbonylbenzyl group,
a $C_{1-3}$-alkyl group substituted by a carboxy or $C_{1-3}$-alkoxycarbonyl group,
a methyl group substituted by a carboxymethylaminocarbonyl or $C_{1-3}$-alkoxycarbonylmethylaminocarbonyl group, or
an n-$C_{2-3}$-alkyl group terminally substituted by a morpholino group;

$R_a$ is a hydrogen atom;

$R_b$ is an $R_3$—CO-(1,1-cyclopropylene), $R_3$—$SO_2$—$NR_4$, $R_3$—CO—$NR_4$, $R_5NR_6$—CO, $R_5NR_6$—$SO_2$, or $R_5NR_6$—CO—$C_{3-5}$-(1,1-cyclopropylene) group, wherein
$R_3$ is a $C_{1-3}$-alkyl, cyclopentyl, or cyclohexyl group,
a methyl group substituted by a tetrazolyl, carboxymethoxy, $C_{1-3}$-alkoxycarbonylmethoxy, carboxy-$C_{1-3}$-alkylamino, or $C_{1-3}$-alkoxycarbonylamino group,
a phenyl, naphthyl, pyridinyl, 1-methyl-5-pyrazolyl, quinolyl, or isoquinolyl group, $R_4$ is a hydrogen atom or a $C_{1-3}$-alkyl or cyclopentyl group,
a $C_{1-5}$-alkyl group substituted by a carboxy group or by a $C_{1-3}$-alkoxycarbonyl group,
a methyl group substituted by a 4-dimethylamino-piperidinocarbonyl, morpholinocarbonyl, 4-methylpiperazino, or 4-morpholinocarbonylmethylpiperazinocarbonyl group,
a $C_{1-3}$-alkyl group substituted by a carboxy-methylaminocarbonyl, N-($C_{1-3}$-alkyl)-carboxymethylamino-carbonyl, $C_{1-3}$-alkoxycarbonylmethylaminocarbonyl, or N-($C_{1-3}$-alkyl)-$C_{1-3}$-alkoxycarbonylmethylaminocarbonyl group,
a $C_{1-3}$-alkyl group substituted by a di-($C_{1-3}$-alkyl)-aminocarbonyl group, wherein an alkyl moiety is additionally substituted in the 2 or 3 position by a di-($C_{1-3}$-alkyl)-amino group,
a $C_{1-3}$-alkyl group substituted by a carboxymethylaminocarbonyl or $C_{1-3}$-alkoxycarbonylmethylaminocarbonyl group, wherein the methyl group of the methylamino moiety is additionally substituted by an aminocarbonylmethyl group,
an n-$C_{2-3}$-alkyl group terminally substituted by a di-($C_{1-3}$-alkyl)-amino, pyrrolidino, or morpholino group, $R_5$ is a $C_{1-5}$alkyl, cyclopentyl, cyclohexyl, phenyl, naphthyl, pyridinyl, quinolyl, or isoquinolyl group, $R_6$ is a $C_{1-5}$-alkyl group unsubstituted or substituted by a carboxy or $C_{1-3}$-alkoxycarbonyl group,
a $C_{1-3}$-alkyl group substituted by a $C_{1-3}$-alkylaminocarbonyl, carboxymethylaminocarbonyl or $C_{1-3}$-alkyloxy-carbonylmethylaminocarbonyl group, or $R_5$ and $R_6$ together with the nitrogen atom between them are a pyrrolidino group substituted by a carboxymethyl or $C_{1-3}$-alkoxymethyl group or a pyrrolidino group onto which a benzene ring is additionally condensed via two adjacent carbon atoms, or $R_b$ is an N-pyrrolidinocarbonyl-methylamino, phenylsulphonyl, 4-oxo-2,3-diaza-spiro[5.5]undec 1-en-1-yl, or $C_{3-5}$-alkyl-tetrazolyl group,
a cyclohexylcarbonyl group substituted by a methyl, carboxymethyl, or $C_{1-3}$-alkoxycarbonylmethyl group,
a cyclohexyl-N-(carboxymethoxy)-iminomethylene or cyclohexyl-N-($C_{1-3}$-alkoxycarbonylmethoxy)-iminomethylene group additionally substituted by a methyl group in the cyclohexyl moiety,
a phosphinyl group substituted by a $C_{3-6}$-alkyl group and by a $C_{1-3}$-alkoxymethoxy group,
a sulphimidoyl group substituted at the sulphur atom by a cyclohexyl group and at the nitrogen atom by a $C_{1-4}$-alkanoyl group, or
a 3-methyl-5-(furan-2-yl)-1-pyrazolyl group; and $R_c$ is an amidino group, or a tautomer or salt thereof.

6. This compound of the formula according to claim 1, wherein

A is a methylene group;

Ar is a 1,4-phenylene group;

X is a nitrogen atom or an —HC= group;

Y is an oxygen or sulphur atom, or an —$R_2N$— group, wherein
$R_2$ is a hydrogen atom or a methyl, benzyl, or $C_{1-3}$-alkoxycarbonylmethyl group;

$R_a$ is a hydrogen atom;

$R_b$ is an $R_5NR_6$—$SO_2$, $R_5NR_6$—CO, $R_3$—$SO_2$—$NR_4$, $R_3$—CO—$NR_4$, or $R_5NR_6$—CO—$C_{3-5}$-(1,1-cyclopropylene) group, wherein
$R_3$ is a cyclopentyl, cyclohexyl, phenyl, naphthyl, 1-methyl-pyrazolyl, quinolyl, or isoquinolyl group, or a methyl group substituted by a carboxymethylamino, $C_{1-3}$-alkoxycarbonyl-methylamino, carboxymethoxy, $C_{1-3}$-alkoxycarbonylmethoxy, or tetrazolyl group, $R_4$ is a hydrogen atom, a methyl group substituted by a carboxy, $C_{1-3}$-alkoxycarbonyl, morpholinocarbonyl, 4-dimethylamino-piperidinocarbonyl, 4-methyl-piperazinocarbonyl, 4-morpholinocarbonylmethyl-piperazinocarbonyl, carboxymethylaminocarbonyl, N-methyl-carboxymethylaminocarbonyl, $C_{1-3}$-alkoxycarbonylmethyl-aminocarbonyl, N-methyl-$C_{1-3}$-alkoxycarbonylmethyl-aminocarbonyl, N-($C_{1-3}$- alkyl)-N-(2-dimethylamino-ethyl)-aminocarbonyl, N-(1-carboxy-2-aminocarbonyl-ethyl)-aminocarbonyl, or N-(1-$C_{1-3}$-alkoxycarbonyl-2-aminocarbonyl-ethyl)-aminocarbonyl group, or a cyclopentyl group, $R_5$ is a $C_{1-5}$-alkyl, phenyl, or pyridyl group, and $R_6$ is a $C_{1-5}$-alkyl group terminally substituted by a carboxy or $C_{1-3}$-alkoxycarbonyl group, or a $C_{1-3}$- alkyl group substituted by a methylaminocarbonyl, carboxymethylaminocarbonyl, or $C_{1-3}$-alkoxycarbonylmethylaminocarbonyl group, or substituted in the 2 or 3 position by a dimethylamino group, or $R_5$ together with $R_6$ and the nitrogen atom between them are a 1-methyl-5-pyrazoyl group, a pyrrolidino group unsubstituted or substituted by a $C_{1-3}$-alkoxycarbonyl group, or a pyrrolidino group onto which a benzene ring is condensed via two adjacent carbon atoms, or $R_b$ is a N-pyrrolidinocarbonyl-methylamino, phenylsulphonyl, 4-oxo-2,3-diaza-spiro[5.5]undec-1-en-1-yl, or $C_{3-5}$-alkyl-tetrazolyl group, a cyclohexylcarbonyl group substituted in the 1 position by a methyl, carboxymethyl, or $C_{1-3}$-alkoxycarbonyl-methyl group, a cyclohexyl-N-(carboxymethoxy)-iminomethylene or cyclohexyl-N-($C_{1-3}$-alkoxycarbonylmethoxy)-iminomethylene group, which is additionally substituted in the cyclohexyl moiety by a methyl group, a phosphinyl group substituted by a $C_{3-6}$-akyl group and by a $C_{1-3}$-alkoxymethoxy group; and $R_c$ is an amidino group, or a tautomer or salt thereof.

7. The compound of the formula I according to claim 1, wherein

A is a methylene group;

Ar is a 1,4-phenylene group;

X is a nitrogen atom or an —HC= group;

Y is an oxygen or sulphur atom, or an —$R_2$N— group, wherein $R_2$ is a hydrogen atom or a methyl, benzyl, or $C_{1-3}$-alkoxycarbonylmethyl group;

$R_a$ is a hydrogen atom;

$R_b$ is a $R_{5a}NR_{6a}$—$SO_2$ group, wherein $R_{5a}$ is a $C_{1-3}$-alkyl or phenyl group, and $R_{6a}$ is a $C_{1-5}$-alkyl group terminally substituted by a carboxy or $C_{1-3}$-alkoxycarbonyl group or substituted in the 2 or 3 position by a dimethylamino group, or $R_{5a}$ together with $R_{6a}$ and the nitrogen atom between them are a pyrrolidino group unsubstituted or substituted by a $C_{1-3}$-alkoxycarbonyl group or a pyrrolidino group onto which a benzene ring is condensed via two adjacent carbon atoms, or an $R_{3a}$—$SO_2$—$NR_{4a}$ group, wherein $R_{3a}$ is a cyclopentyl, cyclohexyl, phenyl, naphthyl, quinolyl, or isoquinolyl group, and $R_{4a}$ is a hydrogen atom or a methyl group substituted by a carboxy, $C_{1-3}$-alkoxycarbonyl, morpholinocarbonyl, 4-dimethylaminopiperidinocarbonyl, 4-methyl-piperazinocarbonyl, 4-morpholinocarbonylmethylpiperazinocarbonyl, carboxymethylaminocarbonyl, N-methyl-carboxymethylaminocarbonyl, $C_{1-3}$-alkoxycarbonylmethyl-aminocarbonyl, N-methyl-$C_{1-3}$-alkoxycarbonylmethylamino-carbonyl, N-($C_{1-3}$-alkyl)-N-(2-dimethylamino-ethyl)-aminocarbonyl, N-(-carboxy-2-aminocarbonyl-ethyl)-aminocarbonyl, or N-(1-$C_{1-3}$-alkoxycarbonyl-2-aminocarbonyl-ethyl)-aminocarbonyl group, or an $R_{5b}$ $NR_{6b}$—CO group, wherein $R_{5b}$ is a $C_3$-alkyl, phenyl, or pyridyl group, and $R_{6b}$ is a $C_{1-5}$-alkyl group or a $C_{1-3}$-alkyl group substituted by a carboxy, $C_{1-3}$-alkoxycarbonyl, methylaminocarbonyl, carboxymethylaminocarbonyl, or $C_{1-3}$-alkoxycarbonylmethylaminocarbonyl group, and in the 2 or 3 position is unsubstituted or substituted by a dimethylamino group, or a $R_{3b}$—CO—$NR_{4b}$ group, wherein $R_{3b}$ is a phenyl group, and $R_{4b}$ is a $C_{1-3}$-alkyl group substituted by a carboxy or $C_{1-3}$-alkoxycarbonyl group, or $R_{3b}$ is a methyl group substituted by a carboxymethylamino, $C_{1-3}$-alkoxycarbonylmethylamino, carboxymethoxy, $C_{1-3}$-alkoxycarbonylmethoxy, or tetrazolyl group, and $R_{4b}$ is a cyclopentyl group, or a $R_{5c}NR_{6c}$—CO—$C_{3-5}$-(1,1-cyclopropylene) group, wherein $R_{5c}$ together with $R_{6c}$ and the nitrogen atom between them are 1-methyl-5-pyrazolyl group, a pyrrolidino group unsubstituted or substituted by a $C_{1-3}$-alkoxycarbonyl group, or a pyrrolidino group onto which a benzene ring is condensed via two adjacent carbon atoms, or $R_b$ is a N-pyrrolidinocarbonyl-methylamino, phenylsulphonyl, 4-oxo-2,3-diaza-spiro[5.5]undec-1-en-1-yl or $C_{3-5}$-alkyl-tetrazolyl group, a cyclohexylcarbonyl group substituted in the 1 position by a methyl, carboxymethyl, or $C_{1-3}$-alkoxycarbonyl-methyl group a cyclohexyl-N-(carboxymethoxy)-iminomethylene or cyclohexyl-N-($C_{1-3}$-alkoxycarbonylmethoxy)-iminomethylene group, which is additionally substituted in the cyclohexyl moiety by a methyl group, a phosphinyl group substituted by a $C_{3-6}$-alkyl group and by a $C_{1-3}$-alkoxymethoxy group, and $R_c$ is an amidino group, or a tautomer or salt thereof.

8. A compound selected from the group consisting of:

(a) 4-[(5-(N-Carboxymethyl-quinolin-8-yl-sulphonylamino)-1-methyl-1H-benzimidazol-2-yl)-methyl]-benzamidine, (b) 4-[(5-(N-Carboxymethylaminoacetyl-quinolin-8-yl-sulphonylamino)-1-methyl-1H-benzimidazol-2-yl)-methyl]-benzamidine, (c) 4-[(5-(N-(2-Dimethylamino-ethyl)-benzenesulphonylamino)-1-benzyl-1H-benzimidazol-2-yl)-methyl]-benzamidine, (d) 4-[(5-(N-(2-Diethylamino-ethyl)-benzenesulphonylamino)-1-(carboxymethylaminocarbonyl)-methyl-1H-benzimidazol-2-yl)-methyl]-benzamidine, (e) 4-[(5-Pyrrolidino-sulphonyl-1-methyl-1H-benzimidazol-2-yl)-methyl]-benzamidine, (f) 4-[(5-(N-Cyclopentyl-methanesulphonylamino)-1-methyl-1H-benzimidazol-2-yl)-methyl]-benzamidine, (g) 4-[(5-(N-Cyclopentyl-3-carboxypropionylamino)-1-methyl-1H-benzimidazol-2-yl)-methyl]-benzamidine, (h) 4-[(5-Pyrrolidinocarbonylcyclopropyl-1-methyl-1H-benzimidazol-2-yl)-methyl]-benzamidine and (i) 4-[(5-(N-Carboxymethyl-quinolin-8-yl-sulphonylamino-benzothiazol-2-yl)-methyl]-benzamidine or a salt thereof.

9. A physiologically acceptable salt of a compound according to claim 1, 2, 3, 4, 5, 6, 7 or 8, wherein $R_c$ is an amidino group as defined in the claim.

10. A pharmaceutical composition comprising a compound according to claim 1, 2, 3, 4, 5, 6, 7 or 8, wherein $R_c$ is an amidino group as defined in the claim, or a physiologically acceptable salt thereof, and one or more inert carriers or diluents.

11. A method of treating or inhibiting thrombus formation which comprises administering to a host in need of such treatment an anti-thrombotic amount of a compound according to claims 1, 2, 3, 4, 5, 6, 7 or 8, wherein $R_c$ is an amidino group as defined in the claim, or a physiologically acceptable salt thereof.

* * * * *